US012605446B2

(12) United States Patent
He

(10) Patent No.: US 12,605,446 B2
(45) Date of Patent: Apr. 21, 2026

(54) PSMA-TARGETED IMMUNOTHERAPIES FOR CANCERS

(71) Applicant: THE METHODIST HOSPITAL, Houston, TX (US)

(72) Inventor: Bin He, Bellaire, TX (US)

(73) Assignee: The Methodist Hospital, Houston, TX (US)

( * ) Notice: Subject to any disclaimer, the term of this patent is extended or adjusted under 35 U.S.C. 154(b) by 556 days.

(21) Appl. No.: 18/032,485

(22) PCT Filed: Aug. 20, 2021

(86) PCT No.: PCT/US2021/046945
§ 371 (c)(1),
(2) Date: Apr. 18, 2023

(87) PCT Pub. No.: WO2022/086620
PCT Pub. Date: Apr. 28, 2022

(65) Prior Publication Data
US 2023/0381316 A1 Nov. 30, 2023

Related U.S. Application Data

(60) Provisional application No. 63/094,005, filed on Oct. 20, 2020.

(51) Int. Cl.
| | |
|---|---|
| *A61K 40/15* | (2025.01) |
| *A61K 40/11* | (2025.01) |
| *A61K 40/31* | (2025.01) |
| *A61K 40/42* | (2025.01) |
| *A61P 35/00* | (2006.01) |
| *C07K 16/30* | (2006.01) |
| *C12N 5/0783* | (2010.01) |

(52) U.S. Cl.
CPC ............. *A61K 40/15* (2025.01); *A61K 40/11* (2025.01); *A61K 40/31* (2025.01); *A61K 40/4211* (2025.01); *A61K 40/4273* (2025.01); *A61K 40/4276* (2025.01); *A61P 35/00* (2018.01); *C07K 16/3069* (2013.01); *C12N 5/0636* (2013.01); *A61K 2239/31* (2023.05); *A61K 2239/38* (2023.05); *A61K 2239/57* (2023.05); *A61K 2239/58* (2023.05); *C07K 2317/622* (2013.01)

(58) Field of Classification Search
CPC ........ A61K 40/15; A61K 40/11; A61K 40/31; A61K 40/4211; A61K 40/4273; A61K 40/4276; A61K 2239/31; A61K 2239/38; A61K 2239/57; A61K 2239/58; A61P 35/00; C07K 16/3069; C07K 2317/622; C07K 2319/03; C07K 14/7051; C12N 5/0636; C12N 2501/15; C12N 2501/515; C12N 2510/00
See application file for complete search history.

(56) References Cited

U.S. PATENT DOCUMENTS

| | | | |
|---|---|---|---|
| 5,399,346 | A | 3/1995 | Anderson et al. |
| 5,580,859 | A | 12/1996 | Felgner et al. |
| 5,589,466 | A | 12/1996 | Felgner et al. |
| 5,858,358 | A | 1/1999 | June et al. |
| 5,883,223 | A | 3/1999 | Gray |
| 6,326,193 | B1 | 12/2001 | Liu et al. |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 9,499,629 | B2 | 11/2016 | June et al. |
| 2006/0121005 | A1 | 6/2006 | Berenson et al. |
| 2009/0214525 | A1 | 8/2009 | Goetsch et al. |
| 2010/0136684 | A1 | 6/2010 | Carroll et al. |
| 2014/0370045 | A1 | 12/2014 | June et al. |
| 2015/0342993 | A1 | 12/2015 | Kloss et al. |
| 2016/0361360 | A1 | 12/2016 | Chang et al. |
| 2018/0057609 | A1 | 3/2018 | June et al. |
| 2018/0187149 | A1 | 7/2018 | Ma et al. |

(Continued)

FOREIGN PATENT DOCUMENTS

| | | |
|---|---|---|
| WO | 2001/029058 | 4/2001 |
| WO | 2001/096584 | 12/2001 |

(Continued)

OTHER PUBLICATIONS

Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.

Bird, Robert E., et al. "Single-chain antigen-binding proteins." Science 242.4877 (1988): 423-426.

Beaucage, S. L., and Marvin H. Caruthers. "Deoxynucleoside phosphoramidites—a new class of key intermediates for deoxypolynucleotide synthesis." Tetrahedron letters 22.20 (1981): 1859-1862.

(Continued)

*Primary Examiner* — Misook Yu
*Assistant Examiner* — Grace H Lunde
(74) *Attorney, Agent, or Firm* — Meunier Carlin & Curfman LLC

(57) ABSTRACT

Disclosed are engineered cells comprising chimeric antigen receptors and uses thereof for treating prostate cancer.

15 Claims, 36 Drawing Sheets

Specification includes a Sequence Listing.

(56) References Cited

U.S. PATENT DOCUMENTS

| | | |
|---|---|---|
| 2018/0258391 A1 | 9/2018 | June et al. |
| 2019/0000881 A1 | 1/2019 | Sadelain et al. |
| 2019/0083534 A1 | 3/2019 | Brentjens et al. |
| 2019/0125797 A1 | 5/2019 | Powell, Jr. et al. |
| 2019/0183932 A1 | 6/2019 | MacKall et al. |

FOREIGN PATENT DOCUMENTS

| | | |
|---|---|---|
| WO | 2012/079000 | 6/2012 |
| WO | 2018115885 A1 | 6/2018 |

OTHER PUBLICATIONS

Matteucci, Mark Douglas, and M. Ho Caruthers. "Synthesis of deoxyoligonucleotides on a polymer support." Journal of the American Chemical Society 103.11 (1981): 3185-3191.

Ui-Tei, Kumiko, et al. "Sensitive assay of RNA interference in *Drosophila* and Chinese hamster cultured cells using firefly luciferase gene as target." FEBS letters 479.3 (2000): 79-82.

Li, Ye, et al. "Human iPSC-derived natural killer cells engineered with chimeric antigen receptors enhance anti-tumor activity." Cell stem cell 23.2 (2018): 181-192.

Liu, Enli, et al. "Use of CAR-transduced natural killer cells in CD19-positive lymphoid tumors." New England Journal of Medicine 382.6 (2020): 545-553.

Zuccolotto et al. (2014), PSMA-Specific CAR-Engineered T Cells Eradicate Disseminated Prostate Cancer in Preclinical Models. PLOS One 9(10): e109427.

Junghans et al., (2016), Phase I Trial of Anti-PSMA Designer CAR-T Cells in Prostate Cancer: Possible Role for Interacting Interleukin 2-T Cell Pharmacodynamics as a Determinant of Clinical Response. Prostate, 76, 1257-1270.

Narayan et al., (2019), A Phase I Clinical Trial of PSMA-directed/TGFβ-insensitive CAR-T Cells in Metastatic Castration-Resistant Prostate Cancer. Journal of Clinical Oncology, 37:7_suppl, TPS347-TPS347. Clinical Trial Information: NCT03089203.

Kloss et al. (2018), Dominant-Negative TGF-β Receptor Enhances PSMA-Targeted Human Car T Cell Proliferation And Augments Prostate Cancer Eradication. Molecular Therapy, 26:7, 1855-1866. Clinical Trial Information: NCT01140373.

Clinical Trial Information: NCT03692663.

American Cancer Society & National Cancer Institute—2019 76 pages.https://www.cancer.org/content/dam/cancer-org/research/cancer-facts-and-statistics/annual-cancer-facts-and-figures/2019/cancer-facts-and-figures-2019.pdf & https://seer.cancer.gov/statfacts/html/prost.html 2019.

World Cancer Research Fund—https://www.wcrf.org/dietandcancer/cancer-trends/prostate-cancer-statistics Mar. 23, 2022.

Cancer Immunotherapy Market Analysis Grand View Research—https://www.grandviewresearch.com/industry-analysis/cancer-immunotherapy-market?utm_source=google&utm_medium=cpc&utm_campaign=AdWords_CancerImmunotherapy_Type2_Healthcare&gclid=Cj0KCQjw1MXpBRDjARIsAHtdN-06yr8hvmHj8ENJDturrRNOUlehtvCdyJRW1FKRv12d7j18Uw3GrNcaAkSrEALw_wcB.

Prostate Cancer Therapeutic Market Analysis Zion Market Research—https://www.globenewswire.com/news-release/2018/09/24/1575060/0/en/Global-Prostate-Cancer-Therapeutics-Market-Will-Reach-USD-17-200-Million-By-2024-Zion-Market-Research.html Sep. 24, 2018.

Grand View Research—https://www.grandviewresearch.com/press-release/global-prostate-cancer-therapeutics-market Oct. 2022.

International Preliminary Report on Patentability dated May 4, 2023.

International Search Report and Written Opinion for corresponding International Application No. PCT/US2021/046945 dated Dec. 16, 2021 by US ISA.

(Cont,d)

Table of Values

| PMC | mAb | ka (1/MS) | kd (1/S) | KD (M) | Best Fit | Chi Sq |
|-----|-----|-----------|----------|--------|----------|--------|
| 444 | 219 | 7.52E+04 | 1.99E-04 | 2.64E-09 | Langmuir | 2.08E+01 |
| 445 | 1377 | 4.45E+04 | 8.29E-04 | 1.86E-08 | Bivalent | 5.66E+00 |
| 446 | 1366 | 3.66E+04 | 1.08E-02 | 2.95E-07 | Bivalent | 5.57E+00 |
| 447 | 1352 | 9.06E+04 | 1.80E-04 | 1.99E-09 | Bivalent | 4.07E+00 |
| 448 | 1207 | 1.20E+05 | 9.75E-04 | 8.13E-09 | Bivalent | 3.51E+01 |
| | | | | | | |
| ScFv Fc | | | | | | |
| 444 | | 3.38E+04 | 1.47E-04 | 4.35E-09 | Bivalent | 4.60E+00 |
| 445 | | 5.68E+04 | 1.45E-04 | 2.55E-09 | Bivalent | 1.99E+00 |
| 446 | | 6.47E+02 | 7.51E-04 | 1.16E-06 | Bivalent | 3.02E+04 |

FIG. 10
(Cont'd)

N0: no regional lymph node metastasis
N1: metastases in 1-3 axillary lymph nodes

| mAB # | Isotype | ka (1/MS) | kd (1/S) | KD (nM) |
|-------|---------|-----------|----------|---------|
| 444 | IgG1 | 7.52E+04 | 1.99E-04 | 2.64 |
| 445 | IgG1 | 4.45E+04 | 8.29E-04 | 18.6 |
| 446 | IgG1 | 3.66E+04 | 1.08E-02 | 295.0 |
| 447 | IgG2b | 9.06E+04 | 1.80E-04 | 1.99 |
| 448 | IgG2a | 1.20E+05 | 9.75E-04 | 8.13 |
| J591* | IgG1 | N.A. | N.A. | 1.83* |

HV-linker-Lv
444-CAR
445-CAR
446-CAR
447-CAR
448-CAR
J591-CAR

LV-linker-Hv
4LH-CAR
5LH-CAR
6LH-CAR
7LH-CAR
8LH-CAR (Cont,d)

Mock:190X: P<0.01 at D7, 11, 16
190S:190X P<0.001 at D7, 11, 16

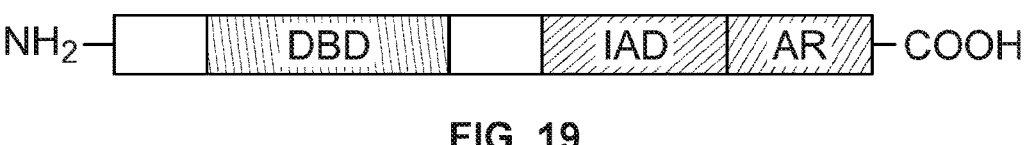
FIG. 19
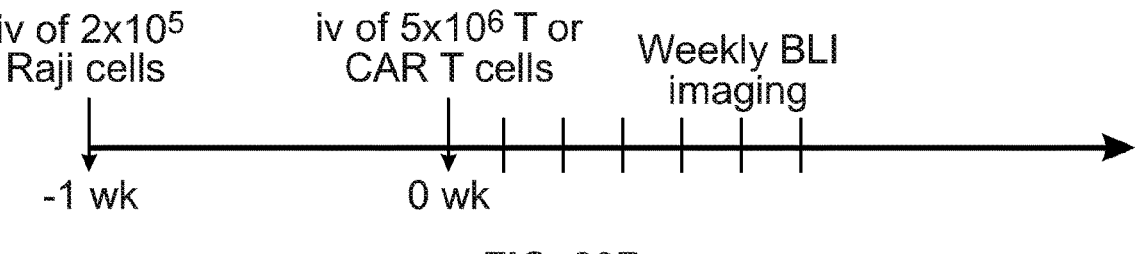
FIG. 20A
iv of $2\times10^5$
Raji cells
iv of $5\times10^6$ T or
CAR T cells
Weekly BLI
imaging
-1 wk          0 wk
FIG. 20B

SEQUENCE LISTING

<160> NUMBER OF SEQ ID NOS: 64

<210> SEQ ID NO 1
<211> LENGTH: 1443
<212> TYPE: DNA
<213> ORGANISM: Artificial Sequence
<220> FEATURE:
<223> OTHER INFORMATION: Synthetic construct

<400> SEQUENCE: 1

```
atggccttac cagtgaccgc cttgctcctg ccgctggcct tgctgctcca cgccgccagg        60
cctgttcagc tgcagcagtc tggacctgaa ctggagaagc ctggcgcttc agtgaagatg       120
tcctgcaagg cttctggtta ctcattcact ggctacaacg taaactgggt gagacagaac       180
aatggaaaga gccttgagtg gattggaaat attgatcctc tccatggtgg tactacctac       240
aaccagaaat tcaaggccaa ggccacattg actgtagaca gatcctccag cacagcctac       300
ttgcagctca gaacctgac atctgaggac tctgcagtct attactgtgc aagatctagt       360
aggtttgact actggggcca aggcaccact ctcacagtct cctcaggtgg cggtggcagc       420
ggcggtggtg gttccggagg cggcggttct gacattgtga tgacccagtc tcacaaattc       480
atgtccacat cagtaggaga cagggtcaac atcacctgca aggccagtca ggatgtgggt       540
actgctgtag cctggtatca acaaaaacca gggcaatctc ctaaactact aatttactgg       600
```

---

-continued

```
gcatccaccc ggcacactgg agtccctgat cgcttcacag gcagtggatc tgggacagat    660
ttcactctca ccattagcaa tgtgcaatct gaagacttgg cagattattt ctgtcaccaa    720
tttaccagct atccattcac gttcggctcg gggacaagct tggaaatgaa acggaccacg    780
acgccagcgc cgcgaccacc aacaccggcg cccaccatcg cgtcgcagcc cctgtccctg    840
cgcccagagg cgtgccggcc agcggcgggg ggcgcagtgc acacgagggg gctggacttc    900
gcctgtgaca tctacatctg ggcgcccctg gccgggactt gtggggtcct tctcctgtca    960
ctggttatca cccttttactg caaacggggc agaaagaaac tcctgtatat attcaaacaa   1020
ccatttatga gaccagtaca aactactcaa gaggaagatg gctgtagctg ccgatttcca   1080
gaagaagaag aaggaggatg tgaactgaga gtgaagttca gcaggagcgc agacgccccc   1140
gcgtacaagc agggccagaa ccagctctat aacgagctca tctaggacg aagagaggag   1200 tacgatgttt tggacaagag acgtggccgg gaccctgaga tggggggaaa gccgagaagg   1260
aagaaccctc aggaaggcct gtacaatgaa ctgcagaaag ataagatggc ggaggcctac   1320
agtgagattg ggatgaaagg cgagcgccgg aggggcaagg ggcacgatgg cctttaccag   1380
ggtctcagta cagccaccaa ggacacctac gacgcccttc acatgcaggc cctgccccct   1440
cgc                                                                                                  1443
```

<210> SEQ ID NO 2
<211> LENGTH: 481
<212> TYPE: PRT
<213> ORGANISM: Artificial Sequence
<220> FEATURE:
<223> OTHER INFORMATION: Synthetic construct

<400> SEQUENCE: 2

```
Met Ala Leu Pro Val Thr Ala Leu Leu Leu Pro Leu Ala Leu Leu Leu
1               5                   10                  15

His Ala Ala Arg Pro Val Gln Leu Gln Gln Ser Gly Pro Glu Leu Glu
            20                  25                  30

Lys Pro Gly Ala Ser Val Lys Met Ser Cys Lys Ala Ser Gly Tyr Ser
        35                  40                  45

Phe Thr Gly Tyr Asn Val Asn Trp Val Arg Gln Asn Asn Gly Lys Ser
    50                  55                  60

Leu Glu Trp Ile Gly Asn Ile Asp Pro Leu His Gly Gly Thr Thr Tyr
65                  70                  75                  80

Asn Gln Lys Phe Lys Ala Lys Ala Thr Leu Thr Val Asp Arg Ser Ser
                85                  90                  95

Ser Thr Ala Tyr Leu Gln Leu Lys Asn Leu Thr Ser Glu Asp Ser Ala
            100                 105                 110

Val Tyr Tyr Cys Ala Arg Ser Ser Arg Phe Asp Tyr Trp Gly Gln Gly
            115                 120                 125

Thr Thr Leu Thr Val Ser Ser Gly Gly Gly Gly Ser Gly Gly Gly Gly
        130                 135                 140

Ser Gly Gly Gly Gly Ser Asp Ile Val Met Thr Gln Ser His Lys Phe
145                 150                 155                 160

Met Ser Thr Ser Val Gly Asp Arg Val Asn Ile Thr Cys Lys Ala Ser
                165                 170                 175

Gln Asp Val Gly Thr Ala Val Ala Trp Tyr Gln Gln Lys Pro Gly Gln
            180                 185                 190

Ser Pro Lys Leu Leu Ile Tyr Trp Ala Ser Thr Arg His Thr Gly Val
        195                 200                 205
```

```
Pro Asp Arg Phe Thr Gly Ser Gly Ser Gly Thr Asp Phe Thr Leu Thr
    210             215             220

Ile Ser Asn Val Gln Ser Glu Asp Leu Ala Asp Tyr Phe Cys His Gln
225             230             235             240

Phe Thr Ser Tyr Pro Phe Thr Phe Gly Ser Gly Thr Ser Leu Glu Met
            245             250             255

Lys Arg Thr Thr Thr Pro Ala Pro Arg Pro Pro Thr Pro Ala Pro Thr
            260             265             270

Ile Ala Ser Gln Pro Leu Ser Leu Arg Pro Glu Ala Cys Arg Pro Ala
        275             280             285

Ala Gly Gly Ala Val His Thr Arg Gly Leu Asp Phe Ala Cys Asp Ile
    290             295             300

Tyr Ile Trp Ala Pro Leu Ala Gly Thr Cys Gly Val Leu Leu Leu Ser
305             310             315             320

Leu Val Ile Thr Leu Tyr Cys Lys Arg Gly Arg Lys Lys Leu Leu Tyr
            325             330             335

Ile Phe Lys Gln Pro Phe Met Arg Pro Val Gln Thr Thr Gln Glu Glu
            340             345             350

Asp Gly Cys Ser Cys Arg Phe Pro Glu Glu Glu Glu Gly Gly Cys Glu
            355             360             365

Leu Arg Val Lys Phe Ser Arg Ser Ala Asp Ala Pro Ala Tyr Lys Gln
    370             375             380

Gly Gln Asn Gln Leu Tyr Asn Glu Leu Asn Leu Gly Arg Arg Glu Glu
385             390             395             400

Tyr Asp Val Leu Asp Lys Arg Arg Gly Arg Asp Pro Glu Met Gly Gly
            405             410             415

Lys Pro Arg Arg Lys Asn Pro Gln Glu Gly Leu Tyr Asn Glu Leu Gln
            420             425             430

Lys Asp Lys Met Ala Glu Ala Tyr Ser Glu Ile Gly Met Lys Gly Glu
            435             440             445

Arg Arg Arg Gly Lys Gly His Asp Gly Leu Tyr Gln Gly Leu Ser Thr
    450             455             460

Ala Thr Lys Asp Thr Tyr Asp Ala Leu His Met Gln Ala Leu Pro Pro
465             470             475             480

Arg
```

```
<210> SEQ ID NO 3
<211> LENGTH: 1470
<212> TYPE: DNA
<213> ORGANISM: Artificial Sequence
<220> FEATURE:
<223> OTHER INFORMATION: Synthetic construct

<400> SEQUENCE: 3
atggccttac cagtgaccgc cttgctcctg ccgctggcct tgctgctcca cgccgccagg        60
cctgtccaat tgcagcagcc tgggggctgcg ctggtgaggc ctggagcttc agtgaggctg       120
tcctgcaagg cttctggata tcccttcacc tactactgga tgaactgggt gatgcagagg       180
cctggccaag gccttgagtg gattggcatg attcatcctt ccgatagtga aactcggtta       240
agtcagaagt tcaggacaa ggccacattg actgtagaca atcttccag cacagtctac        300 atgcaactca acagcccgac atctgatgac tctgcagtct attactgtgc aagagatggt       360
aacttccctt actatgcact agactactgg ggtcaaggaa cctcggtcac cgtctcctca       420
ggtggcggtg gcagcggcgg tggtggttcc ggaggcggcg gttctgatgt tgtgctgacc       480
```

```
caagctccac tctccctgcc tgtcagtctt ggagatcaag cctccatctc ttgcagatct        540
agtcagagcc ttgaatacag taatggaaac acctatttac attggtacct gcagaagcca        600
ggccagtctc cagaactcct gatctacaca gtttccaacc gattttctgg ggtcccagac        660
aggttcagtg gcagtggatc agggacagat ttcacactca agattcacag agtgggaggct       720 gaggatctgg gagtttattt ctgctctcaa agtacacatg ttcccacgtt cggagggggg        780
accaagctgg agataaaacg gaccacgacg ccagcgccgc gaccaccaac accggcgccc        840
accatcgcgt cgcagcccct gtccctgcgc ccagaggcgt gccggccagc ggcggggggc        900
gcagtgcaca cgagggggct ggacttcgcc tgtgacatct acatctgggc gcccctggcc        960
gggacttgtg gggtccttct cctgtcactg gttatcaccc tttactgcaa acggggcaga       1020
aagaaactcc tgtatatatt caaacaacca tttatgagac cagtacaaac tactcaagag       1080
gaagatggct gtagctgccg atttccagaa gaagaagaag aggatgtga actgagagtg        1140 aagttcagca ggagcgcaga cgcccccgcg tacaagcagg gccagaacca gctctataac       1200
gagctcaatc taggacgaag agaggagtac gatgttttgg acaagagacg tggccgggac       1260
cctgagatgg ggggaaagcc gagaaggaag aaccctcagg aaggcctgta caatgaactg       1320
cagaaagata agatggcgga ggcctacagt gagattggga tgaaaggcga gcgccggagg       1380 ggcaagggggc acgatggcct ttaccagggt ctcagtacag ccaccaagga cacctacgac       1440
gcccttcaca tgcaggccct gccccctcgc                                        1470
```

<210> SEQ ID NO 4
<211> LENGTH: 490
<212> TYPE: PRT
<213> ORGANISM: Artificial Sequence
<220> FEATURE:
<223> OTHER INFORMATION: Synthetic construct

<400> SEQUENCE: 4

```
Met Ala Leu Pro Val Thr Ala Leu Leu Leu Pro Leu Ala Leu Leu Leu
1               5                   10                  15

His Ala Ala Arg Pro Val Gln Leu Gln Gln Pro Gly Ala Ala Leu Val
                20                  25                  30

Arg Pro Gly Ala Ser Val Arg Leu Ser Cys Lys Ala Ser Gly Tyr Ser
            35                  40                  45

Phe Thr Tyr Tyr Trp Met Asn Trp Val Met Gln Arg Pro Gly Gln Gly
        50                  55                  60

Leu Glu Trp Ile Gly Met Ile His Pro Ser Asp Ser Glu Thr Arg Leu
65                  70                  75                  80

Ser Gln Lys Phe Arg Asp Lys Ala Thr Leu Thr Val Asp Lys Ser Ser
                85                  90                  95

Ser Thr Val Tyr Met Gln Leu Asn Ser Pro Thr Ser Asp Asp Ser Ala
            100                 105                 110

Val Tyr Tyr Cys Ala Arg Asp Gly Asn Phe Pro Tyr Tyr Ala Leu Asp
        115                 120                 125

Tyr Trp Gly Gln Gly Thr Ser Val Thr Val Ser Ser Gly Gly Gly Gly
        130                 135                 140

Ser Gly Gly Gly Gly Ser Gly Gly Gly Gly Ser Asp Val Val Leu Thr
145                 150                 155                 160

Gln Ala Pro Leu Ser Leu Pro Val Ser Leu Gly Asp Gln Ala Ser Ile
                165                 170                 175

Ser Cys Arg Ser Ser Gln Ser Leu Glu Tyr Ser Asn Gly Asn Thr Tyr
            180                 185                 190
```

```
Leu His Trp Tyr Leu Gln Lys Pro Gly Gln Ser Pro Glu Leu Leu Ile
        195                 200                 205

Tyr Thr Val Ser Asn Arg Phe Ser Gly Val Pro Asp Arg Phe Ser Gly
    210                 215                 220

Ser Gly Ser Gly Thr Asp Phe Thr Leu Lys Ile His Arg Val Glu Ala
225                 230                 235                 240

Glu Asp Leu Gly Val Tyr Phe Cys Ser Gln Ser Thr His Val Pro Thr
                245                 250                 255

Phe Gly Gly Gly Thr Lys Leu Glu Ile Lys Arg Thr Thr Thr Pro Ala
                260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 5
<211> LENGTH: 1446
<212> TYPE: DNA
<213> ORGANISM: Artificial Sequence
<220> FEATURE:
<223> OTHER INFORMATION: Synthetic construct

<400> SEQUENCE: 5
atggccttac cagtgaccgc cttgctcctg ccgctggcct tgctgctcca cgccgccagg    60
cctgtgaagc tgcaggagtc aggacctggc ctggtggcgc cctcacagag cctgtccatc   120
acatgcactg tctcagggtt ctcattaacc gactatggtg tgagttggat tcgccagcct   180
ccaggaaagg gtctggagtg gctgggagta atatggagcg atggaaacac atactataat   240
tcacctctca atccagact gagcatcaac aaggacaact ccaagagcca gtttttctta   300
aaaatgaaca gtctgcaaac tgatgactca gccatgtact actgtgccag acataaggtc   360
```

```
tatactatgg actactgggg tcaaggaacc tcagtcaccg tctcctcagg tggcggtggc    420
agcggcggtg gtggttccgg aggcggcggt tctactgtgc tcacccagtc tccagcaatc    480
atgtctgcat ctccagggga aaaggtcacc atgacctgca gggccagctc aagtgtaagt    540
tccagttact tgcactggta ccagcagaag tcaagtgcct cccccaaact ctggatttat    600
agaacatcca acttggcttc tggagtccct gctcgcttca gtggcagtgg gtctgggacc    660
tcttactctc tcacaatcag cagtttggag gctgaagatg ctgccactta ttactgccag    720
cagtacagtg gttacccact cacgttcggt gctgggacca agctggagct gaaacggacc    780
acgacgccag cgccgcgacc accaacaccg gcgcccacca tcgcgtcgca gcccctgtcc    840
ctgcgcccag aggcgtgccg gccagcggcg gggggcgcag tgcacacgag ggggctggac    900
ttcgcctgtg acatctacat ctgggcgccc ctggccggga cttgtggggt ccttctcctg    960
tcactggtta tcacccttta ctgcaaacgg ggcagaaaga aactcctgta tatattcaaa   1020
caaccattta tgagaccagt acaaactact caagaggaag atggctgtag ctgccgattt   1080
ccagaagaag aagaaggagg atgtgaactg agagtgaagt tcagcaggag cgcagacgcc   1140
cccgcgtaca gcagggcca gaaccagctc tataacgagc tcaatctagg acgaagagag   1200
gagtacgatg ttttggacaa gagacgtggc cgggaccctg agatggggg aaagccgaga   1260 aggaagaacc ctcaggaagg cctgtacaat gaactgcaga agataagat ggcggaggcc   1320 tacagtgaga ttgggatgaa aggcgagcgc cggaggggca aggggcacga tggcctttac   1380
cagggtctca gtacagccac caaggacacc tacgacgccc ttcacatgca ggccctgccc   1440
cctcgc                                                               1446
```

<210> SEQ ID NO 6
<211> LENGTH: 482
<212> TYPE: PRT
<213> ORGANISM: Artificial Sequence
<220> FEATURE:
<223> OTHER INFORMATION: Synthetic construct

<400> SEQUENCE: 6

```
Met Ala Leu Pro Val Thr Ala Leu Leu Leu Pro Leu Ala Leu Leu Leu
1               5                   10                  15

His Ala Ala Arg Pro Val Lys Leu Gln Glu Ser Gly Pro Gly Leu Val
            20                  25                  30

Ala Pro Ser Gln Ser Leu Ser Ile Thr Cys Thr Val Ser Gly Phe Ser
        35                  40                  45

Leu Thr Asp Tyr Gly Val Ser Trp Ile Arg Gln Pro Pro Gly Lys Gly
    50                  55                  60

Leu Glu Trp Leu Gly Val Ile Trp Ser Asp Gly Asn Thr Tyr Tyr Asn
65                  70                  75                  80

Ser Pro Leu Lys Ser Arg Leu Ser Ile Asn Lys Asp Asn Ser Lys Ser
                85                  90                  95

Gln Val Phe Leu Lys Met Asn Ser Leu Gln Thr Asp Asp Ser Ala Met
            100                 105                 110

Tyr Tyr Cys Ala Arg His Lys Val Tyr Thr Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Thr Val Leu Thr Gln Ser Pro Ala Ile
145                 150                 155                 160
```

```
Met Ser Ala Ser Pro Gly Glu Lys Val Thr Met Thr Cys Arg Ala Ser
                165              170              175

Ser Ser Val Ser Ser Ser Tyr Leu His Trp Tyr Gln Gln Lys Ser Ser
            180              185              190

Ala Ser Pro Lys Leu Trp Ile Tyr Arg Thr Ser Asn Leu Ala Ser Gly
            195              200              205

Val Pro Ala Arg Phe Ser Gly Ser Gly Ser Gly Thr Ser Tyr Ser Leu
    210              215              220

Thr Ile Ser Ser Leu Glu Ala Glu Asp Ala Ala Thr Tyr Tyr Cys Gln
225              230              235              240

Gln Tyr Ser Gly Tyr Pro Leu Thr Phe Gly Ala Gly Thr Lys Leu Glu
            245              250              255

Leu Lys Arg Thr Thr Thr Pro Ala Pro Arg Pro Pro Thr Pro Ala Pro
            260              265              270

Thr Ile Ala Ser Gln Pro Leu Ser Leu Arg Pro Glu Ala Cys Arg Pro
            275              280              285

Ala Ala Gly Gly Ala Val His Thr Arg Gly Leu Asp Phe Ala Cys Asp
            290              295              300

Ile Tyr Ile Trp Ala Pro Leu Ala Gly Thr Cys Gly Val Leu Leu Leu
305              310              315              320

Ser Leu Val Ile Thr Leu Tyr Cys Lys Arg Gly Arg Lys Lys Leu Leu
            325              330              335

Tyr Ile Phe Lys Gln Pro Phe Met Arg Pro Val Gln Thr Thr Gln Glu
            340              345              350

Glu Asp Gly Cys Ser Cys Arg Phe Pro Glu Glu Glu Glu Gly Gly Cys
            355              360              365

Glu Leu Arg Val Lys Phe Ser Arg Ser Ala Asp Ala Pro Ala Tyr Lys
            370              375              380

Gln Gly Gln Asn Gln Leu Tyr Asn Glu Leu Asn Leu Gly Arg Arg Glu
385              390              395              400

Glu Tyr Asp Val Leu Asp Lys Arg Arg Gly Arg Asp Pro Glu Met Gly
            405              410              415

Gly Lys Pro Arg Arg Lys Asn Pro Gln Glu Gly Leu Tyr Asn Glu Leu
            420              425              430

Gln Lys Asp Lys Met Ala Glu Ala Tyr Ser Glu Ile Gly Met Lys Gly
            435              440              445

Glu Arg Arg Arg Gly Lys Gly His Asp Gly Leu Tyr Gln Gly Leu Ser
            450              455              460

Thr Ala Thr Lys Asp Thr Tyr Asp Ala Leu His Met Gln Ala Leu Pro
465              470              475              480

Pro Arg
```

<210> SEQ ID NO 7
<211> LENGTH: 1443
<212> TYPE: DNA
<213> ORGANISM: Artificial Sequence
<220> FEATURE:
<223> OTHER INFORMATION: Synthetic construct

<400> SEQUENCE: 7

```
atggccttac cagtgaccgc cttgctcctg ccgctggcct tgctgctcca cgccgccagg      60
cctgtgaagc tgcagcagtc tggacctgaa ctggagaagc ctggcgcatc agtgaagata     120
tcctgcaagg cttcaggtta ctcattcact ggctacaacg tgaactgggt gaagcagagc     180
aatggaaaga gccttgagtg gattggaaat attgatcctt accatggtgg tactacctac     240
```

```
aaccagaaat tcgaggccaa ggccacattg actgtagaca aatcctccag cacagcctac        300
atgcagctca agagccttac atctgaggac tctgcagtct attattgtgc aagatctagt        360
agatttgact actggggcca aggcaccact ctcacagtct cctcaggtgg cggtggcagc        420
ggcggtggtg gttccggagg cggcggttct gacattgtga tgacccagtc tcacaaattc        480
atgtccacat cagtgggaga cagggtcaac atcacctgca aggccagtca ggatgtgggt        540
actgctgtag cctggtatca acagaaacca gggcaatctc ctaaatttct aatttactgg        600
gcatccaccc ggcacactgg agtccctgat cgcttcacag gcagtggatc tgggacagat        660
ttcactctca ccattagcaa tgtgcagtct gaagacttgg cagattattt ctgtcatcag        720
tataccagct atccattcac gttcggctcg gggacaaagt tggaaatgaa acggaccacg        780
acgccagcgc cgcgaccacc aacaccggcg cccaccatcg cgtcgcagcc cctgtccctg        840
cgcccagagg cgtgccggcc agcggcgggg ggcgcagtgc acacgagggg gctggacttc        900
gcctgtgaca tctacatctg ggcgcccctg gccgggactt gtggggtcct tctcctgtca        960
ctggttatca cccttttactg caaacggggc agaaagaaac tcctgtatat attcaaacaa       1020
ccatttatga gaccagtaca aactactcaa gaggaagatg gctgtagctg ccgatttcca       1080
gaagaagaag aaggaggatg tgaactgaga gtgaagttca gcaggagcgc agacgccccc       1140
gcgtacaagc agggccagaa ccagctctat aacgagctca atctaggacg aagagaggag       1200
tacgatgttt tggacaagag acgtggccgg gaccctgaga tggggggaaa gccgagaagg       1260
aagaaccctc aggaaggcct gtacaatgaa ctgcagaaag ataagatggc ggaggcctac       1320
agtgagattg ggatgaaagg cgagcgccgg aggggcaagg ggcacgatgg cctttaccag       1380
ggtctcagta cagccaccaa ggacacctac gacgcccttc acatgcaggc cctgccccct       1440
cgc                                                                    1443
```

<210> SEQ ID NO 8
<211> LENGTH: 481
<212> TYPE: PRT
<213> ORGANISM: Artificial Sequence
<220> FEATURE:
<223> OTHER INFORMATION: Synthetic construct

<400> SEQUENCE: 8

```
Met Ala Leu Pro Val Thr Ala Leu Leu Leu Pro Leu Ala Leu Leu Leu
1               5                   10                  15

His Ala Ala Arg Pro Val Lys Leu Gln Gln Ser Gly Pro Glu Leu Glu
            20                  25                  30

Lys Pro Gly Ala Ser Val Lys Ile Ser Cys Lys Ala Ser Gly Tyr Ser
        35                  40                  45

Phe Thr Gly Tyr Asn Val Asn Trp Val Lys Gln Ser Asn Gly Lys Ser
    50                  55                  60

Leu Glu Trp Ile Gly Asn Ile Asp Pro Tyr His Gly Gly Thr Thr Tyr
65                  70                  75                  80

Asn Gln Lys Phe Glu Ala Lys Ala Thr Leu Thr Val Asp Lys Ser Ser
            85                  90                  95

Ser Thr Ala Tyr Met Gln Leu Lys Ser Leu Thr Ser Glu Asp Ser Ala
            100                 105                 110

Val Tyr Tyr Cys Ala Arg Ser Ser Arg Phe Asp Tyr Trp Gly Gln Gly
        115                 120                 125

Thr Thr Leu Thr Val Ser Ser Gly Gly Gly Gly Ser Gly Gly Gly Gly
    130                 135                 140
```

```
Ser Gly Gly Gly Gly Ser Asp Ile Val Met Thr Gln Ser His Lys Phe
145                 150                 155                 160

Met Ser Thr Ser Val Gly Asp Arg Val Asn Ile Thr Cys Lys Ala Ser
                165                 170                 175

Gln Asp Val Gly Thr Ala Val Ala Trp Tyr Gln Gln Lys Pro Gly Gln
            180                 185                 190

Ser Pro Lys Phe Leu Ile Tyr Trp Ala Ser Thr Arg His Thr Gly Val
        195                 200                 205

Pro Asp Arg Phe Thr Gly Ser Gly Ser Gly Thr Asp Phe Thr Leu Thr
    210                 215                 220

Ile Ser Asn Val Gln Ser Glu Asp Leu Ala Asp Tyr Phe Cys His Gln
225                 230                 235                 240

Tyr Thr Ser Tyr Pro Phe Thr Phe Gly Ser Gly Thr Lys Leu Glu Met
                245                 250                 255

Lys Arg Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Lys Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg
```

<210> SEQ ID NO 9
<211> LENGTH: 1467
<212> TYPE: DNA
<213> ORGANISM: Artificial Sequence
<220> FEATURE:
<223> OTHER INFORMATION: Synthetic construct

<400> SEQUENCE: 9
atggccttac cagtgaccgc cttgctcctg ccgctggcct tgctgctcca cgccgccagg        60
cctgttaagc tgcagcagtc gggacctggc ctggtgaaac cttctcagtc tctgtccctc       120

```
acctgcgctg tcactggcta ctcaatcacc agtgattatg cctggaactg gatccggaag    180
tttccaggaa acaaactgga gtggatgggc tacataagct acagtggtag aactacctac    240
aatccatctc tcgaaagtcg aatctctatc actcgagaca catccaaaaa ccagttcttc    300
ctgcagttga attctgtgac tactgaggac acagccacat attactgtgc aagatgttac    360
tacggtagta gctcccgttg gtatggtatg gactactggg gtcgcggaac ctcagtcgcc    420
gtgtcctcag gtggcggtgg cagcggcggt ggtggttccg gaggcggcgg ttctattgtg    480
ctcacccagt ctccagcaat catgtctgca tctccagggg taaaggtcac catgacctgc    540
agggccagct caagtgtaga ttccagttac ttgcactggt accagcagaa gtcaggtgcc    600
tccccccaag tctggattta tagcacatcc aacttggctt ctggagtccc ggctcgcttc    660
agtggcagtg gtctgggac ctcttactct ctcacaatca gtagtgtgga ggctgaagat    720
gctgccactt attactgcca gcagtacagt ggttatccac tgacgttcgg tggaggcacc    780
aagctggaaa tcaaacggac cacgacgcca gcgccgcgac caccaacacc ggcgcccacc    840
atcgcgtcgc agcccctgtc cctgcgccca gaggcgtgcc ggccagcggc ggggggcgca    900
gtgcacacga gggggctgga cttcgcctgt gacatctaca tctgggcgcc cctggccggg    960
acttgtgggg tccttctcct gtcactggtt atcacccttt actgcaaacg gggcagaaag    1020
aaactcctgt atatattcaa acaaccattt atgagaccag tacaaactac tcaagaggaa    1080
gatggctgta gctgccgatt tccagaagaa gaagaaggag gatgtgaact gagagtgaag    1140
ttcagcagga gcgcagacgc ccccgcgtac aagcagggcc agaaccagct ctataacgag    1200
ctcaatctag gacgaagaga ggagtacgat gtttttggaca agagacgtgg ccgggaccct    1260
gagatggggg gaaagccgag aaggaagaac cctcaggaag gcctgtacaa tgaactgcag    1320
aaagataaga tggcggaggc ctacagtgag attgggatga aaggcgagcg ccggagggggc    1380 aaggggcacg atggccttta ccagggtctc agtacagcca ccaaggacac ctacgacgcc    1440
cttcacatgc aggccctgcc ccctcgc                                        1467
```

```
<210> SEQ ID NO 10
<211> LENGTH: 489
<212> TYPE: PRT
<213> ORGANISM: Artificial Sequence
<220> FEATURE:
<223> OTHER INFORMATION: Synthetic construct

<400> SEQUENCE: 10

Met Ala Leu Pro Val Thr Ala Leu Leu Leu Pro Leu Ala Leu Leu Leu
1               5                   10                  15

His Ala Ala Arg Pro Val Lys Leu Gln Gln Ser Gly Pro Gly Leu Val
            20                  25                  30

Lys Pro Ser Gln Ser Leu Ser Leu Thr Cys Ala Val Thr Gly Tyr Ser
        35                  40                  45

Ile Thr Ser Asp Tyr Ala Trp Asn Trp Ile Arg Lys Phe Pro Gly Asn
    50                  55                  60

Lys Leu Glu Trp Met Gly Tyr Ile Ser Tyr Ser Gly Arg Thr Thr Tyr
65                  70                  75                  80

Asn Pro Ser Leu Glu Ser Arg Ile Ser Ile Thr Arg Asp Thr Ser Lys
                85                  90                  95

Asn Gln Phe Phe Leu Gln Leu Asn Ser Val Thr Thr Glu Asp Thr Ala
            100                 105                 110

Thr Tyr Tyr Cys Ala Arg Cys Tyr Tyr Gly Ser Ser Ser Arg Trp Tyr
```

-continued

```
              115                 120                 125
Gly Met Asp Tyr Trp Gly Arg Gly Thr Ser Val Ala Val Ser Ser Gly
    130                 135                 140

Gly Gly Gly Ser Gly Gly Gly Ser Gly Gly Gly Ser Ile Val
145                 150                 155                 160

Leu Thr Gln Ser Pro Ala Ile Met Ser Ala Ser Pro Gly Val Lys Val
                165                 170                 175

Thr Met Thr Cys Arg Ala Ser Ser Ser Val Asp Ser Ser Tyr Leu His
            180                 185                 190

Trp Tyr Gln Gln Lys Ser Gly Ala Ser Pro Gln Val Trp Ile Tyr Ser
            195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Ser Val Glu Ala Glu Asp
225                 230                 235                 240

Ala Ala Thr Tyr Tyr Cys Gln Gln Tyr Ser Gly Tyr Pro Leu Thr Phe
            245                 250                 255

Gly Gly Gly Thr Lys Leu Glu Ile Lys Arg Thr Thr Thr Pro Ala Pro
            260                 265                 270

Arg Pro Pro Thr Pro Ala Pro Thr Ile Ala Ser Gln Pro Leu Ser Leu
    275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
            325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
    370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
            405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
    435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 11
<211> LENGTH: 342
<212> TYPE: DNA
<213> ORGANISM: Artificial Sequence
<220> FEATURE:
<223> OTHER INFORMATION: Synthetic construct -continued

<400> SEQUENCE: 11

```
gttcagctgc agcagtctgg acctgaactg gagaagcctg gcgcttcagt gaagatgtcc      60
tgcaaggctt ctggttactc attcactggc tacaacgtaa actgggtgag acagaacaat     120
ggaaagagcc ttgagtggat tggaaatatt gatcctctcc atggtggtac tacctacaac     180
cagaaattca aggccaaggc cacattgact gtagacagat cctccagcac agcctacttg     240
cagctcaaga acctgacatc tgaggactct gcagtctatt actgtgcaag atctagtagg     300
tttgactact ggggccaagg caccactctc acagtctcct ca                        342
```

<210> SEQ ID NO 12
<211> LENGTH: 114
<212> TYPE: PRT
<213> ORGANISM: Artificial Sequence
<220> FEATURE:
<223> OTHER INFORMATION: Synthetic construct

<400> SEQUENCE: 12

```
Val Gln Leu Gln Gln Ser Gly Pro Glu Leu Glu Lys Pro Gly Ala Ser
1               5                   10                  15

Val Lys Met Ser Cys Lys Ala Ser Gly Tyr Ser Phe Thr Gly Tyr Asn
            20                  25                  30

Val Asn Trp Val Arg Gln Asn Asn Gly Lys Ser Leu Glu Trp Ile Gly
        35                  40                  45

Asn Ile Asp Pro Leu His Gly Gly Thr Thr Tyr Asn Gln Lys Phe Lys
    50                  55                  60

Ala Lys Ala Thr Leu Thr Val Asp Arg Ser Ser Ser Thr Ala Tyr Leu
65                  70                  75                  80

Gln Leu Lys Asn Leu Thr Ser Glu Asp Ser Ala Val Tyr Tyr Cys Ala
                85                  90                  95

Arg Ser Ser Arg Phe Asp Tyr Trp Gly Gln Gly Thr Thr Leu Thr Val
            100                 105                 110

Ser Ser
```

<210> SEQ ID NO 13
<211> LENGTH: 324
<212> TYPE: DNA
<213> ORGANISM: Artificial Sequence
<220> FEATURE:
<223> OTHER INFORMATION: Synthetic construct

<400> SEQUENCE: 13

```
gacattgtga tgacccagtc tcacaaattc atgtccacat cagtaggaga cagggtcaac      60
atcacctgca aggccagtca ggatgtgggt actgctgtag cctggtatca acaaaaacca     120
gggcaatctc ctaaactact aatttactgg gcatccaccc ggcacactgg agtccctgat     180
cgcttcacag gcagtggatc tgggacagat ttcactctca ccattagcaa tgtgcaatct     240
gaagacttgg cagattattt ctgtcaccaa tttaccagct atccattcac gttcggctcg     300
gggacaagct tggaaatgaa acgg                                            324
```

<210> SEQ ID NO 14
<211> LENGTH: 108
<212> TYPE: PRT
<213> ORGANISM: Artificial Sequence
<220> FEATURE:
<223> OTHER INFORMATION: Synthetic construct

<400> SEQUENCE: 14

```
Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys His Gln Phe Thr Ser Tyr Pro Phe
                85                  90                  95

Thr Phe Gly Ser Gly Thr Ser Leu Glu Met Lys Arg
            100                 105
```

```
<210> SEQ ID NO 15
<211> LENGTH: 357
<212> TYPE: DNA
<213> ORGANISM: Artificial Sequence
<220> FEATURE:
<223> OTHER INFORMATION: Synthetic construct

<400> SEQUENCE: 15
gtccaattgc agcagcctgg ggctgcgctg gtgaggcctg gagcttcagt gaggctgtcc     60
tgcaaggctt ctggatactc cttcacctac tactggatga actgggtgat gcagaggcct    120
ggccaaggcc ttgagtggat tggcatgatt catccttccg atagtgaaac tcggttaagt    180
cagaagttca gggacaaggc cacattgact gtagacaaat cttccagcac agtctacatg    240
caactcaaca gcccgacatc tgatgactct gcagtctatt actgtgcaag agatggtaac    300
ttcccttact atgcactaga ctactggggt caaggaacct cggtcaccgt ctcctca       357
```

```
<210> SEQ ID NO 16
<211> LENGTH: 119
<212> TYPE: PRT
<213> ORGANISM: Artificial Sequence
<220> FEATURE:
<223> OTHER INFORMATION: Synthetic construct

<400> SEQUENCE: 16

Val Gln Leu Gln Gln Pro Gly Ala Ala Leu Val Arg Pro Gly Ala Ser
1               5                   10                  15

Val Arg Leu Ser Cys Lys Ala Ser Gly Tyr Ser Phe Thr Tyr Tyr Trp
            20                  25                  30

Met Asn Trp Val Met Gln Arg Pro Gly Gln Gly Leu Glu Trp Ile Gly
            35                  40                  45

Met Ile His Pro Ser Asp Ser Glu Thr Arg Leu Ser Gln Lys Phe Arg
    50                  55                  60

Asp Lys Ala Thr Leu Thr Val Asp Lys Ser Ser Ser Thr Val Tyr Met
65                  70                  75                  80

Gln Leu Asn Ser Pro Thr Ser Asp Asp Ser Ala Val Tyr Tyr Cys Ala
                85                  90                  95

Arg Asp Gly Asn Phe Pro Tyr Tyr Ala Leu Asp Tyr Trp Gly Gln Gly
            100                 105                 110

Thr Ser Val Thr Val Ser Ser
        115
```

```
<210> SEQ ID NO 17
```

<211> LENGTH: 336
<212> TYPE: DNA
<213> ORGANISM: Artificial Sequence
<220> FEATURE:
<223> OTHER INFORMATION: Synthetic construct

<400> SEQUENCE: 17
gatgttgtgc tgacccaagc tccactctcc ctgcctgtca gtcttggaga tcaagcctcc      60
atctcttgca gatctagtca gagccttgaa tacagtaatg gaaacaccta tttacattgg     120
tacctgcaga agccaggcca gtctccagaa ctcctgatct acacagtttc caaccgattt     180
tctggggtcc cagacaggtt cagtggcagt ggatcaggga cagatttcac actcaagatt     240
cacagagtgg aggctgagga tctgggagtt tatttctgct ctcaaagtac acatgttccc     300
acgttcggag ggggaccaa gctggagata aaacgg                                336

<210> SEQ ID NO 18
<211> LENGTH: 112
<212> TYPE: PRT
<213> ORGANISM: Artificial Sequence
<220> FEATURE:
<223> OTHER INFORMATION: Synthetic construct

<400> SEQUENCE: 18

Asp Val Val Leu Thr Gln Ala Pro Leu Ser Leu Pro Val Ser Leu Gly
1               5                   10                  15

Asp Gln Ala Ser Ile Ser Cys Arg Ser Ser Gln Ser Leu Glu Tyr Ser
            20                  25                  30

Asn Gly Asn Thr Tyr Leu His Trp Tyr Leu Gln Lys Pro Gly Gln Ser
        35                  40                  45

Pro Glu Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

His Arg Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys Arg
            100                 105                 110

<210> SEQ ID NO 19
<211> LENGTH: 345
<212> TYPE: DNA
<213> ORGANISM: Artificial Sequence
<220> FEATURE:
<223> OTHER INFORMATION: Synthetic construct

<400> SEQUENCE: 19
gtgaagctgc aggagtcagg acctggcctg gtggcgccct cacagagcct gtccatcaca      60
tgcactgtct cagggttctc attaaccgac tatggtgtga gttggattcg ccagcctcca     120
ggaaagggtc tggagtggct gggagtaata tggagcgatg gaaacacata ctataattca     180
cctctcaaat ccagactgag catcaacaag gacaactcca gagccaagt tttcttaaaa     240 atgaacagtc tgcaaactga tgactcagcc atgtactact gtgccagaca taaggtctat     300
actatggact actgggggtca aggaacctca gtcaccgtct cctca                     345

<210> SEQ ID NO 20
<211> LENGTH: 115
<212> TYPE: PRT
<213> ORGANISM: Artificial Sequence
<220> FEATURE:

<223> OTHER INFORMATION: Synthetic construct

<400> SEQUENCE: 20

Val Lys Leu Gln Glu Ser Gly Pro Gly Leu Val Ala Pro Ser Gln Ser
1               5                   10                  15

Leu Ser Ile Thr Cys Thr Val Ser Gly Phe Ser Leu Thr Asp Tyr Gly
            20                  25                  30

Val Ser Trp Ile Arg Gln Pro Pro Gly Lys Gly Leu Glu Trp Leu Gly
        35                  40                  45

Val Ile Trp Ser Asp Gly Asn Thr Tyr Tyr Asn Ser Pro Leu Lys Ser
    50                  55                  60

Arg Leu Ser Ile Asn Lys Asp Asn Ser Lys Ser Gln Val Phe Leu Lys
65                  70                  75                  80

Met Asn Ser Leu Gln Thr Asp Asp Ser Ala Met Tyr Tyr Cys Ala Arg
            85                  90                  95

His Lys Val Tyr Thr Met Asp Tyr Trp Gly Gln Gly Thr Ser Val Thr
            100                 105                 110

Val Ser Ser
        115

<210> SEQ ID NO 21
<211> LENGTH: 324
<212> TYPE: DNA
<213> ORGANISM: Artificial Sequence
<220> FEATURE:
<223> OTHER INFORMATION: Synthetic construct

<400> SEQUENCE: 21
actgtgctca cccagtctcc agcaatcatg tctgcatctc caggggaaaa ggtcaccatg      60
acctgcaggg ccagctcaag tgtaagttcc agttacttgc actggtacca gcagaagtca     120
agtgcctccc ccaaactctg gatttataga acatccaact tggcttctgg agtccctgct     180
cgcttcagtg gcagtgggtc tgggacctct tactctctca caatcagcag tttggaggct     240
gaagatgctg ccacttatta ctgccagcag tacagtggtt acccactcac gttcggtgct     300
gggaccaagc tggagctgaa acgg                                           324

<210> SEQ ID NO 22
<211> LENGTH: 108
<212> TYPE: PRT
<213> ORGANISM: Artificial Sequence
<220> FEATURE:
<223> OTHER INFORMATION: Synthetic construct

<400> SEQUENCE: 22

Thr Val Leu Thr Gln Ser Pro Ala Ile Met Ser Ala Ser Pro Gly Glu
1               5                   10                  15

Lys Val Thr Met Thr Cys Arg Ala Ser Ser Ser Val Ser Ser Ser Tyr
            20                  25                  30

Leu His Trp Tyr Gln Gln Lys Ser Ser Ala Ser Pro Lys Leu Trp Ile
        35                  40                  45

Tyr Arg Thr Ser Asn Leu Ala Ser Gly Val Pro Ala Arg Phe Ser Gly
    50                  55                  60

Ser Gly Ser Gly Thr Ser Tyr Ser Leu Thr Ile Ser Ser Leu Glu Ala
65                  70                  75                  80

Glu Asp Ala Ala Thr Tyr Tyr Cys Gln Gln Tyr Ser Gly Tyr Pro Leu
            85                  90                  95

Thr Phe Gly Ala Gly Thr Lys Leu Glu Leu Lys Arg

```
              100                 105
```

<210> SEQ ID NO 23
<211> LENGTH: 342
<212> TYPE: DNA
<213> ORGANISM: Artificial Sequence
<220> FEATURE:
<223> OTHER INFORMATION: Synthetic construct

<400> SEQUENCE: 23
gtgaagctgc agcagtctgg acctgaactg gagaagcctg gcgcatcagt gaagatatcc      60
tgcaaggctt caggttactc attcactggc tacaacgtga actgggtgaa gcagagcaat     120
ggaaagagcc ttgagtggat tggaaatatt gatccttacc atggtggtac tacctacaac     180
cagaaattcg aggccaaggc cacattgact gtagacaaat cctccagcac agcctacatg     240
cagctcaaga gccttacatc tgaggactct gcagtctatt attgtgcaag atctagtaga     300
tttgactact ggggccaagg caccactctc acagtctcct ca                        342

<210> SEQ ID NO 24
<211> LENGTH: 114
<212> TYPE: PRT
<213> ORGANISM: Artificial Sequence
<220> FEATURE:
<223> OTHER INFORMATION: Synthetic construct

<400> SEQUENCE: 24

Val Lys Leu Gln Gln Ser Gly Pro Glu Leu Glu Lys Pro Gly Ala Ser
1               5                   10                  15

Val Lys Ile Ser Cys Lys Ala Ser Gly Tyr Ser Phe Thr Gly Tyr Asn
            20                  25                  30

Val Asn Trp Val Lys Gln Ser Asn Gly Lys Ser Leu Glu Trp Ile Gly
        35                  40                  45

Asn Ile Asp Pro Tyr His Gly Gly Thr Thr Tyr Asn Gln Lys Phe Glu
    50                  55                  60

Ala Lys Ala Thr Leu Thr Val Asp Lys Ser Ser Ser Thr Ala Tyr Met
65                  70                  75                  80

Gln Leu Lys Ser Leu Thr Ser Glu Asp Ser Ala Val Tyr Tyr Cys Ala
                85                  90                  95

Arg Ser Ser Arg Phe Asp Tyr Trp Gly Gln Gly Thr Thr Leu Thr Val
            100                 105                 110

Ser Ser

<210> SEQ ID NO 25
<211> LENGTH: 324
<212> TYPE: DNA
<213> ORGANISM: Artificial Sequence
<220> FEATURE:
<223> OTHER INFORMATION: Synthetic construct

<400> SEQUENCE: 25
gacattgtga tgacccagtc tcacaaattc atgtccacat cagtgggaga cagggtcaac      60
atcacctgca aggccagtca ggatgtgggt actgctgtag cctggtatca acagaaacca     120
gggcaatctc ctaaatttct aatttactgg gcatccaccc ggcacactgg agtccctgat     180
cgcttcacag gcagtggatc tgggacagat ttcactctca ccattagcaa tgtgcagtct     240
gaagacttgg cagattattt ctgtcatcag tataccagct atccattcac gttcggctcg     300
gggacaaagt tggaaatgaa acgg                                            324
```

<210> SEQ ID NO 26
<211> LENGTH: 108
<212> TYPE: PRT
<213> ORGANISM: Artificial Sequence
<220> FEATURE:
<223> OTHER INFORMATION: Synthetic construct

<400> SEQUENCE: 26

```
Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
                20                  25                  30

Val Ala Trp Tyr Gln Gln Lys Pro Gly Gln Ser Pro Lys Phe Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys His Gln Tyr Thr Ser Tyr Pro Phe
                85                  90                  95

Thr Phe Gly Ser Gly Thr Lys Leu Glu Met Lys Arg
            100                 105
```

<210> SEQ ID NO 27
<211> LENGTH: 366
<212> TYPE: DNA
<213> ORGANISM: Artificial Sequence
<220> FEATURE:
<223> OTHER INFORMATION: Synthetic construct

<400> SEQUENCE: 27

```
gttaagctgc agcagtcggg acctggcctg gtgaaacctt ctcagtctct gtccctcacc      60
tgcgctgtca ctggctactc aatcaccagt gattatgcct ggaactggat ccggaagttt     120
ccaggaaaca aactggagtg gatgggctac ataagctaca gtggtagaac tacctacaat     180
ccatctctcg aaagtcgaat ctctatcact cgagacacat ccaaaaacca gttcttcctg     240
cagttgaatt ctgtgactac tgaggacaca gccacatatt actgtgcaag atgttactac     300
ggtagtagct cccgttggta tggtatggac tactggggtc gcggaacctc agtcgccgtg     360
tcctca                                                                366
```

<210> SEQ ID NO 28
<211> LENGTH: 122
<212> TYPE: PRT
<213> ORGANISM: Artificial Sequence
<220> FEATURE:
<223> OTHER INFORMATION: Synthetic construct

<400> SEQUENCE: 28

```
Val Lys Leu Gln Gln Ser Gly Pro Gly Leu Val Lys Pro Ser Gln Ser
1               5                   10                  15

Leu Ser Leu Thr Cys Ala Val Thr Gly Tyr Ser Ile Thr Ser Asp Tyr
                20                  25                  30

Ala Trp Asn Trp Ile Arg Lys Phe Pro Gly Asn Lys Leu Glu Trp Met
            35                  40                  45

Gly Tyr Ile Ser Tyr Ser Gly Arg Thr Thr Tyr Asn Pro Ser Leu Glu
        50                  55                  60

Ser Arg Ile Ser Ile Thr Arg Asp Thr Ser Lys Asn Gln Phe Phe Leu
65                  70                  75                  80
```

```
Gln Leu Asn Ser Val Thr Thr Glu Asp Thr Ala Thr Tyr Tyr Cys Ala
                85                  90                  95

Arg Cys Tyr Tyr Gly Ser Ser Ser Arg Trp Tyr Gly Met Asp Tyr Trp
            100                 105                 110

Gly Arg Gly Thr Ser Val Ala Val Ser Ser
        115                 120

<210> SEQ ID NO 29
<211> LENGTH: 324
<212> TYPE: DNA
<213> ORGANISM: Artificial Sequence
<220> FEATURE:
<223> OTHER INFORMATION: Synthetic construct

<400> SEQUENCE: 29
attgtgctca cccagtctcc agcaatcatg tctgcatctc caggggtaaa ggtcaccatg      60
acctgcaggg ccagctcaag tgtagattcc agttacttgc actggtacca gcagaagtca     120
ggtgcctccc cccaagtctg gatttatagc acatccaact tggcttctgg agtcccggct     180
cgcttcagtg gcagtgggtc tgggacctct tactctctca caatcagtag tgtggaggct     240
gaagatgctg ccacttatta ctgccagcag tacagtggtt atccactgac gttcggtgga     300
ggcaccaagc tggaaatcaa acgg                                            324

<210> SEQ ID NO 30
<211> LENGTH: 108
<212> TYPE: PRT
<213> ORGANISM: Artificial Sequence
<220> FEATURE:
<223> OTHER INFORMATION: Synthetic construct

<400> SEQUENCE: 30

Ile Val Leu Thr Gln Ser Pro Ala Ile Met Ser Ala Ser Pro Gly Val
1               5                   10                  15

Lys Val Thr Met Thr Cys Arg Ala Ser Ser Ser Val Asp Ser Ser Tyr
            20                  25                  30

Leu His Trp Tyr Gln Gln Lys Ser Gly Ala Ser Pro Gln Val Trp Ile
        35                  40                  45

Tyr Ser Thr Ser Asn Leu Ala Ser Gly Val Pro Ala Arg Phe Ser Gly
    50                  55                  60

Ser Gly Ser Gly Thr Ser Tyr Ser Leu Thr Ile Ser Ser Val Glu Ala
65                  70                  75                  80

Glu Asp Ala Ala Thr Tyr Tyr Cys Gln Gln Tyr Ser Gly Tyr Pro Leu
                85                  90                  95

Thr Phe Gly Gly Gly Thr Lys Leu Glu Ile Lys Arg
            100                 105

<210> SEQ ID NO 31
<211> LENGTH: 750
<212> TYPE: PRT
<213> ORGANISM: Homo sapiens

<400> SEQUENCE: 31

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45
```

```
Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
                195                 200                 205

Phe Arg Gly Asn Lys Val Lys Asn Ala Gln Leu Ala Gly Ala Lys Gly
        210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
                275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460
```

```
Asp Cys Thr Pro Leu Met Tyr Ser Leu Val His Asn Leu Thr Lys Glu
465             470             475             480

Leu Lys Ser Pro Asp Glu Gly Phe Glu Gly Lys Ser Leu Tyr Glu Ser
            485             490             495

Trp Thr Lys Lys Ser Pro Ser Pro Glu Phe Ser Gly Met Pro Arg Ile
            500             505             510

Ser Lys Leu Gly Ser Gly Asn Asp Phe Glu Val Phe Phe Gln Arg Leu
            515             520             525

Gly Ile Ala Ser Gly Arg Ala Arg Tyr Thr Lys Asn Trp Glu Thr Asn
            530             535             540

Lys Phe Ser Gly Tyr Pro Leu Tyr His Ser Val Tyr Glu Thr Tyr Glu
545             550             555             560

Leu Val Glu Lys Phe Tyr Asp Pro Met Phe Lys Tyr His Leu Thr Val
            565             570             575

Ala Gln Val Arg Gly Gly Met Val Phe Glu Leu Ala Asn Ser Ile Val
            580             585             590

Leu Pro Phe Asp Cys Arg Asp Tyr Ala Val Val Leu Arg Lys Tyr Ala
            595             600             605

Asp Lys Ile Tyr Ser Ile Ser Met Lys His Pro Gln Glu Met Lys Thr
            610             615             620

Tyr Ser Val Ser Phe Asp Ser Leu Phe Ser Ala Val Lys Asn Phe Thr
625             630             635             640

Glu Ile Ala Ser Lys Phe Ser Glu Arg Leu Gln Asp Phe Asp Lys Ser
            645             650             655

Asn Pro Ile Val Leu Arg Met Met Asn Asp Gln Leu Met Phe Leu Glu
            660             665             670

Arg Ala Phe Ile Asp Pro Leu Gly Leu Pro Asp Arg Pro Phe Tyr Arg
            675             680             685

His Val Ile Tyr Ala Pro Ser Ser His Asn Lys Tyr Ala Gly Glu Ser
            690             695             700

Phe Pro Gly Ile Tyr Asp Ala Leu Phe Asp Ile Glu Ser Lys Val Asp
705             710             715             720

Pro Ser Lys Ala Trp Gly Glu Val Lys Arg Gln Ile Tyr Val Ala Ala
            725             730             735

Phe Thr Val Gln Ala Ala Ala Glu Thr Leu Ser Glu Val Ala
            740             745             750
```

```
<210> SEQ ID NO 32
<211> LENGTH: 255
<212> TYPE: PRT
<213> ORGANISM: Homo sapiens

<400> SEQUENCE: 32

Met Gly Asn Ser Cys Tyr Asn Ile Val Ala Thr Leu Leu Leu Val Leu
1               5               10              15

Asn Phe Glu Arg Thr Arg Ser Leu Gln Asp Pro Cys Ser Asn Cys Pro
            20              25              30

Ala Gly Thr Phe Cys Asp Asn Asn Arg Asn Gln Ile Cys Ser Pro Cys
            35              40              45

Pro Pro Asn Ser Phe Ser Ser Ala Gly Gly Gln Arg Thr Cys Asp Ile
            50              55              60

Cys Arg Gln Cys Lys Gly Val Phe Arg Thr Arg Lys Glu Cys Ser Ser
65              70              75              80

Thr Ser Asn Ala Glu Cys Asp Cys Thr Pro Gly Phe His Cys Leu Gly
            85              90              95
```

```
Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
            165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
            245                 250                 255

<210> SEQ ID NO 33
<211> LENGTH: 42
<212> TYPE: PRT
<213> ORGANISM: Artificial Sequence
<220> FEATURE:
<223> OTHER INFORMATION: Synthetic construct

<400> SEQUENCE: 33

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 34
<211> LENGTH: 18
<212> TYPE: PRT
<213> ORGANISM: Artificial Sequence
<220> FEATURE:
<223> OTHER INFORMATION: Synthetic construct

<400> SEQUENCE: 34

Glu Gly Arg Gly Ser Leu Leu Thr Cys Gly Asp Val Glu Glu Asn Pro
1               5                   10                  15

Gly Pro

<210> SEQ ID NO 35
<211> LENGTH: 451
<212> TYPE: PRT
<213> ORGANISM: Homo sapiens

<400> SEQUENCE: 35

Met Asn Leu Glu Gly Gly Gly Arg Gly Gly Glu Phe Gly Met Ser Ala
1               5                   10                  15

Val Ser Cys Gly Asn Gly Lys Leu Arg Gln Trp Leu Ile Asp Gln Ile
            20                  25                  30
```

```
Asp Ser Gly Lys Tyr Pro Gly Leu Val Trp Glu Asn Glu Glu Lys Ser
        35              40              45

Ile Phe Arg Ile Pro Trp Lys His Ala Gly Lys Gln Asp Tyr Asn Arg
    50              55              60

Glu Glu Asp Ala Ala Leu Phe Lys Ala Trp Ala Leu Phe Lys Gly Lys
65              70              75              80

Phe Arg Glu Gly Ile Asp Lys Pro Asp Pro Pro Thr Trp Lys Thr Arg
                85              90              95

Leu Arg Cys Ala Leu Asn Lys Ser Asn Asp Phe Glu Glu Leu Val Glu
            100             105             110

Arg Ser Gln Leu Asp Ile Ser Asp Pro Tyr Lys Val Tyr Arg Ile Val
        115             120             125

Pro Glu Gly Ala Lys Lys Gly Ala Lys Gln Leu Thr Leu Glu Asp Pro
    130             135             140

Gln Met Ser Met Ser His Pro Tyr Thr Met Thr Thr Pro Tyr Pro Ser
145             150             155             160

Leu Pro Ala Gln Gln Val His Asn Tyr Met Met Pro Pro Leu Asp Arg
            165             170             175

Ser Trp Arg Asp Tyr Val Pro Asp Gln Pro His Pro Glu Ile Pro Tyr
        180             185             190

Gln Cys Pro Met Thr Phe Gly Pro Arg Gly His His Trp Gln Gly Pro
        195             200             205

Ala Cys Glu Asn Gly Cys Gln Val Thr Gly Thr Phe Tyr Ala Cys Ala
    210             215             220

Pro Pro Glu Ser Gln Ala Pro Gly Val Pro Thr Glu Pro Ser Ile Arg
225             230             235             240

Ser Ala Glu Ala Leu Ala Phe Ser Asp Cys Arg Leu His Ile Cys Leu
            245             250             255

Tyr Tyr Arg Glu Ile Leu Val Lys Glu Leu Thr Thr Ser Ser Pro Glu
        260             265             270

Gly Cys Arg Ile Ser His Gly His Thr Tyr Asp Ala Ser Asn Leu Asp
        275             280             285

Gln Val Leu Phe Pro Tyr Pro Glu Asp Asn Gly Gln Arg Lys Asn Ile
    290             295             300

Glu Lys Leu Leu Ser His Leu Glu Arg Gly Val Val Leu Trp Met Ala
305             310             315             320

Pro Asp Gly Leu Tyr Ala Lys Arg Leu Cys Gln Ser Arg Ile Tyr Trp
            325             330             335

Asp Gly Pro Leu Ala Leu Cys Asn Asp Arg Pro Asn Lys Leu Glu Arg
        340             345             350

Asp Gln Thr Cys Lys Leu Phe Asp Thr Gln Gln Phe Leu Ser Glu Leu
        355             360             365

Gln Ala Phe Ala His His Gly Arg Ser Leu Pro Arg Phe Gln Val Thr
    370             375             380

Leu Cys Phe Gly Glu Glu Phe Pro Asp Pro Gln Arg Gln Arg Lys Leu
385             390             395             400

Ile Thr Ala His Val Glu Pro Leu Leu Ala Arg Gln Leu Tyr Tyr Phe
            405             410             415

Ala Gln Gln Asn Ser Gly His Phe Leu Arg Gly Tyr Asp Leu Pro Glu
            420             425             430

His Ile Ser Asn Pro Glu Asp Tyr His Arg Ser Ile Arg His Ser Ser
        435             440             445

Ile Gln Glu
```

450

```
<210> SEQ ID NO 36
<211> LENGTH: 112
<212> TYPE: PRT
<213> ORGANISM: Artificial Sequence
<220> FEATURE:
<223> OTHER INFORMATION: Synthetic construct

<400> SEQUENCE: 36

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 15
<212> TYPE: PRT
<213> ORGANISM: Artificial Sequence
<220> FEATURE:
<223> OTHER INFORMATION: Synthetic construct

<400> SEQUENCE: 37

Gly Gly Gly Gly Ser Gly Gly Gly Gly Ser Gly Gly Gly Gly Ser
1               5                   10                  15

<210> SEQ ID NO 38
<211> LENGTH: 1446
<212> TYPE: DNA
<213> ORGANISM: Artificial Sequence
<220> FEATURE:
<223> OTHER INFORMATION: Synthetic construct

<400> SEQUENCE: 38
atggccttac cagtgaccgc cttgctcctg ccgctggcct tgctgctcca tgcggctcga      60
cctgacatcg tgatgacaca gtctcacaag ttcatgtcca cctctgtggg cgacagggtg     120
aacatcacat gcaaggcctc ccaggatgtg ggcaccgcag tggcctggta tcagcagaag     180
cccggccaga gccctaagct gctgatctat tgggcctcca ccaggcacac aggcgtgcct     240
gaccgcttca caggcagcgg ctccggcacc gacttcaccc tgacaatctc taatgtgcag     300
agcgaggacc tggccgatta cttctgccac cagtttacca gctatccatt cacatttggc     360
tctggcacca gcctggagat gaagagagga ggaggaggca gcggcggagg aggctccggc     420
ggcggcggct ctgtgcagct gcagcagtcc ggaccagagc tggagaagcc aggagcctcc     480
gtgaagatgt cttgtaaggc ctccggctac tctttcacag gctataacgt gaattgggtg     540
cggcagaaca tggcaagag cctggagtgg atcggaaaca tcgacccact gcacggcggc     600
accacataca atcagaagtt taaggccaag gccaccctga cagtggatag aagctcctct     660
acagcctatc tgcagctgaa gaacctgacc agcgaggact ccgccgtgta ctattgtgcc     720
```

-continued

```
cggagcagcc ggtttgatta ctggggccag ggcaccacac tgaccgtgtc tagcaccacg    780
acgccagcgc cgcgaccacc aacaccggcg cccaccatcg cgtcgcagcc cctgtccctg    840
cgcccagagg cgtgccggcc agcggcgggg ggcgcagtgc acacgagggg gctggacttc    900
gcctgtgaca tctacatctg ggcgcccctg gccgggactt gtggggtcct tctcctgtca    960
ctggttatca ccctttactg caaacggggc agaaagaaac tcctgtatat attcaaacaa   1020
ccatttatga gaccagtaca aactactcaa gaggaagatg gctgtagctg ccgatttcca   1080
gaagaagaag aaggaggatg tgaactgaga gtgaagttca gcaggagcgc agacgccccc   1140
gcgtacaagc agggccagaa ccagctctat aacgagctca atctaggacg aagagaggag   1200
tacgatgttt tggacaagag acgtggccgg gaccctgaga tggggggaaa gccgagaagg   1260
aagaaccctc aggaaggcct gtacaatgaa ctgcagaaag ataagatggc ggaggcctac   1320
agtgagattg ggatgaaagg cgagcgccgg aggggcaagg ggcacgatgg cctttaccag   1380
ggtctcagta cagccaccaa ggacacctac gacgcccttc acatgcaggc cctgccccct   1440
cgctag                                                             1446
```

```
<210> SEQ ID NO 39
<211> LENGTH: 481
<212> TYPE: PRT
<213> ORGANISM: Artificial Sequence
<220> FEATURE:
<223> OTHER INFORMATION: Synthetic construct

<400> SEQUENCE: 39

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser His Lys Phe Met
            20                  25                  30

Ser Thr Ser Val Gly Asp Arg Val Asn Ile Thr Cys Lys Ala Ser Gln
        35                  40                  45

Asp Val Gly Thr Ala Val Ala Trp Tyr Gln Gln Lys Pro Gly Gln Ser
    50                  55                  60

Pro Lys Leu Leu Ile Tyr Trp Ala Ser Thr Arg His Thr Gly Val Pro
65                  70                  75                  80

Asp Arg Phe Thr Gly Ser Gly Ser Gly Thr Asp Phe Thr Leu Thr Ile
            85                  90                  95

Ser Asn Val Gln Ser Glu Asp Leu Ala Asp Tyr Phe Cys His Gln Phe
            100                 105                 110

Thr Ser Tyr Pro Phe Thr Phe Gly Ser Gly Thr Ser Leu Glu Met Lys
        115                 120                 125

Arg Gly Gly Gly Gly Ser Gly Gly Gly Gly Ser Gly Gly Gly Gly Ser
    130                 135                 140

Val Gln Leu Gln Gln Ser Gly Pro Glu Leu Glu Lys Pro Gly Ala Ser
145                 150                 155                 160

Val Lys Met Ser Cys Lys Ala Ser Gly Tyr Ser Phe Thr Gly Tyr Asn
                165                 170                 175

Val Asn Trp Val Arg Gln Asn Asn Gly Lys Ser Leu Glu Trp Ile Gly
            180                 185                 190

Asn Ile Asp Pro Leu His Gly Gly Thr Thr Tyr Asn Gln Lys Phe Lys
        195                 200                 205

Ala Lys Ala Thr Leu Thr Val Asp Arg Ser Ser Ser Thr Ala Tyr Leu
    210                 215                 220
```

```
Gln Leu Lys Asn Leu Thr Ser Glu Asp Ser Ala Val Tyr Tyr Cys Ala
225                 230                 235                 240

Arg Ser Ser Arg Phe Asp Tyr Trp Gly Gln Gly Thr Thr Leu Thr Val
                245                 250                 255

Ser Ser Thr Thr Thr Pro Ala Pro Arg Pro Pro Thr Pro Ala Pro Thr
                260                 265                 270

Ile Ala Ser Gln Pro Leu Ser Leu Arg Pro Glu Ala Cys Arg Pro Ala
            275                 280                 285

Ala Gly Gly Ala Val His Thr Arg Gly Leu Asp Phe Ala Cys Asp Ile
        290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
            355                 360                 365

Leu Arg Val Lys Phe Ser Arg Ser Ala Asp Ala Pro Ala Tyr Lys Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
465                 470                 475                 480

Arg
```

```
<210> SEQ ID NO 40
<211> LENGTH: 1473
<212> TYPE: DNA
<213> ORGANISM: Artificial Sequence
<220> FEATURE:
<223> OTHER INFORMATION: Synthetic construct

<400> SEQUENCE: 40
atggccttac cagtgaccgc cttgctcctg ccgctggcct tgctgctcca tgcggctcga        60
cctgacgtgg tgctgaccca ggcaccactg agcctgcccg tgagcctggg cgatcaggcc       120
tccatctctt gcagaagctc ccagtctctg gagtacagca acggcaatac ctacctgcac       180
tggtatctgc agaagccagg ccagagcccc gagctgctga tctatacagt gtccaaccgg       240
ttctctggcg tgcctgaccg gttcagcggc tccggctctg gcaccgattt cacactgaag       300
atccacaggg tggaggcaga ggacctgggc gtgtacttct gcagccagtc cacccacgtg       360
cccacatttg gcggcggcac caagctggag atcaagaggg aggaggagg ctctggagga       420 ggaggcagcg gcggcggcgg ctccgtgcag ctgcagcagc ctggcgccgc cctggtgcgg       480
ccaggagcca gcgtgagact gtcctgtaag gcctccggct attctttcac ctactattgg       540
atgaattggg tcatgcagag gccaggacag ggcctggagt ggatcggcat gatccaccct       600
```

```
tctgatagcg agacaaggct gagccagaag tttcgcgaca aggccaccct gacagtggat    660
aagtctagct ccaccgtgta catgcagctg aacagcccaa catccgacga ttctgccgtg    720
tactattgtg cccgggacgg caattttccc tactatgccc tggattattg gggccagggc    780
acctccgtga cagtgtctag caccacgacg ccagcgccgc gaccaccaac accggcgccc    840
accatcgcgt cgcagcccct gtccctgcgc ccagaggcgt gccggccagc ggcggggggc    900
gcagtgcaca cgagggggct ggacttcgcc tgtgacatct acatctgggc gcccctggcc    960
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
aagttcagca ggagcgcaga cgcccccgcg tacaagcagg gccagaacca gctctataac   1200
gagctcaatc taggacgaag agaggagtac gatgttttgg acaagagacg tggccgggac   1260
cctgagatgg ggggaaagcc gagaaggaag aaccctcagg aaggcctgta caatgaactg   1320
cagaaagata agatggcgga ggcctacagt gagattggga tgaaaggcga gcgccggagg   1380
ggcaaggggc acgatggcct ttaccagggt ctcagtacag ccaccaagga cacctacgac   1440
gcccttcaca tgcaggccct gccccctcgc tag                                1473
```

<210> SEQ ID NO 41
<211> LENGTH: 490
<212> TYPE: PRT
<213> ORGANISM: Artificial Sequence
<220> FEATURE:
<223> OTHER INFORMATION: Synthetic construct

<400> SEQUENCE: 41

```
Met Ala Leu Pro Val Thr Ala Leu Leu Leu Pro Leu Ala Leu Leu Leu
1               5                   10                  15

His Ala Ala Arg Pro Asp Val Val Leu Thr Gln Ala Pro Leu Ser Leu
            20                  25                  30

Pro Val Ser Leu Gly Asp Gln Ala Ser Ile Ser Cys Arg Ser Ser Gln
        35                  40                  45

Ser Leu Glu Tyr Ser Asn Gly Asn Thr Tyr Leu His Trp Tyr Leu Gln
    50                  55                  60

Lys Pro Gly Gln Ser Pro Glu Leu Leu Ile Tyr Thr Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile His Arg Val Glu Ala Glu Asp Leu Gly Val Tyr
            100                 105                 110

Phe Cys Ser Gln Ser Thr His Val Pro Thr Phe Gly Gly Gly Thr Lys
        115                 120                 125

Leu Glu Ile Lys Arg Gly Gly Gly Gly Ser Gly Gly Gly Gly Ser Gly
    130                 135                 140

Gly Gly Gly Ser Val Gln Leu Gln Gln Pro Gly Ala Ala Leu Val Arg
145                 150                 155                 160

Pro Gly Ala Ser Val Arg Leu Ser Cys Lys Ala Ser Gly Tyr Ser Phe
                165                 170                 175

Thr Tyr Tyr Trp Met Asn Trp Val Met Gln Arg Pro Gly Gln Gly Leu
            180                 185                 190

Glu Trp Ile Gly Met Ile His Pro Ser Asp Ser Glu Thr Arg Leu Ser
            195                 200                 205
```

```
Gln Lys Phe Arg Asp Lys Ala Thr Leu Thr Val Asp Lys Ser Ser Ser
    210                 215                 220

Thr Val Tyr Met Gln Leu Asn Ser Pro Thr Ser Asp Asp Ser Ala Val
225                 230                 235                 240

Tyr Tyr Cys Ala Arg Asp Gly Asn Phe Pro Tyr Tyr Ala Leu Asp Tyr
                245                 250                 255

Trp Gly Gln Gly Thr Ser Val Thr Val Ser Ser Thr Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 42
<211> LENGTH: 1449
<212> TYPE: DNA
<213> ORGANISM: Artificial Sequence
<220> FEATURE:
<223> OTHER INFORMATION: Synthetic construct

<400> SEQUENCE: 42

```
atggccttac cagtgaccgc cttgctcctg ccgctggcct tgctgctcca tgcggctcga      60
cctaccgtgc tgacacagtc ccctgccatc atgagcgcct ccccaggaga gaaggtgacc     120
atgacatgca gggccagcag cagcgtgagc agcagctacc tgcactggta tcagcagaag     180
agcagcgcca gccccaagct gtggatctac cggacctcca acctggcctc tggcgtgcct     240
gccagattct ctggcagcgg ctccggcacc tcttatagcc tgacaatctc tagcctggag     300
gcagaggacg cagcaaccta ctattgccag cagtactccg gctatccact gacctttggc     360
gccggcacaa agctggagct gaagagggga ggaggaggca gcggcggagg aggctccggc     420
```

```
ggcggcggct ctgtgaagct gcaggagtcc ggaccaggac tggtggcacc atcccagtct      480
ctgagcatca cctgtacagt gagcggcttc tccctgaccg attacggcgt gtcttggatc      540
aggcagccac ctggcaaggg cctggagtgg ctgggcgtga tctggtctga cggcaacaca      600
tactataata gccccctgaa gtctcgcctg agcatcaaca aggataattc caagtctcag      660
gtgtttctga agatgaatag cctgcagacc gacgattccg ccatgtacta ttgtgcccgg      720
cacaaggtgt acacaatgga ctattggggc caggcacca gcgtgacagt gtcctctacc      780
acgacgccag cgccgcgacc accaacaccg gcgcccacca tcgcgtcgca gcccctgtcc      840
ctgcgcccag aggcgtgccg gccagcggcg ggggcgcag tgcacacgag ggggctggac       900
ttcgcctgtg acatctacat ctgggcgccc ctggccggga cttgtggggt ccttctcctg      960
tcactggtta tcacccttta ctgcaaacgg ggcagaaaga aactcctgta tatattcaaa      1020
caaccattta tgagaccagt acaaactact caagaggaag atggctgtag ctgccgattt      1080
ccagaagaag aagaaggagg atgtgaactg agagtgaagt tcagcaggag cgcagacgcc      1140
cccgcgtaca gcagggcca gaaccagctc tataacgagc tcaatctagg acgaagagag      1200
gagtacgatg tttttggaca gagacgtggc cgggaccctg agatggggg aaagccgaga       1260 aggaagaacc ctcaggaagg cctgtacaat gaactgcaga aagataagat ggcggaggcc      1320
tacagtgaga ttgggatgaa aggcgagcgc cggagggca aggggcacga tggcctttac       1380
cagggtctca gtacagccac caaggacacc tacgacgccc ttcacatgca ggccctgccc      1440
cctcgctag                                                              1449
```

<210> SEQ ID NO 43
<211> LENGTH: 482
<212> TYPE: PRT
<213> ORGANISM: Artificial Sequence
<220> FEATURE:
<223> OTHER INFORMATION: Synthetic construct

<400> SEQUENCE: 43

```
Met Ala Leu Pro Val Thr Ala Leu Leu Leu Pro Leu Ala Leu Leu Leu
1               5                   10                  15

His Ala Ala Arg Pro Thr Val Leu Thr Gln Ser Pro Ala Ile Met Ser
            20                  25                  30

Ala Ser Pro Gly Glu Lys Val Thr Met Thr Cys Arg Ala Ser Ser Ser
        35                  40                  45

Val Ser Ser Ser Tyr Leu His Trp Tyr Gln Gln Lys Ser Ser Ala Ser
    50                  55                  60

Pro Lys Leu Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Leu Glu Ala Glu Asp Ala Ala Thr Tyr Tyr Cys Gln Gln Tyr
            100                 105                 110

Ser Gly Tyr Pro Leu Thr Phe Gly Ala Gly Thr Lys Leu Glu Leu Lys
        115                 120                 125

Arg Gly Gly Gly Gly Ser Gly Gly Gly Gly Ser Gly Gly Gly Gly Ser
    130                 135                 140

Val Lys Leu Gln Glu Ser Gly Pro Gly Leu Val Ala Pro Ser Gln Ser
145                 150                 155                 160

Leu Ser Ile Thr Cys Thr Val Ser Gly Phe Ser Leu Thr Asp Tyr Gly
                165                 170                 175
```

```
Val Ser Trp Ile Arg Gln Pro Pro Gly Lys Gly Leu Glu Trp Leu Gly
        180                 185                 190

Val Ile Trp Ser Asp Gly Asn Thr Tyr Tyr Asn Ser Pro Leu Lys Ser
        195                 200                 205

Arg Leu Ser Ile Asn Lys Asp Asn Ser Lys Ser Gln Val Phe Leu Lys
        210                 215                 220

Met Asn Ser Leu Gln Thr Asp Asp Ser Ala Met Tyr Tyr Cys Ala Arg
225                 230                 235                 240

His Lys Val Tyr Thr Met Asp Tyr Trp Gly Gln Gly Thr Ser Val Thr
                245                 250                 255

Val Ser Ser Thr Thr Thr Pro Ala Pro Arg Pro Pro Thr Pro Ala Pro
        260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
        290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
                340                 345                 350

Glu Asp Gly Cys Ser Cys Arg Phe Pro Glu Glu Glu Glu Gly Gly Cys
                355                 360                 365

Glu Leu Arg Val Lys Phe Ser Arg Ser Ala Asp Ala Pro Ala Tyr Lys
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
        450                 455                 460

Thr Ala Thr Lys Asp Thr Tyr Asp Ala Leu His Met Gln Ala Leu Pro
465                 470                 475                 480

Pro Arg
```

```
<210> SEQ ID NO 44
<211> LENGTH: 1446
<212> TYPE: DNA
<213> ORGANISM: Artificial Sequence
<220> FEATURE:
<223> OTHER INFORMATION: Synthetic construct

<400> SEQUENCE: 44
atggccttac cagtgaccgc cttgctcctg ccgctggcct tgctgctcca tgcggctcga      60
cctgacatcg tgatgacaca gtctcacaag ttcatgtcca cctctgtggg cgaccgggtg     120
aacatcacat gcaaggccag ccaggatgtg ggcaccgcag tggcctggta tcagcagaag     180
cccggccaga gccctaagtt tctgatctat tgggcctcca ccaggcacac aggcgtgcct     240
gaccgcttca caggcagcgg ctccggcacc gacttcaccc tgacaatctc caatgtgcag     300
```

-continued

```
tctgaggacc tggccgatta cttctgccac cagtacacct cctatccatt cacatttggc      360
tctggcacca agctggagat gaagagggga ggaggaggct ccggcggagg aggctctggc      420
ggcggcggca gcgtgaagct gcagcagtcc ggaccagagc tggagaagcc aggagccagc      480
gtgaagatca gctgtaaggc ctctggctac agcttcacag ctataacgt gaattgggtg       540 aagcagtcta acggcaagag cctggagtgg atcggcaata tcgacccta ccacggcggc        600 accacatata accagaagtt tgaggccaag gccaccctga cagtggataa gagcagcagc       660
accgcctaca tgcagctgaa gtccctgacc tctgaggaca cgccgtgta ctattgtgcc        720 cggagcagcc ggtttgatta ttggggccag ggcaccacac tgaccgtgtc tagcaccacg       780
acgccagcgc cgcgaccacc aacaccggcg cccaccatcg cgtcgcagcc cctgtccctg       840 cgccagagg cgtgccggcc agcggcgggg ggcgcagtgc acacgagggg gctggacttc        900
gcctgtgaca tctacatctg ggcgcccctg gccgggactt gtggggtcct tctcctgtca       960
ctggttatca cccttttactg caaacggggc agaaagaaac tcctgtatat attcaaacaa    1020
ccatttatga gaccagtaca aactactcaa gaggaagatg gctgtagctg ccgatttcca     1080
gaagaagaag aaggaggatg tgaactgaga gtgaagttca gcaggagcgc agacgccccc     1140
gcgtacaagc agggccagaa ccagctctat aacgagctca tctaggacg aagagaggag     1200 tacgatgttt tggacaagag acgtggccgg gaccctgaga tggggggaaa gccgagaagg    1260
aagaaccctc aggaaggcct gtacaatgaa ctgcagaaa ataagatggc ggaggcctac     1320
agtgagattg ggatgaaagg cgagcgccgg aggggcaagg ggcacgatgg cctttaccag     1380
ggtctcagta cagccaccaa ggacacctac gacgccttc acatgcaggc cctgcccct      1440 cgctag                                                                  1446
```

<210> SEQ ID NO 45
<211> LENGTH: 481
<212> TYPE: PRT
<213> ORGANISM: Artificial Sequence
<220> FEATURE:
<223> OTHER INFORMATION: Synthetic construct

<400> SEQUENCE: 45

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser His Lys Phe Met
            20                  25                  30

Ser Thr Ser Val Gly Asp Arg Val Asn Ile Thr Cys Lys Ala Ser Gln
        35                  40                  45

Asp Val Gly Thr Ala Val Ala Trp Tyr Gln Gln Lys Pro Gly Gln Ser
    50                  55                  60

Pro Lys Phe Leu Ile Tyr Trp Ala Ser Thr Arg His Thr Gly Val Pro
65                  70                  75                  80

Asp Arg Phe Thr Gly Ser Gly Ser Gly Thr Asp Phe Thr Leu Thr Ile
            85                  90                  95

Ser Asn Val Gln Ser Glu Asp Leu Ala Asp Tyr Phe Cys His Gln Tyr
            100                 105                 110

Thr Ser Tyr Pro Phe Thr Phe Gly Ser Gly Thr Lys Leu Glu Met Lys
        115                 120                 125

Arg Gly Gly Gly Gly Ser Gly Gly Gly Gly Ser Gly Gly Gly Gly Ser
    130                 135                 140

Val Lys Leu Gln Gln Ser Gly Pro Glu Leu Glu Lys Pro Gly Ala Ser
145                 150                 155                 160
```

```
Val Lys Ile Ser Cys Lys Ala Ser Gly Tyr Ser Phe Thr Gly Tyr Asn
                165                 170                 175

Val Asn Trp Val Lys Gln Ser Asn Gly Lys Ser Leu Glu Trp Ile Gly
            180                 185                 190

Asn Ile Asp Pro Tyr His Gly Gly Thr Thr Tyr Asn Gln Lys Phe Glu
        195                 200                 205

Ala Lys Ala Thr Leu Thr Val Asp Lys Ser Ser Ser Thr Ala Tyr Met
    210                 215                 220

Gln Leu Lys Ser Leu Thr Ser Glu Asp Ser Ala Val Tyr Tyr Cys Ala
225                 230                 235                 240

Arg Ser Ser Arg Phe Asp Tyr Trp Gly Gln Gly Thr Thr Leu Thr Val
                245                 250                 255

Ser Ser Thr Thr Thr Pro Ala Pro Arg Pro Pro Thr Pro Ala Pro Thr
                260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
                325                 330                 335

Ile Phe Lys Gln Pro Phe Met Arg Pro Val Gln Thr Thr Gln Glu Glu
                340                 345                 350

Asp Gly Cys Ser Cys Arg Phe Pro Glu Glu Glu Glu Gly Gly Cys Glu
                355                 360                 365

Leu Arg Val Lys Phe Ser Arg Ser Ala Asp Ala Pro Ala Tyr Lys Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
                435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg
```

<210> SEQ ID NO 46
<211> LENGTH: 1470
<212> TYPE: DNA
<213> ORGANISM: Artificial Sequence
<220> FEATURE:
<223> OTHER INFORMATION: Synthetic construct

<400> SEQUENCE: 46

```
atggccttac cagtgaccgc cttgctcctg ccgctggcct tgctgctcca tgcggctcga      60
cctatcgtgc tgacccagag cccagccatc atgagcgcct ccccaggagt gaaggtgacc     120
atgacatgca gggccagctc ctctgtggac agctcctacc tgcactggta tcagcagaag     180
```

-continued

```
tctggcgcca gccctcaagt gtggatctac tctaccagca acctggcctc tggcgtgcca      240
gcacgcttct ccggctctgg cagcggcacc tcctattctc tgacaatctc tagcgtggag      300
gccgaggatg ccgccacata ctattgccag cagtactccg gctatcccct gacctttggc      360
ggcggcacaa agctggagat caagagggga ggaggaggca gcggcggagg aggctccggc      420
ggcggcggct ctgtgaagct gcagcagagc ggaccaggac tggtgaagcc tagccagtcc      480
ctgtctctga cctgtgccgt gacaggctac tccatcacct ctgactatgc ctggaactgg      540
atcagaaagt ccccggcaa taagctggag tggatgggct acatcagcta ttccggcaga      600
accacataca atcctagcct gggagtcccg atctctatca ccagagacac aagcaagaac      660
cagttctttc tgcagctgaa cagcgtgacc acagaggata ccgccacata ctattgcgcc      720
aggtgttact atggctcctc tagccgctgg tacggcatgg attattgggg ccggggcaca      780
tccgtggccg tgtcctctac cacgacgcca gcgccgcgac caccaacacc ggcgcccacc      840
atcgcgtcgc agcccctgtc cctgcgccca gaggcgtgcc ggccagcggc ggggggcgca      900
gtgcacacga gggggctgga cttcgcctgt gacatctaca tctgggcgcc cctggccggg      960
acttgtgggg tccttctcct gtcactggtt atcacccttt actgcaaacg gggcagaaag     1020
aaactcctgt atatattcaa acaaccattt atgagaccag tacaaactac tcaagaggaa     1080
gatggctgta gctgccgatt tccagaagaa gaagaaggag gatgtgaact gagagtgaag     1140
ttcagcagga gcgcagacgc ccccgcgtac aagcagggcc agaaccagct ctataacgag     1200
ctcaatctag gacgaagaga ggagtacgat gttttggaca agagacgtgg ccgggaccct     1260
gagatggggg gaaagccgag aaggaagaac cctcaggaag gcctgtacaa tgaactgcag     1320
aaagataaga tggcggaggc ctacagtgag attgggatga aaggcgagcg ccggaggggc     1380
aaggggcacg atggccttta ccagggtctc agtacagcca ccaaggacac ctacgacgcc     1440
cttcacatgc aggccctgcc ccctcgctag                                      1470
```

<210> SEQ ID NO 47
<211> LENGTH: 489
<212> TYPE: PRT
<213> ORGANISM: Artificial Sequence
<220> FEATURE:
<223> OTHER INFORMATION: Synthetic construct

<400> SEQUENCE: 47

```
Met Ala Leu Pro Val Thr Ala Leu Leu Leu Pro Leu Ala Leu Leu Leu
1               5                   10                  15

His Ala Ala Arg Pro Ile Val Leu Thr Gln Ser Pro Ala Ile Met Ser
            20                  25                  30

Ala Ser Pro Gly Val Lys Val Thr Met Thr Cys Arg Ala Ser Ser Ser
        35                  40                  45

Val Asp Ser Ser Tyr Leu His Trp Tyr Gln Gln Lys Ser Gly Ala Ser
    50                  55                  60

Pro Gln Val Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Val Glu Ala Glu Asp Ala Ala Thr Tyr Tyr Cys Gln Gln Tyr
            100                 105                 110

Ser Gly Tyr Pro Leu Thr Phe Gly Gly Gly Thr Lys Leu Glu Ile Lys
        115                 120                 125

Arg Gly Gly Gly Gly Ser Gly Gly Gly Gly Ser Gly Gly Gly Gly Ser
```

```
           130                 135                 140

Val Lys Leu Gln Gln Ser Gly Pro Gly Leu Val Lys Pro Ser Gln Ser
145                 150                 155                 160

Leu Ser Leu Thr Cys Ala Val Thr Gly Tyr Ser Ile Thr Ser Asp Tyr
                165                 170                 175

Ala Trp Asn Trp Ile Arg Lys Phe Pro Gly Asn Lys Leu Glu Trp Met
            180                 185                 190

Gly Tyr Ile Ser Tyr Ser Gly Arg Thr Thr Tyr Asn Pro Ser Leu Glu
            195                 200                 205

Ser Arg Ile Ser Ile Thr Arg Asp Thr Ser Lys Asn Gln Phe Phe Leu
        210                 215                 220

Gln Leu Asn Ser Val Thr Thr Glu Asp Thr Ala Thr Tyr Tyr Cys Ala
225                 230                 235                 240

Arg Cys Tyr Tyr Gly Ser Ser Ser Arg Trp Tyr Gly Met Asp Tyr Trp
                245                 250                 255

Gly Arg Gly Thr Ser Val Ala Val Ser Ser Thr Thr Thr Pro Ala Pro
            260                 265                 270

Arg Pro Pro Thr Pro Ala Pro Thr Ile Ala Ser Gln Pro Leu Ser Leu
            275                 280                 285

Arg Pro Glu Ala Cys Arg Pro Ala Ala Gly Gly Ala Val His Thr Arg
        290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
        370                 375                 380

Ala Asp Ala Pro Ala Tyr Lys Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 48
<211> LENGTH: 63
<212> TYPE: DNA
<213> ORGANISM: Artificial Sequence
<220> FEATURE:
<223> OTHER INFORMATION: Synthetic construct

<400> SEQUENCE: 48
atggccttac cagtgaccgc cttgctcctg ccgctggcct tgctgctcca cgccgccagg      60
ccg                                                                      63

<210> SEQ ID NO 49
<211> LENGTH: 21
<212> TYPE: PRT
<213> ORGANISM: Artificial Sequence
<220> FEATURE:
<223> OTHER INFORMATION: Synthetic construct

<400> SEQUENCE: 49

Met Ala Leu Pro Val Thr Ala Leu Leu Leu Pro Leu Ala Leu Leu Leu
1               5                   10                  15

His Ala Ala Arg Pro
            20

<210> SEQ ID NO 50
<211> LENGTH: 726
<212> TYPE: DNA
<213> ORGANISM: Artificial Sequence
<220> FEATURE:
<223> OTHER INFORMATION: Synthetic construct

<400> SEQUENCE: 50
gacatccaga tgacacagac tacatcctcc ctgtctgcct ctctgggaga cagagtcacc      60
atcagttgca gggcaagtca ggacattagt aaatatttaa attggtatca gcagaaacca     120
gatggaactg ttaaactcct gatctaccat acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggactaagt tggaaataac aggtggcggt ggcagcggcg gtggtggttc cggaggcggc     360
ggttctgagg tgaaactgca ggagtcagga cctggcctgg tggcgccctc acagagcctg     420
tccgtcacat gcactgtctc aggggtctca ttacccgact atggtgtaag ctggattcgc     480
cagcctccac gaaagggtct ggagtggctg ggagtaatat ggggtagtga aaccacatac     540
tataattcag ctctcaaatc cagactgacc atcatcaagg acaactccaa gagccaagtt     600
ttcttaaaaa tgaacagtct gcaaactgat gacacagcca tttactactg tgccaaacat     660
tattactacg gtggtagcta tgctatggac tactggggtc aaggaacctc agtcaccgtc     720
tcctca                                                                 726

<210> SEQ ID NO 51
<211> LENGTH: 242
<212> TYPE: PRT
<213> ORGANISM: Artificial Sequence
<220> FEATURE:
<223> OTHER INFORMATION: Synthetic construct

<400> SEQUENCE: 51

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

-continued

```
Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

```
<210> SEQ ID NO 52
<211> LENGTH: 207
<212> TYPE: DNA
<213> ORGANISM: Artificial Sequence
<220> FEATURE:
<223> OTHER INFORMATION: Synthetic construct

<400> SEQUENCE: 52
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgatatcta catctgggcg cccctggccg ggacttgtgg ggtccttctc     180
ctgtcactgg ttatcaccct ttactgc                                        207
```

```
<210> SEQ ID NO 53
<211> LENGTH: 69
<212> TYPE: PRT
<213> ORGANISM: Artificial Sequence
<220> FEATURE:
<223> OTHER INFORMATION: Synthetic construct

<400> SEQUENCE: 53

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
    50                  55                  60

Ile Thr Leu Tyr Cys
65
```

```
<210> SEQ ID NO 54
<211> LENGTH: 126
```

-continued

```
<212> TYPE: DNA
<213> ORGANISM: Artificial Sequence
<220> FEATURE:
<223> OTHER INFORMATION: Synthetic construct

<400> SEQUENCE: 54
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                  126

<210> SEQ ID NO 55
<211> LENGTH: 335
<212> TYPE: DNA
<213> ORGANISM: Artificial Sequence
<220> FEATURE:
<223> OTHER INFORMATION: Synthetic construct

<400> SEQUENCE: 55
gagtgaagtt cagcaggagc gcagacgccc ccgcgtacaa gcagggccag aaccagctct        60
ataacgagct caatctagga cgaagagagg agtacgatgt tttggacaag agacgtggcc       120
gggaccctga gatgggggga aagccgagaa ggaagaaccc tcaggaaggc ctgtacaatg       180
aactgcagaa agataagatg gcggaggcct acagtgagat tgggatgaaa ggcgagcgcc       240
ggaggggcaa ggggcacgat ggcctttacc agggtctcag tacagccacc aaggacacct       300
acgacgccct tcacatgcag gccctgcccc ctcgc                                  335

<210> SEQ ID NO 56
<211> LENGTH: 54
<212> TYPE: DNA
<213> ORGANISM: Artificial Sequence
<220> FEATURE:
<223> OTHER INFORMATION: Synthetic construct

<400> SEQUENCE: 56
gagggcagag gcagcctgct gacatgtggc gacgttgaag agaatcctgg gccc              54

<210> SEQ ID NO 57
<211> LENGTH: 1356
<212> TYPE: DNA
<213> ORGANISM: Artificial Sequence
<220> FEATURE:
<223> OTHER INFORMATION: Synthetic construct

<400> SEQUENCE: 57
atgaacctgg agggcggcgg ccgaggcgga gagttcggca tgagcgcggt gagctgcggc        60
aacgggaagc tccgccagtg gctgatcgac cagatcgaca gcggcaagta ccccgggctg       120
gtgtgggaga cgaggagaa gagcatcttc cgcatcccct ggaagcacgc gggcaagcag       180
gactacaacc gcgaggagga cgccgcgctc ttcaaggctt gggcactgtt taaaggaaag       240
ttccgagaag gcatcgacaa gccggaccct cccacctgga gacgcgcct gcggtgcgct       300 ttgaacaaga gcaatgactt tgaggaactg gttgagcgga gccagctgga catctcagac       360
ccgtacaaag tgtacaggat tgttcctgag ggagccaaaa aaggagccaa gcagctcacc       420
ttggaggacc cgcagatgtc catgagccac ccctacacca tgacaacgcc ttacccttcg       480
ctcccagccc agcaggttca caactacatg atgccacccc tcgaccgaag ctggagggac       540
tacgtcccgg atcagccaca cccggaaatc ccgtaccaat gtcccatgac gtttggaccc       600
cgcggccacc actggcaagg cccagcttgt gaaaatggtt gccaggtgac aggaaccttt       660
```

-continued

```
tatgcttgtg ccccacctga gtcccaggct cccggagtcc ccacagagcc aagcataagg       720
tctgccgaag ccttggcgtt ctcagactgc cggctgcaca tctgcctgta ctaccgggaa       780
atcctcgtga aggagctgac cacgtccagc cccgagggct gccggatctc ccatggacat       840
acgtatgacg ccagcaacct ggaccaggtc ctgttcccct acccagagga caatggccag       900
aggaaaaaca ttgagaagct gctgagccac ctggagaggg gcgtggtcct ctggatggcc       960
cccgacgggc tctatgcgaa aagactgtgc cagagcagga tctactggga cgggcccctg      1020
gcgctgtgca acgaccggcc caacaaactg gagagagacc agacctgcaa gctctttgac      1080
acacagcagt tcttgtcaga gctgcaagcg tttgctcacc acggccgctc cctgccaaga      1140
ttccaggtga ctctatgctt tggagaggag tttccagacc ctcagaggca agaaagctc       1200 atcacagctc acgtagaacc tctgctagcc agacaactat attattttgc tcaacaaaac      1260
agtggacatt tcctgagggg ctacgattta ccagaacaca tcagcaatcc agaagattac      1320
cacagatcta tccgccattc ctctattcaa gaatga                                1356
```

```
<210> SEQ ID NO 58
<211> LENGTH: 451
<212> TYPE: PRT
<213> ORGANISM: Artificial Sequence
<220> FEATURE:
<223> OTHER INFORMATION: Synthetic construct

<400> SEQUENCE: 58

Met Asn Leu Glu Gly Gly Gly Arg Gly Gly Glu Phe Gly Met Ser Ala
1               5                   10                  15

Val Ser Cys Gly Asn Gly Lys Leu Arg Gln Trp Leu Ile Asp Gln Ile
                20                  25                  30

Asp Ser Gly Lys Tyr Pro Gly Leu Val Trp Glu Asn Glu Glu Lys Ser
            35                  40                  45

Ile Phe Arg Ile Pro Trp Lys His Ala Gly Lys Gln Asp Tyr Asn Arg
        50                  55                  60

Glu Glu Asp Ala Ala Leu Phe Lys Ala Trp Ala Leu Phe Lys Gly Lys
65                  70                  75                  80

Phe Arg Glu Gly Ile Asp Lys Pro Asp Pro Thr Trp Lys Thr Arg
                85                  90                  95

Leu Arg Cys Ala Leu Asn Lys Ser Asn Asp Phe Glu Glu Leu Val Glu
            100                 105                 110

Arg Ser Gln Leu Asp Ile Ser Asp Pro Tyr Lys Val Tyr Arg Ile Val
            115                 120                 125

Pro Glu Gly Ala Lys Lys Gly Ala Lys Gln Leu Thr Leu Glu Asp Pro
        130                 135                 140

Gln Met Ser Met Ser His Pro Tyr Thr Met Thr Thr Pro Tyr Pro Ser
145                 150                 155                 160

Leu Pro Ala Gln Gln Val His Asn Tyr Met Met Pro Pro Leu Asp Arg
                165                 170                 175

Ser Trp Arg Asp Tyr Val Pro Asp Gln Pro His Pro Glu Ile Pro Tyr
            180                 185                 190

Gln Cys Pro Met Thr Phe Gly Pro Arg Gly His His Trp Gln Gly Pro
            195                 200                 205

Ala Cys Glu Asn Gly Cys Gln Val Thr Gly Thr Phe Tyr Ala Cys Ala
        210                 215                 220

Pro Pro Glu Ser Gln Ala Pro Gly Val Pro Thr Glu Pro Ser Ile Arg
225                 230                 235                 240
```

```
Ser Ala Glu Ala Leu Ala Phe Ser Asp Cys Arg Leu His Ile Cys Leu
            245                 250                 255

Tyr Tyr Arg Glu Ile Leu Val Lys Glu Leu Thr Thr Ser Ser Pro Glu
            260                 265                 270

Gly Cys Arg Ile Ser His Gly His Thr Tyr Asp Ala Ser Asn Leu Asp
            275                 280                 285

Gln Val Leu Phe Pro Tyr Pro Glu Asp Asn Gly Gln Arg Lys Asn Ile
        290                 295                 300

Glu Lys Leu Leu Ser His Leu Glu Arg Gly Val Val Leu Trp Met Ala
305                 310                 315                 320

Pro Asp Gly Leu Tyr Ala Lys Arg Leu Cys Gln Ser Arg Ile Tyr Trp
                325                 330                 335

Asp Gly Pro Leu Ala Leu Cys Asn Asp Arg Pro Asn Lys Leu Glu Arg
                340                 345                 350

Asp Gln Thr Cys Lys Leu Phe Asp Thr Gln Gln Phe Leu Ser Glu Leu
            355                 360                 365

Gln Ala Phe Ala His His Gly Arg Ser Leu Pro Arg Phe Gln Val Thr
        370                 375                 380

Leu Cys Phe Gly Glu Glu Phe Pro Asp Pro Gln Arg Gln Arg Lys Leu
385                 390                 395                 400

Ile Thr Ala His Val Glu Pro Leu Leu Ala Arg Gln Leu Tyr Tyr Phe
                405                 410                 415

Ala Gln Gln Asn Ser Gly His Phe Leu Arg Gly Tyr Asp Leu Pro Glu
                420                 425                 430

His Ile Ser Asn Pro Glu Asp Tyr His Arg Ser Ile Arg His Ser Ser
            435                 440                 445

Ile Gln Glu
    450

<210> SEQ ID NO 59
<211> LENGTH: 2868
<212> TYPE: DNA
<213> ORGANISM: Artificial Sequence
<220> FEATURE:
<223> OTHER INFORMATION: Synthetic construct

<400> SEQUENCE: 59
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
ggggggacta gttggaaat aacaggtggc ggtggcagcg gcggtggtgg ttccggaggc     420
ggcggttctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc acgaaaggg tctggagtgg ctgggagtaa tatggggtag tgaaaccaca     600
tactataatt cagctctcaa atccagactg accatcatca ggacaactc caagagccaa     660 gttttcttaa aaatgaacag tctgcaaact gatgacacag ccatttacta ctgtgccaaa     720
cattattact acggtggtag ctatgctatg gactactggg gtcaaggaac ctcagtcacc     780
gtctcctcaa ccacgacgcc agcgccgcga ccaccaacac cggcgcccac catcgcgtcg     840
```

-continued

```
cagcccctgt ccctgcgccc agaggcgtgc cggccagcgg cggggggcgc agtgcacacg      900 aggggggctgg acttcgcctg tgatatctac atctgggcgc ccctggccgg gacttgtggg     960
gtccttctcc tgtcactggt tatcacccctt tactgcaaac ggggcagaaa gaaactcctg    1020
tatatattca aacaaccatt tatgagacca gtacaaacta ctcaagagga agatggctgt     1080
agctgccgat ttccagaaga agaagaagga ggatgtgaac tgagagtgaa gttcagcagg    1140
agcgcagacg cccccgcgta caagcagggc cagaaccagc tctataacga gctcaatcta     1200
ggacgaagag aggagtacga tgttttggac aagagacgtg gccgggaccc tgagatgggg     1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380 gatggcccttt accagggtct cagtacagcc accaaggaca cctacgcgc ccttcacatg    1440 caggccctgc cccctcgcga gggcagaggc agcctgctga catgtggcga cgttgaagag    1500
aatcctgggc ccatgaacct ggagggcggc ggccgaggcg gagagttcgg catgagcgcg     1560
gtgagctgcg gcaacgggaa gctccgccag tggctgatcg accagatcga cagcggcaag     1620
taccccgggc tggtgtggga gaacgaggag aagagcatct tccgcatccc ctggaagcac    1680
gcgggcaagc aggactacaa ccgcgaggag gacgccgcgc tcttcaaggc ttgggcactg    1740
tttaaaggaa agttccgaga aggcatcgac aagccggacc ctcccacctg gaagacgcgc    1800
ctgcggtgcg ctttgaacaa gagcaatgac tttgaggaac tggttgagcg gagccagctg    1860
gacatctcag acccgtacaa agtgtacagg attgttcctg agggagccaa aaaaggagcc    1920
aagcagctca ccttggagga cccgcagatg tccatgagcc accctacac catgacaacg    1980 ccttacccctt cgctcccagc ccagcaggtt cacaactaca tgatgccacc cctcgaccga    2040
agctggaggg actacgtccc ggatcagcca cacccggaaa tcccgtacca atgtcccatg    2100
acgtttggac cccgcggcca ccactggcaa ggcccagctt gtgaaaatgg ttgccaggtg    2160
acaggaacct tttatgcttg tgccccacct gagtcccagg ctcccggagt ccccacagag    2220
ccaagcataa ggtctgccga agccttggcg ttctcagact gccggctgca catctgcctg    2280
tactaccggg aaatcctcgt gaaggagctg accacgtcca gccccgaggg ctgccggatc    2340
tcccatggac atacgtatga cgccagcaac ctggaccagg tcctgttccc ctacccagag    2400
gacaatggcc agaggaaaaa cattgagaag ctgctgagcc acctggagag gggcgtggtc    2460
ctctggatgg cccccgacgg gctctatgcg aaaagactgt gccagagcag gatctactgg    2520
gacgggcccc tggcgctgtg caacgaccgg cccaacaaac tggagagaga ccagacctgc    2580
aagctctttg acacacagca gttcttgtca gagctgcaag cgtttgctca ccacggccgc    2640
tccctgccaa gattccaggt gactctatgc tttggagagg agtttccaga ccctcagagg    2700
caaagaaagc tcatcacagc tcacgtagaa cctctgctag ccagacaact atattatttt    2760
gctcaacaaa acagtggaca tttcctgagg ggctacgatt taccagaaca catcagcaat    2820
ccagaagatt accacagatc tatccgccat tcctctattc aagaatga               2868
```

<210> SEQ ID NO 60
<211> LENGTH: 955
<212> TYPE: PRT
<213> ORGANISM: Artificial Sequence
<220> FEATURE:
<223> OTHER INFORMATION: Synthetic construct

<400> SEQUENCE: 60

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Gly Ser Gly Gly Gly Gly Ser Glu
        130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
        370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
```

```
                420              425              430

Tyr Asn Glu Leu Gln Lys Asp Lys Met Ala Glu Ala Tyr Ser Glu Ile
        435              440              445

Gly Met Lys Gly Glu Arg Arg Arg Gly Lys Gly His Asp Gly Leu Tyr
    450              455              460

Gln Gly Leu Ser Thr Ala Thr Lys Asp Thr Tyr Asp Ala Leu His Met
465              470              475              480

Gln Ala Leu Pro Pro Arg Glu Gly Arg Gly Ser Leu Leu Thr Cys Gly
                485              490              495

Asp Val Glu Glu Asn Pro Gly Pro Met Asn Leu Glu Gly Gly Gly Arg
            500              505              510

Gly Gly Glu Phe Gly Met Ser Ala Val Ser Cys Gly Asn Gly Lys Leu
            515              520              525

Arg Gln Trp Leu Ile Asp Gln Ile Asp Ser Gly Lys Tyr Pro Gly Leu
        530              535              540

Val Trp Glu Asn Glu Glu Lys Ser Ile Phe Arg Ile Pro Trp Lys His
545              550              555              560

Ala Gly Lys Gln Asp Tyr Asn Arg Glu Glu Asp Ala Ala Leu Phe Lys
                565              570              575

Ala Trp Ala Leu Phe Lys Gly Lys Phe Arg Glu Gly Ile Asp Lys Pro
            580              585              590

Asp Pro Pro Thr Trp Lys Thr Arg Leu Arg Cys Ala Leu Asn Lys Ser
            595              600              605

Asn Asp Phe Glu Glu Leu Val Glu Arg Ser Gln Leu Asp Ile Ser Asp
        610              615              620

Pro Tyr Lys Val Tyr Arg Ile Val Pro Glu Gly Ala Lys Lys Gly Ala
625              630              635              640

Lys Gln Leu Thr Leu Glu Asp Pro Gln Met Ser Met Ser His Pro Tyr
            645              650              655

Thr Met Thr Thr Pro Tyr Pro Ser Leu Pro Ala Gln Gln Val His Asn
            660              665              670

Tyr Met Met Pro Pro Leu Asp Arg Ser Trp Arg Asp Tyr Val Pro Asp
        675              680              685

Gln Pro His Pro Glu Ile Pro Tyr Gln Cys Pro Met Thr Phe Gly Pro
    690              695              700

Arg Gly His His Trp Gln Gly Pro Ala Cys Glu Asn Gly Cys Gln Val
705              710              715              720

Thr Gly Thr Phe Tyr Ala Cys Ala Pro Pro Glu Ser Gln Ala Pro Gly
            725              730              735

Val Pro Thr Glu Pro Ser Ile Arg Ser Ala Glu Ala Leu Ala Phe Ser
            740              745              750

Asp Cys Arg Leu His Ile Cys Leu Tyr Tyr Arg Glu Ile Leu Val Lys
        755              760              765

Glu Leu Thr Thr Ser Ser Pro Glu Gly Cys Arg Ile Ser His Gly His
    770              775              780

Thr Tyr Asp Ala Ser Asn Leu Asp Gln Val Leu Phe Pro Tyr Pro Glu
785              790              795              800

Asp Asn Gly Gln Arg Lys Asn Ile Glu Lys Leu Leu Ser His Leu Glu
                805              810              815

Arg Gly Val Val Leu Trp Met Ala Pro Asp Gly Leu Tyr Ala Lys Arg
            820              825              830

Leu Cys Gln Ser Arg Ile Tyr Trp Asp Gly Pro Leu Ala Leu Cys Asn
        835              840              845
```

-continued

_____

```
Asp Arg Pro Asn Lys Leu Glu Arg Asp Gln Thr Cys Lys Leu Phe Asp
    850             855             860

Thr Gln Gln Phe Leu Ser Glu Leu Gln Ala Phe Ala His His Gly Arg
865             870             875             880

Ser Leu Pro Arg Phe Gln Val Thr Leu Cys Phe Gly Glu Glu Phe Pro
            885             890             895

Asp Pro Gln Arg Gln Arg Lys Leu Ile Thr Ala His Val Glu Pro Leu
            900             905             910

Leu Ala Arg Gln Leu Tyr Tyr Phe Ala Gln Gln Asn Ser Gly His Phe
        915             920             925

Leu Arg Gly Tyr Asp Leu Pro Glu His Ile Ser Asn Pro Glu Asp Tyr
    930             935             940

His Arg Ser Ile Arg His Ser Ser Ile Gln Glu
945             950             955
```

```
<210> SEQ ID NO 61
<211> LENGTH: 738
<212> TYPE: DNA
<213> ORGANISM: Artificial Sequence
<220> FEATURE:
<223> OTHER INFORMATION: Synthetic construct

<400> SEQUENCE: 61
gtccagctcc aacagccggg tgctgcactg gttcggccag gagcttcagt gaggctgtcc        60
tgcaaggctt ctggatactc cttcacctac tactggatga actgggtgat gcagaggcct       120
ggccaaggcc ttgagtggat tggcatgatt catccttccg atagtgaaac tcggttaagt       180
cagaagttca gggacaaggc cacattgact gtagacaaat cttccagcac agtctacatg       240
caactcaaca gcccgacatc tgatgactct gcagtctatt actgtgcaag agatggtaac       300
ttcccttact atgcactaga ctactggggt caaggaacct cggtcaccgt ctcctcaggt       360
ggcggtggca gcggcggtgg tggttccgga ggcggcggtt ctgatgttgt gctgacccaa       420
gctccactct ccctgcctgt cagtcttgga gatcaagcct ccatctcttg cagatctagt       480
cagagccttg aatacagtaa tggaaacacc tatttacatt ggtacctgca gaagccaggc       540
cagtctccag aactcctgat ctacacagtt tccaaccgat tttctggggt cccagacagg       600
ttcagtggca gtggatcagg gacagatttc acactcaaga ttcacagagt ggaggctgag       660
gatctgggag tttatttctg ctctcaaagt acacatgttc ccacgttcgg aggggggacc       720
aagctggaga taaaacgg                                                     738
```

```
<210> SEQ ID NO 62
<211> LENGTH: 246
<212> TYPE: PRT
<213> ORGANISM: Artificial Sequence
<220> FEATURE:
<223> OTHER INFORMATION: Synthetic construct

<400> SEQUENCE: 62

Val Gln Leu Gln Gln Pro Gly Ala Ala Leu Val Arg Pro Gly Ala Ser
1               5               10              15

Val Arg Leu Ser Cys Lys Ala Ser Gly Tyr Ser Phe Thr Tyr Tyr Trp
            20              25              30

Met Asn Trp Val Met Gln Arg Pro Gly Gln Gly Leu Glu Trp Ile Gly
        35              40              45

Met Ile His Pro Ser Asp Ser Glu Thr Arg Leu Ser Gln Lys Phe Arg
    50              55              60
```

```
Asp Lys Ala Thr Leu Thr Val Asp Lys Ser Ser Ser Thr Val Tyr Met
65              70              75              80

Gln Leu Asn Ser Pro Thr Ser Asp Asp Ser Ala Val Tyr Tyr Cys Ala
                85              90              95

Arg Asp Gly Asn Phe Pro Tyr Tyr Ala Leu Asp Tyr Trp Gly Gln Gly
            100             105             110

Thr Ser Val Thr Val Ser Ser Gly Gly Gly Gly Ser Gly Gly Gly Gly
            115             120             125

Ser Gly Gly Gly Gly Ser Asp Val Val Leu Thr Gln Ala Pro Leu Ser
    130             135             140

Leu Pro Val Ser Leu Gly Asp Gln Ala Ser Ile Ser Cys Arg Ser Ser
145             150             155             160

Gln Ser Leu Glu Tyr Ser Asn Gly Asn Thr Tyr Leu His Trp Tyr Leu
                165             170             175

Gln Lys Pro Gly Gln Ser Pro Glu Leu Leu Ile Tyr Thr Val Ser Asn
            180             185             190

Arg Phe Ser Gly Val Pro Asp Arg Phe Ser Gly Ser Gly Ser Gly Thr
            195             200             205

Asp Phe Thr Leu Lys Ile His Arg Val Glu Ala Glu Asp Leu Gly Val
    210             215             220

Tyr Phe Cys Ser Gln Ser Thr His Val Pro Thr Phe Gly Gly Gly Thr
225             230             235             240

Lys Leu Glu Ile Lys Arg
            245
```

```
<210> SEQ ID NO 63
<211> LENGTH: 2880
<212> TYPE: DNA
<213> ORGANISM: Artificial Sequence
<220> FEATURE:
<223> OTHER INFORMATION: Synthetic construct

<400> SEQUENCE: 63
atggccttac cagtgaccgc cttgctcctg ccgctggcct tgctgctcca tgcggctcga      60
cctgtccagc tccaacagcc gggtgctgca ctggttcggc caggagcttc agtgaggctg     120
tcctgcaagg cttctggata ctccttcacc tactactgga tgaactgggt gatgcagagg     180
cctggccaag gccttgagtg gattggcatg attcatcctt ccgatagtga aactcggtta     240
agtcagaagt tcaggacaa ggccacattg actgtagaca aatcttccag cacagtctac      300
atgcaactca cagcccgac atctgatgac tctgcagtct attactgtgc aagagatggt      360
aacttccctt actatgcact agactactgg ggtcaaggaa cctcggtcac cgtctcctca      420
ggtggcggtg gcagcggcgg tggtggttcc ggaggcggcg gttctgatgt tgtgctgacc      480
caagctccac tctccctgcc tgtcagtctt ggagatcaag cctccatctc ttgcagatct      540
agtcagagcc ttgaatacag taatggaaac acctatttac attggtacct gcagaagcca      600
ggccagtctc cagaactcct gatctacaca gtttccaacc gattttctgg ggtcccagac      660
aggttcagtg gcagtggatc agggacagat ttcacactca agattcacag agtggaggct      720
gaggatctgg gagtttattt ctgctctcaa agtacacatg ttcccacgtt cggagggggg      780
accaagctgg agataaaacg gaccacgacg ccagcgccgc gaccaccaac accggcgccc      840
accatcgcgt cgcagcccct gtccctgcgc ccagaggcgt gccggccagc ggcggggggc      900
gcagtgcaca cgaggggggct ggacttcgcc tgtgatatct acatctgggc gcccctggcc      960
```

-continued

```
gggacttgtg gggtccttct cctgtcactg gttatcaccc tttactgcaa acggggcaga      1020
aagaaactcc tgtatatatt caaacaacca tttatgagac cagtacaaac tactcaagag      1080
gaagatggct gtagctgccg atttccagaa gaagaagaag gaggatgtga actgagagtg      1140
aagttcagca ggagcgcaga cgcccccgcg tacaagcagg gccagaacca gctctataac      1200
gagctcaatc taggacgaag agaggagtac gatgttttgg acaagagacg tggccgggac      1260
cctgagatgg ggggaaagcc gagaaggaag aaccctcagg aaggcctgta caatgaactg      1320
cagaaagata agatggcgga ggcctacagt gagattggga tgaaaggcga gcgccggagg      1380
ggcaaggggc acgatggcct ttaccagggt ctcagtacag ccaccaagga cacctacgac      1440
gcccttcaca tgcaggccct gcccctcgc gagggcagag gcagcctgct gacatgtggc       1500
gacgttgaag agaatcctgg gcccatgaac ctggagggcg cggccgagg cggagagttc       1560 ggcatgagcg cggtgagctg cggcaacggg aagctccgcc agtggctgat cgaccagatc      1620
gacagcggca gtaccccgg gctggtgtgg gagaacgagg agaagagcat cttccgcatc       1680
ccctggaagc acgcgggcaa gcaggactac aaccgcgagg aggacgccgc gctcttcaag      1740
gcttgggcac tgtttaaagg aaagttccga gaaggcatcg acaagccgga ccctcccacc      1800
tggaagacgc gcctgcggtg cgctttgaac aagagcaatg actttgagga actggttgag      1860
cggagccagc tggacatctc agacccgtac aaagtgtaca ggattgttcc tgagggagcc      1920
aaaaaaggag ccaagcagct caccttggag gacccgcaga tgtccatgag ccacccctac      1980
accatgacaa cgccttaccc ttcgctccca gcccagcagg ttcacaacta catgatgcca      2040
cccctcgacc gaagctggag ggactacgtc ccggatcagc cacacccgga aatcccgtac      2100
caatgtccca tgacgtttgg accccgcggc caccactggc aaggcccagc ttgtgaaaat      2160
ggttgccagt gacaggaac cttttatgct tgtgccccac ctgagtccca ggctcccgga      2220
gtccccacag agccaagcat aaggtctgcc gaagccttgg cgttctcaga ctgccggctg      2280
cacatctgcc tgtactaccg ggaaatcctc gtgaaggagc tgaccacgtc cagccccgag      2340
ggctgccgga tctcccatgg acatacgtat gacgccagca acctggacca ggtcctgttc      2400
ccctacccag aggacaatgg ccagaggaaa aacattgaga agctgctgag ccacctggag      2460
aggggcgtgg tcctctggat ggcccccgac gggctctatg cgaaaagact gtgccagagc      2520
aggatctact gggacgggcc cctggcgctg tgcaacgacc ggcccaacaa actggagaga      2580
gaccagacct gcaagctctt tgacacacag cagttcttgt cagagctgca agcgtttgct      2640
caccacggcc gctccctgcc aagattccag gtgactctat gctttggaga ggagtttcca      2700
gaccctcaga ggcaaagaaa gctcatcaca gctcacgtag aacctctgct agccagacaa      2760
ctatattatt ttgctcaaca aaacagtgga catttcctga ggggctacga tttaccagaa      2820
cacatcagca atccagaaga ttaccacaga tctatccgcc attcctctat tcaagaatga      2880
```

```
<210> SEQ ID NO 64
<211> LENGTH: 959
<212> TYPE: PRT
<213> ORGANISM: Artificial Sequence
<220> FEATURE:
<223> OTHER INFORMATION: Synthetic construct

<400> SEQUENCE: 64

Met Ala Leu Pro Val Thr Ala Leu Leu Leu Pro Leu Ala Leu Leu Leu
1               5                   10                  15

His Ala Ala Arg Pro Val Gln Leu Gln Gln Pro Gly Ala Ala Leu Val
            20                  25                  30
```

```
Arg Pro Gly Ala Ser Val Arg Leu Ser Cys Lys Ala Ser Gly Tyr Ser
        35              40              45

Phe Thr Tyr Tyr Trp Met Asn Trp Val Met Gln Arg Pro Gly Gln Gly
        50              55              60

Leu Glu Trp Ile Gly Met Ile His Pro Ser Asp Ser Glu Thr Arg Leu
65              70              75              80

Ser Gln Lys Phe Arg Asp Lys Ala Thr Leu Thr Val Asp Lys Ser Ser
                85              90              95

Ser Thr Val Tyr Met Gln Leu Asn Ser Pro Thr Ser Asp Asp Ser Ala
                100             105             110

Val Tyr Tyr Cys Ala Arg Asp Gly Asn Phe Pro Tyr Tyr Ala Leu Asp
                115             120             125

Tyr Trp Gly Gln Gly Thr Ser Val Thr Val Ser Ser Gly Gly Gly Gly
        130             135             140

Ser Gly Gly Gly Gly Ser Gly Gly Gly Gly Ser Asp Val Val Leu Thr
145             150             155             160

Gln Ala Pro Leu Ser Leu Pro Val Ser Leu Gly Asp Gln Ala Ser Ile
                165             170             175

Ser Cys Arg Ser Ser Gln Ser Leu Glu Tyr Ser Asn Gly Asn Thr Tyr
                180             185             190

Leu His Trp Tyr Leu Gln Lys Pro Gly Gln Ser Pro Glu Leu Leu Ile
        195             200             205

Tyr Thr Val Ser Asn Arg Phe Ser Gly Val Pro Asp Arg Phe Ser Gly
        210             215             220

Ser Gly Ser Gly Thr Asp Phe Thr Leu Lys Ile His Arg Val Glu Ala
225             230             235             240

Glu Asp Leu Gly Val Tyr Phe Cys Ser Gln Ser Thr His Val Pro Thr
                245             250             255

Phe Gly Gly Gly Thr Lys Leu Glu Ile Lys Arg Thr Thr Thr Pro Ala
        260             265             270

Pro Arg Pro Pro Thr Pro Ala Pro Thr Ile Ala Ser Gln Pro Leu Ser
        275             280             285

Leu Arg Pro Glu Ala Cys Arg Pro Ala Ala Gly Gly Ala Val His Thr
        290             295             300

Arg Gly Leu Asp Phe Ala Cys Asp Ile Tyr Ile Trp Ala Pro Leu Ala
305             310             315             320

Gly Thr Cys Gly Val Leu Leu Leu Ser Leu Val Ile Thr Leu Tyr Cys
                325             330             335

Lys Arg Gly Arg Lys Lys Leu Leu Tyr Ile Phe Lys Gln Pro Phe Met
        340             345             350

Arg Pro Val Gln Thr Thr Gln Glu Glu Asp Gly Cys Ser Cys Arg Phe
        355             360             365

Pro Glu Glu Glu Glu Gly Gly Cys Glu Leu Arg Val Lys Phe Ser Arg
        370             375             380

Ser Ala Asp Ala Pro Ala Tyr Lys Gln Gly Gln Asn Gln Leu Tyr Asn
385             390             395             400

Glu Leu Asn Leu Gly Arg Arg Glu Glu Tyr Asp Val Leu Asp Lys Arg
                405             410             415

Arg Gly Arg Asp Pro Glu Met Gly Gly Lys Pro Arg Arg Lys Asn Pro
        420             425             430

Gln Glu Gly Leu Tyr Asn Glu Leu Gln Lys Asp Lys Met Ala Glu Ala
        435             440             445
```

```
Tyr Ser Glu Ile Gly Met Lys Gly Glu Arg Arg Arg Gly Lys Gly His
    450             455             460

Asp Gly Leu Tyr Gln Gly Leu Ser Thr Ala Thr Lys Asp Thr Tyr Asp
465             470             475             480

Ala Leu His Met Gln Ala Leu Pro Pro Arg Glu Gly Arg Gly Ser Leu
                485             490             495

Leu Thr Cys Gly Asp Val Glu Glu Asn Pro Gly Pro Met Asn Leu Glu
                500             505             510

Gly Gly Gly Arg Gly Gly Glu Phe Gly Met Ser Ala Val Ser Cys Gly
            515             520             525

Asn Gly Lys Leu Arg Gln Trp Leu Ile Asp Gln Ile Asp Ser Gly Lys
    530             535             540

Tyr Pro Gly Leu Val Trp Glu Asn Glu Glu Lys Ser Ile Phe Arg Ile
545             550             555             560

Pro Trp Lys His Ala Gly Lys Gln Asp Tyr Asn Arg Glu Glu Asp Ala
                565             570             575

Ala Leu Phe Lys Ala Trp Ala Leu Phe Lys Gly Lys Phe Arg Glu Gly
                580             585             590

Ile Asp Lys Pro Asp Pro Pro Thr Trp Lys Thr Arg Leu Arg Cys Ala
            595             600             605

Leu Asn Lys Ser Asn Asp Phe Glu Glu Leu Val Glu Arg Ser Gln Leu
    610             615             620

Asp Ile Ser Asp Pro Tyr Lys Val Tyr Arg Ile Val Pro Glu Gly Ala
625             630             635             640

Lys Lys Gly Ala Lys Gln Leu Thr Leu Glu Asp Pro Gln Met Ser Met
            645             650             655

Ser His Pro Tyr Thr Met Thr Thr Pro Tyr Pro Ser Leu Pro Ala Gln
            660             665             670

Gln Val His Asn Tyr Met Met Pro Pro Leu Asp Arg Ser Trp Arg Asp
    675             680             685

Tyr Val Pro Asp Gln Pro His Pro Glu Ile Pro Tyr Gln Cys Pro Met
    690             695             700

Thr Phe Gly Pro Arg Gly His His Trp Gln Gly Pro Ala Cys Glu Asn
705             710             715             720

Gly Cys Gln Val Thr Gly Thr Phe Tyr Ala Cys Ala Pro Pro Glu Ser
            725             730             735

Gln Ala Pro Gly Val Pro Thr Glu Pro Ser Ile Arg Ser Ala Glu Ala
            740             745             750

Leu Ala Phe Ser Asp Cys Arg Leu His Ile Cys Leu Tyr Tyr Arg Glu
    755             760             765

Ile Leu Val Lys Glu Leu Thr Thr Ser Ser Pro Glu Gly Cys Arg Ile
    770             775             780

Ser His Gly His Thr Tyr Asp Ala Ser Asn Leu Asp Gln Val Leu Phe
785             790             795             800

Pro Tyr Pro Glu Asp Asn Gly Gln Arg Lys Asn Ile Glu Lys Leu Leu
                805             810             815

Ser His Leu Glu Arg Gly Val Val Leu Trp Met Ala Pro Asp Gly Leu
            820             825             830

Tyr Ala Lys Arg Leu Cys Gln Ser Arg Ile Tyr Trp Asp Gly Pro Leu
            835             840             845

Ala Leu Cys Asn Asp Arg Pro Asn Lys Leu Glu Arg Asp Gln Thr Cys
    850             855             860

Lys Leu Phe Asp Thr Gln Gln Phe Leu Ser Glu Leu Gln Ala Phe Ala
```

-continued

```
865                 870             875             880

His His Gly Arg Ser Leu Pro Arg Phe Gln Val Thr Leu Cys Phe Gly
                885             890             895

Glu Glu Phe Pro Asp Pro Gln Arg Gln Arg Lys Leu Ile Thr Ala His
            900             905             910

Val Glu Pro Leu Leu Ala Arg Gln Leu Tyr Tyr Phe Ala Gln Gln Asn
        915             920             925

Ser Gly His Phe Leu Arg Gly Tyr Asp Leu Pro Glu His Ile Ser Asn
    930             935             940

Pro Glu Asp Tyr His Arg Ser Ile Arg His Ser Ser Ile Gln Glu
945             950             955
```

PSMA-TARGETED IMMUNOTHERAPIES FOR CANCERS

CROSS-REFERENCE TO RELATED APPLICATIONS

This application claims the benefit of U.S. Provisional Application No. 63/094,005, filed Oct. 20, 2020, which is expressly incorporated herein by reference in its entirety.

SEQUENCE LISTING

This application contains a Sequence Listing which has been submitted electronically in xml format and is hereby incorporated by reference in its entirety. Said xml copy, created on Apr. 25, 2023, is named "18032485_1_1.txt" and is 134,169 bytes in size.

STATEMENT REGARDING FEDERALLY SPONSORED RESEARCH OR DEVELOPMENT

This invention was made with Government support under grant number CA211861 awarded by the National Institutes of Health. The Government has certain rights in the invention.

FIELD

The present disclosure relates to compositions and methods for treating prostate cancer.

BACKGROUND

Prostate cancer affects approximately 11% of American men and is the second leading cause of cancer death in the U.S. While the overall 5-year survival rate of men with prostate cancer is nearly 98%, these rates drop significantly to 30% once the cancer has metastasized. The currently available therapeutic interventions for metastatic prostate cancer are highly ineffective at treating the disease, indicating a need for targeted treatment strategies. What are needed are new compositions and methods for treating prostate cancer. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to methods for treating prostate cancer.

The details of one or more embodiments of the invention are set forth in the accompanying drawings and the description below. Other features, objects, and advantages of the invention will be apparent from the description and drawings, and from the claims.

In some aspects, disclosed herein is a recombinant nucleic acid sequence encoding a chimeric antigen receptor (CAR), wherein the CAR comprises a CD3 zeta signaling domain, a costimulatory signaling domain, a CD8α domain, a transmembrane domain, and a prostate-specific membrane antigen (PSMA) binding domain, wherein the PSMA binding domain comprises a heavy chain variable region (VH) comprising an amino acid sequence 90% identity to SEQ ID NO: 12, 16, 20, 24, or 28 and a light chain variable region (VL) comprising an amino acid sequence 90% identity to SEQ ID NO: 14, 18, 22, 26, or 30.

In some embodiments, the VH is encoded by the nucleic acid sequence of SEQ ID NO: 11, 15, 19, 23, or 27 and the VL is encoded by the nucleic acid sequence of SEQ ID NO: 13, 17, 21, 25, or 29.

In some embodiments, the PSMA binding domain is an antibody or an antigen-binding fragment thereof. In some embodiments, the antigen-binding fragment is a single-chain variable (scFv).

In some embodiments, the costimulatory signaling domain is 4-1BB.

In some embodiments, the CAR comprises the amino acid sequence of SEQ ID NO: 2, 4, or 6.

In some embodiments, the recombinant nucleic acid sequence of any preceding aspect comprises the nucleic acid sequence of SEQ ID NO: 1, 3, 5, 7, 9, 38, 40, 42, 44, or 46.

In some embodiments, the recombinant nucleic acid sequence of any preceding aspect further comprises a nucleic acid sequence encoding interferon regulatory factor 4 (IRF4) or a dominant negative TGFβ receptor (TGFβRDN). In some embodiments, the recombinant nucleic acid sequence comprises the sequence of SEQ ID NO: 63.

In some embodiments, the recombinant nucleic acid sequence of ai preceding aspect further comprises one or more promoters. In some embodiments, the one or more promoters are selected from the group consisting of an EF1α promoter, a PGK promoter, a CMV promoter, or a CAG promoter.

In some aspects, disclosed herein is a vector comprising the recombinant nucleic acid sequence of any preceding aspect.

In some aspects, disclosed herein is a genetically modified T cell comprising recombinant nucleic acid sequence encoding a chimeric antigen receptor (CAR), wherein the CAR comprises a CD3 zeta signaling domain, a costimulatory signaling domain, a CD8α domain, a transmembrane domain, and a prostate-specific membrane antigen (PSMA) binding domain, wherein the PSMA binding domain comprises a heavy chain variable region (VH) comprising an amino acid sequence 90% identity to SEQ ID NO: 12, 16, 20, 24, or 28 and a light chain variable region (VL) comprising an amino acid sequence 90% identity to SEQ ID NO: 14, 18, 22, 26, or 30.

In some aspects, disclosed herein is a method of treating prostate cancer, comprising administering to a subject in need a therapeutically effective amount of the genetically modified T cell of any preceding aspect.

In some aspects, disclosed herein is a genetically modified natural killer (NK) cell comprising a recombinant nucleic acid sequence encoding a chimeric antigen receptor (CAR), wherein the CAR comprises a CD3 zeta signaling domain, a costimulatory signaling domain, a CD8α domain, a transmembrane domain, and a prostate-specific membrane antigen (PSMA) binding domain, wherein the PSMA binding domain comprises a heavy chain variable region (VH) comprising an amino acid sequence 90% identity to SEQ ID NO: 12, 16, 20, 24, or 28 and a light chain variable region (VL) comprising an amino acid sequence 90% identity to SEQ ID NO: 14, 18, 22, 26, or 30.

In some aspects, disclosed herein is a method of treating prostate cancer, comprising administering to a subject in need a therapeutically effective amount of the genetically modified NK cell of any preceding aspect.

In some aspects, disclosed herein is a method of treating prostate cancer, comprising administering to a subject in need a therapeutically effective amount of a polypeptide that comprises a prostate-specific membrane antigen (PSMA) binding domain, wherein the PSMA binding domain comprises a heavy chain variable region (VH) comprising an amino acid sequence 90% identity to SEQ ID NO: 12, 16, 20, 24, or 28 and a light chain variable region (VL) comprising an amino acid sequence 90% identity to SEQ ID NO: 14, 18, 22, 26, or 30.

BRIEF DESCRIPTION OF FIGURES

The accompanying figures, which are incorporated in and constitute a part of this specification, illustrate several aspects described below.

FIG. 9A shows that PSMA mRNA levels were increased in LNCaP and VCaP cells when treated 10 μM of enzalutamide for 48 hours, but reduced when treated with 10 nM R1881. FIG. 9B shows that PSMA protein levels were increased in VCaP (1) and LNCaP (2) cells treated with antiandrogen Enzalutamide for 72 hrs. (3) PSMA protein was expressed in Enzalutamide-resistant C4-2B stable cell line, comparable with its expression in LNCaP cells.

FIG. 12A shows PSMA mRNA expression profile across tumor samples and paired normal tissues. The height of bar represents the median expression level of different tumor types or normal tissues. This figure was generated from GEPIA. FIG. 12B shows expression levels of PSMA in normal prostate tissues and prostate tumors with different nodal metastasis status. This figure was generated at UALCAN. PRAD, prostate adenocarcinoma.

FIG. 13A shows flowchart of the development of PSMA-CAR T cell therapy in my laboratory at Houston Methodist Research Institute. FIG. 13B shows binding affinities and kinetics of five anti-PSMA mAbs to purified recombinant human PSMA protein were measured by Biacore SPR. *Affinity of J591 antibody was previously reported. FIG. 13C shows construction of 11 PSMA CARs, including 10 CAR s based on scFv sequences derived from our 5 anti-PSMA mAbs, and one J591-CAR based on published murine J591 scFv sequence. FIG. 13D shows western blot analysis to verify PSMA-CAR expression in HEK293T cells 3 days after transient transfection.

FIG. 14A shows that in vitro killing of PSM-CAR T cells against LNCaP cells was measured in 20-hr luciferase-based lysis assay at different ET ratios. LNCaP cells that stably expresses firefly luciferase were used as target cells. FIG. 14B shows in vitro killing of four representative PSMA-CARs (445-, 447-, 4LH-, J591-CAR) and non-transduced T cells were presented. FIG. 14C shows ELISA quantification of the released IFNγ in the culture supernatants from the killing assay. FIG. 14D shows IFNγ levels from four representative PSMA-CARs (445-, 447-, J591-CAR) are presented for clarity. The error bars represent SEM.

FIG. 15A shows schematic diagram showing the treatment regimen and IVIS imaging. FIG. 15B shows flow cytometry analysis of PSMA-CAR T cells using Fluorescence-labeled PSMA protein as probe. The percentages of CART cells positive for PSMA-binding are: 0.48% (non-transduced), 38.8% (445-CAR), 43.9% (4-LH-CAR), and 38.2% (J591-CAR). FIG. 15C shows bioluminescent images showing tumor progression after adoptive transfer of PSMA-CAR T cells. FIG. 15D shows quantification of BLI signals as surrogate of tumor growth over the course of treatment. Non-transduced vs 445-CAR: $p<0.01$ at week 2; $p<0.001$ at week 3. Non-transduced vs 4LH-CAR: $p<0.01$ at week 2; $p<0.001$ at week 3. Non-transduced vs J591-CAR: $p<0.01$ at week 3. 445-CAR vs J1591-CAR: $p<0.05$ at week 2. 4LH-CAR vs J1591-CAR: $p<0.01$ at week 2. There is no statistically significant difference between 445-CAR and 4LH-CAR treatments.

FIG. 16A shows diagram of in vivo B16-F10 subcutaneous xenograft tumor growth in wild type B6 mice and Pmel-1 T cell treatment. FIG. 16B shows flow cytometry analysis of the retrovirus transduction efficacy. FIGS. 16C-16D show B16-F10 subcutaneous xenograft tumor growth in mice treated with IRF4-overexpressing Pmel-1 T cells or control Pmel-1 T cells. FIGS. 16E-16F show flow cytometry analysis of tumor infiltrating CD45+ cells. $**p<0.01$.

FIG. 18A shows that IRF4 is co-expressed with PSMA-CAR or CD19-CAR by a "self-cleaving" T2A peptide conjugation. PSMA-CAR contains 445-scFv, whereas CD19-CAR contains FMC63-sav (same as Kymriah®). FIG. 18B shows validation of transcription activator activity of IRF4 co-expressed from CAR viral vectors. IRF4 transcriptional activity was measured as reported. 100 ng (TTTCCTTT)3-Luc reporter plasmid was co-transfected with 50 ng of CAR-GFP, CAR-IRF4, or wild type TRH plasmid into HEK293T cells in 96 well plate. The positive control wild type IRF4 plasmid was from Origene (cat #MR226642). FIG. 18C shows in vitro expansion of PSMA-CAR T cells with or without exogenous IRF4. FIG. 18D shows in vitro expansion of CD19-CAR and CD19-CAR-IRF4 T cells. The error bars represent ±SEM. $*P<0.05$; $**P<0.01$.

FIG. 19 shows that IRF4 is a transcription factor critical for T cell activation and function. IRF4 domains: DNA binding domain (DBD), interferon activating domain (IAD), auto inhibitory region (AR).

FIGS. 20A-20C show that IRF4 enhanced in vivo anti-lymphoma activity of CD19-CAR T cells

DETAILED DESCRIPTION

Figure 1:
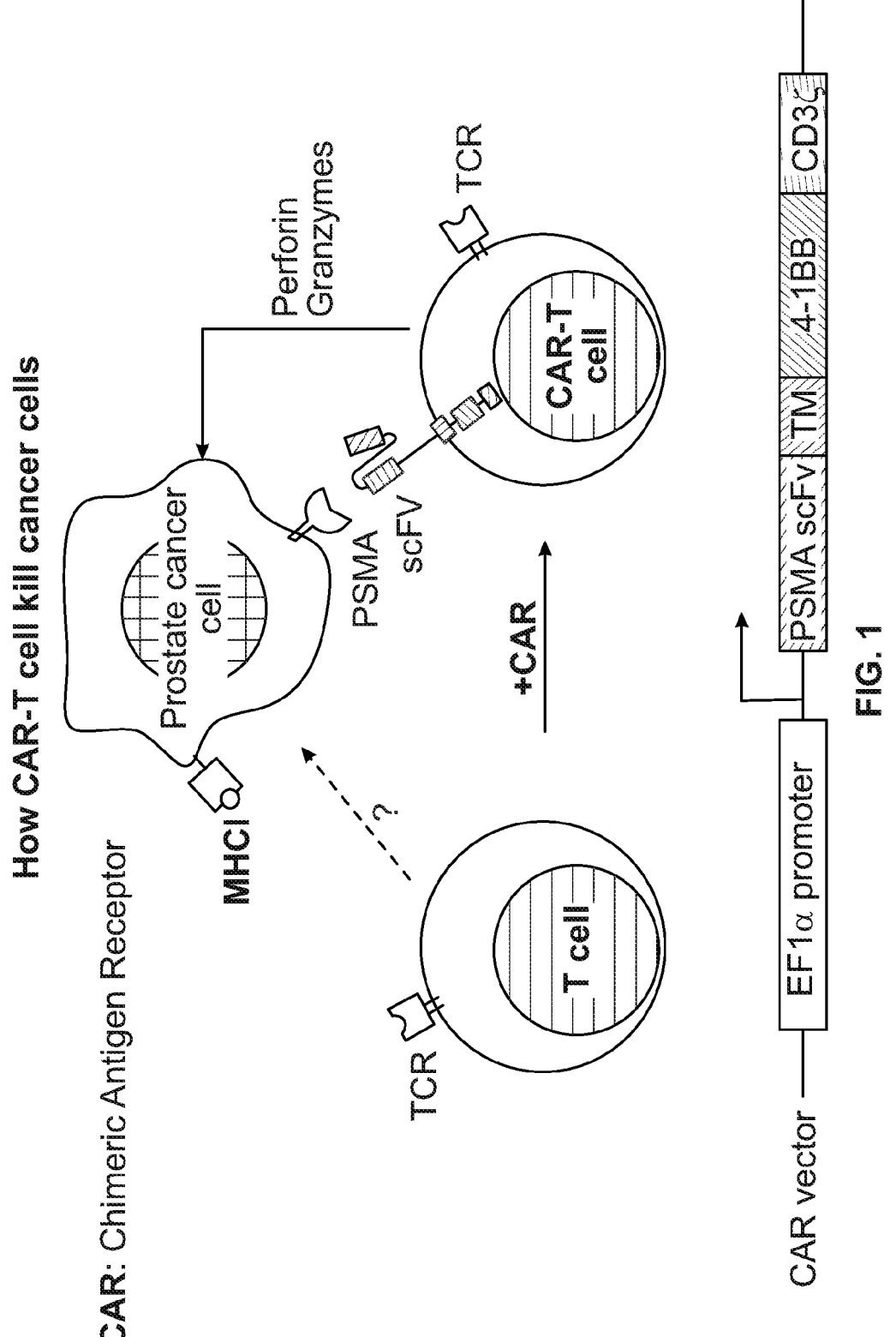
FIG. 1 shows a schematic diagram of CAR-mediated prostate cancer immunotherapy. (top panel) Due to lack of immunogenic mutations in prostate cancer cells, T lymphocytes cannot recognize cancer cells through TCR/MHCI interaction. In contrast, CAR-engineered T cells can specifically kill cancer cells by recognizing the PSMA antigen on cancer cell surfice through PSMA scFv domain, regardless of mutation status in cancer cells. (bottom panel) PSMA CAR is composed of the scFv domain derived from anti-PSMA mouse monoclonal antibody, transmembrane domain (TM), 4-BB (CD137) signal transduction domain, and CD3ζ signaling domain.
Figure 2:
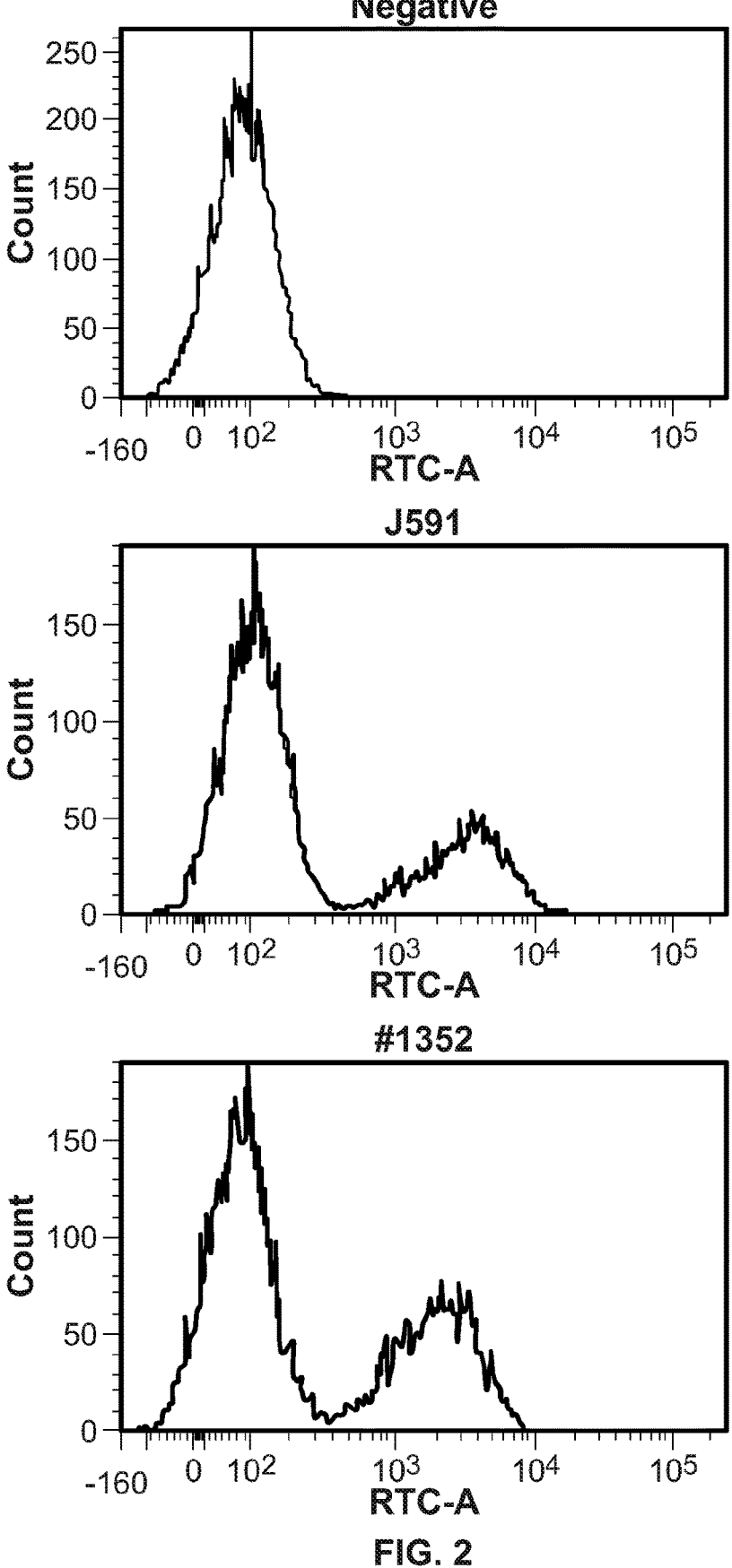
FIG. 2 shows generation of hybridomas that produce IgG mAbs specifically binding to PSMA-positive LNCaP cells, but not PSMA-negative PC3 cells. PC3 cells and UNCaP cells are mixed and incubated with 20 μg of J591, our home-made mAb #1352, or no, mal serum as a negative control. Next, the cells were incubated with FITC anti-mouse IgG secondary antibody (Biolegend, cat #406001), followed by flow cytometric analysis. LNCaP cells in the mixed cell populations were similarly detected as the FITC positive cells by J591 and mAb clone #1352, but not by normal serum control. In addition to hybridoma clone #1352, four more cloned hybridoma lines #219, #1207, #1366, and #1377 also produced antibodies that can bind to LNCaP cells with high affinity.
Figure 2:
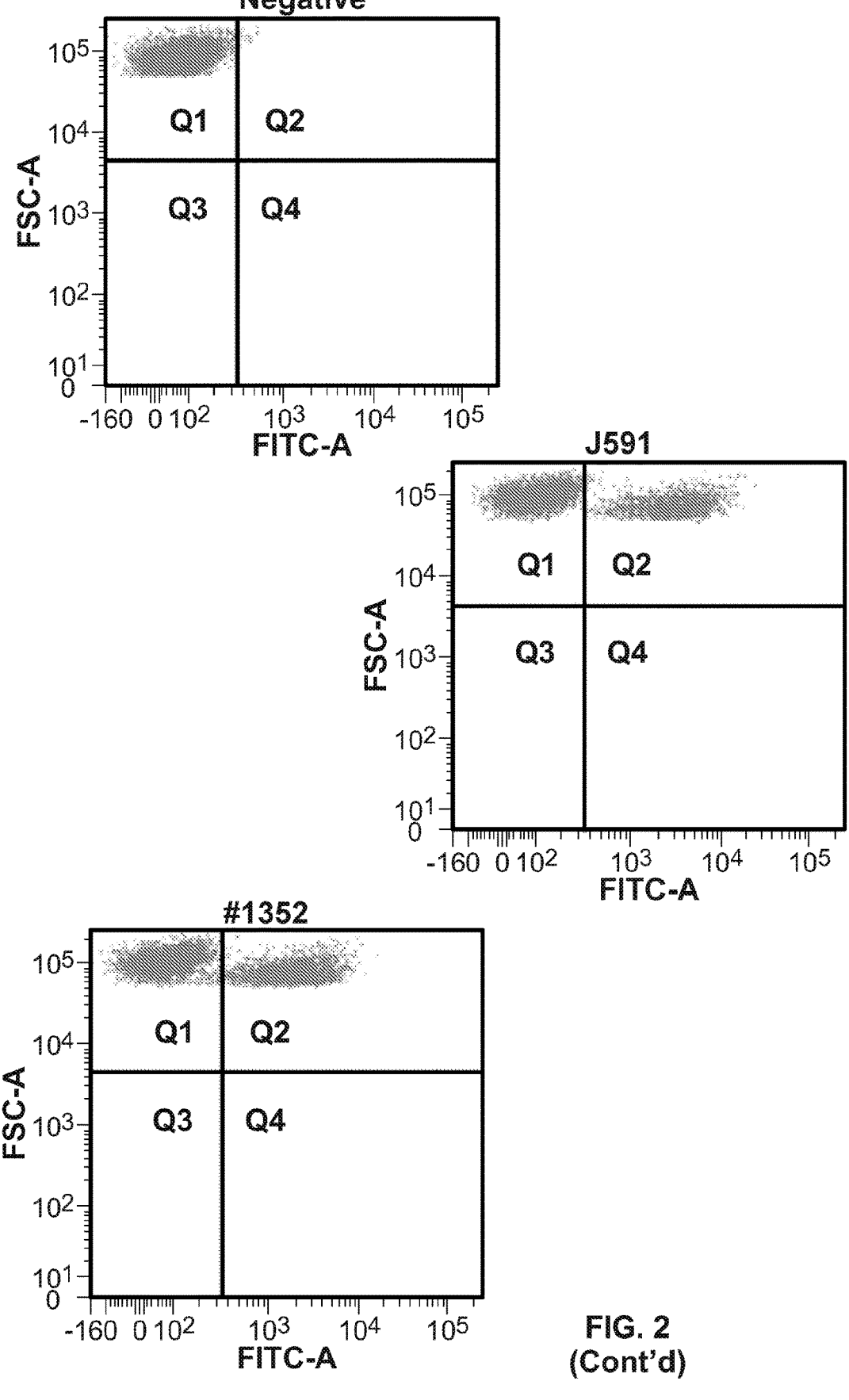
Figure 3:
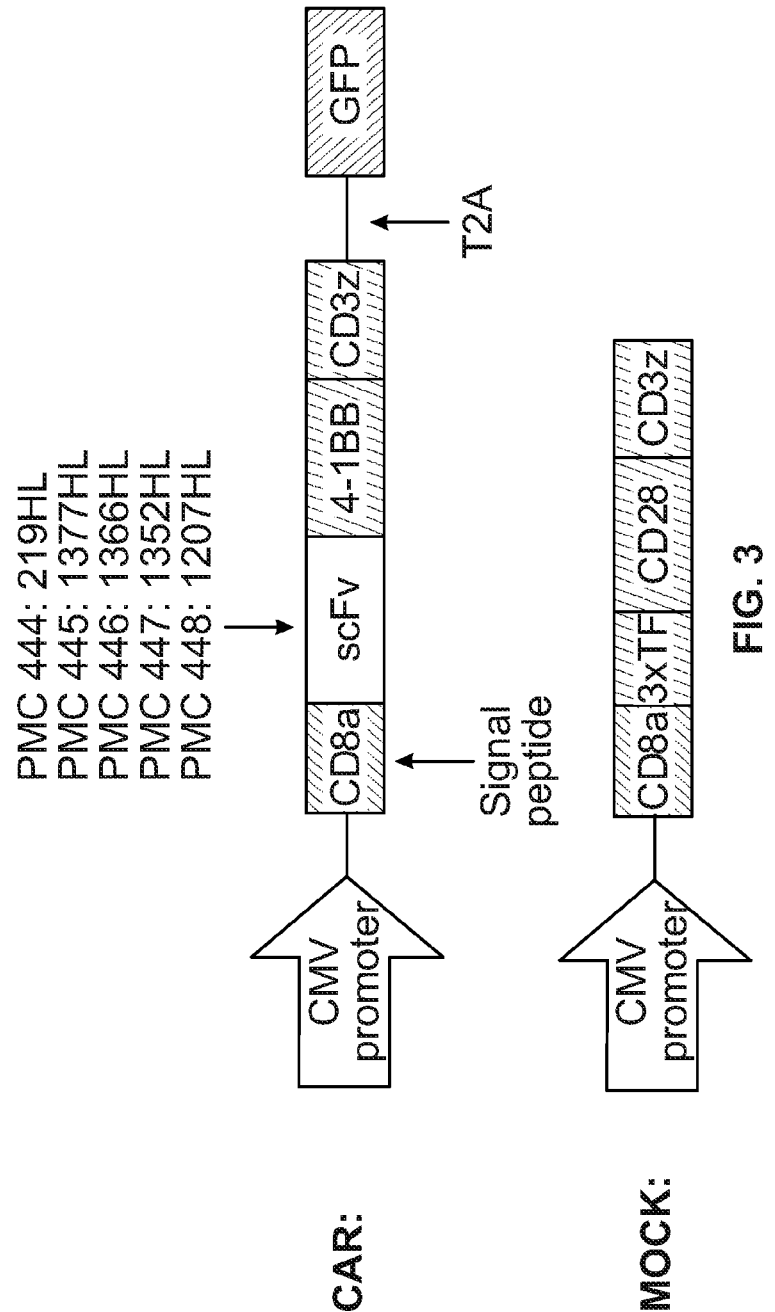
FIG. 3 shows construction of PSMA CAR lentiviral vectors and validation of CAR (GFP) expression on T cells by FACS. A schematic diagram of PSMA CAR and mock CAR constructs. Shown here are five different CAR lentiviral vectors. The PSMA CAR also contain a carboxyl-terminal GFP tag linked by a T2A self-cleaving peptide. Mock CAR is similar to PSMA CARS, except for lack of PSMA scFv domain and GFP tag.
Figure 4:
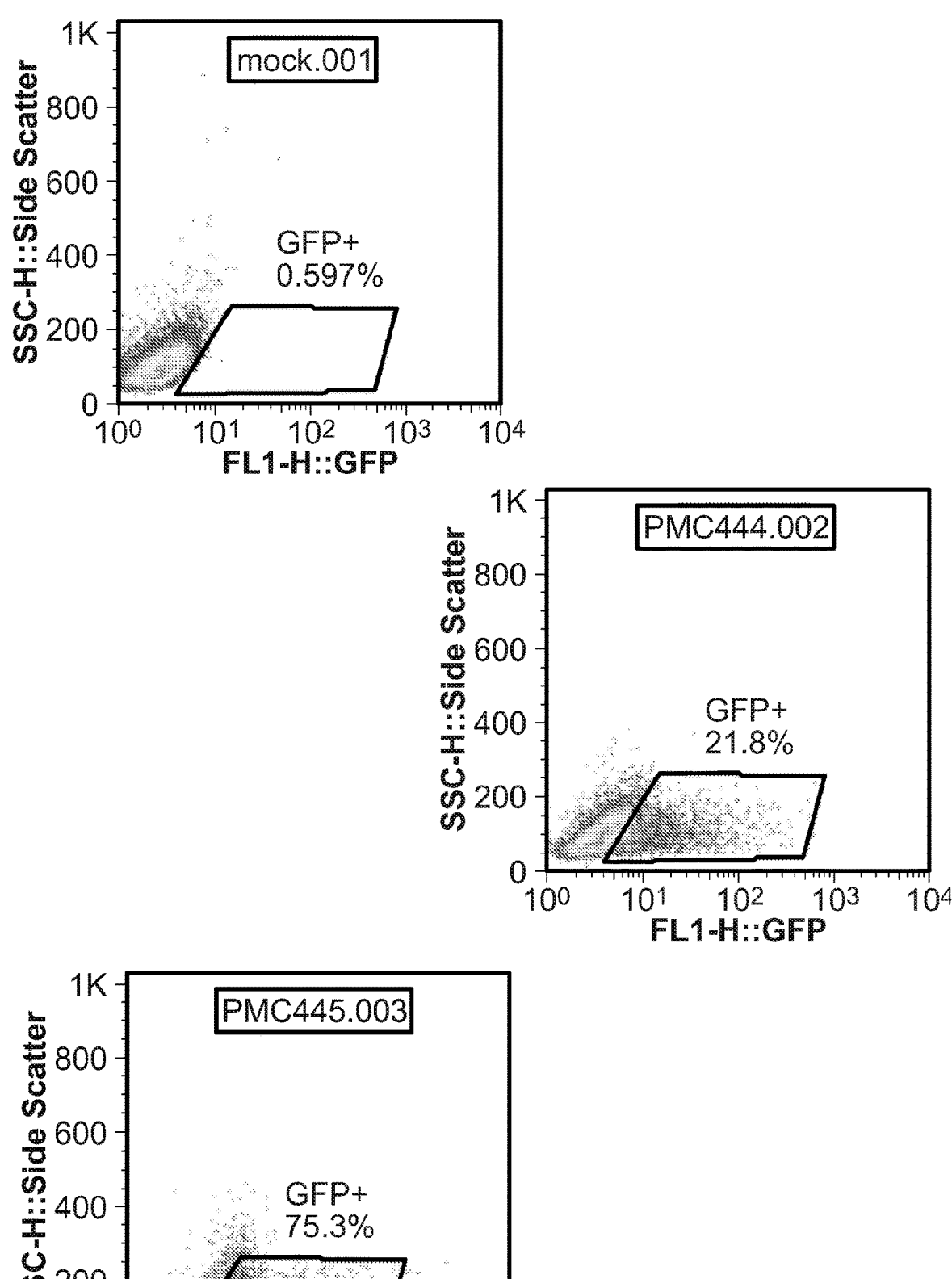
FIG. 4 shows validation of CAR (GFP) expression in T cells by FACS. Human T cells were isolated from PBMC, activated by Dynabeads human T-Activator CD3/CD28 (Thermo Fisher Scientific), then transduced with lentiviruses expressing PSMA CAR or mock CAR. Expression levels of GFP (i.e. CAR) in lentivirus-transduced T cells were analyzed by flow cytometry: Mock CAR, PMC444 CAR, PMC445. CAR, PMC446 CAR, PMC447 CAR, and PMC448 CAR.
Figure 4:
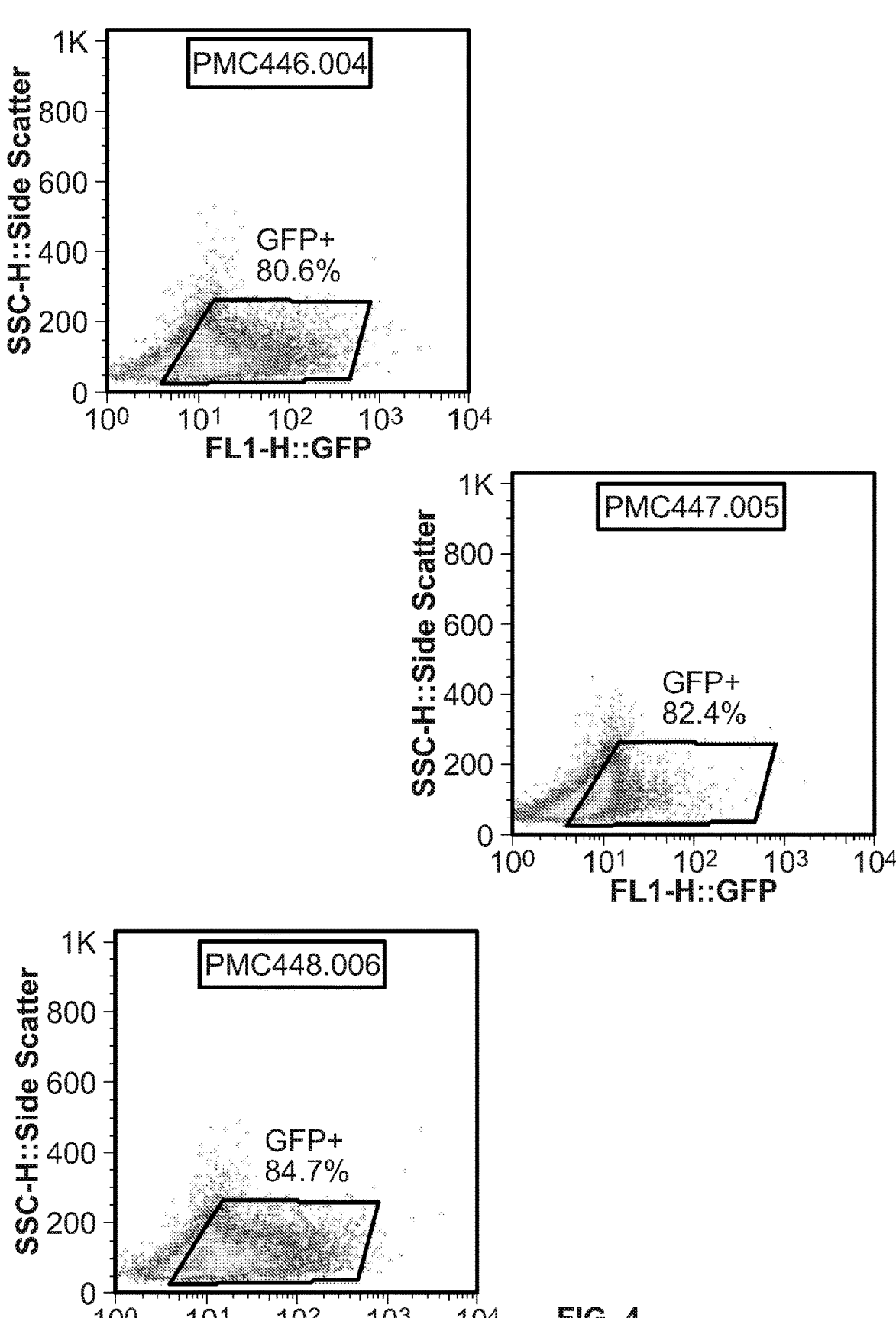
Figure 5:
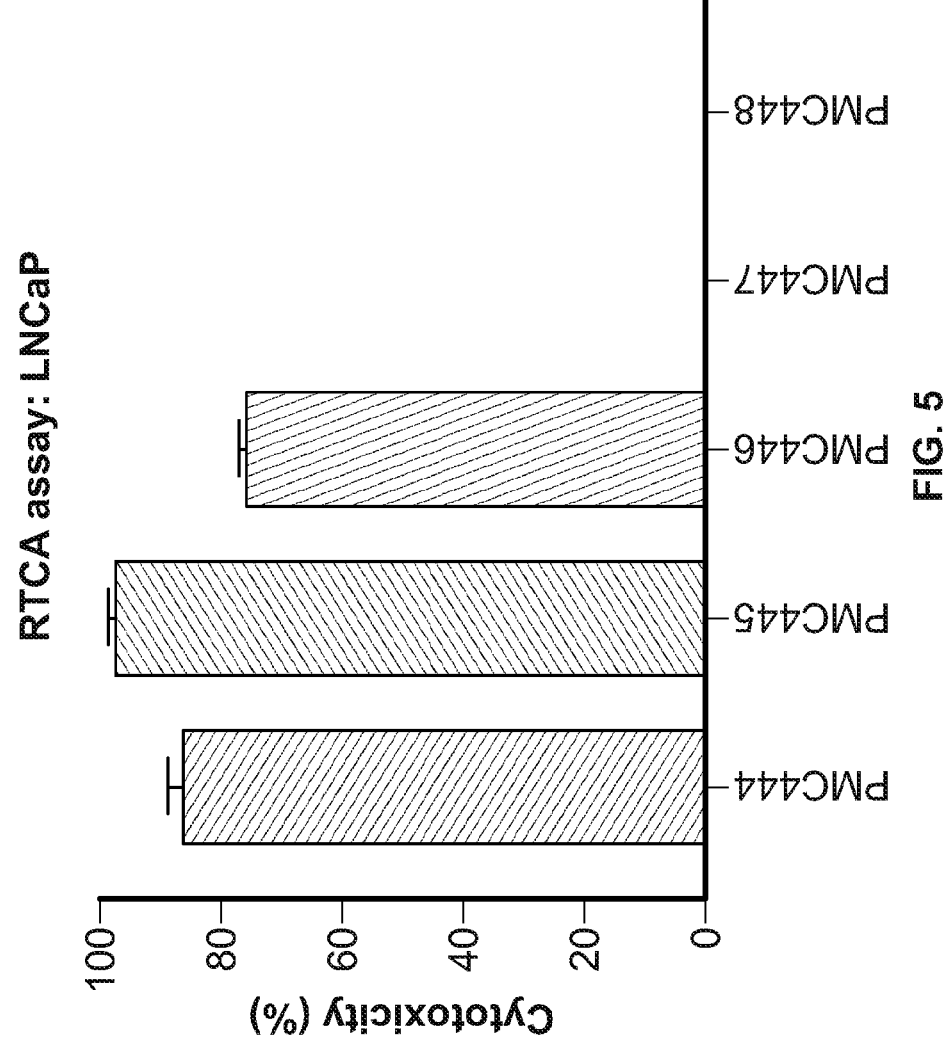
FIG. 5 shows quantification of in vitro cytotoxicity PSMA CAR T-cells determined by Real-Time Cell Analysis (RTCA) assay. PSMA-negative PC3 cells were not killed by any CAR T-cells. Killing of PSMA-positive LNCaP cells by five PSMA CART-cells, relative to mock CAR T-cells. PMC447 and PMC448 did not kill LNCaP cells. PMC444, PMC445, and PMC446 kill more than mock CAR-T cells.
Figure 6:
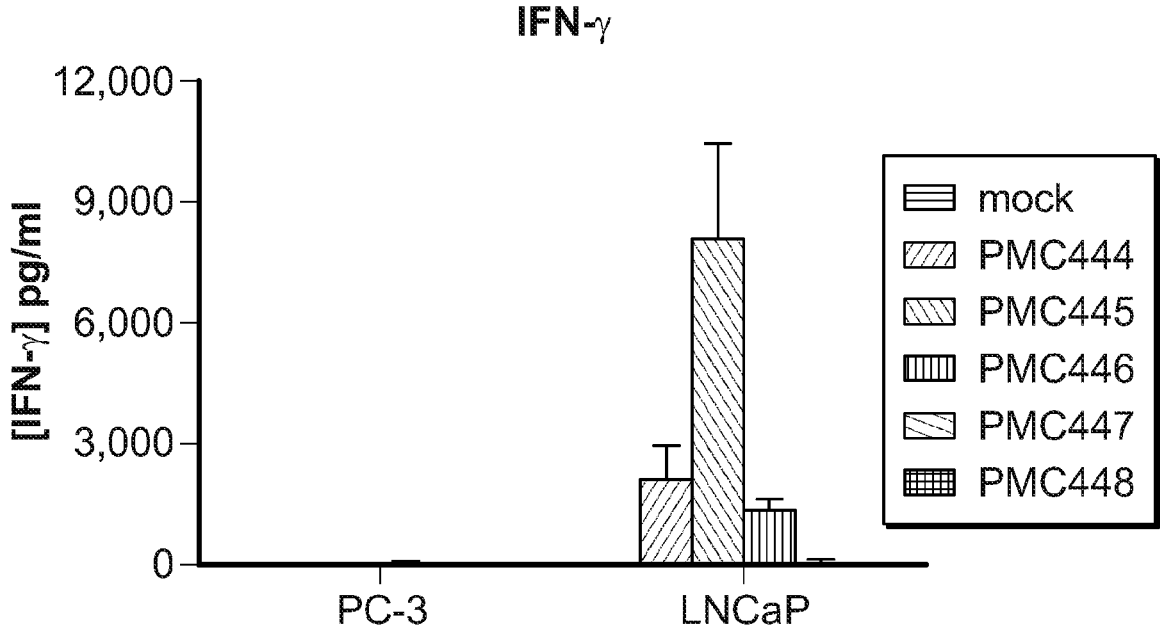
FIG. 6 shows quantification of the release of cytokine IFNγ (left panel) and granzyme B (right panel) from CAR T-cells in the presence of PC3 or LNCaP cells.
Figure 6:
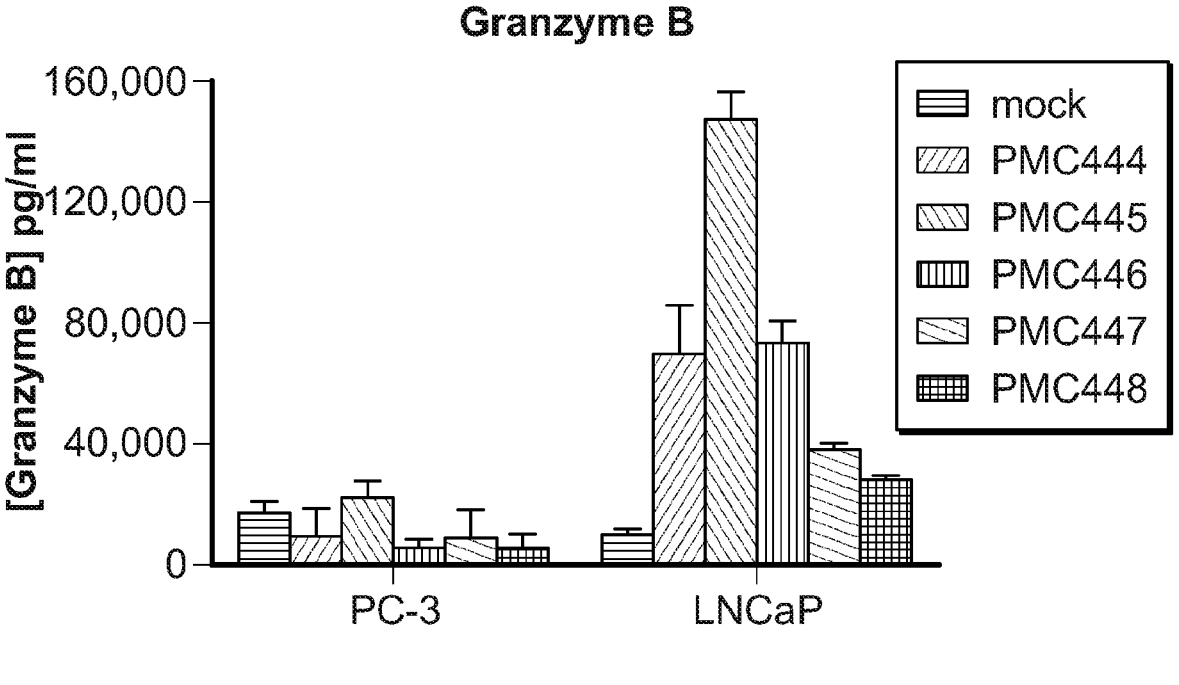
Figure 7:
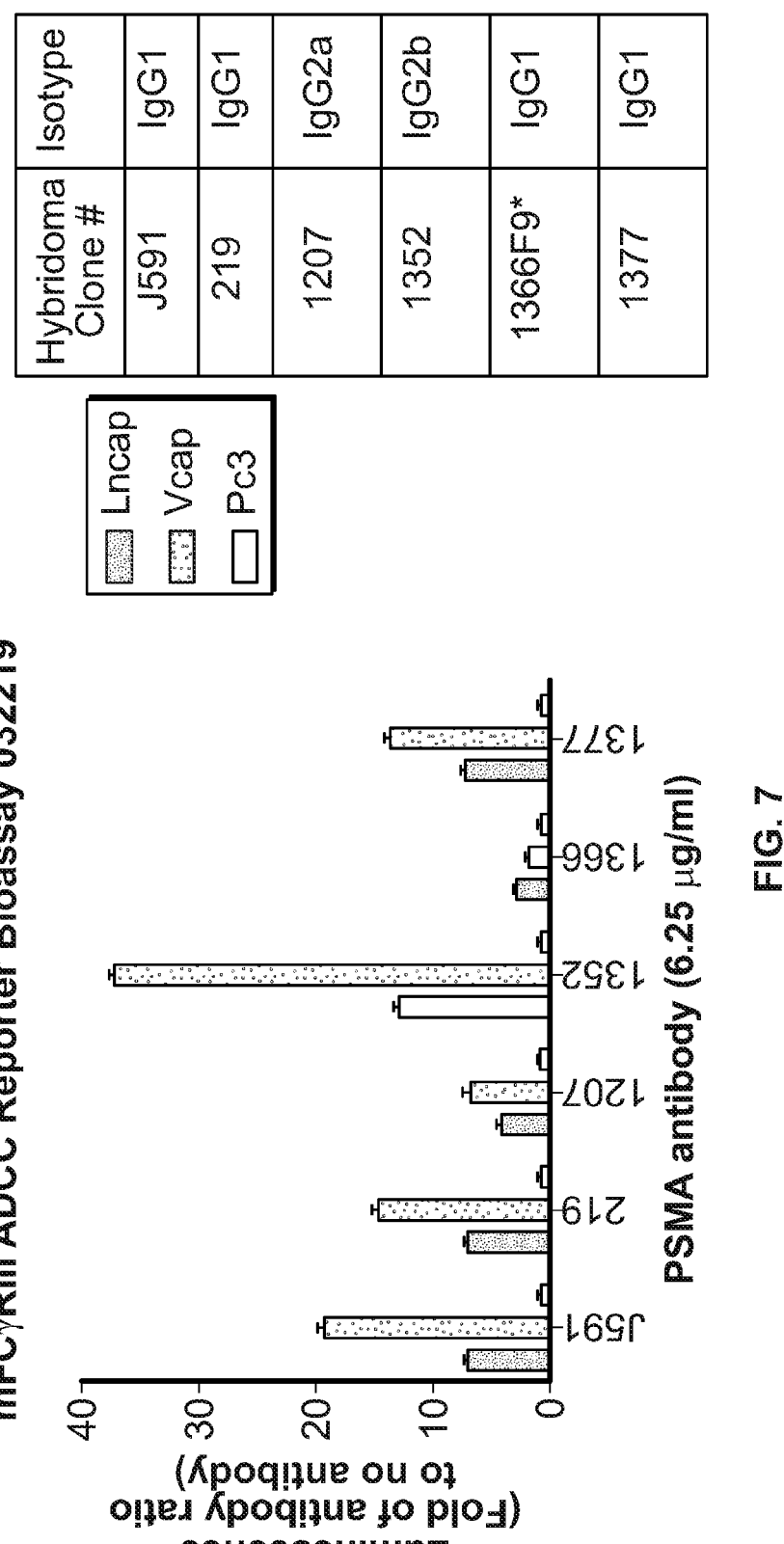
FIG. 7 shows induction of Antibody-Dependent Cellular Cytotoxicity (ADCC) by PSMA antibodies tested in murine FCγRIII ADCC reporter bioassay (Promega, cat #CS1779B08). The left panel shows that induction of ADCC activity was tested on two PSMA-positive prostate cancer cell lines LNCaP and VCaP, and one PSMA-negative PC3 cells. The right panel shows isotype of different PSMA antibodies.
Figure 8:
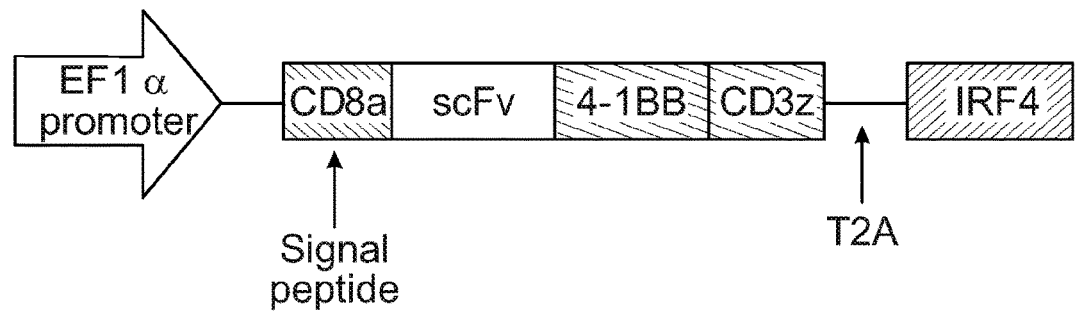
FIG. 8 shows T2A self-cleaving peptide-mediated co-expression of PSMA CAR and IRF4.
Figure 9A:
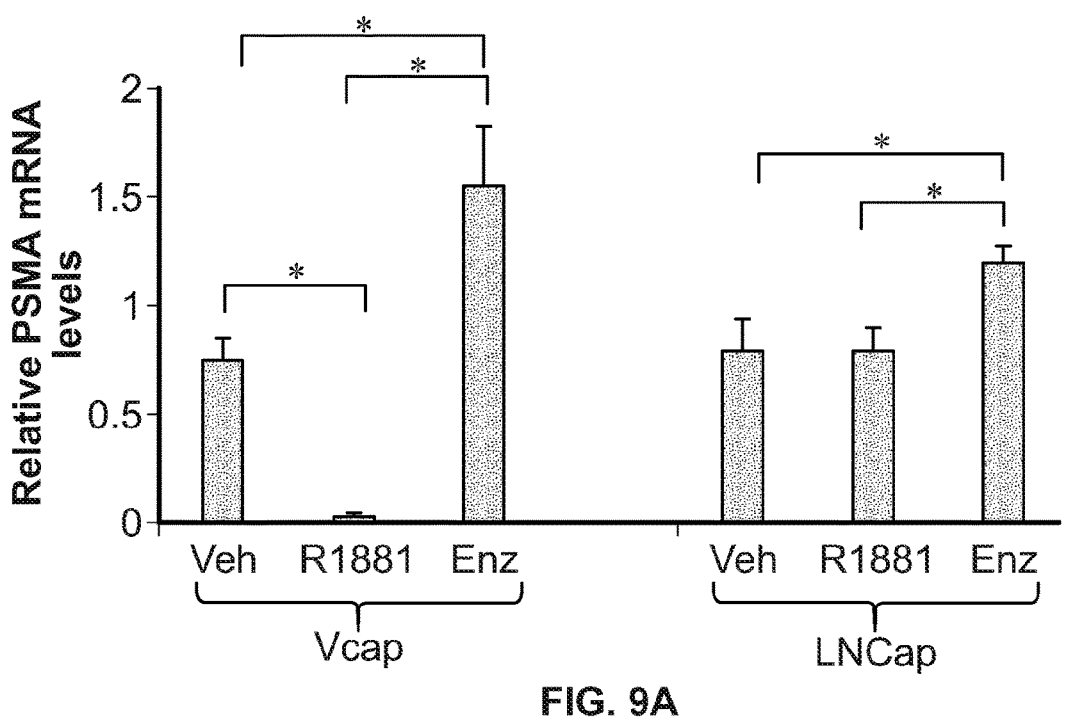
FIGS. 9A and 9B show that PSMA expression was upregulated by antiandrogens.
Figure 9B:
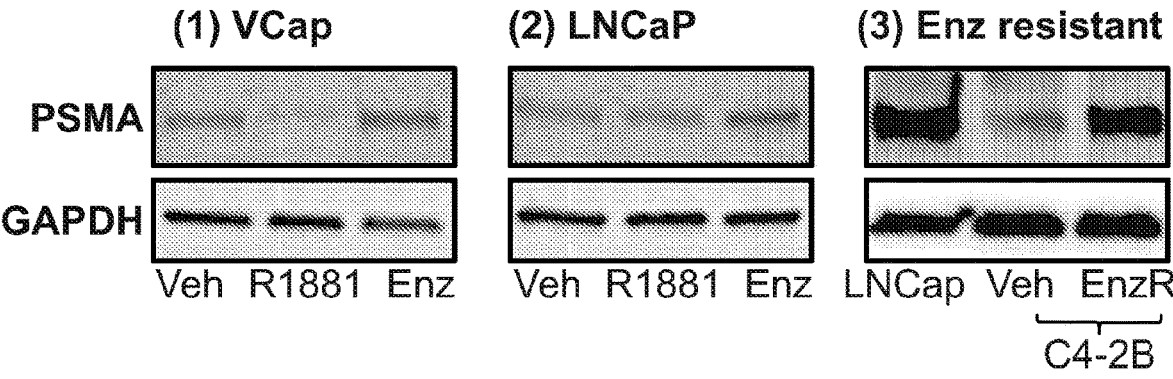
Figure 10:
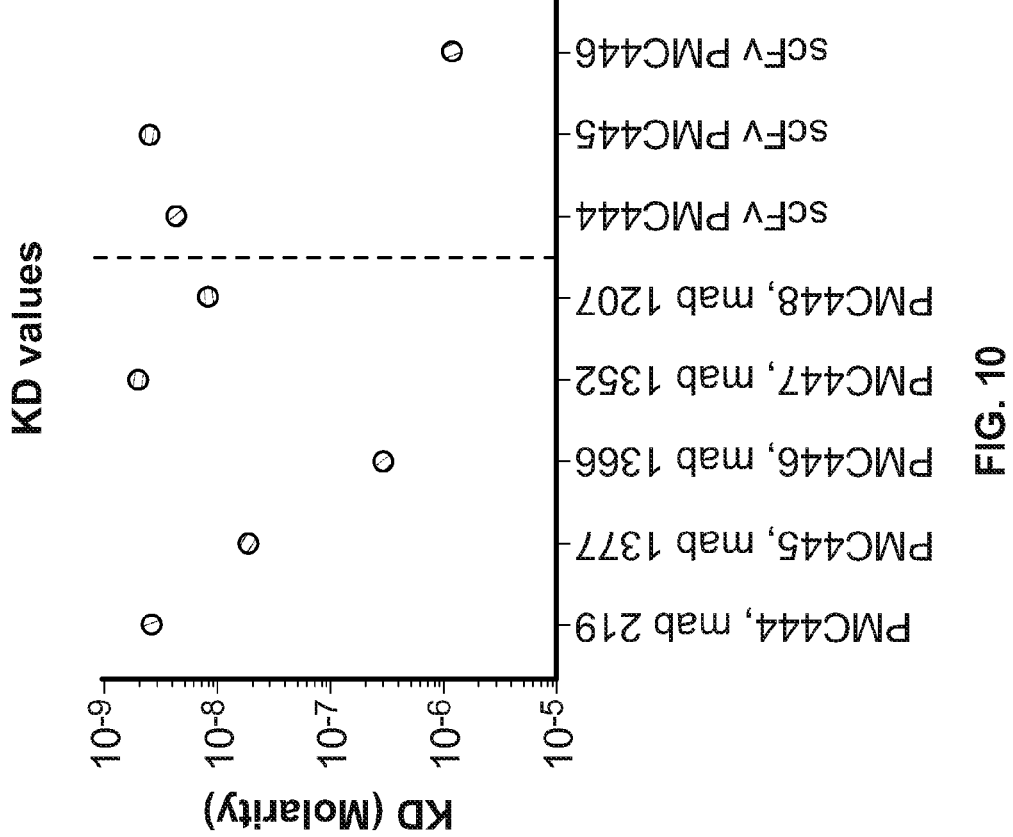
FIG. 10 shows binding affinity of five PSMA full length antibodies and three purified scFv-Fe fusion recombinant proteins. The Ka and Kd values were determined by Biacore system based on surface plasmon resonance (SPR) technology.
Figure 11:
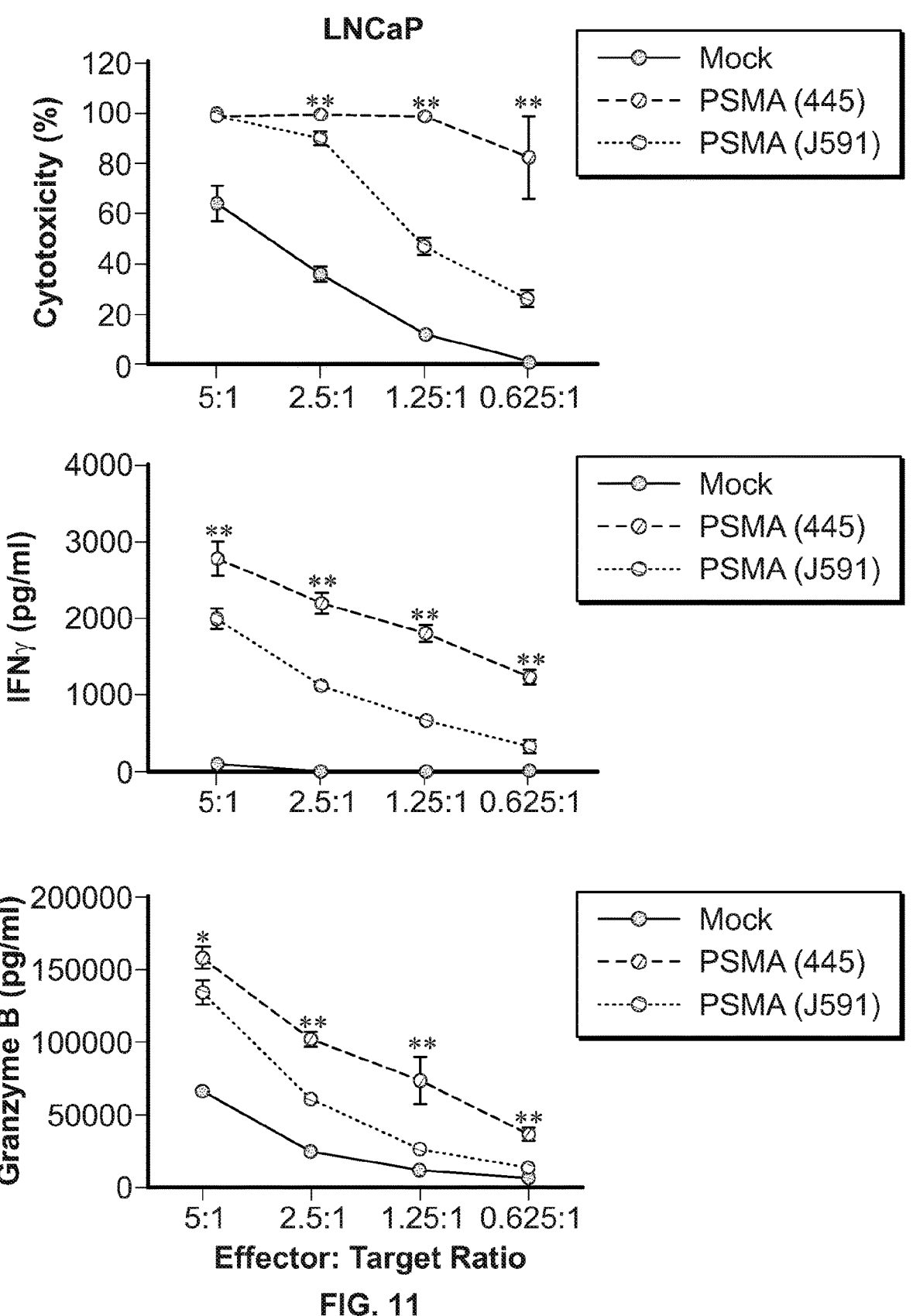
FIG. 11 shows comparison between PSMA(445)-CAR with PSMA(J59)-CAR, which was derived from J591 antibody. The result showed that PSMA(445)-CAR is much more potent. The same J591 antibody has been used by Carl June to construct their PSMA-CAR. In vitro cytotoxicity of PSMA(445)-CAR-T and PSMA(J1591)-CAR-T cells determined by luciferase-based lysis assay. (top 4 panels.) In vitro killing activity was measured in 20-hr luciferase-based lysis assay at different effector to target (E:T) ratios. LNCaP and VCaP cells express endogenous PSMA, whereas PC3-PSMA express exogenous PSMA. Wild type PC3 cell are PSMA-negative. All four cell lines have been engineered to express luciferase. (middle 4 panels) ELISA quantification of the released IFNγ in the culture supernatants from the in vitro killing assay. (bottom 4 panels) ELISA quantification of the released Granzyme B in the culture supernatants from the in vitro killing assay. Mock control is activated but not transduced T cells. The error bars represent±SD. Statistical differences between PSMA(445)-CAR and PSMA(J591)-CAR were obtained. **p<0.01.
Figure 11:
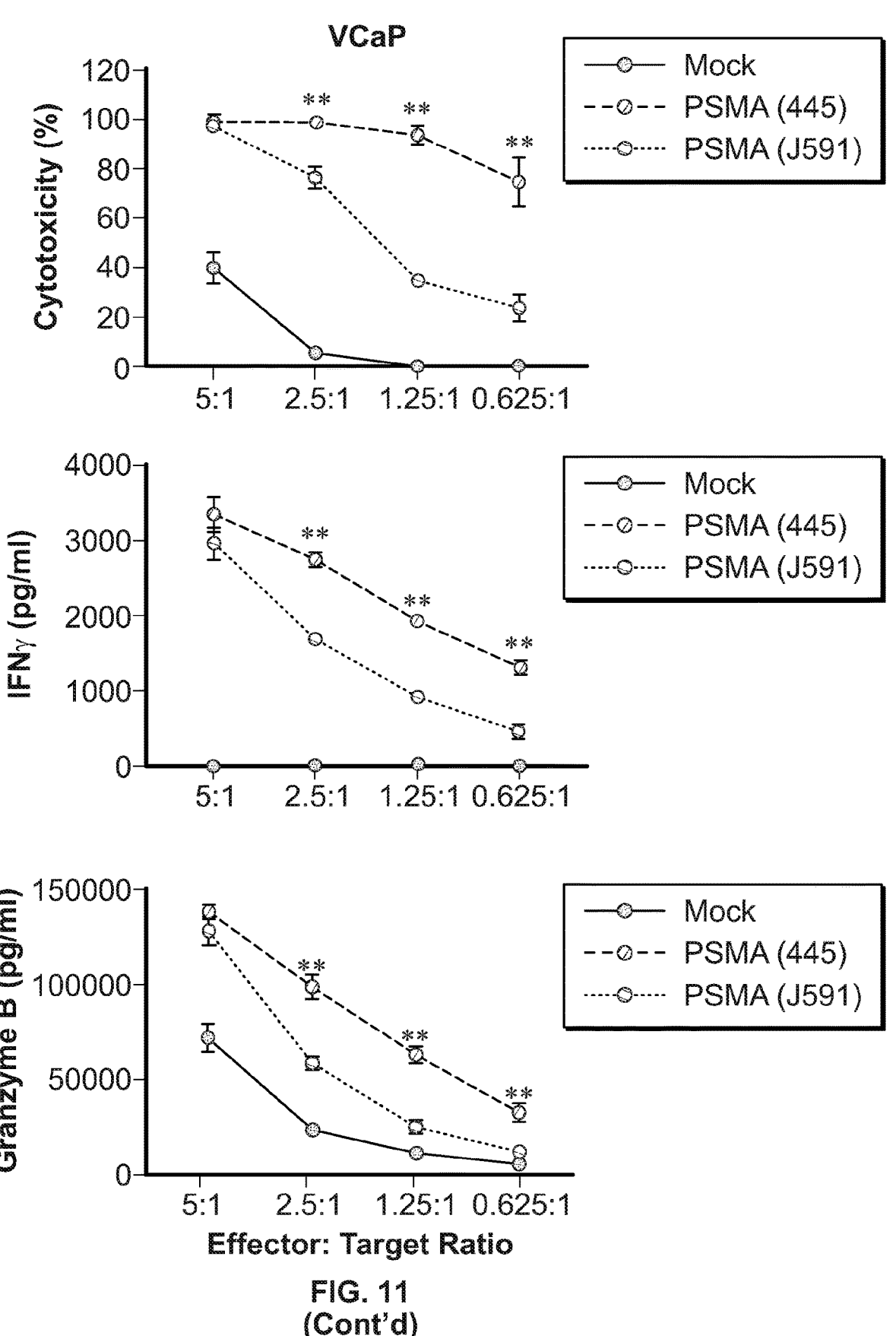
Figure 11:
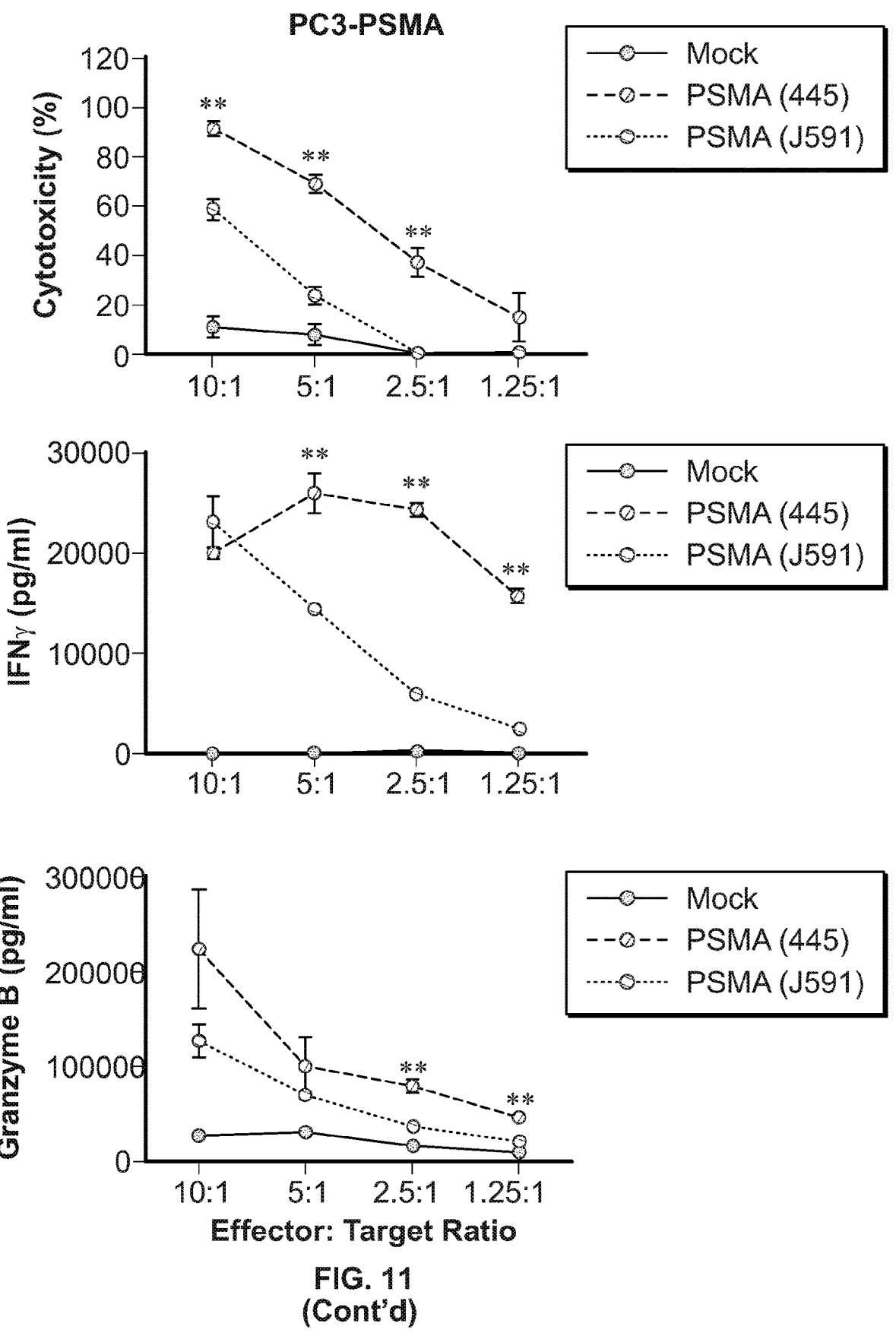
Figure 11:
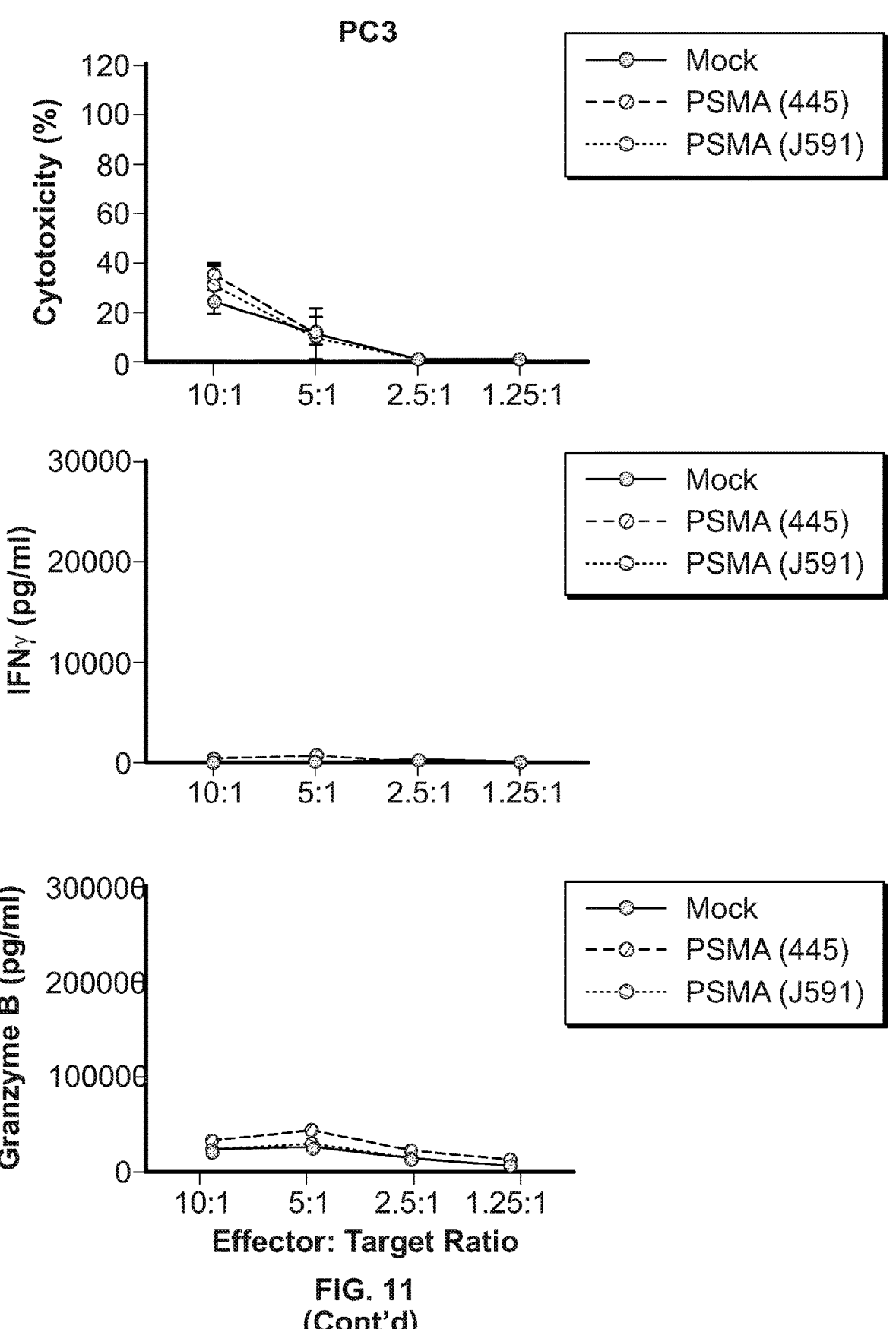

In some aspects, disclosed herein is a chimeric antigen receptor (CAR) and a recombinant nucleic acid sequence encoding the CAR, wherein the CAR comprises a CD3 zeta signaling domain, a costimulatory signaling domain, a CD8α signal peptide, a CD8α transmembrane domain, and a prostate-specific membrane antigen (PSMA) binding domain. In some aspects, disclosed herein is an engineered T cell or an engineered natural killer (NK) cell comprising the CAR, a polypeptide comprising the PSMA hinging domain sequence, and uses thereof for treating prostate cancer. Such engineered immune cells show effective effector function to prostate cancer cells. In one example, the CAR can further comprise an interferon regulatory factor 4 (IRF4) domain or a dominant negative TGFβ receptor (TGFβRDN) domain that improves the anti-cancer effect of the engineered T cell and/or engineered NK cell.

Terms used throughout this application are to be construed with ordinary and typical meaning to those of ordinary skill in the art. However, Applicant desires that the following terms be given the particular definition as defined below.

Terminology

As used in the specification and claims, the singular form "a," "an," and "the" include plural references unless the context clearly dictates otherwise. For example, the term "a particle" includes a plurality of particles, including mixtures thereof.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

"Administration" to a subject includes any route of introducing or delivering to a subject an agent. Administration can be carried out by any suitable route, including oral, intravenous, intraperitoneal, intranasal, by inhalation, intravitreal, intraocular, and the like. Administration includes self-administration and the administration by another.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies. Fv, Fab and F(ab)2, as well as single chain antibodies, VHH single domain antibody and humanized antibodies (Harlow et al, 1999, In: Using Antibodies: A Laboratory Manual, Cold Spring Harbor Laboratory Press, NY, Harlow et al., 1989, in: Antibodies: A Laboratory Manual, Cold Spring Harbor, New York; Houston et al., 1988, *Proc. Natl. Acad. Sci. USA* 85:5879-5883; Bird et al., 1988. Science 242:423-426).

An antibody "heavy chain", as used herein, refers to the larger of the two types of polypeptide chains present in all antibody molecules in their naturally occurring conformations.

An antibody "light chain", as used herein, refers to the smaller of the two types of polypeptide chains present in all antibody molecules in their naturally occurring conformations, κ and λ light chains refer to the two major antibody light chain isotypes.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

As used herein, the term "antibody or fragments thereof" encompasses chimeric antibodies and hybrid antibodies, with dual or multiple antigen or epitope specificities, and fragments, such as F(ab')2, Fab', Fab, Fv, scFv, VHH, single domain antibody, and the like, including hybrid fragments. Thus, fragments of the antibodies that retain the ability to bind their specific antigens are provided. For example, fragments of antibodies which maintain prostate-specific membrane antigen (PSMA) binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)).

The term "antigen" or "Ag" as used herein is defined as a molecule that provokes an immune response. This immune response may involve either antibody production, or the activation of specific immunologically-competent cells (e.g., T cells or NK cells), or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. In one example, the antigen described herein is a PSMA or a functional fragment thereof.

The term "anti-cancer effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-cancer effect" can also be manifested by the ability of the peptides, polynucleotides, cells and antibodies of the invention in prevention of the occurrence of tumor in the first place.

The term "cancer" as used herein is defined as disease characterized by the rapid and uncontrolled growth of aberrant cells. Cancer cells can spread locally or through the bloodstream and lymphatic system to other parts of the body, Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, the cancer is prostate cancer.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell (e.g., a T cell or an NK cell). In some embodiments, CARs comprise an intracellular domain, a transmembrane domain, and an extracellular domain comprising a tumor associated antigen binding region.

The term "CDR" as used herein refers to the "complementarity determining regions" of the antibody which consist of the antigen binding loops as defined by Kabat E. A. et al., (1991) Sequences of proteins of immunological interest. NIH Publication 91-3242.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The phrases "concurrent administration", "administration in combination", "simultaneous administration" or "administered simultaneously" as used herein, means that the compounds are administered at the same point in time or immediately following one another.

"Costimulatory ligand," as the term is used herein, includes a molecule on an antigen presenting cell (e.g., dendritic cell, B cell, and the like) that specifically binds a cognate costimulatory molecule on a T cell or an NK cell, thereby providing a signal which, in addition to the primary signal, mediates a T cell or an NK cell response, including, but not limited to, proliferation, activation, differentiation, and the like. The primary signal can be provided by, for instance, binding of a T cell receptor (TCR)/CD3 complex with an MHC molecule loaded with peptide or binding of an NK cell receptor with a ligand thereof. A costimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6. ILT3, ILT4, HVEM, an agonist or antibody that binds Toll ligand receptor and a ligand that specifically binds with B7-H3.

A "costimulatory molecule," refers to the cognate binding partner on a T cell or an NK cell that specifically binds with a costimulatory ligand, thereby mediating a costimulatory response by the T cell or the NK cell, respectively.

A "costimulatory signal", as used herein, refers to a signal, which in combination with a primary signal, such as T cell receptor (TCR)/CD3 ligation or an NK cell receptor ligation, leads to the immune cell proliferation and/or upregulation or downregulation of key molecules. The "costimulatory signaling domain" refers to a portion of the CAR comprising the intracellular domain of a costimulatory molecule.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom, Thus, a gene encodes a protein if transcription and translation of mRNA.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22: 1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPSTM technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third. Ed., (1988), incorporated herein by reference for all purposes.

As used herein, "operatively linked" can indicate that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and/or transcription control elements (e.g. promoters, enhancers, and termination elements), and/or selectable markers in an expression vector. The term "operatively linked" can also refer to the arrangement of polypeptide segments within a single polypeptide chain, where the individual polypeptide segments can be, without limitation, a protein, fragments thereof, linking peptides, and/or signal peptides. The term operatively linked can refer to direct fusion of different individual polypeptides within the single polypeptides or fragments thereof where there are no intervening amino acids between the different segments as well as when the individual polypeptides are connected to one another via one or more intervening amino acids.

The term "polynucleotide" refers to a single or double stranded polymer composed of nucleotide monomers.

The term "polypeptide" refers to a compound made up of a single chain of D- or L-amino acids or a mixture of D- and L-amino acids joined by peptide bonds.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) nucleotide sequence identity is defined as the percentage of amino acids in a candidate sequence that are identical to the nucleotides in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "reduced", "reduce", "reduction", or "decrease" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

"Pharmaceutically acceptable" can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, tiller, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

As used herein, the terms "prevent", "preventing" and "prevention" refer to the prevention of the recurrence or the onset of one or more symptoms of a disorder or disease, especially in individuals which have been analyzed to be susceptible or likely to develop the disease.

The term "promoter" as used herein is defined as a DNA sequence recognized by the synthetic machinery of the cell, or introduced synthetic machinery, required to initiate the specific transcription of a polynucleotide sequence.

"Recombinant" used in reference to a gene refers herein to a sequence of nucleic acids that are not naturally occurring in the genome of the bacterium. The non-naturally occurring sequence may include a recombination, substitution, deletion, or addition of one or more bases with respect to the nucleic acid sequence originally present in the natural genome of the bacterium.

The term "specificity" refers to the number of different types of antigens or antigenic determinants to which a particular antigen-binding molecule (such as the CAR, single-chain variable fragment, or PSMA binding domain of the invention) can bind. By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species, But, such cross-species reactivity does not itself alter the classification of an antibody as specific, in another example, an antibody that specifically binds to an antigen may also bind to different allelic forms of the antigen, However, such cross reactivity does not itself alter the classification of an antibody as specific.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex.

The term "subject" refers to a human in need of treatment for any purpose, and more preferably a human in need of treatment to treat prostate cancer. The term "subject" can also refer to non-human animals, such as non-human primates.

As used herein, an "scFv" is a single chain variable fragment of immunoglobulin or antigen receptor. A variable domain of each of the heavy (VH) and light (VL) chain connected in some embodiments by a multi-residue peptide linker.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder (e.g., prostate cancer). The terms "treating" and "treatment" can also refer to reduction in severity and/or frequency of symptoms, elimination of symptoms and/or underlying cause, and improvement or remediation of damage.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of prostate cancer. In some embodiments, a desired therapeutic result is the control of prostate cancer, a decrease of tumor volume, or a symptom of prostate cancer. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, lentiviral vectors, adenoviral vectors, adeno-associated virus vectors, retroviral vectors, and the like.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Chimeric Antigen Receptors (CARs)

In some aspects, disclosed herein is a chimeric antigen receptor (CAR) that comprising an extracellular domain and an intracellular domain, and transmembrane domain, wherein the extracellular comprises a prostate-specific membrane antigen (PSMA) binding domain, and wherein the intracellular domain or otherwise the cytoplasmic domain comprises a CD3 zeta signaling domain and a costimulatory signaling domain. In some embodiments, the CAR further comprises a signal peptide domain. In some embodiments, the signal peptide domain is a CD8α domain.

Accordingly, in some aspects, disclosed herein is a chimeric antigen receptor (CAR) comprising comprises a CD3 zeta signaling domain, a costimulatory signaling domain, a CD8α domain, a transmembrane domain, and a prostate-specific membrane antigen (PSMA) binding domain, wherein these domains are directly linked or operatively linked via linkers.

In some embodiments, the disclosed CAR is defined by the formula:

CD8α-PSMA BD-TM-CSD-CD3;

wherein "CD8α" represents a CD8α domain,
wherein "PSMA BD" represents a prostate-specific membrane antigen (PSMA) binding domain;
wherein "TM" represents a transmembrane domain;
wherein "CSD" represents a costimulatory signaling domain;
wherein "CD3" represents a CD3 zeta signaling domain; and
wherein "-" represents a linker.

In some embodiments, the disclosed CAR is defined by the formula:

PSMA BD-TM-CSD-CD3;

wherein "PSMA BD" represents a prostate-specific membrane antigen (PSMA) binding domain;

wherein "TM" represents a transmembrane domain;

wherein "CSD" represents a costimulatory signaling domain, wherein "CD3" represents a CD3 zeta signaling domain; and wherein "-" represents a linker.

In some embodiments. "CD3 zeta signaling domain", "CD8α domain", "transmembrane domain", and "linker" are known in the art. See, e.g., US Published Patent Application NOs: 2018/0057609 and 2016/0361360, and U.S. Pat. No. 9,499,629B2, which are incorporated by reference herein in their entireties. The terms "CD8α domain" and "CD8 leader sequence" are used interchangeably herein and in the cited references.

PSMA is a type II cell surface membrane-bound glyco-protein with −110 kD molecular weight, including an intra-cellular segment (amino acids 1-18), a transmembrane domain (amino acids 19-43), and an extensive extracellular domain (amino acids 44-750). PSMA is also sometimes referred to as an N-acetyl alpha linked acidic dipeptidase (NAALADase), folate hydrolase I (FOLK I) or glutamate carboxypeptidase (GCP PSMA is named largely due to its higher level of expression on prostate cancer cells. In addition, PSMA is over-expressed in the malignant prostate tissues when compared to other organs in the human body such as kidney, proximal small intestine, and salivary glands. PSMA also express in the neo-vasculature of most of the solid tumors, "PSMA" refers herein to a polypeptide that synthesizes and hydrolyzes cyclic adenosine 5'-diphosphate-ribose, and in humans, is encoded by the FOLH1 gene. In some embodiments, the PSMA polypeptide is that identified in one or more publicly available databases as follows: HGNC: 3788, Entrez Gene: 2346, Ensembl: ENSG00000086205, OMIM: 600934, UniProtKB: Q04609. In some embodiments, the PSMA polypeptide comprises the sequence of SEQ ID NO: 31, or a polypeptide sequence having at or greater than about 80%, about 85%, about 90%, about 95%, or about 98% homology with SEQ ID NO: 31, or a polypeptide comprising a portion of SEQ ID NO: 31. The PSMA polypeptide of SEQ NO: 31 may represent an immature or pre-processed form of mature PSMA, and accordingly, included herein are mature or processed portions of the PSMA polypeptide in SEQ ID NO: 31.

The terms "antigen binding site", "binding site" or "binding domain" of an amino acid sequence (such as an antibody, a scFv a polypeptide of the invention, or generally an antigen binding protein or polypeptide or a fragment thereof) refers to the specific elements, parts or amino acid residues of the amino acid sequence with which said amino acid sequence interacts with a specific antigenic determinant, epitope, antigen or protein (or for at least one part, fragment or epitope thereof). Accordingly, the term "PSMA binding domain" used herein refers to the specific elements, parts or amino acid residues of an amino acid sequence with which said amino acid sequence specifically bind to a PSMA or an epitope thereof, Accordingly, in some embodiments, disclosed herein is a CAR comprising a PSMA binding domain comprising a light chain variable region (VL) and a heavy chain variable region (VII). In some embodiments, the PSMA binding domain is an antibody or an antigen-binding fragment thereof. In some embodiments, the antigen-binding fragment is a single chain variable fragment (scFv).

In some embodiments, the PSMA binding domain disclosed herein comprises a VL and a VH, wherein the VH comprises an amino acid sequence at least about 80%, at least about 85%, at least about 90%, at least about 95%, at least about 98%, or at least about 99% identity to SEQ ID NO: 12, 16, 20, 24, or 28, or a fragment thereof, and wherein the VL comprises an amino acid sequence at least about 80%, at least about 85%, at least about 90%, at least about 95%, at least about 98%, or at least about 99% identity to SEQ ID NO: 14, 18, 22, 26, or 30, or a fragment thereof. In some embodiments, the PSMA binding domain disclosed herein comprises a VH comprising the amino acid sequence of SEQ ID NO: 12, 16, 20, 24, or 28, or a fragment thereof and a VL comprising the amino acid sequence of SEQ ID NO: 14, 18, 22, 26, or 30, or a fragment thereof. In some embodiments, the PSMA binding domain disclosed herein comprises a VH comprising the amino acid sequence of SEQ ID NO: 12 and a VL comprising the amino acid sequence of SEQ ID NO: 14. In some embodiments, the PSMA binding domain disclosed herein comprises a VH comprising the amino acid sequence of SEQ ID NO: 16 and a VL comprising the amino acid sequence of SEQ ID NO: 18. In some embodiments, the PSMA binding domain disclosed herein comprises a VH comprising the amino acid sequence of SEQ ID NO: 20 and a VL comprising the amino acid sequence of SEQ ID NO: 22. In some embodiments, the PSMA binding domain disclosed herein comprises a VH comprising the amino acid sequence of SEQ ID NO: 24 and a VL comprising the amino acid sequence of SEQ ID NO: 26. In some embodiments, the PSMA binding domain disclosed herein comprises a VH comprising the amino acid sequence of SEQ ID NO: 28 and a VL comprising the amino acid sequence of SEQ ID NO: 30.

In some embodiments, the VH disclosed herein is encoded by a nucleic acid sequence at least about 80%, at least about 85%, at least about 90%, at least about 95%, at least about 98%, or at least about 99% identity to SEQ ID NO: 11, 15, 19, 23, or 27, or a fragment thereof. In some embodiments, the VL disclosed herein is encoded by a nucleic acid sequence at least about 80%, at least about 85%, at least about 90%, at least about 95%, at least about 98%, or at least about 99% identity to SEQ ID NO: 13, 17, 21, 25, or 29, or a fragment thereof. In some embodiments, the VH disclosed herein is encoded by the nucleic acid sequence of SEQ ID NO: 11, 15, 19, 23, or 27, or a fragment thereof and the VL disclosed herein is encoded by the nucleic acid sequence of SEQ ID NO: 13, 17, 21, 25, or 29, or a fragment thereof.

In some embodiments, the svFv described herein comprises an amino acid sequence at least about 80%, at least about 85%, at least about 90%, at least about 95%, at least about 98%, or at least about 99% identity to SEQ ID NO: 62 or a sequence comprising a portion of SEQ ID NO: 62. In some embodiments, the scFv is encoded by the nucleic acid sequence at least about 80%, at least about 85%, at least about 90%, at least about 95%, at least about 98%, or at least about 99% identity to SEQ ID NO: 61 or a sequence comprising a portion of SEQ ID NO: 61.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National institutes of Health, Bethesda, Md, (1987)). The constant domains are not involved directly in binding an antibody to an antigen, but exhibit various effector functions, such as participation of the antibody in antibody-dependent cellular toxicity.

Accordingly, in some embodiments, the PSMA binding domain disclosed herein comprises a VL and a VH, wherein the VL comprises a CDR1, a CDR2, and/or a CDR3, and wherein the VH comprises a CDR4, a CDR5, and/or a CDR6.

The intracellular domain or otherwise the intracellular signaling domain of the CAR of the invention is responsible for activation of at least about one of the normal effector functions of the immune cell in which the CAR has been placed in. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. Preferred examples of intracellular signaling domains for use in the CAR of the invention include the intracellular signaling domain sequences of the T cell receptor (TCR) and costimulatory molecule that act in concert to initiate signal transduction following antigen receptor engagement, as well as any derivative or variant of these sequences and any synthetic sequence that has the same functional capability. In some embodiments, the intracellular signaling domains for use in the CAR of the invention comprises the intracellular signaling domain sequences of NK cell receptor, T cell receptor, and/or costimulatory molecules.

In some embodiments, the intracellular domain of the CAR can be designed to comprise the CD3-zeta signaling domain by itself or combined with any other desired intracellular domain(s) useful in the context of the CAR of the invention. For example, the intracellular domain of the CAR can comprise a CD3 zeta chain portion and a costimulatory signaling domain. Examples of costimulatory molecules include CD27, CD28, 4-1BB (CD137), OX40, CD30, CD40, PD-1, ICOS, lymphocyte function-associated antigen-1 (LEA-1), CD2, CD7, LIGHT, NKG2C, B7-H3, and a ligand that specifically binds with CD83, and the like. Thus, while the invention in exemplified primarily with 4-1BB as the costimulatory signaling molecule, other costimulatory molecules are within the scope of the invention. In some embodiments, the intracellular domain of the CAR can comprise a DAP10 or DAP12 chain portion and a costimulatory signaling domain, such as the costimulatory signaling domain of 4-1BB. In some embodiments, the CD3-zeta signaling domain described herein comprises the sequence of SEQ ID NO: 36, or a polypeptide sequence having at or greater than about 80%, about 85%, about 90%, about 95%, or about 98% homology with SEQ ID NO: 36, or a polypeptide comprising a portion of SEQ ID NO: 36. In some embodiments, the CD3-zeta signaling domain described herein is encoded by the sequence of SEQ ID NO: 55, or a polynucleotide sequence having at or greater than about 80%, about 85%, about 90%, about 95%, or about 98% homology with SEQ ID NO: 55, or a polynucleotide sequence comprising a portion of SEQ ID NO: 55.

In some embodiments, the CD8α signal peptide described herein comprises the sequence of SEQ ID NO: 49, or a polypeptide sequence having at or greater than about 80%, about 85%, about 90%, about 95%, or about 98% homology with SEQ ID NO: 49, or a polypeptide comprising a portion of SEQ ID NO: 49. In some embodiments, the CD8α signal peptide described herein is encoded by the sequence of SEQ ID NO: 48, or a polynucleotide sequence having at or greater than about 80%, about 85%, about 90%, about 95%, or about 98% homology with SEQ ID NO: 48, or a polynucleotide sequence comprising a portion of SEQ ID NO: 48.

In some embodiments, the transmembrane domain (TM) is a CD8α transmembrane domain. In some embodiments, the CD8α transmembrane domain described herein comprises the sequence of SEQ ID NO: 53, or a polypeptide sequence having at or greater than about 80%, about 85%, about 90%, about 95%, or about 98% homology with SEQ ID NO: 53, or a polypeptide comprising a portion of SEQ ID NO: 53. In some embodiments, the CD8α transmembrane domain described herein is encoded by the sequence of SEQ ID NO: 52, or a polynucleotide sequence having at or greater than about 80%, about 85%, about 90%, about 95%, or about 98% homology with SEQ ID NO: 52, or a polynucleotide sequence comprising a portion of SEQ ID NO: 52.

"4-1BB" refers herein to a polypeptide that synthesizes and hydrolyzes cyclic adenosine 5'-diphosphate-ribose, and in humans, is encoded by the TNFRSF9 gene. In some embodiments, the 4-1BB polypeptide is that identified in one or more publicly available databases as follows: HGNC: 11924, Entrez Gene: 3604, Ensembl: ENSG00000049249, OMIM: 602250, UniProtKB: Q07011. In some embodiments, the 4-1BB polypeptide comprises the sequence of SEQ ID NO: 32, or a polypeptide sequence having at or greater than about 80%, about 85%, about 90%, about 95%, or about 98% homology with SEQ ID NO: 32, or a polypeptide comprising a portion of SEQ ID NO: 32. The 4-1BB polypeptide of SEQ ID NO: 32 may represent an immature or pre-processed form of mature 4-1BB, and accordingly, included herein are mature or processed portions of the 4-1BB polypeptide in SEQ ID NO: 32. In some embodiments, the 4-1BB polypeptide comprises an intracellular signaling domain of 4-1BB comprising a sequence having at or greater than about 80%, about 85%, about 90%, about 95%, or about 98% homology with SEQ ID NO: 33, or a polypeptide comprising a portion of SEQ ID NO: 33. In some embodiments, the 4-1BB polypeptide described herein is encoded by the sequence of SEQ ID NO: 54, or a polynucleotide sequence having at or greater than about 80%, about 85%, about 90%, about 95%, or about 98% homology with SEQ ID NO: 54, or a polynucleotide sequence comprising a portion of SEQ ID NO: 54.

In some embodiments, the CAR disclosed herein comprises the amino acid sequence at least about 80%, at least about 85%, at least about 90%, at least about 95%, at least about 98%, or at least about 99% identity to SEQ ID NO: 2, 4, 6, 8, 10, 39, 41, 43, 45, or 47 or a fragment thereof. In some embodiments, the CAR disclosed herein comprises the amino acid sequence of SEQ ID NO: 2, 4, 6, 8, 10, 39, 41, 43, 45, or 47 or a fragment thereof.

In some embodiments, the CAR disclosed herein is encoded by a nucleic acid sequence at least about 80%, at least about 85%, at least about 90%, at least about 95%, at least about 98%, or at least about 99% identity to SEQ ID NO: 1, 3, 5, 7, 9, 38, 40, 42, 44, or 46 or a fragment thereof. In some embodiments, the CAR disclosed herein is encoded by the nucleic acid sequence of SEQ ID NO: 1, 3, 5, 7, 9, 38, 40, 42, 44, or 46 or a fragment thereof.

In some embodiments, the CAR disclosed herein is operatively linked to a polypeptide comprising interferon regulatory factor 4 (IRF4) or a dominant negative TGFβ receptor (TGFβRDN). In some embodiments, the CAR and the polypeptide are operatively linked via a linker that comprises a self-cleaving peptide. In some embodiments, the self-cleaving peptide is T2A. T2A is an 18 to 22 amino acid-long polypeptide derived from Thosea asigna virus 2A. T2A can be used to cleave a longer polypeptide into two shorter polypeptides (e.g., CAR and IRF4). In some embodiments, the T2A polypeptide used herein comprises a sequence at least about 80%, at least about 85%, at least about 90%, at least about 95%, at least about 98%, or at least about 99% identity to SEQ ID NO: 34, or a portion of SEQ ID NO: 34. In some embodiments, the T2A polypeptide used herein is encoded by a sequence at least about 80%, at least about 85%, at least about 90%, at least about 95%, at least about 98%, or at least about 99% identity to SEQ ID NO: 56, or a portion of SEQ ID NO: 56.

Accordingly, in some embodiments, the disclosed CAR can be defined by the formula:

$$\text{CD8α-PSMA BD-TM-CSD-CD3-T2A-IRF4/}$$
$$\text{TGFβRDN;}$$

wherein "CD8α" represents a CD8α domain,
wherein "PSMA BD" represents a prostate-specific membrane antigen (PSMA) binding domain;
wherein "TM" represents a transmembrane domain;
wherein "CSD" represents a costimulatory signaling domain;
wherein "CD3" represents a CD3 zeta signaling domain; and
wherein "-" represents a linker.

In some embodiments, the disclosed CAR can be defined by the formula:

$$\text{Tumor BD-TM-CSD-CD3-T2A-IRF4/TGFβRDN;}$$

wherein "Tumor BD" represents a tumor binding domain;
wherein "TM" represents a transmembrane domain;
wherein "CSD" represents a costimulatory signaling domain;
wherein "CD3" represents a CD3 zeta signaling domain; and
wherein "-" represents a linker.

In some embodiments, the tumor BD specific binds to a tumor antigen, including, for examples, CD19 or PSMA. In some embodiments, the BD is a svFV specific for CD19 or PSMA. In some embodiments, the svFv comprises an amino acid sequence at least about 80%, at least about 85%, at least about 90%, at least about 95%, at least about 98%, or at least about 99% identity to SEQ ID NO: 51 or 62 or a sequence comprising a portion of SEQ ID NO: 51 or 62. In some embodiments, the scFv is encoded by the nucleic acid sequence of SEQ ID NO: 50 or 61 or a sequence comprising a portion of SEQ ID NO: 50 or 61.

"IRF4" refers herein to a polypeptide that synthesizes and hydrolyzes cyclic adenosine 5'-diphosphate-ribose, and in humans, is encoded by the IRF4 gene. In some embodiments, the IRF4 polypeptide is that identified in one or more publicly available databases as follows: HGNC: 6119, Entrez Gene: 3662, Ensembl: ENSG00000137265, OMIM: 601900, UniProtKB: Q15306. In some embodiments, the IRF4 polypeptide comprises the sequence of SEQ ID NO: 35, or a polypeptide sequence having at or greater than about 80%, about 85%, about 90%, about 95%, or about 98% homology with SEQ ID NO: 35 or SEQ ID NO: 58, or a polypeptide comprising a portion of SEQ ID NO: 35 or SEQ ID NO: 58. The IRF4 polypeptide of SEQ ID NO: 35 or SEQ ID NO: 58 may represent an immature or pre-processed form of mature IRF4, and accordingly, included herein are mature or processed portions of the IRF4 polypeptide in SEQ ID NO: 35 or SEQ ID NO: 58. In some embodiments, the IRF4 polypeptide used herein is encoded by a sequence at least about 80%, at least about 85%, at least about 90%, at least about 95%, at least about 98%, or at least about 99% identity to SEQ ID NO: 57, or a sequence comprising a portion of SEQ ID NO: 57. In some embodiments, the CAR comprises the amino acid sequence at least about 80%, at least about 85%, at least about 90%, at least about 95%, at least about 98%, or at least about 99% identity to SEQ ID NO: 60 or 64 or a sequence comprising a portion of SEQ ID NO: 60 or 64. In some embodiments, the CAR disclosed herein comprises the amino acid sequence of SEQ ID NO: 60 or 64. In some embodiments, the CAR is encoded by a nucleic acid sequence at least about 80%, at least about 85%, at least about 90%, at least about 95%, at least about 98%, or at least about 99% identity to SEQ ID NO: 59 or 63 or a sequence comprising a portion of SEQ ID NO: 59 or 63. In some embodiments, the CAR is encoded by the nucleic acid sequence of SEQ ID NO: 59 or 63.

Nucleic Acids and Vectors

In some aspects, disclosed herein is a recombinant nucleic acid sequence encoding a chimeric antigen receptor (CAR) that comprising an extracellular domain and an intracellular domain, and transmembrane domain, wherein the extracellular comprises a prostate-specific membrane antigen (PSMA) binding domain, and wherein the intracellular domain or otherwise the cytoplasmic domain comprises a CD3 zeta signaling domain and a costimulatory signaling domain. In some embodiments, the CAR further comprises a signal peptide domain. In some embodiments, the signal peptide domain is a CD8α domain.

An exemplary intracellular domain that can be used in the CAR of the invention includes but is not limited to the intracellular domain of CD3 zeta and 4-1BB, and the like.

Accordingly, in one aspect, disclosed herein is a recombinant nucleic acid sequence encoding a CAR, wherein the recombinant nucleic acid sequence comprises a nucleic acid sequence encoding a CD3 zeta signaling domain, a nucleic acid sequence encoding a costimulatory signaling domain, a nucleic acid sequence encoding a transmembrane domain, a nucleic acid sequence encoding a CD8α domain, and a nucleic acid sequence encoding a PSMA binding domain, wherein these domains are directly linked or operatively linked via linkers.

In another aspect, disclosed herein is a recombinant nucleic acid sequence encoding a CAR, wherein the recombinant nucleic acid sequence comprises a nucleic acid sequence encoding DAP10 or DAP12 signaling domain, a nucleic acid sequence encoding a costimulatory signaling domain, a nucleic acid sequence encoding a transmembrane domain, a nucleic acid sequence encoding a CD8α domain, and a nucleic acid sequence encoding a PSMA binding domain, wherein these domains are directly linked or operatively linked via linkers.

As noted above, in some embodiments, the PSMA binding domain comprises a light chain variable region (VL) and a heavy chain variable region (VH), wherein the VH is encoded by a nucleic acid sequence at least about 80%, at least about 85%, at least about 90%, at least 95%, at least about 98%, or at least about 99% identity to SEQ ID NO: 11, 15, 19, 23, or 27 and wherein the VL is encoded by a nucleic acid sequence at about least 80%, at about least 85%, at least about 90%, at least 95%, at least about 98%, or at least about 99% identity to SEQ ID NO: 13, 17, 21, 25, or 29.

Accordingly, in some embodiments, the nucleic acid sequence encoding the PSMA binding domain disclosed herein comprises a first nucleic acid sequence encoding a VH and a second nucleic acid sequence encoding a VL, wherein the first nucleic acid sequence is at least about 80%, at least about 85%, at least about 90%, at least about 95%, at least about 98%, or at least about 99% identity to SEQ ID NO: 11, 15, 19, 23, or 27 and the second nucleic acid sequence is at least about 80%, at least about 85%, at least about 90%, at least about 95%, at least about 98%, or at least about 99% identity to SEQ ID NO: 13, 17, 21, 25, or 29.

In some embodiments, the nucleic acid sequence encoding the PSMA binding domain disclosed herein comprises a first nucleic acid sequence encoding a VH and a second nucleic acid sequence encoding a VL, wherein the first nucleic acid sequence is at least about 80%, at least about 85%, at least about 90%, at least about 95%, at least about 98%, or at least about 99% identity to SEQ ID NO: 11 and the second nucleic acid sequence is at least about 80%, at least about 85%, at least about 90%, at least about 95%, at least about 98%, or at least about 99% identity to SEQ ID NO: 13.

In some embodiments, the nucleic acid sequence encoding the PSMA binding domain disclosed herein comprises a first nucleic acid sequence encoding a VH and a second nucleic acid sequence encoding a VL, wherein the first nucleic acid sequence is at least about 80%, at least about 85%, at least about 90%, at least about 95%, at least about 98%, or at least about 99% identity to SEQ ID NO: 15 and the second nucleic acid sequence is at least about 80%, at least about 85%, at least about 90%, at least about 95%, at least about 98%, or at least about 99% identity to SEQ ID NO: 17.

Accordingly, in some embodiments, the nucleic acid sequence encoding the PSMA binding domain disclosed herein comprises a first nucleic acid sequence encoding a VH and a second nucleic acid sequence encoding a VL, wherein the first nucleic acid sequence is at least about 80%, at least about 85%, at least about 90%, at least about 95%, at least about 98%, or at least about 99% identity to SEQ ID NO: 19 and the second nucleic acid sequence is at least about 80%, at least about 85%, at least about 90%, at least about 95%, at least about 98%, or at least about 99% identity to SEQ ID NO: 21.

Accordingly, in some embodiments, the nucleic acid sequence encoding the PSMA binding domain disclosed herein comprises a first nucleic acid sequence encoding a VH and a second nucleic acid sequence encoding a VL, wherein the first nucleic acid sequence is at least about 80%, at least about 85%, at least about 90%, at least about 95%, at least about 98%, or at least about 99% identity to SEQ ID NO: 23 and the second nucleic acid sequence is at least about 80%, at least about 85%, at least about 90%, at least about 95%, at least about 98%, or at least about 99% identity to SEQ ID NO: 25.

Accordingly, in some embodiments, the nucleic acid sequence encoding the PSMA binding domain disclosed herein comprises a first nucleic acid sequence encoding a VH and a second nucleic acid sequence encoding a VL, wherein the first nucleic acid sequence is at least about 80%, at least about 85%, at least about 90%, at least about 95%, at least about 98%, or at least about 99% identity to SEQ ID NO: 27 and the second nucleic acid sequence is at least about 80%, at least about 85%, at least about 90%, at least about 95%, at least about 98%, or at least about 99% identity to SEQ ID NO: 29.

In some embodiments, the nucleic acid sequence encoding the PSMA binding domain disclosed herein comprises a first nucleic acid sequence encoding a VH and a second nucleic acid sequence encoding a VL, wherein the first nucleic acid sequence is set forth in SEQ ID NO: 11, 15, 19, 23, or 27 and the second nucleic acid sequence is set for the in SEQ ID NO: 13, 17, 21, 25, or 29.

In some embodiments, the linker sequence is at least about 80%, at least about 85%, at least about 90%, at least about 95%, at least about 98%, or at least about 99% identity to SEQ ID NO: 37.

In some embodiments, the recombinant nucleic acid sequence encoding a CAR disclosed herein comprises a nucleic acid sequence at least about 80%, at least about 85%, at least about 90%, at least about 95%, at least about 98%, or at least about 99% identity to SEQ ID NO: 1, 3, 5, 7, 9, 38, 40, 42, 44, or 46. In some embodiments, the recombinant nucleic acid sequence encoding the CAR disclosed herein comprises the nucleic acid sequence set forth in SEQ ID NO: 1, 3, 5, 7, 9, 38, 40, 42, 44, or 46.

In some embodiments, the recombinant nucleic acid sequence disclosed herein further comprises a nucleic acid encoding interferon regulatory factor 4 (IRF4) or a dominant negative TGFβ receptor (TGFβRDN). In some embodiments, the recombinant nucleic acid sequence disclosed herein further comprises a nucleic acid sequence encoding a self-cleaving peptide that is located upstream of the 5' terminus of the nucleic acid encoding IRF4 or a TGFβRDN. In Kale embodiments, the self-cleaving peptide is T2A. In some embodiments, the recombinant nucleic acid sequence encoding a CAR disclosed herein comprises a nucleic acid sequence at least about 80%, at least about 85%, at least about 90%, at least about 95%, at least about 98%, or at least about 99% identity to SEQ ID NO: 63. In some embodiments, the recombinant nucleic acid sequence encoding the CAR disclosed herein comprises the nucleic acid sequence set forth in SEQ ID NO: 63.

In some embodiments, the recombinant nucleic acid disclosed herein further comprises additional promoter elements, e.g., enhancers, regulate the frequency of transcriptional initiation. Typically, these are located in the region 30-110 bp upstream of the start site of the nucleic acid sequence mentioned above (e.g., the nucleic acid sequence encoding CD8α), although a number of promoters have recently been shown to contain functional elements downstream of the start site as well. In some embodiments, the recombinant nucleic acid disclosed herein comprises one promoter. In some embodiments, the recombinant nucleic acid disclosed herein comprises more than one promoter. In some embodiments, the recombinant nucleic acid disclosed herein comprises two promoters, wherein the first promoter is located upstream of the 5' terminus of the nucleic acid sequence encoding CD8α, and wherein the second promoter is located downstream of the 3' terminus of the nucleic acid encoding the CDS zeta and upstream of the 5' terminus of the nucleic acid encoding IRF4 or a TGFβRDN.

The spacing between promoter elements frequently is flexible, so that promoter function is preserved when elements are inverted or moved relative to one another. Depending on the promoter, it appears that individual elements can function either cooperatively or independently to activate transcription, One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor −1 alpha (EF-1α). However, other promoter sequences may also be used, including, but not limited to the simian virus 40 (SV40), early promoter, mouse mammary tumor virus (MMTV), human immunodeficiency virus (HIV) long terminal repeat (LTR) promoter, MoMuLV promoter. PGK-1 promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter as well as synthetic protein, such as a CAG promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to mod late promoter-driven transcription. In some embodiments, the recombinant nucleic acid disclosed herein further comprises a reporter gene. In some embodiments, the reporter gene in invention is GFP.

In brief summary, the expression of natural or synthetic nucleic acids encoding CARs is typically achieved by operably linking a nucleic acid encoding the CAR polypeptide or portions thereof to a promoter and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties.

The nucleic acid can be cloned into a number of types of vectors. For example, the nucleic acid can be cloned into a vector including, but not limited to a plasmid, a phagemid, phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endomiclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Accordingly, in some embodiments, disclosed herein is a vector comprising the recombinant nucleic acid sequence disclosed herein. In some embodiments, the vector is a lentivirus vector.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. See, e.g., WO2012079000A1, incorporated by reference herein in their entireties.

Engineered T Cells, NK Cells, and Uses Thereof

In some aspects, disclosed herein is a genetically modified T cell comprising a recombinant nucleic acid sequence encoding a chimeric antigen receptor (CAR), wherein the recombinant nucleic acid sequence comprises a nucleic acid sequence encoding a CD3 zeta signaling domain, a nucleic acid sequence encoding a costimulatory signaling domain, a nucleic acid sequence encoding a transmembrane domain, a nucleic acid sequence encoding a CD8α domain, and a nucleic acid sequence encoding a PSMA binding domain, wherein these nucleic acid sequences are directly linked or operatively linked via linkers. In some embodiments, the PSMA binding domain comprises a light chain variable region (VL) and a heavy chain variable region (VH), wherein the VH is encoded by a nucleic acid sequence at least about 80%, at least about 85%, at least about 90%, at least about 95%, at least about 98%, or at least about 99% identity to SEQ ID NO: 11, 15, 19, 23, or 27 and wherein the VL is encoded by a nucleic acid sequence at least about 80%, at least about 85%, at least about 90%, at least about 95%, at least about 98%, or at least about 99% identity to SEQ ID NO: 13, 17, 21, 25, or 29.

In some aspects, disclosed herein is a genetically modified T cell comprising a chimeric antigen receptor (CAR), wherein the CAR comprises a CD3 zeta signaling domain, a costimulatory signaling domain, a CD8α domain, a transmembrane domain, and a prostate-specific membrane antigen (PSMA) binding domain comprising a light chain variable region (VL) and a heavy chain variable region (VH), wherein the VH comprises an amino acid sequence at least about 80%, at least about 85%, at least about 90%, at least about 95%, at least about 98%, or at least about 99% identity to SEQ ID NO: 12, 16, 20, 24, or 28, and wherein the VL comprises an amino acid sequence at least about 80%, at least about 85%, at least about 90%, at least about 95%, at least about 98%, or at least about 99% identity to SEQ ID NO: 14, 18, 22, 26, or 30.

In some aspects, disclosed herein is a genetically modified T cell comprising a chimeric antigen receptor (CAR), wherein the CAR comprises an amino acid sequence at least about 80%, at least about 85%, at least about 90%, at least about 95%, at least about 98%, or at least about 99% identity to SEQ ID NO: 2, 4, 6, 8, 10, 39, 41, 43, 45, 47, 60, or 64.

In some aspects, disclosed herein is a genetically modified natural killer (NK) cell comprising a recombinant nucleic acid sequence encoding a chimeric antigen receptor (CAR), wherein the recombinant nucleic acid sequence comprises a nucleic acid sequence encoding a CD3 zeta signaling domain, a nucleic acid sequence encoding an NK cell signaling domain, a nucleic acid sequence encoding a costimulatory signaling domain, a nucleic acid sequence encoding a transmembrane domain, a nucleic acid sequence encoding a CD8α domain, and/or a nucleic acid sequence encoding a PSMA binding domain, wherein these domains are directly linked or operatively linked via linkers, wherein the NK cell signaling domain comprises CD3zeta, DAP10 or DAP12. In some embodiments, the PSMA binding domain comprises a light chain variable region (VL) and a heavy chain variable region (VH), wherein the VH is encoded by a nucleic acid sequence at least about 80%, at least about 85%, at least about 90%, at least about 95%, at least about 98%, or at least about 99% identity to SEQ ID NO: 11, 15, 19, 23, or 27 and wherein the VL is encoded by a nucleic acid sequence at least about 80%, at least about 85%, at least about 90%, at least about 95%, at least about 98%, or at least about 99% identity to SEQ ID NO: 13, 17, 21, 25, or 29.

In some aspects, disclosed herein is a genetically modified NK cell comprising a chimeric antigen receptor (CAR), wherein the CAR comprises a CD3 zeta signaling domain or an NK cell receptor signaling domain, a costimulatory signaling domain, a CD8α domain, a transmembrane domain, and a prostate-specific membrane antigen (PSMA) binding domain comprising a light chain variable region (VL) and a heavy chain variable region (VH), wherein the VH comprises an amino acid sequence at least about 80%, at least about 85%, at least about 90%, at least about 95%, at least about 98%, or at least about 99% identity to SEQ ID NO: 12, 16, 20, 24, or 28, wherein the VL comprises an amino acid sequence at least about 80%, at least about 85%, at least about 90%, at least about 95%, at least about 98%, or at least about 99% identity to SEQ ID NO: 14, 18, 22, 26, or 30, and wherein the NK cell receptor signaling domain comprises DAP12 or DAP10.

In some aspects, disclosed herein is a genetically modified NK cell comprising a chimeric antigen receptor (CAR), wherein the CAR comprises an amino acid sequence at least about 80%, at least about 85%, at least about 90%, at least about 95%, at least about 98%, or at least about 99% identity to SEQ ID NO: 2, 4, 6, 8, 10, 39, 41, 43, 45, 47, 60, or 64.

Prior to expansion and genetic modification of the NK cells and T cells of the invention, a source of NK cells and T cells is obtained from a subject. NK cells and T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, the T cells and NK cells used herein are T cell lines and NK cell lines.

Whether prior or after genetic modification of the NK cell and T cell to express a desirable CAR, the T cells can be isolated, stimulated cryopreserved, activated, and/or expanded. Methods of isolating, stimulating, cryopreserving, activating, and expansion of T cells have been generally described, for examples in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5.883,223; 6,905,874; 6,797,514; 6,867,041; and U.S. Patent Application Publication No. 20060121005, US20160361360A1, US20150342993A1, incorporated by reference herein in their entireties.

In some aspects, disclosed herein are methods of preventing, reducing, inhibiting, and/or treating prostate cancer, comprising administering to the subject in need a therapeutically effective amount of the genetically modified T cell disclosed herein.

In some aspects, disclosed herein are method of preventing, reducing, inhibiting, and/or treating prostate cancer, comprising administering to the subject in need a therapeutically effective amount of the genetically modified NK cell disclosed herein.

In some aspects, disclosed herein are method of preventing, reducing, inhibiting, and/or treating prostate cancer, comprising administering to the subject in need a therapeutically effective amount of a polypeptide that comprises a prostate-specific membrane antigen (PSMA) binding domain comprising a light chain variable region (VL) and a heavy chain variable region (VH), wherein the VH comprises an amino acid sequence at least about 80%, at least about 85%, at least about 90%, at least about 95%, at least about 98%, or at least about 99% identity to SEQ ID NO: 12, 16, 20, 24, or 28, and wherein the VL comprises an amino acid sequence at least about 80%, at least about 85%, at least about 90%, at least about 95%, at least about 98%, or at least about 99% identity to SEQ ID NO: 14, 18, 22, 26, or 30. In some embodiments, the PSMA binding domain is an antibody or an antigen-binding fragment thereof. In some embodiments, the antigen-binding fragment is a single-chain variable fragment (scfv).

In some embodiments, the genetically modified T cell, NK cell or the polypeptide described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavemous, intrathecal, intravitreal, intracerebral, gingival, subgingival, intracerebroventricular, and intradermal. Such formulations may be prepared by any method known in the art.

The disclosed methods can be performed any time prior to and/or after the onset of prostate cancer. In some aspects, the disclosed methods can be employed 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 years; 12, 11, 10, 9, 8, 7, 6, 5, 4, 3, 2, or 1 months; 30, 29, 28, 27, 26, 25, 24, 23, 22, 21, 20, 19, 18, 17, 16, 15, 14, 13, 12, 11, 10, 9, 8, 7, 6, 5, 4, or 3 days; 60, 48, 36, 30, 24, 18, 15, 12, 10, 9, 8, 7, 6, 5, 4, 3, or 2 hours prior to the onset of prostate cancer; or 1, 2, 3, 4, 5, 6, 7, 8, 9, 10, 15, 25, 30, 35, 40, 45, 50, 55, 60, 75, 90, 105, 120 minutes; 3, 4, 5, 6, 7, 8, 9, 10, 11, 12, 15, 18, 24, 30, 36, 48, 60 hours; 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days; 4, 5, 6, 7, 8, 9, 10, 11, 12 or more months; 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 years after the onset of prostate cancer.

Dosing frequency for the genetically modified T cell, NK cell or the polypeptide composition disclosed herein, includes, but is not limited to, at least once every 12 months, once every 11 months, once every 10 months, once every 9 months, once every 8 months, once every 7 months, once every 6 months, once every 5 months, once every 4 months, once every 3 months, once every two months, once every month; or at least once every three weeks, once every two weeks, once a week, twice a week, three times a week, four times a week, five times a week, six times a week, or daily. In some embodiment, the interval between each administration is less than about 4 months, less than about 3 months, less than about 2 months, less than about a month, less than about 3 weeks, less than about 2 weeks, or less than less than about a week, such as less than about any of 6, 5, 4, 3, 2, or 1 day. In some embodiment, the dosing frequency for the genetically modified T cell, NK cell or the polypeptide composition disclosed herein includes, but is not limited to, at least once a day, twice a day, or three times a day. In some embodiment, the interval between each administration is less than about 48 hours, 36 hours, 24 hours, 22 hours, 20 hours, 18 hours, 16 hours, 14 hours, 12 hours, 10 hours, 9 hours, 8 hours, or 7 hours. In some embodiment, the interval between each administration is less than about 24 hours, 22 hours, 20 hours, 18 hours, 16 hours, 14 hours, 12 hours, 10 hours, 9 hours, 8 hours, 7 hours, or 6 hours. In some embodiment, the interval between each administration is constant. For example, the administration can be carried out daily, every two days, every three days, every four days, every five days, or weekly. Administration can also be continuous and adjusted to maintaining a level of the compound within any desired and specified range.

As noted above, PSMA is also expressed on other types of malignant cells. Therefore, in some aspects, disclosed herein are methods of preventing, reducing, inhibiting, and/or treating a cancer. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer. In some embodiments, the cancer cell has an increased level of PSMA in comparison to a reference level (e.g., levels of PSMA in a normal cell or in a healthy subject).

CD19 is expressed on B cell. In some aspects, disclosed herein are compositions and methods of preventing, reducing, inhibiting, and/or treating B cell malignancy in a subject in need. A representative but non-limiting list of cancers that the disclosed compositions can be used to treat is the following: non-Hodgkin lymphoma, chronic lymphocytic leukemia (CLL), diffuse large B-cell lymphoma (DLBCL), acute lymphocytic leukemia (ALL), or Burkitt lymphoma. In some embodiments, the cancer cell has an increased level of CD19 in comparison to a reference level (e.g., levels of CD19 in a normal cell or in a healthy subject). In some embodiments, the subject in need has an increased level of CD19+ cells in comparison to a reference level (e.g., the amounts of CD19+ cell in a healthy subject).

EXAMPLES

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Example 1

PSMA-Targeted Immunotherapies for Human Cancers

Prostate-specific membrane antigen (PSMA) is a plasma membrane glycoprotein. It is highly expressed in normal prostate epithelial cells, human primary prostate cancer cells (98.5%), castration-resistant prostate cancer, and neovasculature of all solid tumors. It is expressed in prostate, kidney, small intestine, ganglia of nervous system but not in heart or lung. Importantly PSMA is not an essential gene for animal development as indicated by the fact that PSMA knockout mice appear normal. Therefore, PSMA is a valuable therapeutic target for solid tumors including prostate cancer. In this disclosure, amuse monoclonal antibodies that can specifically recognize the PSMA on prostate cancer cells were generated. Based on these antibodies, several immunotherapies were developed for treatment of solid tumors including prostate cancer.

(1) Based on five mouse monoclonal antibodies that recognize PSMA on prostate cancer cells, single-chain fragment variable (scFv) domains were derived which retain the ability to binding to PSMA antigen. Using these PSMA scFv, chimeric antigen receptor (CAR)-engineered T cells were developed, which showed potent anti-prostate cancer activity in vitro. (2) In addition to CAR T-cell therapy, CAR-engineered natural killer (NK) cells are developed. These CAR-NK cells have anti-solid cancer activities. (3) The full length PSMA antibodies have anti-cancer activities based on an in vitro antibody-dependent cellular cytotoxicity (ADCC) assay. Altogether, these PSMA antibodies disclosed herein can be used as monotherapy for solid cancers or in combination with other cancer therapies.

For PSMA-specific CAR-T cells, five lentiviral vectors expressing PSMA-specific CARS were developed for infecting human T cells. Three out of five CAR constructs rendered the infected T cells potent in vitro anti-cancer activities of specifically killing prostate cancer LNCaP cells. These three clones of PSMA-specific CAR T cells are tested for their in vivo anti-cancer activities.

Based on the success of the PSMA-specific CAR-T cells, PSMA-specific CAR NK therapy is developed. First, the CAR lentivirus mentioned above can be used to generate CAR-NK cells and their in vitro anti-cancer activities are tested, followed with testing their in vivo anti-cancer activities in mice. Second, the current CAR vectors are optimized for NK cells, then the in vitro and in vivo anticancer activities are tested.

All five PSMA mouse monoclonal antibodies showed anticancer activities based on an in vitro ADCC assay. The most potent clone #1352 was chosen to perform subclass switch from the IgG2b subtype to the IgG2a subtype, given that mouse IgG2a subtype is known as having the most potent anti-cancer activities in vivo in mice. The in vivo anti-cancer activities of the purified recombinant antibody #1353 (IgG2a) are tested in mice.

Example 2

The Prominent Effects of the Engineered CAR-T and CAR-NK Cells in Treating Prostate Cancer Castration-resistant prostate cancer (CRPC) is deadly and currently there is effective treatment. In addition, because prostate cancer cells harbor small amount of somatic mutations, prostate cancers are not sensitive to current immuno-therapies including anti-PD1/anti-CTLA4 checkpoint blockade and tumor infiltrating lymphocyte (TIL) therapy. Because CAR-engineered lymphocytes (CAR-T) and NK cells (CAR-NK) recognize cancer cells through cancer cell surface antigens, their anti-cancer activities are not dependent on mutations in cancer cells. Therefore, the CAR-T cells and CAR-NK cells developed herein meet the urgent need for CRPC.

Example 3

Engineering CAR-T and CAR-NK Cells to Co-Express IRF4

The CAR T cell immunotherapy has recently been approved by FDA for treatment of refractory pre-B cell acute lymphoblastic leukemia and diffuse large B cell lymphoma. However, CAR-T therapy has not been successful in treating solid tumors. Here, PSMA-specific CAR-T cells were modified by co-expressing IRF in T cells. IRF4 is a key regulator of (i) effector T cell activity and (ii) tissue infiltration. Constitutive expression of IRF4 in mouse T cells can enhance tissue infiltration and anticancer activity in a melanoma mouse model. Co-express IRF4 in the PSMA-specific CAR-T cells disclosed herein can enhance the anti-cancer activities of CAR-T and CAR-NK cells.

In a recent report (Li et al., Human iPSC-Derived Natural Killer Cells Engineered with Chimeric Antigen Receptors Enhance Anti-tumor Activity, *Cell Stem Cell,* 2018, 23:181-192), a CAR that contains NKG2D transmembrane domain and 2B4 co-stimulatory domain conferred NK cells more potent anti-cancer activity. However, in another report (Liu et al., Use of CAR-Transduced Natural Killer Cells in CD19-Positive Lymphoid Tumors, *N Engl J Med,* 2020, 382:545-553), treatment with CD19-CAR-NK cells achieved partial or complete response in the majority of 11 patients with relapsed or refractory CD19-positive cancers. In this clinical trial, the CD19-CAR was the same CAR which was originally designed for CAR-T therapy and contains CD28 and CD3zeta signaling domains, not NKG2D or 2B4 domain.

In the present study, when the NKG2D transmembrane domain and 2B4 co-stimulatory domain were tested in the CAR-NK cells disclosed herein, no increase in anti-tumor effect was not observed. Instead, the original CAR was much more potent. Therefore, the original PSMA-CAR was used for CAR-NK work.

Example 4

Invigorating Chimeric Antigen Receptor T Cells for Treatment of Metastatic Prostate Cancer Recent advances in immunotherapy are revolutionizing the treatment of cancer. The checkpoint blockade therapies using antibodies to block CTLA-4 or PD-1 have achieved durable clinical benefits and a cure in a subset of cancers. Unfortunately, prostate cancer is notoriously resistant to this type of immunotherapy probably due to its immunologically "cold" nature. Less than 5% of metastatic prostate cancer responds to anti-PD-2 therapy. Therefore, currently there is no cure for most of the late stage metastatic prostate cancer.

T cells are a type of cytotoxic lymphocytes critical to the anti-cancer immunity. T cells can recognize and destroy some cancer cells such as melanoma, because those cancer cells contain a large number of mutations and are thus treated by the immune system as 'non-self' antigens. However, prostate cancer cells contain only a small number of mutations and cannot be distinguished by our T cells as 'non-self'.

The Chimeric Antigen Receptor (CAR) T-cell therapy is an emerging immunotherapy with tremendous potential. It has recently been approved by FDA for treatment of refractory pre-B cell acute lymphoblastic leukemia and diffuse large B cell lymphoma and multiple myeloma.

The current study developed PSMA-targeted CAR-engineered T-cells, which already showed potent in vitro and in vivo anti-prostate cancer activity. PSMA stands for Prostate-Specific Membrane Antigen, and is highly expressed on prostate cancer cells, but not in any essential tissues. The engineered CAR T-cells can now recognize prostate cancer cells based on their PSMA expression and kill them effectively, regardless of mutation status in cancer cells.

It is demonstrated herein that a transcription factor IRF4 can boost T cell activity. Therefore, IRF4 expression is engineered in the PSMA CAR T-cells to achieve more potent and durable anti-cancer activity.

Prostate cancer can be made amenable to CAR T cell therapy based on its unique features. First, prostate is not a vital organ for human survival; therefore, collateral damage to normal prostate tissue during therapy can be tolerated. Second, prostate-specific membrane antigen (PSMA) has been identified as a prostate cancer-selective surface antigen and is required for optimal prostate cancer progression.

CAR T cells can thus be engineered to target PSMA on prostate cancer cells. Third, PSMA is expressed across all stages of prostate cancer, but not in other vital tissues in adults. Mice deficient in PSMA appear to be normal. Therefore, no fatal toxicity is anticipated for PSMA-specific CAR T therapy. Finally, based on the proprietary mouse monoclonal antibodies against human PSMA, two PSMA-CARs were developed which conferred upon human T cells potent in vitro and in vivo anti-prostate cancer activity. These PSMA-CARs are more potent than the PSMA-CAR derived from the famous J591 antibody, which is currently in phase I/II clinical trials.

Although CAR T cell therapy has achieved success against hematological cancers, solid tumors remain a big challenge. Weaknesses with current CAR T cells against solid tumors are lack of in vivo CAR T cell expansion and T cell dysfunction within the tumor microenvironment. How to achieve potent and durable T cell activity in vivo is critical for the success of CAR-T immunotherapy for solid tumors. Studies recently made an important discovery by demonstrating that interferon regulatory factor 4 (IRF4) is a key regulator of effector T cell activity. Deletion of IRF4 in CD4+ T cells leads to T cell dysfunction; whereas constitutive overexpression of IRF4 in murine Pmel-1 CD8+ T cells dramatically increased the anti-melanoma activity.

The present study shows that (i) PSMA-targeted CAR T cells can specifically kill prostate cancer cells by recognizing the PSMA antigen on cancer cell membrane, bypassing the requirement of TCR/MHCI interaction; and (ii) PSMA-CAR T cells with engineered IRF4 expression can achieve more potent and durable in vivo cytotoxicity against metastatic prostate cancer. The data shown herein made a striking observation that overexpression of IRF4 tremendously increased the in vitro expansion of PSMA-CAR T cell and CD19-CAR T cells.

Here, IRF4-invigorated PSMA-specific CAR T cells are developed and tested for their in vitro and in vivo anti-prostate cancer activity. In addition, the function of PSMA-IRF4 CAR T cells is tested by: (1) RNA-sequencing to identify IRF4-regulated genes in CAR T cells; (2) single cell RNA-seq analysis to characterize tumor-infiltrating CAR T cells; (3) studying the impact of IRF4 deficiency on PSMA-CAR T cell activity.

Background. Prostate cancer is one of the most common cancers in men, with an estimated 248,530 newly diagnosed cases and 34,130 deaths in the United States in 2021 according to American Cancer Society. The second-generation anti-androgens such as Enzalutamide and Darolutamide have been successful in prolonging the survival of men with metastatic prostate cancer; however cancers invariably relapse and become deadly. Recent advances in immunotherapy are revolutionizing the treatment of cancer. The checkpoint blockade therapies using antibodies to block CTLA-4 or PD-1 have achieved long-term clinical benefits, or even a cure in a subset of cancers. Unfortunately, prostate cancer is notoriously resistant to checkpoint blockade immunotherapy, as less than 5% of metastatic prostate cancer responds to anti-PD-1 therapy [4]. The checkpoint blockade therapies are particularly successful for cancers like melanoma, because those cancers contain many mutations, and thus can be recognized by T cells as 'non-self' antigens. In contrast, most of prostate tumors contain fewer missense mutations in their genome, and therefore cannot be distinguished by our T cells as 'non-self' (FIG. 1).

In addition to checkpoint blockade, the chimeric antigen receptor (CAR)-T cell immunotherapy has recently been approved by FDA for treatment of refractory pre-B cell acute lymphoblastic leukemia, diffuse large B cell lymphoma and multiple myeloma. CAR-engineered T cells can specifically kill cancer cells by recognizing the membrane antigen on cancer cell surface through anti-antigen single-chain variable fragment (scFv) domain, regardless of mutation status in cancer cells. Therefore, for CAR T cell therapy to succeed, cancer cells need to express a membrane antigen that can be recognized by chimeric antigen receptor. Additionally, this membrane antigen cannot be expressed in vital organs. Otherwise, fatal toxicity can occur when the vital organs are targeted by CAR T cells.

Prostate cancer can be made amenable to CAR T cell therapy owing to its unique features. First, prostate is not a vital organ for human survival; therefore, collateral damage to normal prostate tissue during therapy can be tolerated. Second, prostate-specific membrane antigen (PSMA) has been identified as a prostate cancer-selective surface antigen, and is required for optimal prostate cancer progression. CAR T cells can thus be engineered to target PSMA on prostate cancer cells. Third, PSMA is expressed across all stages of prostate cancer, but not in other vital tissues in adults. Mice deficient in PSMA (also known as GCPII/Folh1) appear to be normal. Therefore, no fatal toxicity is anticipated for PSMA-specific CAR T immunotherapy. Finally, based on the proprietary five mouse monoclonal antibodies (mAbs) against human PSMA extracellular domain, multiple PSMA-specific CARs have been developed which conferred upon human T cells potent in vitro and in vivo anti-prostate cancer activity (FIG. 16).

Figure 17:
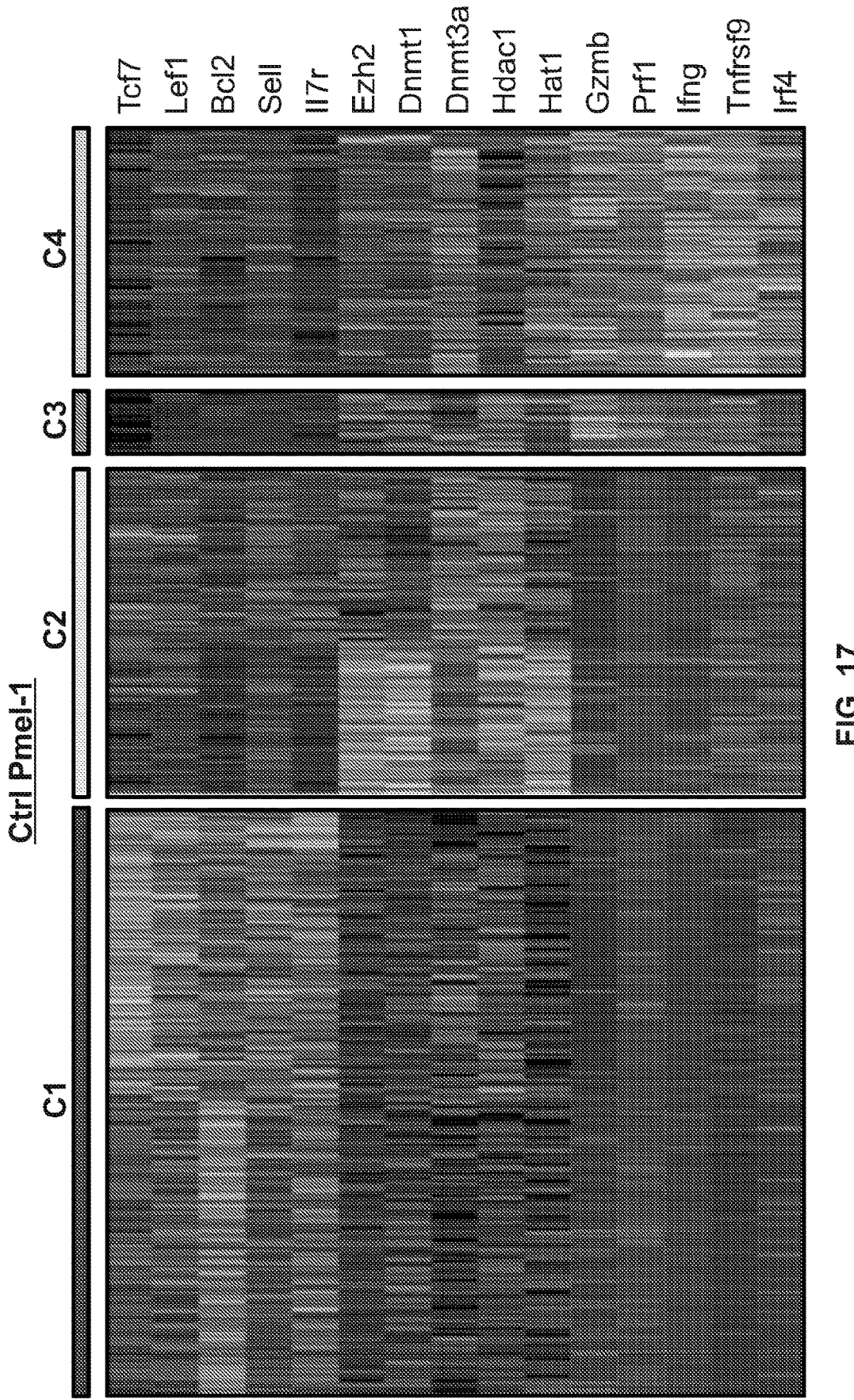
FIG. 17 shows the cluster heat map of single cell RNA-seq analysis of tumor infiltrating control and IRF4-ovexpressing pmel-1 CD8-f T cells. The tumors were isolated from mice treated with pmel-1 CD8+ T cells transduced with GFP control retrovirus. Tumor infiltrating pmel-1 CD8+ T cells are classified based on the expression profiles of signature genes.
Figure 17:
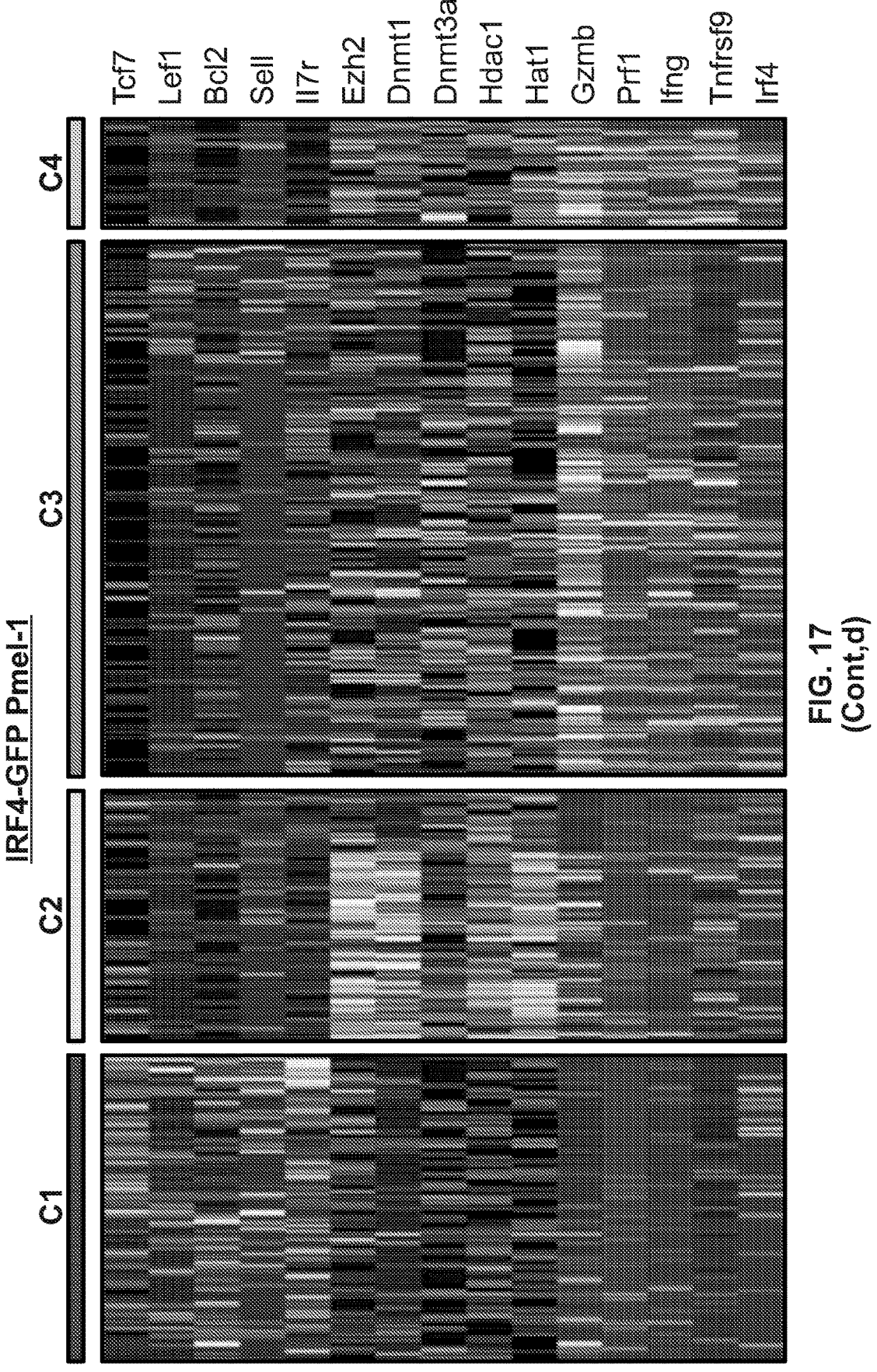

Although CAR T cell therapy has achieved success in hematological cancers, solid tumors remain a big challenge. Weaknesses with current CAR cell therapy against solid tumors include: lack of in viva CAR T cell expansion, short duration of anti-tumor activity, and T cell dysfunction within the tumor microenvironment. How to achieve potent and durable T cell activity in vivo is critical for the success of CAR-T therapy for solid tumors. IRF4 is a member of the IRF family of transcription factors and is specifically expressed in hematopoietic cells. Ablation of IRF4 in CD4+ T cells leads to T cell dysfunction; whereas constitutive overexpression of IRF4 in Pmel-1 CD8+ T cells dramatically increased tumor infiltration and anti-melanoma activity (FIG. 17).

Multiple lines of PSMA-targeted CAR T cells have been developed, which showed potent in vitro and in vivo anti-prostate cancer activity, more potent than a positive control PSMA-CAR derived from the famous J591 antibody, which is currently under phase I/II clinical trials. The present study shows (i) PSMA-targeted CAR T cells can specifically kill prostate cancer cells by recognizing the PSMA antigen on cancer cell membrane, bypassing the requirement of TCR/MHCI interaction; and (ii) PSMA-CAR T cells with engineered IRF4 expression can achieve more potent and durable in vivo cytotoxicity against metastatic prostate cancer.

Figure 18A:
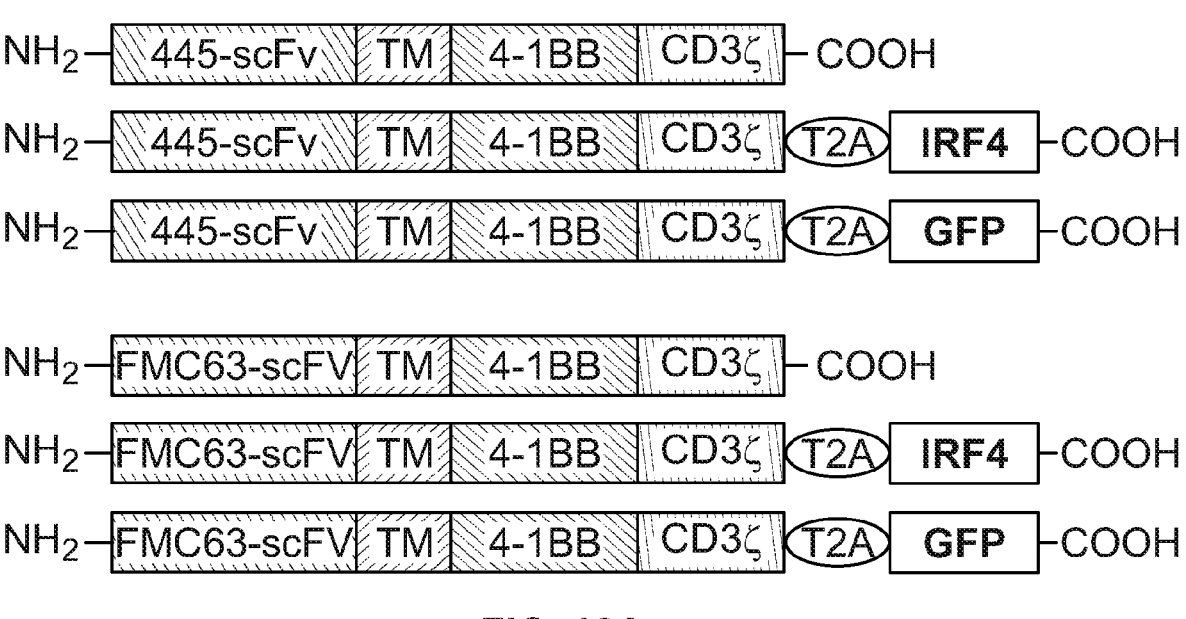
FIGS. 18A-18D show that IRF4 overexpression dramatically enhanced in vitro CAR T cell expansion.

The strategy shown herein is innovative. First, many strategies have been reported to enhance the efficacy of CAR T cell therapy against solid tumors, including co-expression of c-Jun, CD40 ligand (CD40L), OX40. IRF4 was identified as a key regulator of T cell activity. IRF4 ablation in CD4+ T cells results in T cell dysfunction and transplant acceptance in mice, whereas IRF4 overexpression in murine Pmel-1 CD8+ T cells resulted in more potent and durable in vivo anti-melanoma activity. Here, IRF4 was overexpressed in CAR T cells to achieve more potent anti-prostate cancer efficacy. Compared to CD40L or OX40 which requires interaction with receptor molecule CD40 or OX40L to be activated, TRH confers upon CAR T cells autonomous activation. Indeed, it was found that overexpression of IRF4 alone dramatically increased the in vitro expansion of PSMA-CAR T cells and CD19-CAR T cells (FIGS. 18C, 18D).

Second, there are a few reports of PSMA-CAR T cells in the literature. These PSMA-CARs were designed based on one PSMA antibody such as J591. In the current study, based on five anti-PSMA mAbs, 10 PSMA-CARs were constructed, and their in vitro cytotoxicity and cytokine induction was tested. The most active PSMA-CARs were then tested for their in vivo anti-cancer activity in mice. As a result, the two most potent PSMA-CARs are more effective than the positive control PSMA(J591)-CAR, which was developed by Dr. Carl June and is currently in Phase I/II clinical trials.

Figure 12A:
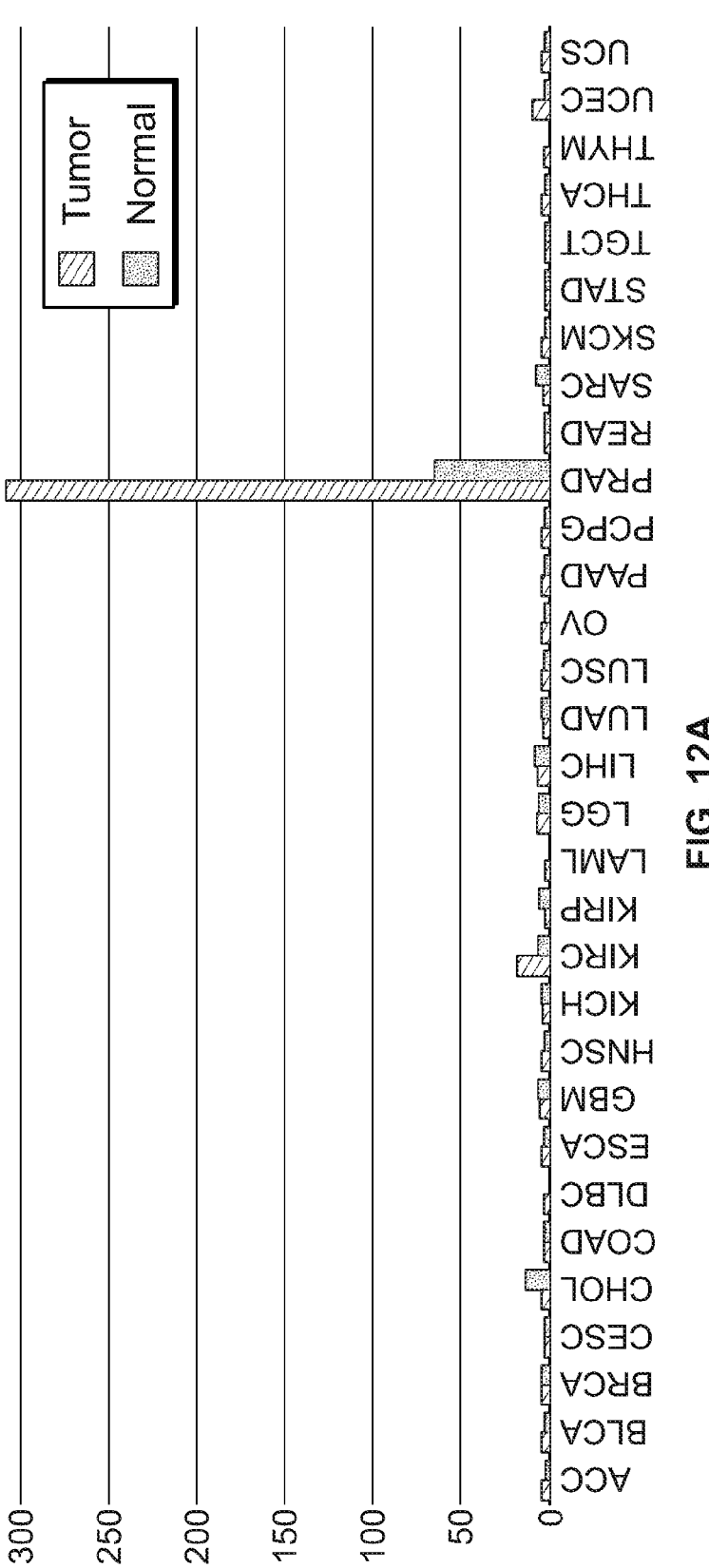
FIGS. 12A-12B show PSMA snRNA levels in human normal tissues and tumor samples.
Figure 12B:
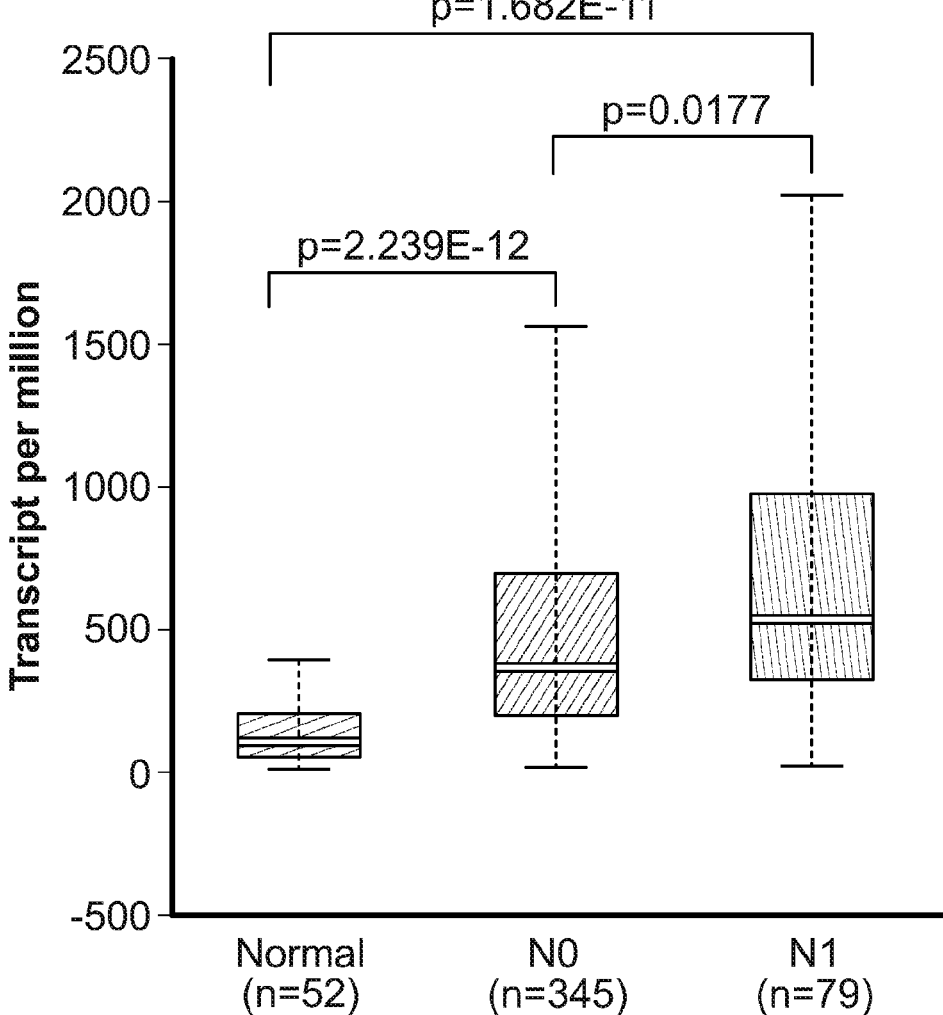

RESEARCH STRATEGY. (A1). Selective PSMA expression in normal prostate tissue and prostate cancer. Prostate-specific membrane antigen (PSMA) has been identified as a prostate cancer-selective surface antigen. PSMA mRNA expression levels in normal human tissues and tumor samples were analyzed based on an interactive web server GEPIA (Gene Expression Profiling interactive Analysis) for the RNA sequencing expression data of 9,736 tumors and 8,587 normal samples from the TCGA and GTEx projects, and another interactive web resource UALCAN for cancer TCGA OMICS data. Shown in FIG. 12A, PSMA mRNA is selectively expressed in normal prostate and its expression is much higher in prostate tumors. Shown in FIG. 12B, compared with normal prostate tissues, PSMA mRNA level is increased in primary prostate tumors (N0), and further increased in metastatic prostate tumors (N1).

Figures 13A, 13B:
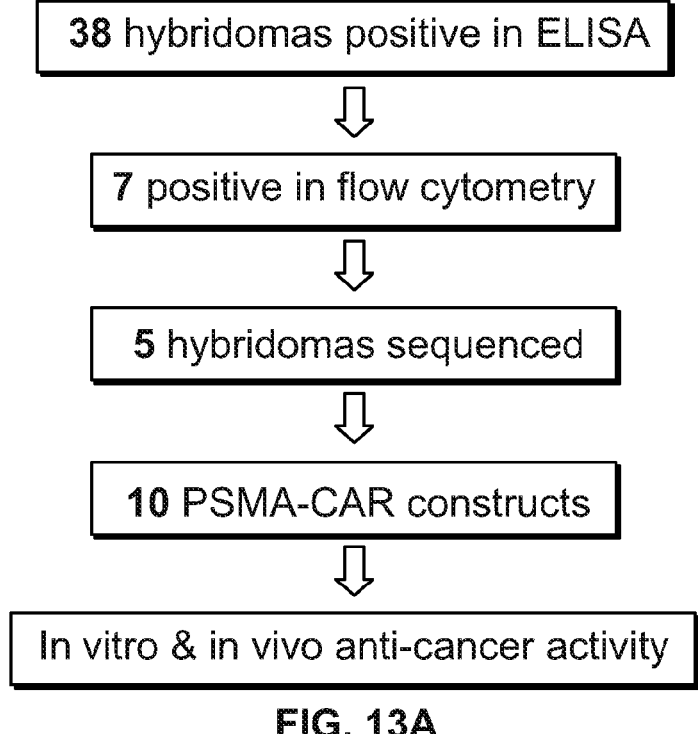
FIGS. 13A-13D show work flowchart and construction of PSMA-CARs.

(A2). Development of anti-PSMA mAbs and construction of PSMA-CARs. The process of PSMA-CAR T cell therapy development is shown in the flowchart (FIG. 13A). PSMA extracellular domain was produced in baculovirus-insect cell expression system as reported. Purified recombinant PSMA protein was used to immunized BALB/c mice. Out of 38 ELISA-positive hybridomas, seven were confirmed by flow cytometry for their antibody-specific binding to PSMA-positive LNCaP and VCaP cells, but not to PSMA-negative PC3 cells. Five mAbs were purified and their binding affinities and kinetics were measured by Biacore SPR, which showed moderate to high affinities to the recombinant PSMA protein (FIG. 13B), J591 antibody was included as a control, and its affinity was previously reported.

Figure 13C:
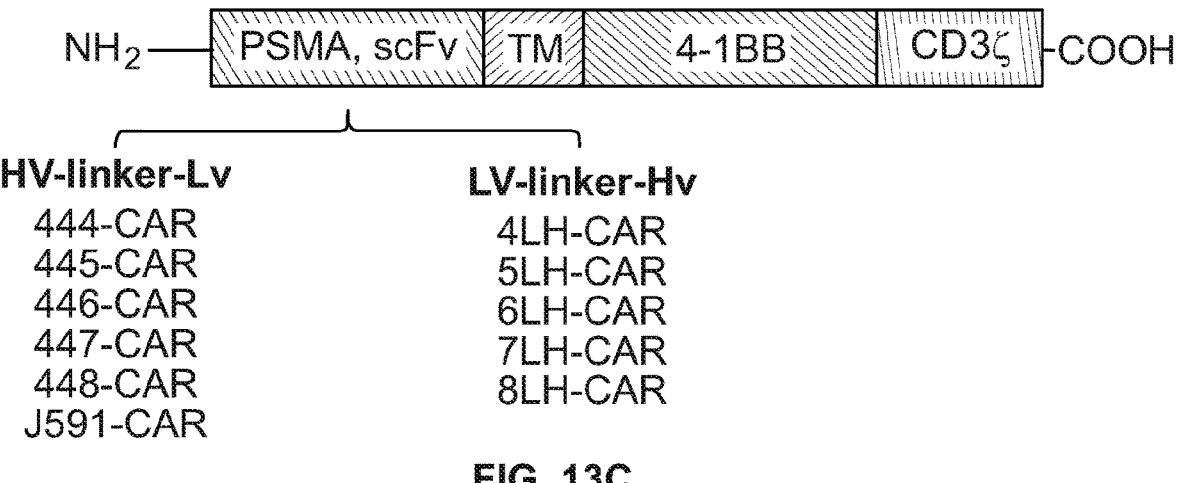
Figure 13D:
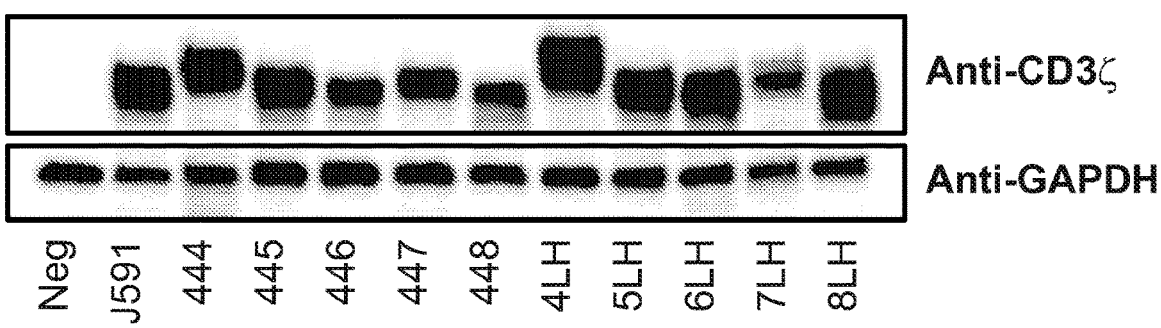

Next, the variable regions of heavy and light chains for five hybridomas were sequenced, and 10 scFv sequences were produced, with each antibody resulting in two scFvs in either heavy chain-linker-light chain (Hv-linker-Lv) or Lv-linker-Hv orientation. PSMA-CARs were designed using the same strategy as reported by Dr. Carl June, and placed in self-inactivating lentiviral vector under the control of EF1α promoter. PSMA(J591)-CAR was constructed as a positive control based on the published murine J591 scFv sequence. Shown in FIG. 13C, CAR contains a short signal peptide (not shown in the diagram), scFv domain, CD8a transmembrane domain (TM), 4-1BB signaling domain, and CD3ζ signaling domain. PSMA-CAR constructs were transiently transfected into HEK293T cells, and Western blot was performed to confirm the expression of PSMA-CARs using anti-CD3ζ antibody (FIG. 13D).

(A3). In vitro cytotoxicity of PSMA-CAR T cells. Human peripheral blood mononuclear cells (PBMC) were isolated from leukopak following a SOP published by Hanc (HIV/ADIS Network Coordination). T cells including CD4+ and CD8+ T cells were isolated from PBMC with human T cell isolation kit (Miltenyi Biotec). T cells were activated by Dynabeads human T-Activator CD3/CD28 (ThermoFisher) for 24 hrs, then transduced with lentiviruses expressing PSMA-CARs. Transduced cells were expanded for 8 to 21 days in culture. Flow cytometry was performed to determine the percentage of T cells that express functional CAR. To prepare home-made fluorescent probe, we labeled purified PSMA protein with biotin using EZ link Sulfo-NHS-Biotin (ThermoFisher), then incubated with Alexa Fluor® 647 Streptavidin (BioLegend) to obtain the probe.

The in vitro cytotoxicity was measured using luciferase-based lysis assay as reported. Briefly, cancer cells were plated in black clear bottom 96-well plates. CAR T cells were added next day in varying effector-to-target (E:T) ratios. Plates were incubated for another 20 hrs, then washed with PBS before luciferin substrate was added. Luciferase activity was measured using BioTek microplate reader. The formula to calculate the percent cytotoxicity is as follows; % killing=(total luciferase−X)/(total luciferase−spontaneous luciferase)*100. Total luciferase is the luciferase activity in untreated well, whereas X is luciferase activity in assay well. Specific release of IFNγ and granzyme B into the cell culture supernatant was measured using human IFNγ and Granzyme B DuoSet ELISA (R&D Systems).

Figures 14A, 14B:
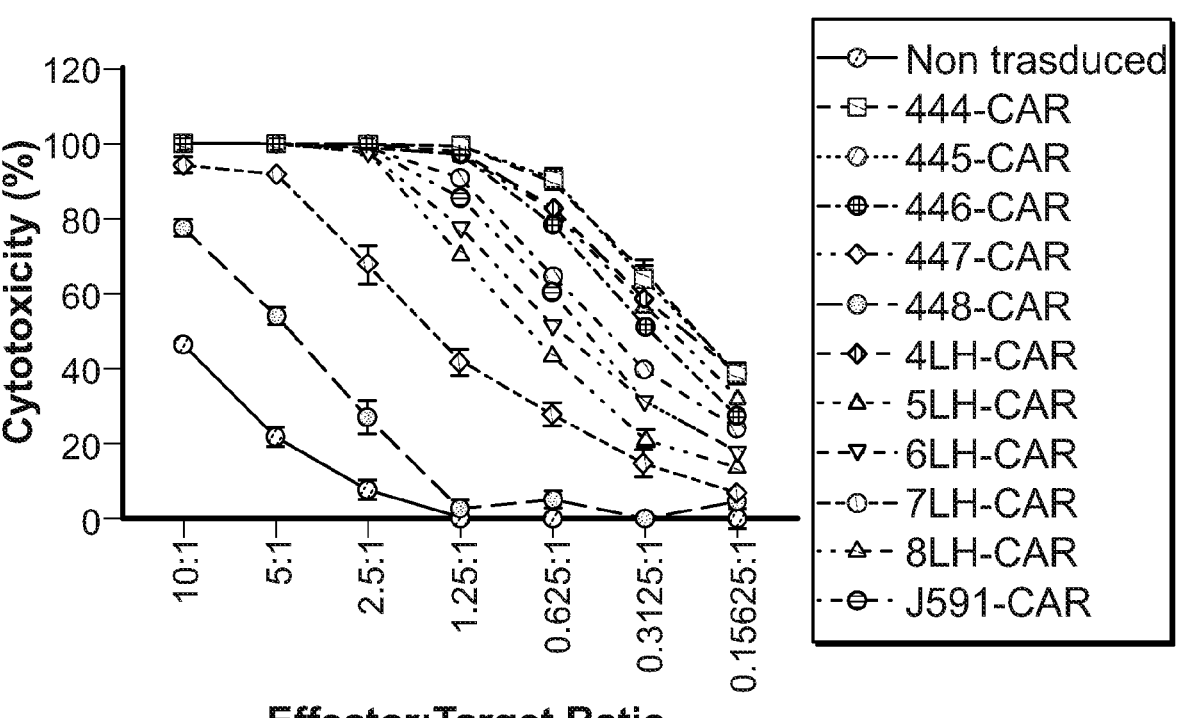
FIGS. 14A-14D show in vitro anti-prostate cancer activity of 11 lines of PSMA-CAR T cells.
Figure 14C:
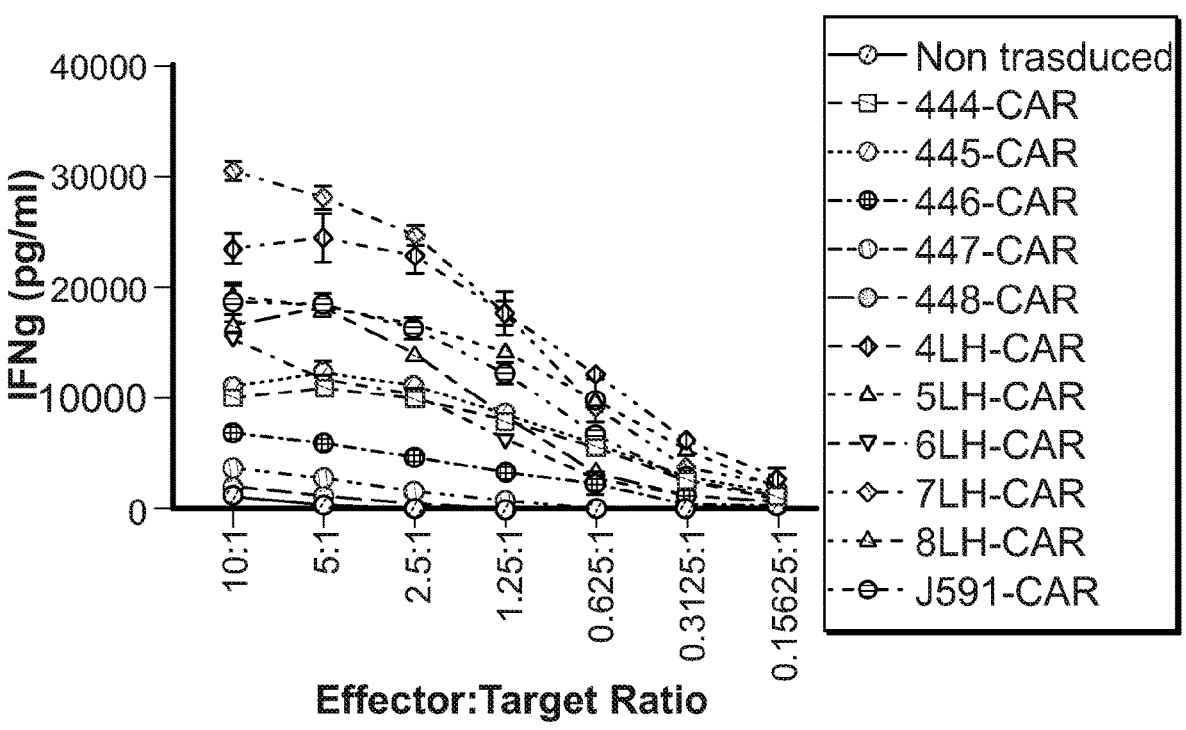
Figure 14D:
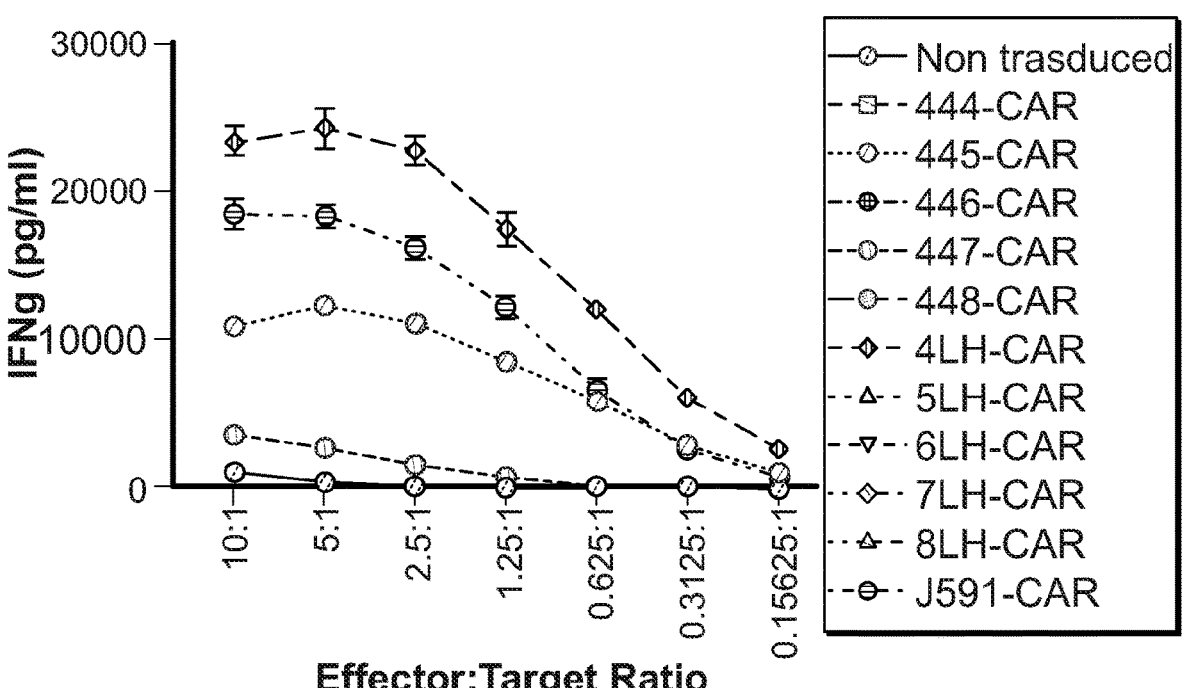
Figure 15A:
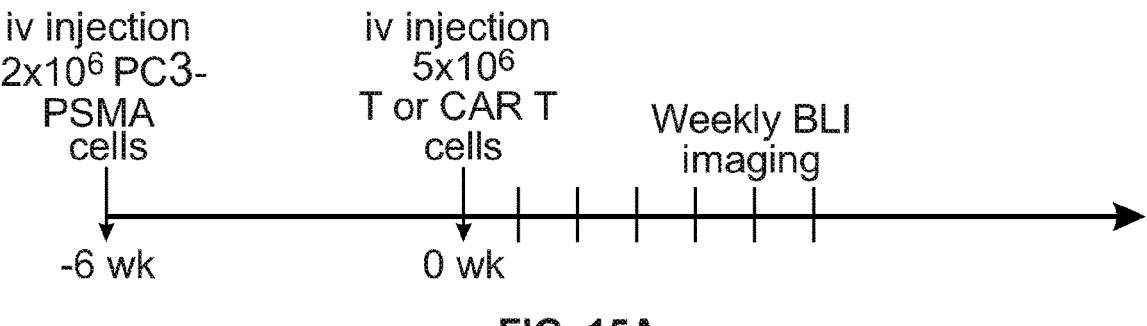
FIGS. 15A-15D show in vivo anti-prostate cancer efficacy of PSMA-CAR T cells.
Figure 15B:
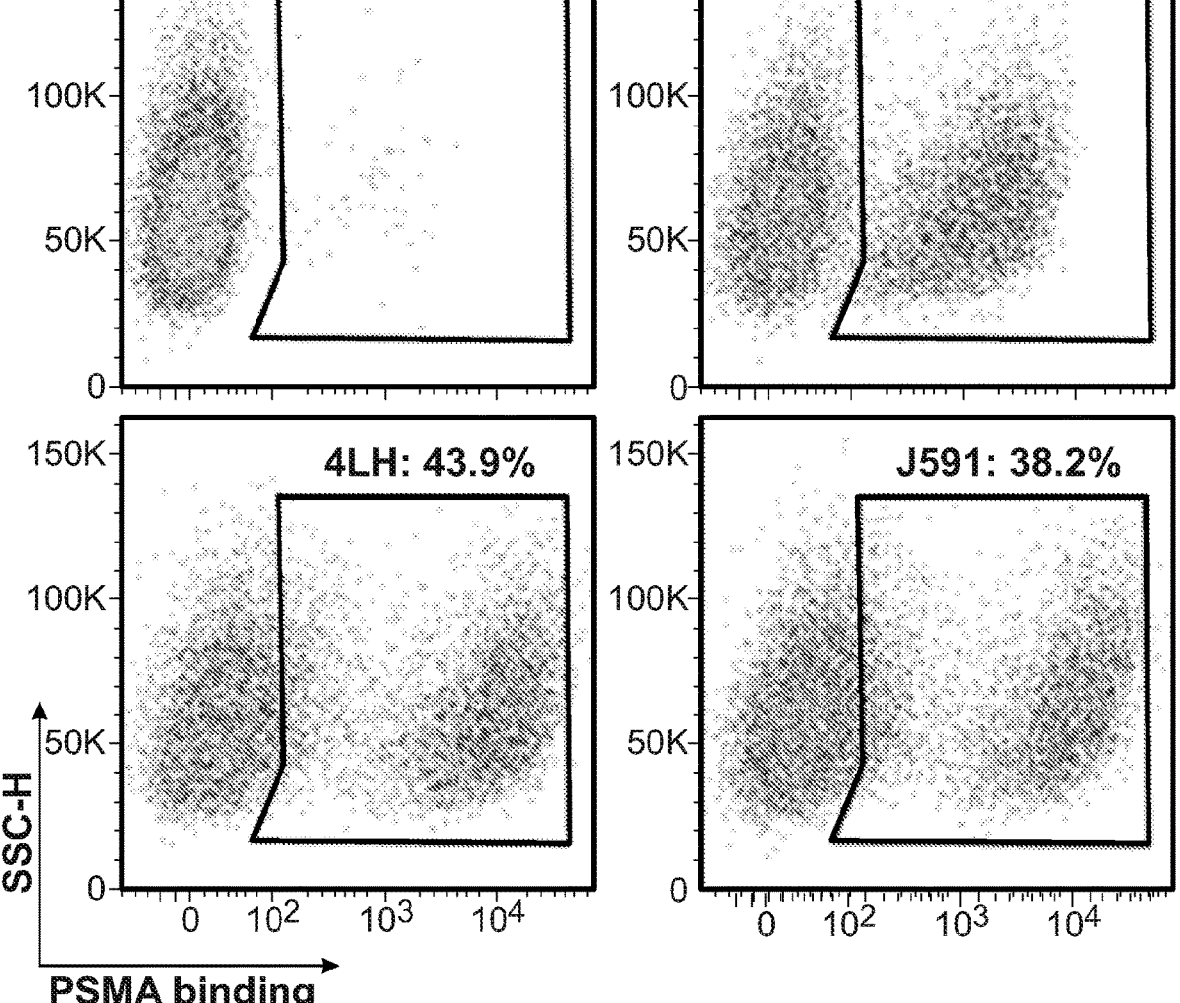

Shown in FIGS. 14A and 14B, among 11 PSMA-CARS, 445-CAR, 444-CAR, and 4L H-CAR showed the highest cytotoxicity, whereas J591-CAR was in the middle. For IFNγ induction (FIGS. 14C, 14D)), 4LH-CAR, 7LH-CAR, 5LH-CAR appeared to be the strongest. 445-CAR and J591-CAR also induced very high levels of IFNγ, but not as high as 4LH-CAR. We also tested the in vitro killing on PSMA-positive VCaP cells, PSMA-negative wild type PC3 cells, and PSMA-positive PC3-PSMA stable cells. As anticipated, the PSMA-CAR T cell cytotoxicity IFNγ induction were strictly PSMA-dependent. Moreover, using fluorescence labeled recombinant PSMA protein as probe, flow cytometry analysis was performed on non-transduced and 11 PSMA-CAR T cells. The percentages of CAR T cells positive for PSMA binding are as follows: 0.48%, 38.2%, 47.1%, 38.8%, 19.6%, 3.08%, 2.23%, 43.9%, 53.0%, 17.8%, 35.5%, 16.0%, in the same order as the Western blot samples shown in FIG. 13D. Representative contour plots are shown in FIG. 15B.

(A4). PSMA-CAR T cells showed potent anti-prostate cancer efficacy in NSG mice. Based on in vitro cytotoxicity and IFNγ induction, we chose 445-CAR and 4LH-CAR to investigate their in vivo anti-cancer activity along with the control J591-CAR, 8-14-week-old male NSG mice were intravenously injected with 2×10⁶ luciferase-expressing PC3-PSMA stable cells. LNCaP or VCaP cells were not used because they cannot grow metastatic tumors when intravenously injected into NSG mice. PC3-PSMA metastatic tumors were established 6 weeks later. Tumor burden was determined by IVIS imaging after 150 mg/kg D-Luciferin was injected intraperitoneally. Mice were separated into four groups to ensure each group has similar tumor burden.

Shown in FIG. 15, two weeks after CAR T cell injection, 445-CAR and 4LH-CAR T cells eradicated cancers in all the mice, whereas J591-CAR T cells killed vast majority of cancer cells, as compared to the non-transduced control group. These data indicate that PSMA-CAR T cells effectively eliminated metastatic prostate cancer in mice, and our 445-CAR and 4LH-CAR were more effective than J591-CAR.

Figure 16A:
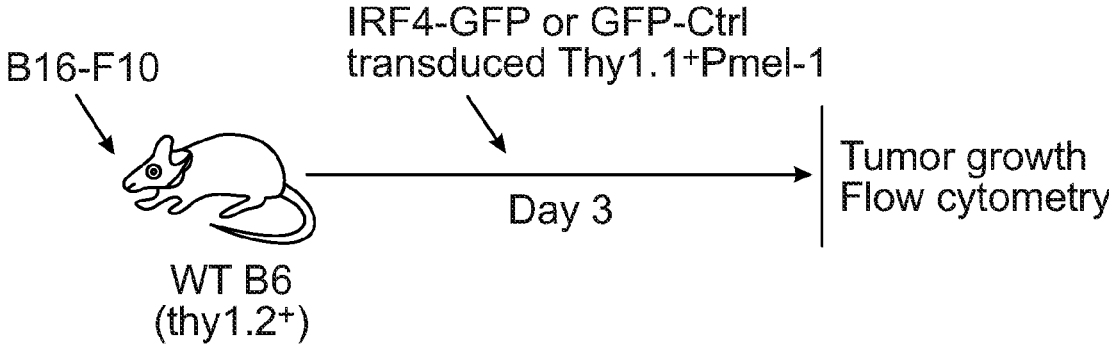
FIGS. 16A-16F shows that IRF4 overexpression increased tumor infiltration and anti-tumor activity of therapeutic CD8+ T cells.
Figure 16B:
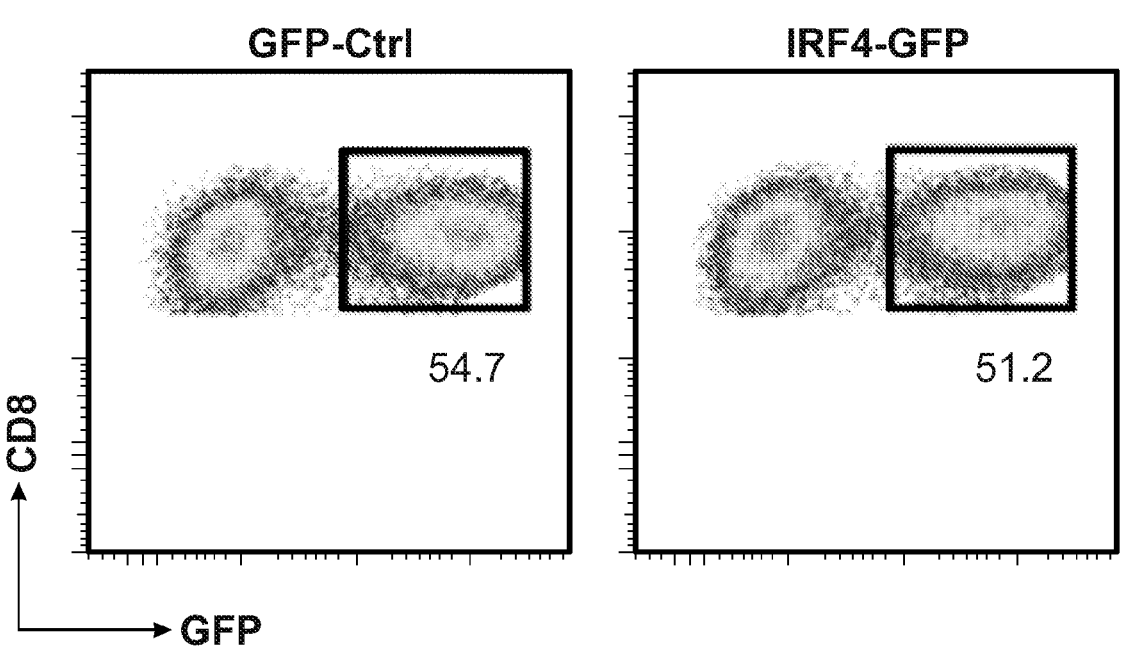
Figure 16C:
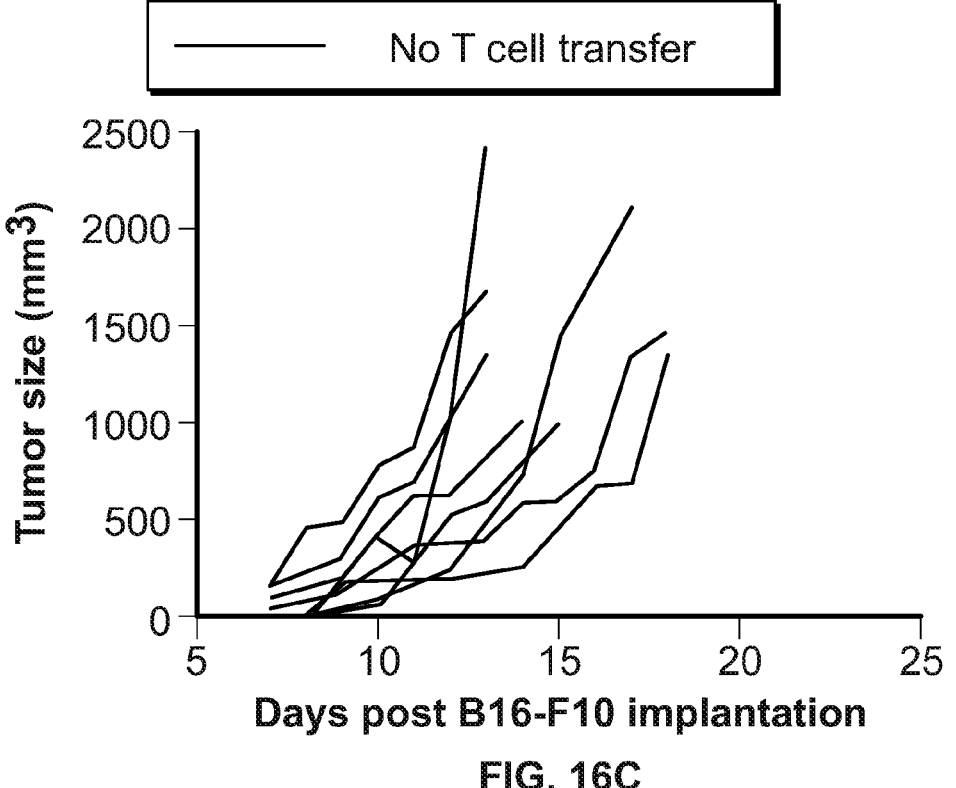
Figures 16C, 16D:
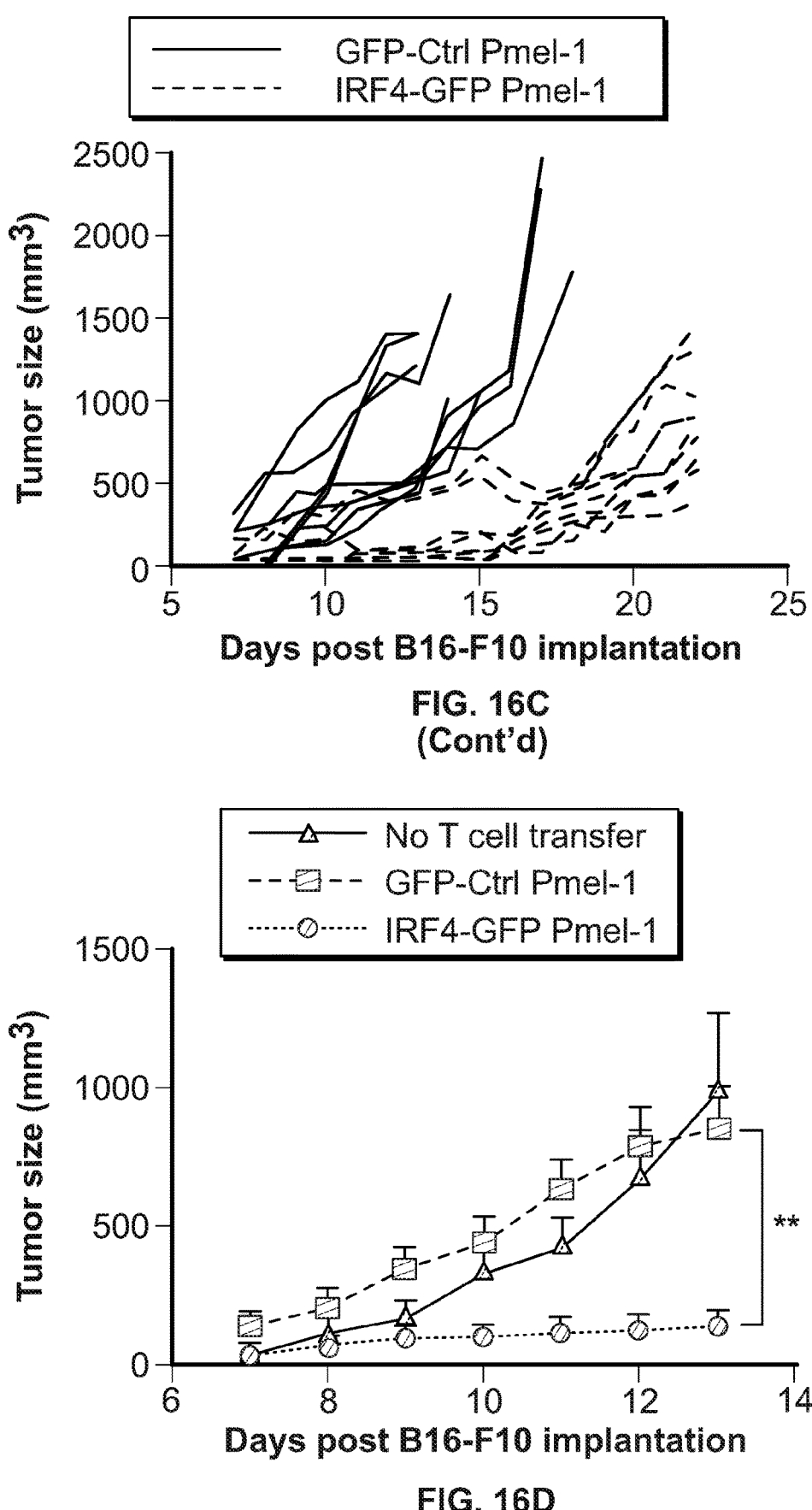
Figure 16E:
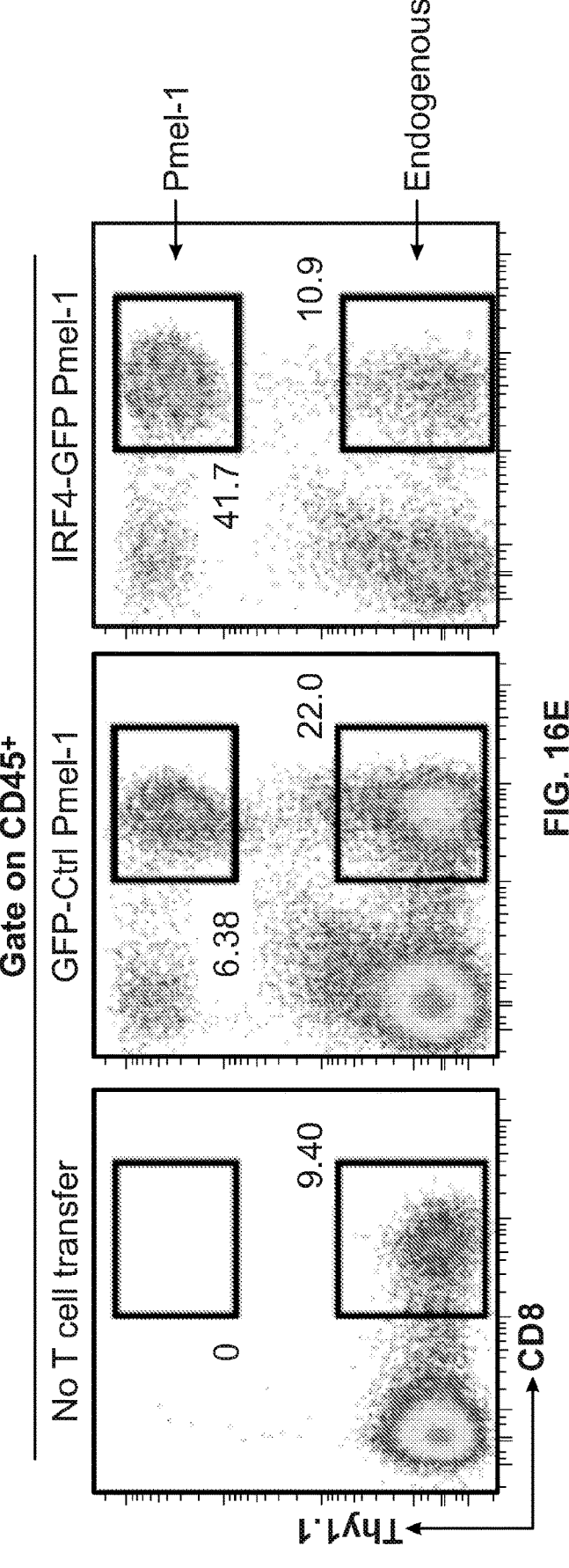

(A5). IRF4 overexpression in antigen specific CD8+ T cells increased the anti-cancer activity. To test whether IRF4 overexpression can enhance CD8+ T cell activity, the Pmel-1 TCR transgenic mouse model was utilized, which is a well-established mouse model to study anti-cancer activity of CD8+ T cells. This mouse contains melanoma-reactive CD8+ T cells that are specific to H2-D$^b$-restricted nonmutated-self/tumor-antigen gp100$_{25-33}$. Splenocytes from Panel-1 transgenic mice were first stimulated with 1 μM hgp100$_{25-33}$ peptide for 24 hrs, and transduced with retroviruses expressing IRF4-GFP or GFP-alone. 24 hrs later, more than 50% Pmel-1 T cells were found to be positive for GFP expression (FIG. 16B). On day 3 after subcutaneous implantation of 0.5×10$^6$ B16-F10 cells. Thy1.2+B6 host mice were adoptively transferred with 1×10$^6$ IRF4-GFP-Pmel-1 or GFP-Panel-1 T cells or untreated. Tumor growth was measured using a vernier caliper. Transferred Pmel-1 T cells were analyzed by flow cytometry (FIG. 16E). It was found that adoptive transfer of IRF4-GFP-Pmel-1 T cells, but not GFP-Pmel-1 T cells, significantly inhibited B16-F10 melanoma growth in mice (FIGS. 16C, 16D).

Figure 16F:
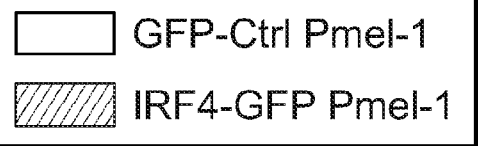
Figure 16F:
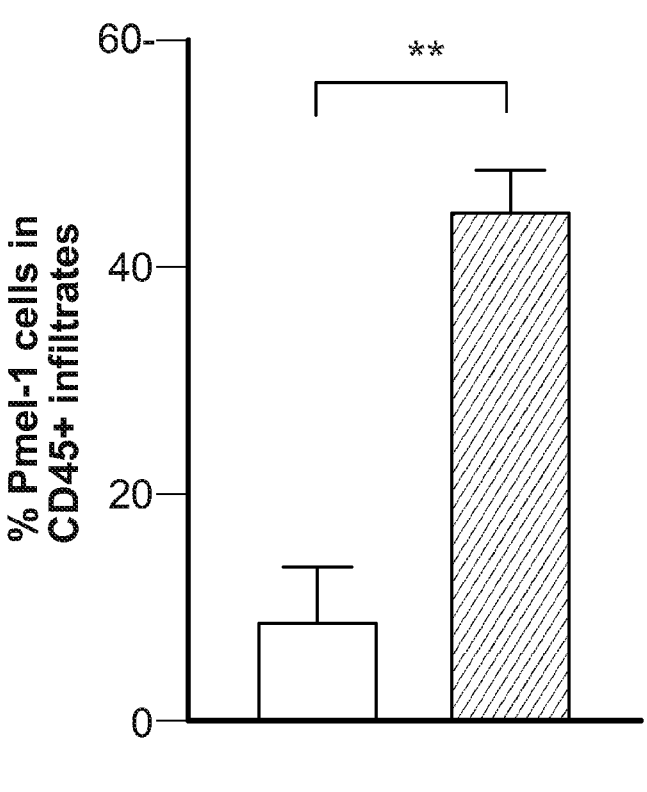

On day 14 post B16-F10 implantation, the transferred Thy1.1+Pmel-1 T cells from both IRF4-GFP and GFP-control groups were present in spleens and draining lymph nodes (DLN)s, and maintained GFP expression after infiltrating into B16-F10 tumors. Of note, more than 40% of CD45+ tumor-infiltrating leukocytes were the transferred Thy1.1+Pmel-1 T cells in the IRF4-GFP group, a percentage that was significantly higher than that in the GFP-control group, which was about 10% (FIGS. 16E and 16F). Compared with those in the GFP-control group, tumor-infiltrating Pmel-1 T cells in the IRF4-GFP group expressed significantly higher levels of IRF4 as anticipated and the proliferation marker Ki67. Moreover, tumor-infiltrating GFP+ Pmel-1 T cells in the IRF4-GFP group produced significantly higher levels of pro-inflammatory cytokines IFN-γ and TNF-α than those in the GFP-control group. Collectively, IRF4 overexpression in Pmel-1 CD8+ T cells increased their tumor infiltration and anti-cancer activity, and inhibited melanoma progression in mice.

(A6). Single cell RNA-sequencing analysis of tumor infiltrating lymphocytes. To understand the underlying mechanisms by which IRF4-expressing Pmel-1 CD8+ T cells have more potent anti-cancer activity, single cell RNA-seq analysis was performed on the infiltrating lymphocytes isolated from B16-F10 melanoma tumor tissues. As described in FIG. 16, subcutaneous B16-F10 melanoma tumors were isolated from mice 15 days after Pmel-1 CD8+ T cells injection. Tumor infiltrating lymphocytes were isolated from the tumor tissues using Lympholyte®-M Cell separation media (CL5035, Cedarlane) following the manufacturer's instructions. 10× Genomics RNA-sequencing was performed by the Single Cell Genomics Core at the Baylor College of Medicine. Shown in FIG. 17 left panel, tumor infiltrating Pmel-1 CD8+ T cells can be classified into four major groups based on unsupervised clustering: C1, TCF7-positive naïve like memory T cells; C2, transition T cells; C3 type I effector T cells; and C4, type 2 effector T cells. The type 2 effector T cells express high levels of IRF4, Granzyme B (Gzmb), perforin 1 (Prf1), interferon gamma (Ifng), and low levels of PD1 (pdcd1). This group of T cells consist of ~20% of total tumor infiltrating Pmel-1 CD8+ T cells and are believed to be the major functional effector T cells.

In addition, single cell RNA-seq was performed on tumor infiltrating lymphocytes isolated from mice treated with IRF4-expressing Pmel-1 CD8+ T cells (FIG. 16, right panel). It shows that ~40% of tumor infiltrating T cells are functional effector T cells in IRF4-expressing group, in comparison to ~20% of tumor infiltrating T cells in GFP-expressing group. This result shows that forced IRF4 expression in CD8+ T cells helps more functional effector T cells to infiltrate solid tumors. Forced IRF4 expression can help T cells to maintain the functional effector status inside the solid tumors. This result provides a mechanism by which IRF4-expressing Pmel-1 CD8+ T cells have more potent anti-cancer activity against solid tumor melanoma.

Research Design and Methods.

1) Develop IRF4-Invigorated PSMA-Specific CAR-T Cells and Test Their In Vitro and In Vivo Anti-Prostate Cancer Activity.

Generation of CAR constructs that co-express IRF4. Co-expression of IRF4 was done by linking IRF4 to CAR with a self-cleaving T2A peptide (FIG. 18A). This strategy has been used to co-express dominant-negative TGFβ receptor or CD40 L in CAR T cells. Co-expression of IRF4 with PSMA(445)-CAR was first tested. The transcriptional activity of IRF4 expressed from the PSMA(445)-CAR-IRF4 was verified by transient transfection luciferase reporter assay (FIG. 19B). IRF4-overexpressing PSMA(445)-CAR showed dramatically increased in vitro expansion (FIG. 18C). IRF4 was also co-expressed with CD19-CAR, and similarly, IRF4 overexpression caused significantly increased in vitro expansion (FIG. 18D).

Accumulating evidence indicates that IFNγ is critical for in viva CAR T cell cytotoxicity and IFNγ signaling is essential for the anti-cancer efficacy of anti-PD-1 and anti-CTLA4 therapies. Because 4LH-CAR exhibited the highest IFNγ induction (FIG. 14D), both PSMA(445)-CAR-IRF4 and PSMA(4LH)-CAR-TRF4 are generated and tested in the following experiments.

In vitro cytotoxicity assay. Similar to the studies described above, human T cells are isolate from PBMC and transduced with viruses expressing PSMA(445)-CAR, PSMA(445)-CAR-IRF4, PSMA(4LH)-CAR, and PSMA(4LH)-CAR-IRF4. Because these new CAR constructs do not contain GFP, after transduction, the CAR expression on T cells can be confirmed by flow cytometry using home-made Fluor-conjugated recombinant PSMA proteins (FIG. 16B). The in vitro cytotoxicity of PSMA(445)-CAR, PSMA(445)-CAR-IRF4, PSMA(4LH)-CAR, and PSMA(4LH)-CAR-IRF4T-cells against LNCaP cells is measured in the 20-hr luciferase based assay as performed in the studies (FIG. 14). The E:T ratios are from 10:1 to 0.15625:1. Cell culture supernatant is collected, and IFNγ and Granzyme B levels measured by ELISA assays.

Figure 15C:
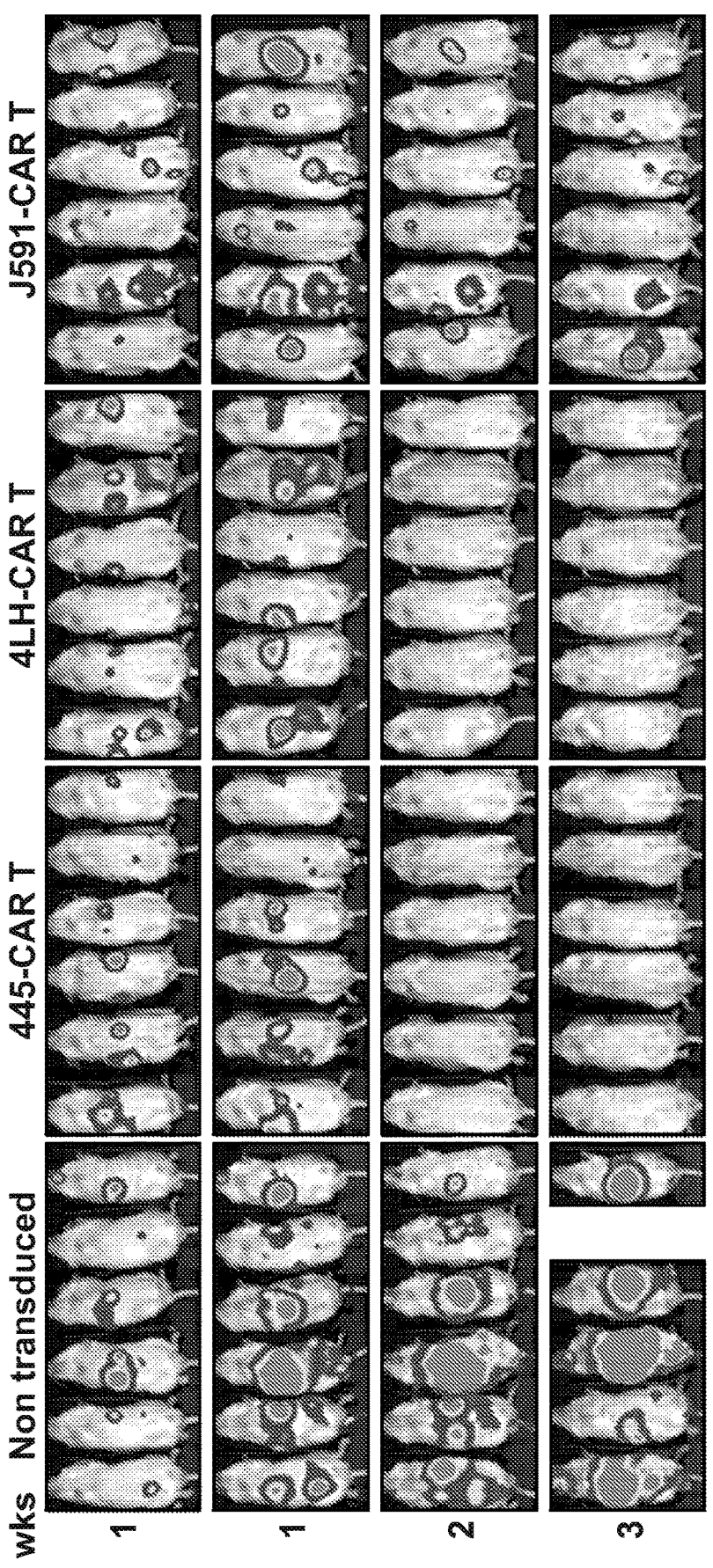
Figure 15D:
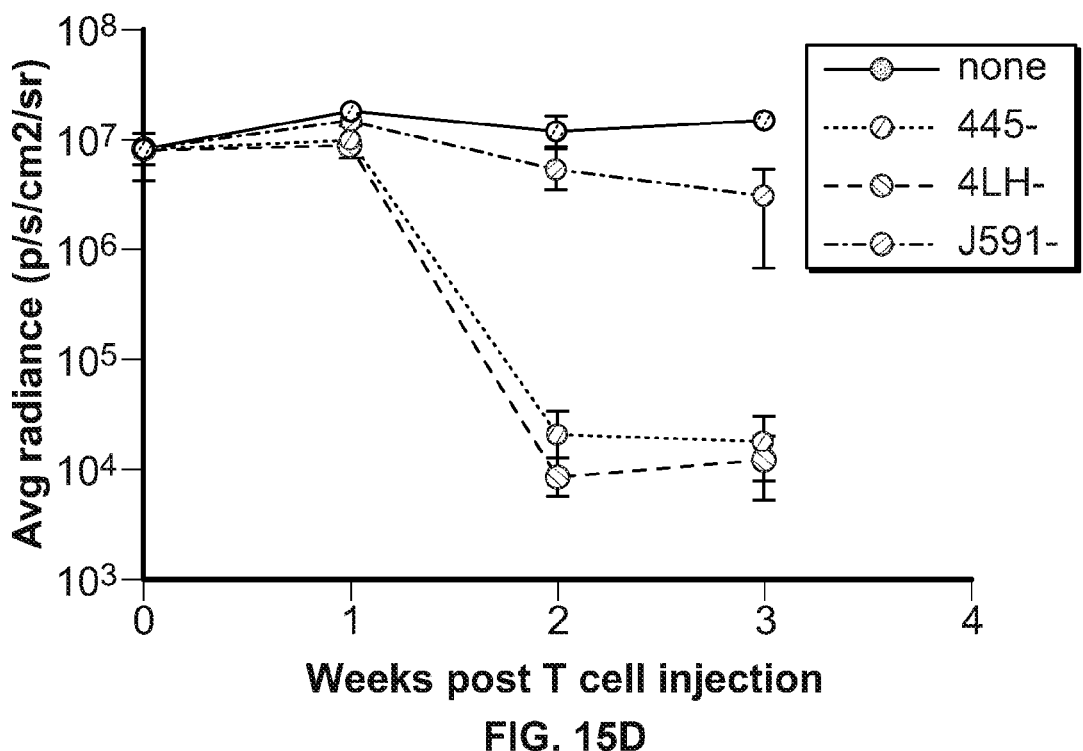

In vivo anti-cancer activity using metastatic prostate cancer mouse model. 8- to 14-week-old NSG male mice are intravenously injected with 2×10$^6$ firefly luciferase-expressing PC3-PSMA cells. Cancers are established systemically for 6 weeks. Then the mice are injected intravenously with 2×10$^6$ human T cells transduced with viruses which express PSMA(445)-CAR, PSMA(445)-CAR-IRF4, PSMA(4LH)-CAR, and PSMA(4LH)-CAR-IRF4. Non-transduced T cells are used as control. Tumor growth is indirectly assessed weekly by bioluminescent imaging until all the control group mice treated with non-transduced T cells die. In this experiment, 2×10$^6$, instead of 5×10$^6$, CAR T cells are use, because 5×10$^6$ PSMA-CAR T cells eliminate all cancer cells within 2 weeks of injection (FIG. 15C). Under this condition, it is difficult to see if IRF4 overexpression can further enhance cancer killing efficacy.

In vivo anti-prostate cancer activity using subcutaneous xenograft prostate cancer mouse model. Although prostate cancer never metastasizes to the skin, subcutaneous xenograft tumor model has been used traditionally to test the efficacy of anti-cancer drugs, especially small-molecule compounds. The PSMA-CARs, particularly PSMA-CAR- IRF4 are tested in the subcutaneous xenograft tumor model in NSG mice. 8-14-week-old NSG male mice are implanted subcutaneously in the left flank regions with LNCaP cells ($5 \times 10^6$ cells/mouse) that stably express luciferase in 100 µl of basement Matrigel. Seven days later, mice will be divided into groups based on tumor size, and receive adoptive transfer treatment with non-transduced T cells, PSMA(445)-CAR, PSMA(445)-CAR-IRF4, PSMA(4LH)-CAR, and PSMA(4LH)-CAR-IRF4 T cells ($5 \times 10^6$ cells/mouse) by intravenous injection. Tumor sizes are measured weekly using a vernier caliper. Tumor volume is determined using the following formula: volume (cm$^3$)=0.5×length×(width)$^2$. Mice are sacrificed 3 weeks after the adoptive transfer or until the tumor diameter reaches 2 cm.

Figure 18B:
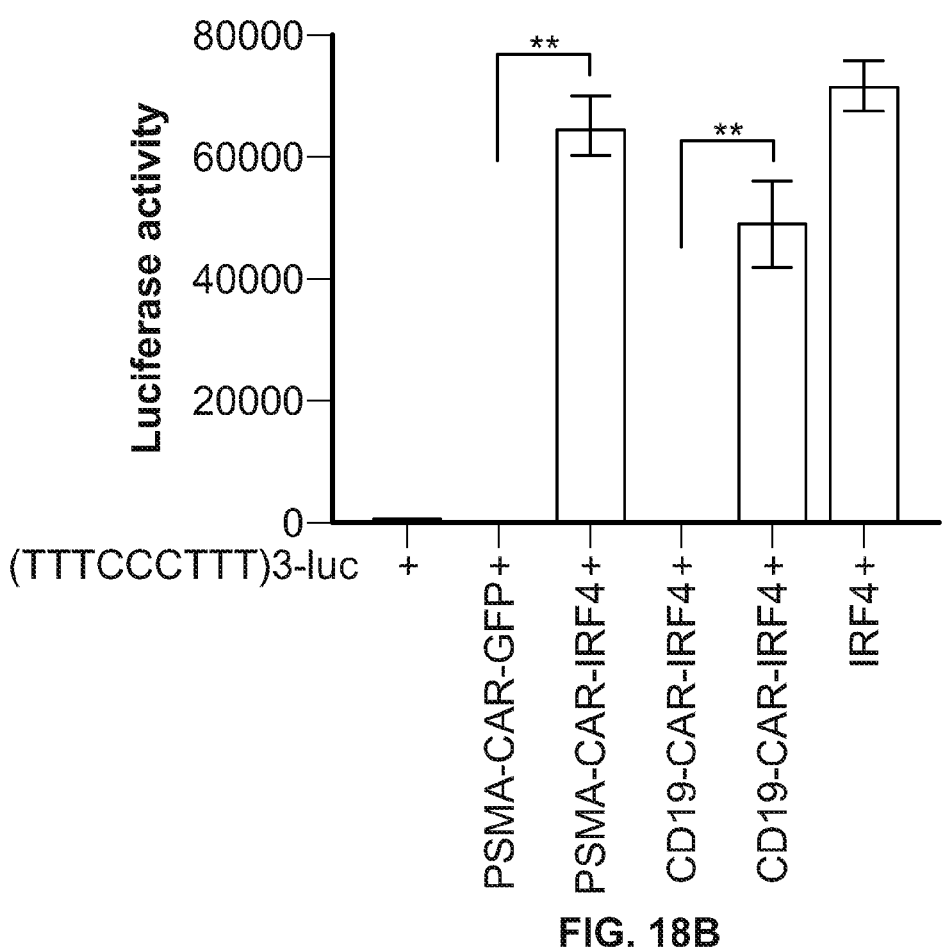
Figures 18C, 18D:
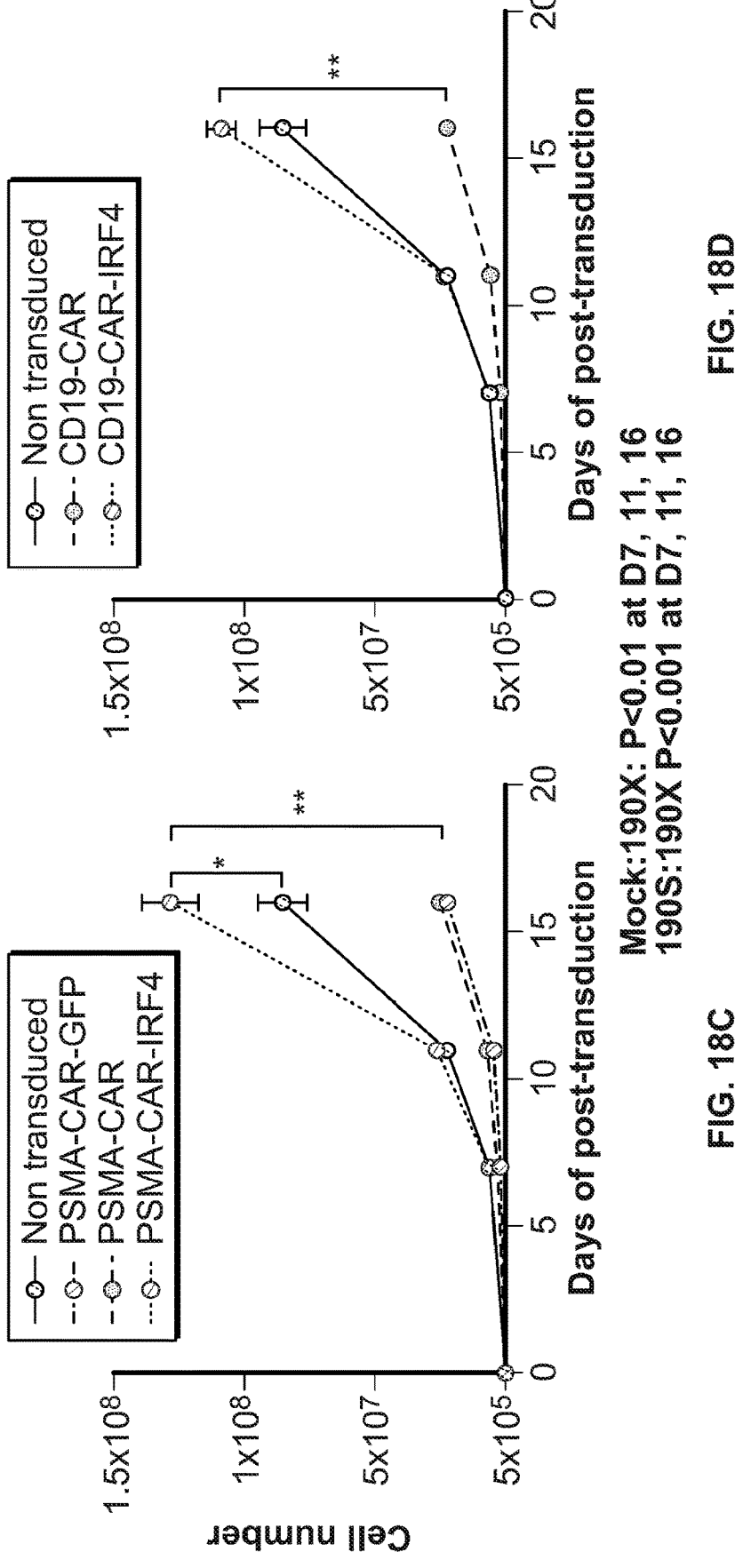
Figure 20C:
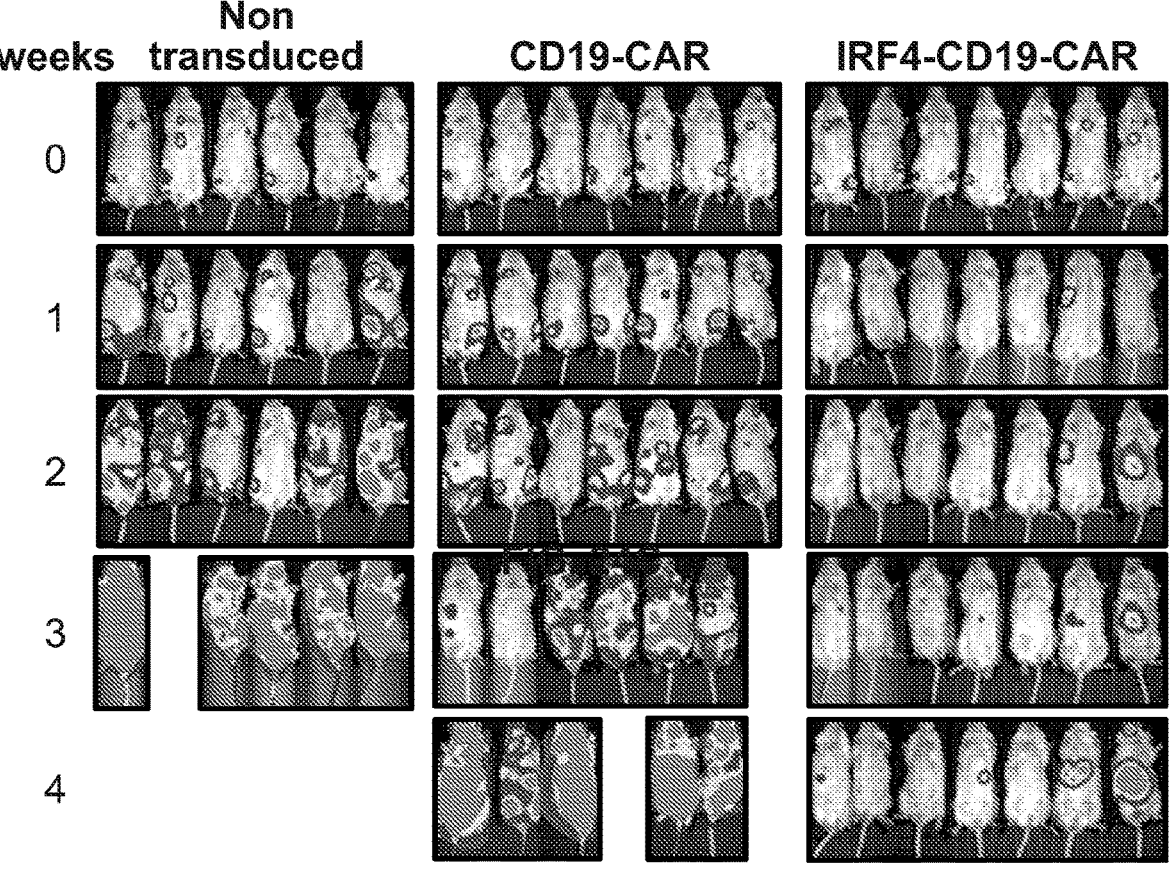
Figure 21:
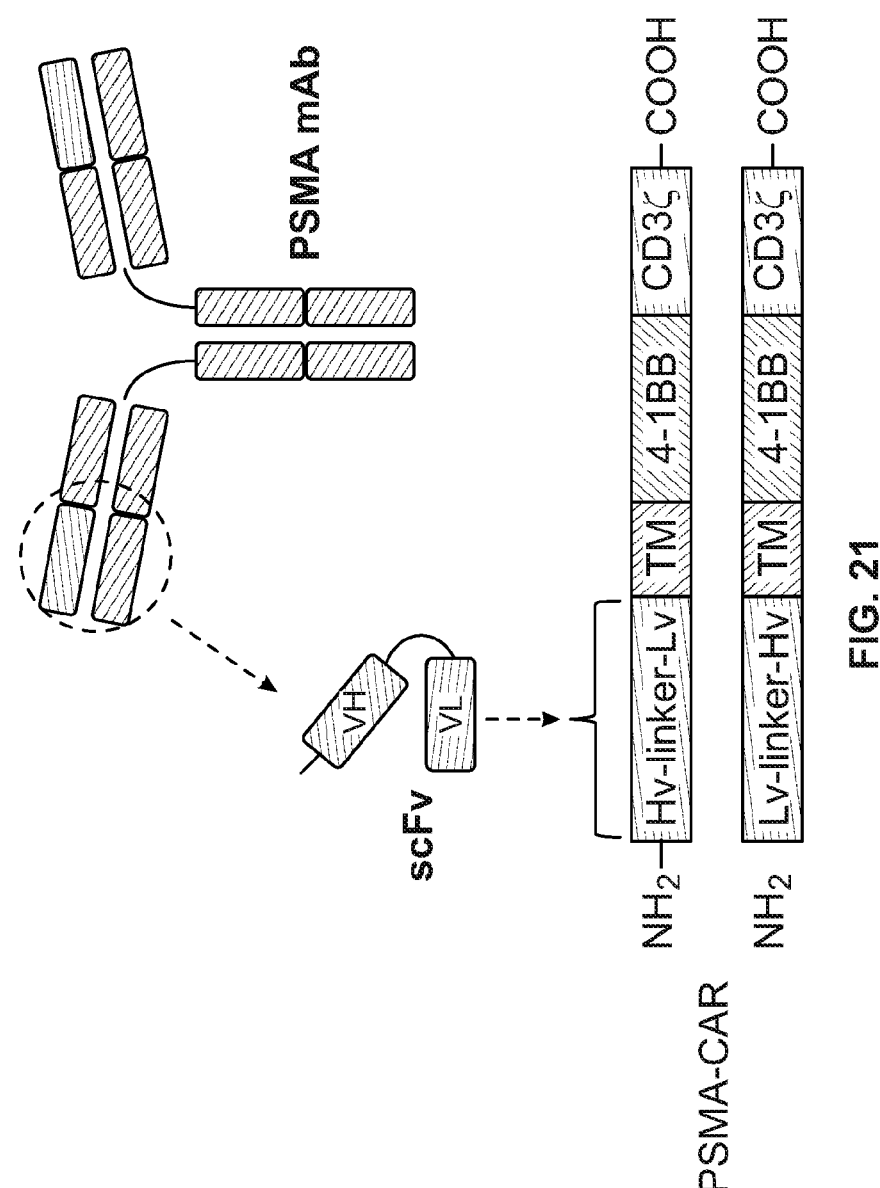
FIG. 21 shows that scFv, derived from monoclonal antibody, retains antigen binding affinity and specificity.

As shown in FIG. 18, IRF4 overexpression dramatically increased in vitro CAR T cell expansion. This effect was also observed in CD19-CAR T cells, indicating that IRF4-induced expansion is not limited to PSMA-CAR. Interestingly, this finding is in line with a previous report that IRF4 is a limiting factor for the clonal expansion of antigen-specific CD8+ T cells, and OT-1 T cells overexpressing IRF4 expanded much better than control T cells in vivo. Moreover, IRF4-overexpressing Pmel-1 T cells also expanded much better than in mice than control Pmel-1 cells, 6.38% vs 41.7% (FIG. 16E). Therefore, IRF4-overexpressing PSMA-CAR T cells can achieve better in vivo expansion and tumor infiltration, resulting in more potent and durable anti-cancer efficacy.

Subcutaneous xenograft tumors are known to be resistant to CAR T therapy. Combination therapies to combine the PSMA-CAR T with oncolytic virus or immunogenic chemotherapy can be applied.

2) Characterize the function of PSMA-CAR-IRF4 T cells by: (i) RNA-seq to identify IRF4-regulated genes in CAR T cells; (ii) single cell RNA-seq to characterize tumor-infiltrating CAR T cells; (iii) studying the effect of IRF4 deficiency on PSMA-CAR T cell activity.

RNA-seq to identify IRF4-regulated genes in human CAR-T cells. IRF4-regulated genes are systematically identified in human CAR T cells by RNA-seq to profile the gene expression in PSMA-CAR and PSMA-CAR-IRF4 T cells. Briefly, human T cells are activated and transduced with viruses expressing PSMA-CAR or PSMA-CAR-IRF4. The resulting CAR T cells are expanded for eight days before being harvested for RNA purification. The mRNA sequencing is based on Illumina NovaSeq platforms with paired-end 150 bp sequencing strategy and 15G raw data per sample. DESeq2 R package is used for differential gene expression analysis of total mRNA transcripts. mRNA sequencing is performed by Novogene, an industrial leader in next-generation sequencing, and the Biostatistics and Bioinformatics Core Laboratory at Houston Methodist will perform the data analysis. IRF4-regulated genes are verified by Western blot analysis, compared with mouse IRF4 target genes, and KEGG pathway analysis is performed with DAVID Bioinformatics Resources.

Single cell RNA-sequencing analysis. Fresh subcutaneous xenograft tumor tissues are isolated from mice treated with non-transduced T cells, PSMA-CAR, or PSMA-CAR-IRF4 T cells, and immediately minced into small pieces using a scalpel, followed by enzymatic digestion the using the tumor dissociation kit (Miltenyi Biotec). Debris is removed by filtering through a 100 µM cell strainer. Dissociated cells will be layered onto a 5-ml density gradient (Cedarlane), followed by centrifuge at 1500 g at room temperature to remove dead cells and red blood cells. The resulting lymphocytes are stained with anti-human CD45

(BioLegend, clone 2D1) and DAPI following Fe receptor blockade (BioLegend). Viable single CD45+ immune cells are sorted on a FACSARIA sorter (BD Biosciences) into 96-well plates containing cold TCL buffer (Qiagen), snap frozen on dry ice, and stored at −80° C. Up to 10,000 cells each sample in biological triplicates are subjected to whole transcriptome amplification, library preparation, and high throughput sequencing by the Single Cell Genomics Core at the Baylor College of Medicine The effect of IRF4 deficiency on PSMA-CAR T cell activity. First, IRF4-deficient T cells are purified from CD4cre;IRF4$^{flox/flox}$ conditional KO mice and IRF4$^{flox/flox}$ control mice using the Dynabeads Untouched Mouse T cells kit (ThermoFisher). Next, IRF4−/− and IRF4+/+ murine T cells are transduced with viruses expressing PSM-CAR or PSMA-CAR-IRF4. The resulting PSMA-CAR murine T cells are tested for their in vitro cytotoxicity against LNCaP, VCaP, PC3-PSMA, and PC3 cells using the 20-hr luciferase-based assay.

In murine T cells, IRF4 is a key regulator of effector T cell function. It suppresses genes involved in T cell dysfunction, while increases the expression of genes involved in cytotoxicity. IRF4 can perform similar function in human CAR T cells. The mRNA-seq experiment provides mechanistic insight into the role of IRF4 in human CAR T-cells by identifying its target genes. IRF4 can have different roles in these two subtypes of CAR T cells. To address this, CD4+ CAR T cells and CD8+ CAR T cells are generated and RNA-seq is performed on them separately to identify IRF4-regulated genes in subtype-dependent manner.

As shown in FIG. 16, IRF4-expressing Pmel-1 CD8+ T cells showed more potent anti-cancer activity. Consistently, more functional effector Pmel-1 T cells were present inside melanoma as revealed by the single cell RNA-seq (FIG. 17). PSMA-CAR-IRF4 T cells have more potent in vivo anti-prostate cancer activity than PSMA-CAR cells, and more functional effector CAR-T cells are identified inside the subcutaneously implanted prostate tumors.

Given the critical role of IRF4 in CD4+ T cell and Pmel1 CD8+ T cells (FIG. 16), IRF4 deficiency in murine T cells ablates the anti-cancer activity of PSMA-CAR cells. Co-expression of IRF4 can rescue PSMA-CAR T activity in the IRF4-deficient T cells.

The anti-human CD45 antibody (BioLegend, clone 2D1) is used to purify tumor infiltrating lymphocytes for single cell RNA-seq. Because this antibody does not recognize mouse CD45, only human PSMA-CAR T cells are adoptively transferred, but not host murine hematopoietic cells. Moreover, NSG mice are severely immunodeficient and deficient in T cell, B cell, NK cells and other innate immunity. Therefore, the impact of IRF4 expression on the differentiation status of tumor infiltrating PSMA-CAR T cells is studied by single cell RNA-seq analysis.

Tumor infiltrating lymphocytes (TILs) are studied in subcutaneous xenograft LNCaP tumors. If there are not enough infiltrating CAR T cells for single cell RNA-seq analysis, metastatic PC3-PSMA tumor model is used. Shown in FIG. 15C, one week after T cell injection, there were still metastatic tumors in mice treated with PSMA-CAR T cells. As an alternative strategy, metastatic tumor samples can be obtained at this time point to perform single cell RNA-seq analysis. Metastatic tumors can be grown longer (8 instead of 6 weeks) before CAR T cell injection in order to get larger tumor tissues to retrieve more TILs for single cell RNA-seq analysis.

Vertebrate Animals and Statistical Plan

Description of procedures. Approximately 255 male NSG mice and 6 genetically engineered B6 male mice are used for the experiments. 8 to 14-week old male NSG immunodeficient mice (the Jackson Laboratories) are used as xenograft hosts for prostate cancer cells growth and test the effect of CAR T-cells on tumor growth and metastasis.

Number of mice. The number of mice needed to achieve the objectives is based on power analyses. In study 1), 8 to 14-week-old male NOD-scid IL2rγnull (NSG) mice are used for xenograft models. Based on previously published data on tumor weight for VCaP-Luc-shCon mice, sample sizes of 35 mice per group achieve 80.7% power to detect a 50% difference in tumor weight means between the two group (0.1676 mg for VCaP control group vs. 0.0838 mg for VCaP treated group) with estimated group standard deviations of 0.1164 and 0.1280 (10% larger to account for unlikely yet possible variability increase) respectively and with alpha of 0.05 using a two-sided two-sample t-test. Planned sample size is 42 mice per group.

To calculate the number of NSG mice to be used: (1) For LNCaP subcutaneous xenograft model, five groups of mice: non-transduced, PSMA(445)-CAR, PSMA(445)-CAR-IRF4, PSMA(4LH)-CAR, and PSMA(4LH)-CAR-IRF4. 42×5=210 mice. (2) For metastatic cancer experiment, prostate cancer PC3-PSM stable cell line is tested. Five groups of mice are required: non-transduced control. PSMA(445)-

CAR, PSMA(445)-CAR-IRF4, PSMA(4LH)-CAR, and PSMA(4LH)-CAR-IRF4. CAR T cells can eliminate the metastatic cancer cells. Six mice each group are used achieve statistical significance, as shown in FIG. 15. 6×5=30 mice, (3) For single cell RNA-seq analysis, 5 mice each group are used for mice treated with non-transduced T cells, PSMA-CAR-T cells, and PSMA-CAR-IRF4 T cells. 5×3=15 mice. Therefore, total number of NSG mice: 210+30+15=255 mice. For T cell-specific IRF4 knockout mice for purification of murine T cells for PSMA-CAR-T assays, three CD4Cre;IRF4$^{flox/flox}$ and three IRF4$^{flox/flox}$ mice in B6 background are used. Total genetically engineered B6 mice: 3+3=6 mice.

Minimization of Pain and Distress, and Euthanasia. All efforts are made to minimize discomfort to these animals. Surgical procedures are performed under isoflurane general anesthesia. Animals injected with tumor cells are monitored daily and sacrificed upon displaying signs of morbidity as determined by a weight loss of >30%, rigidity of the thorax, shortness of breath, hind limb paralysis, and anemia as judged by paleness of limbs. Animals that develop signs of discomfort, or have a tumor growth at or above 1.5 cm diameter, or otherwise exhibit weight loss in excess of 20% are euthanatized by $CO_2$ asphyxiation, in accordance with recommendations approved by the 2000 Report of the American Veterinary Medical Association panel on euthanasia and the IACUC Committee at HMRI.

---

SEQUENCES

```
SEQ ID NO: 1 (nucleic acid sequence of CAR PMC 444_clone 219)
ATGGCCTTACCAGTGACCGCCTTGCTCCTGCCGCTGGCCTTGCTGCTCCACGCCGCC
AGGCCTGTTCAGCTGCAGCAGTCTGGACCTGAACTGGAGAAGCCTGGCGCTTCAGT
GAAGATGTCCTGCAAGGCTTCTGGTTACTCATTCACTGGCTACAACGTAAACTGGGT
GAGACAGAACAATGGAAAGAGCCTTGAGTGGATTGGAAATATTGATCCTCTCCATG
GTGGTACTACCTACAACCAGAAATTCAAGGCCAAGGCCACATTGACTGTAGACAGA
TCCTCCAGCACAGCCTACTTGCAGCTCAAGAACCTGACATCTGAGGACTCTGCAGTC
TATTACTGTGCAAGATCTAGTAGGTTTGACTACTGGGGCCAAGGCACCACTCTCACA
GTCTCCTCAGGTGGCGGTGGCAGCGGCGGTGGTGGTTCCGGAGGCGGCGGTTCTGA
CATTGTGATGACCCAGTCTCACAAATTCATGTCCACATCAGTAGGAGACAGGGTCA
ACATCACCTGCAAGGCCAGTCAGGATGTGGGTACTGCTGTAGCCTGGTATCAACAA
AAACCAGGGCAATCTCCTAAACTACTAATTTACTGGGCATCCACCCGGCACACTGG
AGTCCCTGATCGCTTCACAGGCAGTGGATCTGGGACAGATTTCACTCTCACCATTAG
CAATGTGCAATCTGAAGACTTGGCAGATTATTTCTGTCACCAATTTACCAGCTATCC
ATTCACGTTCGGCTCGGGGACAAGCTTGGAAATGAAACGGACCACGACGCCAGCGC
CGCGACCACCAACACCGGCGCCCACCATCGCGTCGCAGCCCCTGTCCCTGCGCCCA
GAGGCGTGCCGGCCAGCGGCGGGGGGCGCAGTGCACACGAGGGGGCTGGACTTCG
CCTGTGAcATCTACATCTGGGCGCCCCTGGCCGGGACTTGTGGGGTCCTTCTCCTGTC
ACTGGTTATCACCCTTTACTGCAAACGGGGCAGAAAGAAACTCCTGTATATATTCAA
ACAACCATTTATGAGACCAGTACAAACTACTCAAGAGGAAGATGGCTGTAGCTGCC
GATTTCCAGAAGAAGAAGAAGGAGGATGTGAACTGAGAGTGAAGTTCAGCAGGAG
CGCAGACGCCCCCGCGTACAAGCAGGGCCAGAACCAGCTCTATAACGAGCTCAATC
TAGGACGAAGAGAGGAGTACGATGTTTTGGACAAGAGACGTGGCCGGGACCCTGA
GATGGGGGGAAAGCCGAGAAGGAAGAACCCTCAGGAAGGCCTGTACAATGAACTG
CAGAAAGATAAGATGGCGGAAGGCCTACAGTGAGATTGGGATGAAAGGCGAGCGCC
GGAGGGGCAAGGGGCACGATGGCCTTTACCAGGGTCTCAGTACAGCCACCAAGGAC
ACCTACGACGCCCTTCACATGCAGGCCCTGCCCCCTCGC
```

```
SEQ ID NO: 2 (amino acid sequence of CAR PMC 444_clone 219)
MALPVTALLLPLALLLHAARPVQLQQSGPELEKPGASVKMSCKASGYSFTGYNVNWVR
QNNGKSLEWIGNIDPLHGGTTYNQKFKAKATLTVDRSSSTAYLQLKNLTSEDSAVYYC
ARSSRFDYWGQGTTLTVSSGGGGSGGGGSGGGGSDIVMTQSHKFMSTSVGDRVNITCK
ASQDVGTAVAWYQQKPGQSPKLLIYWASTRHTGVPDRFTGSGSGTDFTLTISNVQSEDL
ADYFCHQFTSYPFTFGSGTSLEMKRTTTPAPRPPTPAPTIASQPLSLRPEACRPAAGGAVH
TRGLDFACDIYIWAPLAGTCGVLLLSLVITLYCKRGRKKLLYIFKQPFMRPVQTTQEEDG
CSCRFPEEEEGGCELRVKFSRSADAPAYKQGQNQLYNELNLGRREEYDVLDKRRGRDP
EMGGKPRRKNPQEGLYNELQKDKMAEAYSEIGMKGERRRGKGHDGLYQGLSTATKDT
YDALHMQALPPR
```

```
SEQ ID NO: 3 (nucleic acid sequence of CAR PMC 445_clone 219)
ATGGCCTTACCAGTGACCGCCTTGCTCCTGCCGCTGGCCTTGCTGCTCCACGCCGCC
AGGCCTGTTCCAATTGCAGCAGCCTGGGGCTGCGCTGGTGAGGCCTGGAGCTTCAGT
GAGGCTGTCCTGCAAGGCTTCTGGATACTCCTTCACCTACTACTGGATGAACTGGGT
GATGCAGAGGCCTGGCCAAGGCCTTGAGTGGATTGGCATGATTCATCCTTCCGATAG
```

| SEQUENCES |
| --- |

```
TGAAACTCGGTTAAGTCAGAAGTTCAGGGACAAGGCCACATTGACTGTAGACAAAT
CTTCCAGCACAGTCTACATGCAACTCAACAGCCCGACATCTGATGACTCTGCAGTCT
ATTACTGTGCAAGAGATGGTAACTTCCCTTACTATGCACTAGACTACTGGGGTCAAG
GAACCTCGGTCACCGTCTCCTCAGGTGGCGGTGGCAGCGGCGGTGGTGGTTCCGGA
GGCGGCGGTTCTGATGTTGTGCTGACCCAAGCTCCACTCTCCCTGCCTGTCAGTCTT
GGAGATCAAGCCTCCATCTCTTGCAGATCTAGTCAGAGCCTTGAATACAGTAATGGA
AACACCTATTTACATTGGTACCTGCAGAAGCCAGGCCAGTCTCCAGAACTCCTGATC
TACACAGTTTCCAACCGATTTTCTGGGGTCCCAGACAGGTTCAGTGGCAGTGGATCA
GGGACAGATTTCACACTCAAGATTCACAGAGTGGAGGCTGAGGATCTGGGAGTTTA
TTTCTGCTCTCAAAGTACACATGTTCCCACGTTCGGAGGGGGGACCAAGCTGGAGAT
AAAACGGACCACGACGCCAGCGCCGCGACCACCAACACCGGCGCCCACCATCGCGT
CGCAGCCCCTGTCCCTGCGCCCAGAGGCGTGCCGGCCAGCGGCGGGGGGCGCAGTG
CACACGAGGGGGCTGGACTTCGCCTGTGAcATCTACATCTGGGCGCCCCTGGCCGGG
ACTTGTGGGGTCCTTCTCCTGTCACTGGTTATCACCCTTTACTGCAAACGGGGCAGA
AAGAAACTCCTGTATATATTCAAACAACCATTTATGAGACCAGTACAAACTACTCAA
GAGGAAGATGGCTGTAGCTGCCGATTTCCAGAAGAAGAAGAAGGAGGATGTGAAC
TGAGAGTGAAGTTCAGCAGGAGCGCAGACGCCCCCGCGTACAAGCAGGGCCAGAA
CCAGCTCTATAACGAGCTCAATCTAGGACGAAGAGAGGAGTACGATGTTTTGGACA
AGAGACGTGGCCGGGACCCTGAGATGGGGGGGAAAGCCGAGAAGGAAGAACCCTCA
GGAAGGCCTGTACAATGAACTGCAGAAAGATAAGATGGCGGAGGCCTACAGTGAG
ATTGGGATGAAAGGCGAGCGCCGGAGGGGCAAGGGGCACGATGGCCTTTACCAGG
GTCTCAGTACAGCCACCAAGGACACCTACGACGCCCTTCACATGCAGGCCCTGCCCC
CTCGC
```

```
SEQ ID NO: 4 (amino acid sequence of CAR PMC 445_clone 219)
MALPVTALLLPLALLLHAARPVQLQQPGAALVRPGASVRLSCKASGYSFTYYWMNWV
MQRPGQGLEWIGMIHPSDSETRLSQKFRDKATLTVDKSSSTVYMQLNSPTSDDSAVYY
CARDGNFPYYALDYWGQGTSVTVSSGGGGSGGGGSGGGGSDVVLTQAPLSLPVSLGD
QASISCRSSQSLEYSNGNTYLHWYLQKPGQSPELLIYTVSNRFSGVPDRFSGSGSGTDFT
LKIHRVEAEDLGVYFCSQSTHVPTFGGGTKLEIKRTTTPAPRPPTPAPTIASQPLSLRPEAC
RPAAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGHDGL
YQGLSTATKDTYDALHMQALPPR
```

```
SEQ ID NO: 5 (nucleic acid sequence of CAR PMC 446_clone 1366)
ATGGCCTTACCAGTGACCGCCTTGCTCCTGCCGCTGGCCTTGCTGCTGCTCCACGCCGCC
AGGCCTGTGAAGCTGCAGGAGTCAGGACCTGGCCTGGTGGCGCCCTCACAGAGCCT
GTCCATCACATGCACTGTCTCAGGGTTCTCATTAACCGACTATGGTGTGAGTTGGAT
TCGCCAGCCTCCAGGAAAGGGTCTGGAGTGGCTGGGAGTAATATGGAGCGATGGAA
ACACATACTATAATTCACCTCTCAAATCCAGACTGAGCATCAACAAGGACAACTCC
AAGAGCCAAGTTTTCTTAAAAATGAACAGTCTGCAAACTGATGACTCAGCCATGTA
CTACTGTGCCAGACATAAGGTCTATACTATGGACTACTGGGGTCAAGGAACCTCAGT
CACCGTCTCCTCAGGTGGCGGTGGCAGCGGCGGTGGTGGTTCCGGAGGCGGCGGTT
CTACTGTGCTCACCCAGTCTCCAGCAATCATGTCTGCATCTCCAGGGGAAAAGGTCA
CCATGACCTGCAGGGCCAGCTCAAGTGTAAGTTCCAGTTACTTGCACTGGTACCAGC
AGAAGTCAAGTGCCTCCCCCAAACTCTGGATTTATAGAACATCCAACTTGGCTTCTG
GAGTCCCTGCTCGCTTCAGTGGCAGTGGGTCTGGGACCTCTTACTCTCTCACAATCA
GCAGTTTGGAGGCTGAAGATGCTGCCACTTATTACTGCCAGCAGTACAGTGGTTACC
CACTCACGTTCGGTGCTGGGACCAAGCTGGAGCTGAAACGGACCACGACGCCAGCG
CCGCGACCACCAACACCGGCGCCCACCATCGCGTCGCAGCCCCTGTCCCTGCGCCCA
GAGGCGTGCCGGCCAGCGGCGGGGGGCGCAGTGCACACGAGGGGGCTGGACTTCG
CCTGTGAcATCTACATCTGGGCGCCCCTGGCCGGGACTTGTGGGGTCCTTCTCCTGTC
ACTGGTTATCACCCTTTACTGCAAACGGGGCAGAAAGAAACTCCTGTATATATTCAA
ACAACCATTTATGAGACCAGTACAAACTACTCAAGAGGAAGATGGCTGTAGCTGCC
GATTTCCAGAAGAAGAAGAAGGAGGATGTGAACTGAGAGTGAAGTTCAGCAGGAG
CGCAGACGCCCCCGCGTACAAGCAGGGCCAGAACCAGCTCTATAACGAGCTCAATC
TAGGACGAAGAGAGGAGTACGATGTTTTGGACAAGAGACGTGGCCGGGACCCTGA
GATGGGGGGAAAGCCGAGAAGGAAGAACCCTCAGGAAGGCCTGTACAATGAACTG
CAGAAAGATAAGATGGCGGAGGCCTACAGTGAGATTGGGATGAAAGGCGAGCGCC
GGAGGGGCAAGGGGCACGATGGCCTTTACCAGGGTCTCAGTACAGCCACCAAGGAC
ACCTACGACGCCCTTCACATGCAGGCCCTGCCCCCTCGC
```

```
SEQ ID NO: 6 (amino acid sequence of CAR PMC 446_clone 1366)
MALPVTALLLPLALLLHAARPVKLQESGPGLVAPSQSLSITCTVSGFSLTDYGVSWIRQP
PGKGLEWLGVIWSDGNTYYNSPLKSRLSINKDNSKSQVFLKMNSLQTDDSAMYYCARH
KVYTMDYWGQGTSVTVSSGGGGSGGGGSGGGGSTVLTQSPAIMSASPGEKVTMTCRA
SSSVSSSYLHWYQQKSSASPKLWIYRTSNLASGVPARFSGSGSGTSYSLTISSLEAEDAAT
YYCQQYSGYPLTFGAGTKLELKRTTTPAPRPPTPAPTIASQPLSLRPEACRPAAGGAVHT
RGLDFACDIYIWAPLAGTCGVLLLSLVITLYCKRGRKKLLYIFKQPFMRPVQTTQEEDGC
SCRFPEEEEGGCELRVKFSRSADAPAYKQGQNQLYNELNLGRREEYDVLDKRRGRDPE
MGGKPRRKNPQEGLYNELQKDKMAEAYSEIGMKGERRRGKGHDGLYQGLSTATKDT
YDALHMQALPPR
```

SEQUENCES

SEQ ID NO: 7 (nucleic acid sequence of CAR PMC 447_clone 1352)
ATGGCCTTACCAGTGACCGCCTTGCTCCTGCCGCTGGCCTTGCTGCTCCACGCCGCC
AGGCCTGTGAAGCTGCAGCAGTCTGGACCTGAACTGGAGAAGCCTGGCGCATCAGT
GAAGATATCCTGCAAGGCTTCAGGTTACTCATTCACTGGCTACAACGTGAACTGGGT
GAAGCAGAGCAATGGAAAGAGCCTTGAGTGGATTGGAAATATTGATCCTTACCATG
GTGGTACTACCTACAACCAGAAATTCGAGGCCAAGGCCACATTGACTGTAGACAAA
TCCTCCAGCACAGCCTACATGCAGCTCAAGAGCCTTACATCTGAGGACTCTGCAGTC
TATTATTGTGCAAGATCTAGTAGATTTGACTACTGGGGCCAAGGCACCACTCTCACA
GTCTCCTCAGGTGGCGGTGGCAGCGGCGGTGGTGGTTCCGGAGGCGGCGGTTCTGA
CATTGTGATGACCCAGTCTCACAAATTCATGTCCACATCAGTGGGAGACAGGGTCA
ACATCACCTGCAAGGCCAGTCAGGATGTGGGTACTGCTGTAGCCTGGTATCAACAG
AAACCAGGGCAATCTCCTAAATTTCTAATTTACTGGGCATCCACCCGGCACACTGGA
GTCCCTGATCGCTTCACAGGCAGTGGATCTGGGACAGATTTCACTCTCACCATTAGC
AATGTGCAGTCTGAAGACTTGGCAGATTATTTCTGTCATCAGTATACCAGCTATCCA
TTCACGTTCGGCTCGGGGACAAAGTTGGAAATGAAACGGACCACGACGCCAGCGCC
GCGACCACCAACACCGGCGCCCACCATCGCGTCGCAGCCCCTGTCCCTGCGCCCAG
AGGCGTGCCGGCCAGCGGCGGGGGGCGCAGTGCACACGAGGGGGCTGGACTTCGC
CTGTGAcATCTACATCTGGGCGCCCCTGGCCGGGACTTGTGGGGTCCTTCTCCTGTCA
CTGGTTATCACCCTTTACTGCAAACGGGGCAGAAAGAAACTCCTGTATATATTCAAA
CAACCATTTATGAGACCAGTACAAACTACTCAAGAGGAAGATGGCTGTAGCTGCCG
ATTTCCAGAAGAAGAAGAAGGAGGATGTGAACTGAGAGTGAAGTTCAGCAGGAGC
GCAGACGCCCCCGCGTACAAGCAGGGCCAGAACCAGCTCTATAACGAGCTCAATCT
AGGACGAAGAGAGGAGTACGATGTTTTGGACAAGAGACGTGGCCGGGACCCTGAG
ATGGGGGGAAAGCCGAGAAGGAAGAACCCTCAGGAAGGCCTGTACAATGAACTGC
AGAAAGATAAGATGGCGGAGGCCTACAGTGAGATTGGGATGAAAGGCGAGCGCCG
GAGGGGCAAGGGGCACGATGGCCTTTACCAGGGTCTCAGTACAGCCACCAAGGACA
CCTACGACGCCCTTCACATGCAGGCCCTGCCCCCTCGC SEQ ID NO: 8 (amino acid sequence of CAR PMC 447_clone 1352)
MALPVTALLLPLALLLHAARPVKLQQSGPELEKPGASVKISCKASGYSFTGYNVNWVK
QSNGKSLEWIGNIDPYHGGTTYNQKFEAKATLTVDKSSSTAYMQLKSLTSEDSAVYYC
ARSSRFDYWGQGTTLTVSSGGGGSGGGGSGGGGSDIVMTQSHKFMSTSVGDRVNITCK
ASQDVGTAVAWYQQKPGQSPKFLIYWASTRHTGVPDRFTGSGSGTDFTLTISNVQSEDL
ADYFCHQYTSYPFTFGSGTKLEMKRTTTPAPRPPTPAPTIASQPLSLRPEACRPAAGGAV
HTRGLDFACDIYIWAPLAGTCGVLLLSLVITLYCKRGRKKLLYIFKQPFMRPVQTTQEED
GCSCRFPEEEEGGCELRVKFSRSADAPAYKQGQNQLYNELNLGRREEYDVLDKRRGRD
PEMGGKPRRKNPQEGLYNELQKDKMAEAYSEIGMKGERRRGKGHDGLYQGLSTATKD
TYDALHMQALPPR SEQ ID NO: 9 (nucleic acid sequence of CAR PMC 448_clone 1207)
ATGGCCTTACCAGTGACCGCCTTGCTCCTGCCGCTGGCCTTGCTGCTCCACGCCGCC
AGGCCTGTTAAGCTGCAGCAGTCGGGACCTGGCCTGGTGAAACCTTCTCAGTCTCTG
TCCCTCACCTGCGCTGTCACTGGCTACTCAATCACCAGTGATTATGCCTGGAACTGG
ATCCGGAAGTTTCCAGGAAACAAACTGGAGTGGATGGGCTACATAAGCTACAGTGG
TAGAACTACCTACAATCCATCTCTCGAAAGTCGAATCTCTATCACTCGAGACACATC
CAAAAACCAGTTCTTCCTGCAGTTGAATTCTGTGACTACTGAGGACACAGCCACATA
TTACTGTGCAAGATGTTACTACGGTAGTAGCTCCCGTTGGTATGGTATGGACTACTG
GGGTCGCGGAACCTCAGTCGCCGTGTCCTCAGGTGGCGGTGGCAGCGGCGGTGGTG
GTTCCGGAGGCGGCGGTTCTATTGTGCTCACCCAGTCTCCAGCAATCATGTCTGCAT
CTCCAGGGGTAAAGGTCACCATGACCTGCAGGGCCAGCTCAAGTGTAGATTCCAGT
TACTTGCACTGGTACCAGCAGAAGTCAGGTGCCTCCCCCCAAGTCTGGATTTATAGC
ACATCCAACTTGGCTTCTGGAGTCCCGGCTCGCTTCAGTGGCAGTGGGTCTGGGACC
TCTTACTCTCTCACAATCAGTAGTGTGGAGGCTGAAGATGCTGCCACTTATTACTGC
CAGCAGTACAGTGGTTATCCACTGACGTTCGGTGGAGGCACCAAGCTGGAAATCAA
ACGGACCACGACGCCAGCGCCGCGACCACCAACACCGGCGCCCACCATCGCGTCGC
AGCCCCTGTCCCTGCGCCCAGAGGCGTGCCGGCCAGCGGCGGGGGGCGCAGTGCAC
ACGAGGGGGCTGGACTTCGCCTGTGAcATCTACATCTGGGCGCCCCTGGCCGGGACT
TGTGGGGTCCTTCTCCTGTCACTGGTTATCACCCTTTACTGCAAACGGGGCAGAAAG
AAACTCCTGTATATATTCAAACAACCATTTATGAGACCAGTACAAACTACTCAAGAG
GAAGATGGCTGTAGCTGCCGATTTCCAGAAGAAGAAGAAGGAGGATGTGAACTGA
GAGTGAAGTTCAGCAGGAGCGCAGACGCCCCCGCGTACAAGCAGGGCCAGAACCA
GCTCTATAACGAGCTCAATCTAGGACGAAGAGAGGAGTACGATGTTTTGGACAAGA
GACGTGGCCGGGACCCTGAGATGGGGGGAAAGCCGAGAAGGAAGAACCCTCAGGA
AGGCCTGTACAATGAACTGCAGAAAGATAAGATGGCGGAGGCCTACAGTGAGATTG
GGATGAAAGGCGAGCGCCGGAGGGGCAAGGGGCACGATGGCCTTTACCAGGGTCT
CAGTACAGCCACCAAGGACACCTACGACGCCCTTCACATGCAGGCCCTGCCCCCTCGC SEQ ID NO: 10 (amino acid sequence of CAR PMC 448_clone 1207)
MALPVTALLLPLALLLHAARPVKLQQSGPGLVKPSQSLSLTCAVTGYSITSDYAWNWIR
KFPGNKLEWMGYISYSGRTTYNPSLESRISITRDTSKNQFFLQLNSVTTEDTATYYCARC
YYGSSSRWYGMDYWGRGTSVAVSSGGGGSGGGGSGGGGSIVLTQSPAIMSASPGVKV
TMTCRASSSVDSSYLHWYQQKSGASPQVWIYSTSNLASGVPARFSGSGSGTSYSLTISSV
EAEDAATYYCQQYSGYPLTFGGGTKLEIKRTTTPAPRPPTPAPTIASQPLSLRPEACRPAA
GGAVHTRGLDFACDIYIWAPLAGTCGVLLLSLVITLYCKRGRKKLLYIFKQPFMRPVQT
TQEEDGCSCRFPEEEEGGCELRVKFSRSADAPAYKQGQNQLYNELNLGRREEYDVLDK
RRGRDPEMGGKPRRKNPQEGLYNELQKDKMAEAYSEIGMKGERRRGKGHDGLYQGLS
TATKDTYDALHMQALPPR

SEQUENCES

SEQ ID NO: 11 (nucleic acid sequence of heavy chain variable region sequence
H-1, 2, 3, 4, 6 of 219)
GTTCAGCTGCAGCAGTCTGGACCTGAACTGGAGAAGCCTGGCGCTTCAGTGAAGAT
GTCCTGCAAGGCTTCTGGTTACTCATTCACTGGCTACAACGTAAACTGGGTGAGACA
GAACAATGGAAAGAGCCTTGAGTGGATTGGAAATATTGATCCTCTCCATGGTGGTA
CTACCTACAACCAGAAATTCAAGGCCAAGGCCACATTGACTGTAGACAGATCCTCC
AGCACAGCCTACTTGCAGCTCAAGAACCTGACATCTGAGGACTCTGCAGTCTATTAC
TGTGCAAGATCTAGTAGGTTTGACTACTGGGGCCAAGGCACCACTCTCACAGTCTCC
TCA SEQ ID NO: 12 (amino acid sequence of heavy chain variable region sequence
H-1, 2, 3, 4, 6 of 219)
VQLQQSGPELEKPGASVKMSCKASGYSFTGYNVNWVRQNNGKSLEWIGNIDPLHGGTT
YNQKFKAKATLIVDRSSSTAYLQLKNLTSEDSAVYYCARSSRFDYWGQGTTLTVSS SEQ ID NO: 13 (nucleic acid sequence of Light chain variable region sequence
K-21, 22, 25, 29, 30 of 219)
GACATTGTGATGACCCAGTCTCACAAATTCATGTCCACATCAGTAGGAGACAGGGT
CAACATCACCTGCAAGGCCAGTCAGGATGTGGGTACTGCTGTAGCCTGGTATCAAC
AAAAACCAGGGCAATCTCCTAAACTACTAATTTACTGGGCATCCACCCGGCACACT
GGAGTCCCTGATCGCTTCACAGGCAGTGGATCTGGGACAGATTTCACTCTCACCATT
AGCAATGTGCAATCTGAAGACTTGGCAGATTATTTCTGTCACCAATTTACCAGCTAT
CCATTCACGTTCGGCTCGGGGACAAGCTTGGAAATGAAACGG SEQ ID NO: 14 (amino acid sequence of Light chain variable region sequence
K-21, 22, 25, 29, 30 of 219)
DIVMTQSHKFMSTSVGDRVNITCKASQDVGTAVAWYQQKPGQSPKLLIYWASTRHTG
VPDRFTGSGSGTDFTLTISNVQSEDLADYFCHQFTSYPFTFGSGTSLEMKR SEQ ID NO: 15 (nucleic acid sequence of heavy chain variable region sequence
H-1, 3, 4, 5, 6 of 1377)
GTCCAATTGCAGCAGCCTGGGGCTGCGCTGGTGAGGCCTGGAGCTTCAGTGAGGCT
GTCCTGCAAGGCTTCTGGATACTCCTTCACCTACTACTGGATGAACTGGGTGATGCA
GAGGCCTGGCCAAGGCCTTGAGTGGATTGGCATGATTCATCCTTCCGATAGTGAAAC
TCGGTTAAGTCAGAAGTTCAGGGACAAGGCCACATTGACTGTAGACAAATCTTCCA
GCACAGTCTACATGCAACTCAACAGCCCGACATCTGATGACTCTGCAGTCTATTACT
GTGCAAGAGATGGTAACTTCCCTTACTATGCACTAGACTACTGGGGTCAAGGAACCT
CGGTCACCGTCTCCTCA SEQ ID NO: 16 (amino acid sequence of heavy chain variable region sequence
H-1, 3, 4, 5, 6 of 1377)
VQLQQPGAALVRPGASVRLSCKASGYSFTYYWMNWVMQRPGQGLEWIGMIHPSDSET
RLSQKFRDKATLIVDKSSSTVYMQLNSPTSDDSAVYYCARDGNFPYYALDYWGQGTS
VTVSS SEQ ID NO: 17 (nucleic acid sequence of light chain variable region sequence
K-6, 8, 9, 10, 12 of 1377)
GATGTTGTGCTGACCCAAGCTCCACTCTCCCTGCCTGTCAGTCTTGGAGATCAAGCC
TCCATCTCTTGCAGATCTAGTCAGAGCCTTGAATACAGTAATGGAAACACCTATTTA
CATTGGTACCTGCAGAAGCCAGGCCAGTCTCCAGAACTCCTGATCTACACAGTTTCC
AACCGATTTTCTGGGGTCCCAGACAGGTTCAGTGGCAGTGGATCAGGGACAGATTT
CACACTCAAGATTCACAGAGTGGAGGCTGAGGATCTGGGAGTTTATTTCTGCTCTCA
AAGTACACATGTTCCCACGTTCGGAGGGGGGACCAAGCTGGAGATAAAACGG SEQ ID NO: 18 (amino acid sequence of light chain variable region sequence
K-6, 8, 9, 10, 12 of 1377)
DVVLTQAPLSLPVSLGDQASISCRSSQSLEYSNGNTYLHWYLQKPGQSPELLIYTVSNRF
SGVPDRFSGSGSGTDFTLKIHRVEAEDLGVYFCSQSTHVPTFGGGTKLEIKR SEQ ID NO: 19 (nucleic acid sequence of heavy chain variable region sequence
H-7, 8, 9, 10, 11 of 1366)
GTGAAGCTGCAGGAGTCAGGACCTGGCCTGGTGGCGCCCTCACAGAGCCTGTCCAT
CACATGCACTGTCTCAGGGTTCTCATTAACCGACTATGGTGTGAGTTGGATTCGCCA
GCCTCCAGGAAAGGGTCTGGAGTGGCTGGGAGTAATATGGAGCGATGGAAACACAT
ACTATAATTCACCTCTCAAATCCAGACTGAGCATCAACAAGGACAACTCCAAGAGC
CAAGTTTTCTTAAAAATGAACAGTCTGCAAACTGATGACTCAGCCATGTACTACTGT
GCCAGACATAAGGTCTATACTATGGACTACTGGGGTCAAGGAACCTCAGTCACCGT
CTCCTCA SEQ ID NO: 20 (amino acid sequence of heavy chain variable region sequence
H-7, 8, 9, 10, 11 of 1366)
VKLQESGPGLVAPSQSLSITCTVSGFSLTDYGVSWIRQPPGKGLEWLGVIWSDGNTYYN
SPLKSRLSINKDNSKSQVFLKMNSLQTDDSAMYYCARHKVYTMDYWGQGTSVTVSS -continued

SEQUENCES

SEQ ID NO: 21 (nucleic acid sequence of light chain variable region sequence
K-1, 2, 3, 5, 8 of 1366)
ACTGTGCTCACCCAGTCTCCAGCAATCATGTCTGCATCTCCAGGGGAAAAGGTCACC
ATGACCTGCAGGGCCAGCTCAAGTGTAAGTTCCAGTTACTTGCACTGGTACCAGCAG
AAGTCAAGTGCCTCCCCCAAACTCTGGATTTATAGAACATCCAACTTGGCTTCTGGA
GTCCCTGCTCGCTTCAGTGGCAGTGGGTCTGGGACCTCTTACTCTCTCACAATCAGC
AGTTTGGAGGCTGAAGATGCTGCCACTTATTACTGCCAGCAGTACAGTGGTTACCCA
CTCACGTTCGGTGCTGGGACCAAGCTGGAGCTGAAACGG SEQ ID NO: 22 (amino acid sequence of light chain variable region sequence
K-1, 2, 3, 5, 8 of 1366)
TVLTQSPAIMSASPGEKVTMTCRASSSVSSSYLHWYQQKSSASPKLWIYRTSNLASGVP
ARFSGSGSGTSYSLTISSLEAEDAATYYCQQYSGYPLTFGAGTKLELKR SEQ ID NO: 23 (nucleic acid sequence of heavy chain variable region sequence
H-2, 3, 6, 7, 9 of 1352)
GTGAAGCTGCAGCAGTCTGGACCTGAACTGGAGAAGCCTGGCGCATCAGTGAAGAT
ATCCTGCAAGGCTTCAGGTTACTCATTCACTGGCTACAACGTGAACTGGGTGAAGCA
GAGCAATGGAAAGAGCCTTGAGTGGATTGGAAATATTGATCCTTACCATGGTGGTA
CTACCTACAACCAGAAATTCGAGGCCAAGGCCACATTGACTGTAGACAAATCCTCC
AGCACAGCCTACATGCAGCTCAAGAGCCTTACATCTGAGGACTCTGCAGTCTATTAT
TGTGCAAGATCTAGTAGATTTGACTACTGGGGCCAAGGCACCACTCTCACAGTCTCC
TCA SEQ ID NO: 24 (amino acid sequence of heavy chain variable region sequence
H-2, 3, 6, 7, 9 of 1352)
VKLQQSGPELEKPGASVKISCKASGYSFTGYNVNWVKQSNGKSLEWIGNIDPYHGGTT
YNQKFEAKATLTVDKSSSTAYMQLKSLTSEDSAVYYCARSSRFDYWGQGTTLTVSS SEQ ID NO: 25 (nucleic acid sequence of light chain variable region sequence
K-2, 3, 6, 8, 10 of 1352)
GACATTGTGATGACCCAGTCTCACAAATTCATGTCCACATCAGTGGGAGACAGGGT
CAACATCACCTGCAAGGCCAGTCAGGATGTGGGTACTGCTGTAGCCTGGTATCAAC
AGAAACCAGGGCAATCTCCTAAATTTCTAATTTACTGGGCATCCACCCGGCACACTG
GAGTCCCTGATCGCTTCACAGGCAGTGGATCTGGGACAGATTTCACTCTCACCATTA
GCAATGTGCAGTCTGAAGACTTGGCAGATTATTTCTGTCATCAGTATACCAGCTATC
CATTCACGTTCGGCTCGGGGACAAAGTTGGAAATGAAACGG SEQ ID NO: 26 (amino acid sequence of light chain variable region sequence
K-2, 3, 6, 8, 10 of 1352)
DIVMTQSHKFMSTSVGDRVNITCKASQDVGTAVAWYQQKPGQSPKFLIYWASTRHTGV
PDRFTGSGSGTDFTLTISNVQSEDLADYFCHQYTSYPFTFGSGTKLEMKR SEQ ID NO: 27 (nucleic acid sequence of heavy chain variable region sequence
H-2, 4, 7, 9, 14 of 1207)
GTTAAGCTGCAGCAGTCGGGACCTGGCCTGGTGAAACCTTCTCAGTCTCTGTCCCTC
ACCTGCGCTGTCACTGGCTACTCAATCACCAGTGATTATGCCTGGAACTGGATCCGG
AAGTTTCCAGGAAACAAACTGGAGTGGATGGGCTACATAAGCTACAGTGGTAGAAC
TACCTACAATCCATCTCTCGAAAGTCGAATCTCTATCACTCGAGACAATCCAAAAA
CCAGTTCTTCCTGCAGTTGAATTCTGTGACTACTGAGGACACAGCCACATATTACTG
TGCAAGATGTTACTACGGTAGTAGCTCCCGTTGGTATGGTATGGACTACTGGGGTCG
CGGAACCTCAGTCGCCGTGTCCTCA SEQ ID NO: 28 (amino acid sequence of heavy chain variable region sequence
H-2, 4, 7, 9, 14 of 1207)
VKLQQSGPGLVKPSQSLSLTCAVTGYSITSDYAWNWIRKFPGNKLEWMGYISYSGRTTY
NPSLESRISITRDTSKNQFFLQLNSVTTEDTATYYCARCYYGSSSRWYGMDYWGRGTSV
AVSS SEQ ID NO: 29 (nucleic acid sequence of light chain variable region sequence
K-2, 3, 5, 6, 7 of 1207)
ATTGTGCTCACCCAGTCTCCAGCAATCATGTCTGCATCTCCAGGGGTAAAGGTCACC
ATGACCTGCAGGGCCAGCTCAAGTGTAGATTCCAGTTACTTGCACTGGTACCAGCAG
AAGTCAGGTGCCTCCCCCCAAGTCTGGATTTATAGCACATCCAACTTGGCTTCTGGA
GTCCCGGCTCGCTTCAGTGGCAGTGGGTCTGGGACCTCTTACTCTCTCACAATCAGT
AGTGTGGAGGCTGAAGATGCTGCCACTTATTACTGCCAGCAGTACAGTGGTTATCCA
CTGACGTTCGGTGGAGGCACCAAGCTGGAAATCAAACGG SEQ ID NO: 30 (amino acid sequence of light chain variable region sequence
K-2, 3, 5, 6, 7 of 1207)
IVLTQSPAIMSASPGVKVTMTCRASSSVDSSYLHWYQQKSGASPQVWIYSTSNLASGVP
ARFSGSGSGTSYSLTISSVEAEDAATYYCQQYSGYPLTFGGGTKLEIKR SEQ ID NO: 31 (amino acid sequence of PSMA)
MWNLLHETDSAVATARRPRWLCAGALVLAGGFFLLGFLFGWFIKSSNEATNITPKHNM
KAFLDELKAENIKKFLYNFTQIPHLAGTEQNFQLAKQIQSQWKEFGLDSVELAHYDVLL
SYPNKTHPNYISIINEDGNEIFNTSLFEPPPPGYENVSDIVPPFSAFSPQGMPEGDLVYVNY

SEQUENCES

ARTEDFFKLERDMKINCSGKIVIARYGKVFRGNKVKNAQLAGAKGVILYSDPADYFAP
GVKSYPDGWNLPGGGVQRGNILNLNGAGDPLTPGYPANEYAYRRGIAEAVGLPSIPVH
PIGYYDAQKLLEKMGGSAPPDSSWRGSLKVPYNVGPGFTGNFSTQKVKMHIHSTNEVT
RIYNVIGTLRGAVEPDRYVILGGHRDSWVFGGIDPQSGAAVVHEIVRSFGTLKKEGWRP
RRTILFASWDAEEFGLLGSTEWAEENSRLLQERGVAYINADSSIEGNYTLRVDCTPLMY
SLVHNLTKELKSPDEGFEGKSLYESWTKKSPSPEFSGMPRISKLGSGNDFEVFFQRLGIAS
GRARYTKNWETNKFSGYPLYHSVYETYELVEKFYDPMFKYHLTVAQVRGGMVFELAN
SIVLPFDCRDYAVVLRKYADKIYSISMKHPQEMKTYSVSFDSLFSAVKNFTEJASKFSER
LQDFDKSNPIVLRMMNDQLMFLERAFIDPLGLPDRPFYRHVIYAPSSHNKYAGESFPGTY
DALFDIESKVDPSKAWGEVKRQIYVAAFTVQAAAETLSEVA

SEQ ID NO: 32 (amino acid sequence of human 4-1BB)
MGNSCYNIVATLLLVLNFERTRSLQDPCSNCPAGTFCDNNRNQICSPCPPNSFSSAGGQR
TCDICRQCKGVFRTRKECSSTSNAECDCTPGFHCLGAGCSMCEQDCKQGQELTKKGCK
DCCFGTFNDQKRGICRPWTNCSLDGKSVLVNGTKERDVVCGPSPADLSPGASSVTPPAP
AREPGHSPQUISFFLALTSTALLFLLFFLTLRFSVVKRGRKKLLYIFKQPFMRPVQTTQEED
GCSCRFPEEEEGGCEL SEQ ID NO: 33 (amino acid sequence intracellular signaling domain of 4-1BB)
KRGRKKLLYIFKQPFMRPVQTTQEEDGCSCRFPEEEEGGCEL SEQ ID NO: 34 (amino acid sequence of T2A cleaving peptide)
EGRGSLLTCGDVEENPGP SEQ ID NO: 35 (amino acid sequence of human IRF4)
MNLEGGGRGGEFGMSAVSCGNGKLRQWLIDQIDSGKYPGLVWENEEKSIFRIPWKHAG
KQDYNREEDAALFKAWALFKGKFREGIDKPDPPTWKTRLRCALNKSNDFEELVERSQL
DISDPYKVYRIVPEGAKKGAKQLTLEDPQMSMSHPYTMTTPYPSLPAQQVHNYMMPPL
DRSWRDYVPDQPHPEIPYQCPMTFGPRGHHWQGPACENGCQVTGTFYACAPPESQAPG
VPTEPSIRSAEALAFSDCRLHICLYYREILVKELTTSSPEGCRISHGHTYDASNLDQVLFPY
PEDNGQRKNIEKLLSHLERGVVLWMAPDGLYAKRLCQSRIYWDGPLALCNDRPNKLER
DQTCKLFDTQQFLSELQAFAHHGRSLPRFQVTLCFGEEFPDPQRQRKLITAHVEPLLARQ
LYYFAQQNSGHFLRGYDLPEHISNPEDYHRSIRHSSIQE SEQ ID NO: 36 (amino acid sequence of CD3zeta)
RVKFSRSADAPAYKQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR SEQ ID NO: 37 (linker sequence)
GGGGSGGGGSGGGGS SEQ ID NO: 38 (nucleic acid sequence for PSMA(4LH)-CAR, derived from antibody #219)
ATGGCCTTACCAGTGACCGCCTTGCTCCTGCCGCTGGCCTTGCTGCTCCATGCGGCT
CGACCTGACATCGTGATGACACAGTCTCACAAGTTCATGTCCACCTCTGTGGGCGAC
AGGGTGAACATCACATGCAAGGCCTCCCAGGATGTGGGCACCGCAGTGGCCTGGTA
TCAGCAGAAGCCCGGCCAGAGCCCTAAGCTGCTGATCTATTGGGCCTCCACCAGGC
ACACAGGCGTGCCTGACCGCTTCACAGGCAGCGGCTCCGGCACCGACTTCACCCTG
ACAATCTCTAATGTGCAGAGCGAGGACCTGGCCGATTACTTCTGCCACCAGTTTACC
AGCTATCCATTCACATTTGGCTCTGGCACCAGCCTGGAGATGAAGAGGAGGAGGAGG
AGGCAGCGGCGGAGGAGGCTCCGGCGGCGGCGGCTCTGTGCAGCTGCAGCAGTCCG
GACCAGAGCTGGAGAAGCCAGGAGCCTCCGTGAAGATGTCTTGTAAGGCCTCCGGC
TACTCTTTCACAGGCTATAACGTGAATTGGGTGCGGCAGAACAATGGCAAGAGCCT
GGAGTGGATCGGAAACATCGACCCACTGCACGGCGGCACCACATACAATCAGAAGT
TTAAGGCCAAGGCCACCCTGACAGTGGATAGAAGCTCCTCTACAGCCTATCTGCAG
CTGAAGAACCTGACCAGCGAGGACTCCGCCGTGTACTATTGTGCCCGGAGCAGCCG
GTTTGATTACTGGGGCCAGGGCACCACACTGACCGTGTCTAGCACCACGACGCCAG
CGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTT
CGCCTGTGACATCTACATCTGGGCGCCCCTGGCCGGGACTTGTGGGGTCCTTCTCCT
GTCACTGGTTATCACCCTTTACTGCAAACGGGGCAGAAAGAAACTCCTGTATATATT
CAAACAACCATTTATGAGACCAGTACAAACTACTCAAGAGGAAGATGGCTGTAGCT
GCCGATTTCCAGAAGAAGAAGAAGGAGGATGTGAACTGAGAGTGAAGTTCAGCAG
GAGCGCAGACGCCCCCGCGTACAAGCAGGGCCAGAACCAGCTCTATAACGAGCTCA
ATCTAGGACGAAGAGAGGAGTACGATGTTTTGGACAAGAGACGTGGCCGGGACCCT
GAGATGGGGGGAAAGCCGAGAAGGAAGAACCCTCAGGAAGGCCTGTACAATGAAC
TGCAGAAAGATAAGATGGCGGAGGCCTACAGTGAGATTGGGATGAAAGGCGAGCG
CCGGAGGGGCAAGGGGCACGATGGCCTTTACCAGGGTCTCAGTACAGCCACCAAGG
ACACCTACGACGCCCTTCACATGCAGGCCCTGCCCCCTCGCTAG SEQ ID NO: 39 (amino acid sequence for PSMA(4LH)-CAR, derived from antibody #219)
MALPVTALLLPLALLLHAARPDIVMTQSHKFMSTSVGDRVNITCKASQDVGTAVAWYQ
QKPGQSPKLLIYWASTRHTGVPDRFTGSGSGTDFTLTISNVQSEDLADYFCHQFTSYPFT
FGSGTSLEMKRGGGGSGGGGSGGGGSVQLQQSGPELEKPGASVKMSCKASGYSFTGYN
VNWVRQNNGKSLEWIGNIDPLHGGTTYNQKFKAKATLTVDRSSSTAYLQLKNLTSEDS
AVYYCARSSRFDYWGQGTTLTVSSTTTPAPRPPTPAPTIASQPLSLRPEACRPAAGGAVH
TRGLDFACDIYIWAPLAGTCGVLLLSLVITLYCKRGRKKLLYIFKQPFMRPVQTTQEEDG
CSCRFPEEEEGGCELRVKFSRSADAPAYKQGQNQLYNELNLGRREEYDVLDKRRGRDP

SEQUENCES

EMGGKPRRKNPQEGLYNELQKDKMAEAYSEIGMKGERRRGKGHDGLYQGLSTATKDT
YDALHMQALPPR

SEQ ID NO: 40 (nucleic acid sequence for PSMA(SLH)-CAR, derived from antibody #1377)
ATGGCCTTACCAGTGACCGCCTTGCTCCTGCCGCTGGCCTTGCTGCTCCATGCGGCT
CGACCTGACGTGGTGCTGACCCAGGCACCACTGAGCCTGCCCGTGAGCCTGGGCGA
TCAGGCCTCCATCTCTTGCAGAAGCTCCCAGTCTCTGGAGTACAGCAACGGCAATAC
CTACCTGCACTGGTATCTGCAGAAGCCAGGCCAGAGCCCCGAGCTGCTGATCTATAC
AGTGTCCAACCGGTTCTCTGGCGTGCCTGACCGGTTCAGCGGCTCCGGCTCTGGCAC
CGATTTCACACTGAAGATCCACAGGGTGGAGGCAGAGGACCTGGGCGTGTACTTCT
GCAGCCAGTCCACCCACGTGCCCACATTTGGCGGCGGCACCAAGCTGGAGATCAAG
AGGGGAGGAGGAGGCTCTGGAGGAGGAGGCAGCGGCGGCGGCGGCTCCGTGCAGC
TGCAGCAGCCTGGCGCCGCCCTGGTGCGGCCAGGAGCCAGCGTGAGACTGTCCTGT
AAGGCCTCCGGCTATTCTTTCACCTACTATTGGATGAATTGGGTCATGCAGAGGCCA
GGACAGGGCCTGGAGTGGATCGGCATGATCCACCCTTCTGATAGCGAGACAAGGCT
GAGCCAGAAGTTTCGCGACAAGGCCACCCTGACAGTGGATAAGTCTAGCTCCACCG
TGTACATGCAGCTGAACAGCCCAACATCCGACGATTCTGCCGTGTACTATTGTGCCC
GGGACGGCAATTTTCCCTACTATGCCCTGGATTATTGGGGCCAGGGCACCTCCGTGA
CAGTGTCTAGCACCACGACGCCAGCGCCGCGACCACCAACACCGGCGCCCACCATC
GCGTCGCAGCCCCTGTCCCTGCGCCCAGAGGCGTGCCGGCCAGCGGCGGGGGGCGC
AGTGCACACGAGGGGGCTGGACTTCGCCTGTGACATCTACATCTGGGCGCCCCTGG
CCGGGACTTGTGGGGTCCTTCTCCTGTCACTGGTTATCACCCTTTACTGCAAACGGG
GCAGAAAGAAACTCCTGTATATATTCAAACAACCATTTATGAGACCAGTACAAACT
ACTCAAGAGGAAGATGGCTGTAGCTGCCGATTTCCAGAAGAAGAAGAAGGAGGAT
GTGAACTGAGAGTGAAGTTCAGCAGGAGCGCAGACGCCCCCGCGTACAAGCAGGG
CCAGAACCAGCTCTATAACGAGCTCAATCTAGGACGAAGAGAGGAGTACGATGTTT
TGGACAAGAGACGTGGCCGGGACCCTGAGATGGGGGGAAAGCCGAGAAGGAAGAA
CCCTCAGGAAGGCCTGTACAATGAACTGCAGAAAGATAAGATGGCGGAGGCCTACA
GTGAGATTGGGATGAAAGGCGAGCGCCGGAGGGGCAAGGGGCACGATGGCCTTTA
CCAGGGTCTCAGTACAGCCACCAAGGACACCTACGACGCCCTTCACATGCAGGCCC
TGCCCCCTCGCTAG SEQ ID NO: 41 (amino acid sequence for PSMA(5LH)-CAR, derived from antibody #1377)
MALPVTALLLPLALLLHAARPDVVLTQAPLSLPVSLGDQASISCRSSQSLEYSNGNTYLH
WYLQKPGQSPELLIYTVSNRFSGVPDRFSGSGSGTDFTLKIHRVEAEDLGVYFCSQSTHV
PTFGGGTKLEIKRGGGGSGGGGSGGGGSVQLQQPGAALVRPGASVRLSCKASGYSFTY
YWMNWVMQRPGQGLEWIGMIHPSDSETRLSQKFRDKATLTVDKSSSTVYMQLNSPTS
DDSAVYYCARDGNFPYYALDYWGQGTSVTVSSTTTPAPRPPTPAPTIASQPLSLRPEAC
RPAAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGHDGL
YQGLSTATKDTYDALHMQALPPR SEQ ID NO: 42 (nucleic acid sequence for PSMA(6LH)-CAR, derived from antibody #1366)
ATGGCCTTACCAGTGACCGCCTTGCTCCTGCCGCTGGCCTTGCTGCTCCATGCGGCT
CGACCTACCGTGCTGACACAGTCCCCTGCCATCATGAGCGCCTCCCCAGGAGAGAA
GGTGACCATGACATGCAGGGCCAGCAGCAGCGTGAGCAGCAGCTACCTGCACTGGT
ATCAGCAGAAGAGCAGCGCCAGCCCCAAGCTGTGGATCTACCGGACCTCCAACCTG
GCCTCTGGCGTGCCTGCCAGATTCTCTGGCAGCGGCTCCGGCACCTCTTATAGCCTG
ACAATCTCTAGCCTGGAGGCAGAGGACGCAGCAACCTACTATTGCCAGCAGTACTC
CGGCTATCCACTGACCTTTGGCGCCGGCACAAAGCTGGAGCTGAAGAGGGGAGGAG
GAGGCAGCGGCGGAGGAGGCTCCGGCGGCGGCGGCTCTGTGAAGCTGCAGGAGTC
CGGACCAGGACTGGTGGCACCATCCCAGTCTCTGAGCATCACCTGTACAGTGAGCG
GCTTCTCCCTGACCGATTACGGCGTGTCTTGGATCAGGCAGCCACCTGGCAAGGGCC
TGGAGTGGCTGGGCGTGATCTGGTCTGACGGCAACACATACTATAATAGCCCCCTG
AAGTCTCGCCTGAGCATCAACAAGGATAATTCCAAGTCTCAGGTGTTTCTGAAGATG
AATAGCCTGCAGACCGACGATTCCGCCATGTACTATTGTGCCCGGCACAAGGTGTAC
ACAATGGACTATTGGGGCCAGGGCACCAGCGTGACAGTGTCCTCTACCACGACGCC
AGCGCCGCGACCACCAACACCGGCGCCCACCATCGCGTCGCAGCCCCTGTCCCTGC
GCCCAGAGGCGTGCCGGCCAGCGGCGGGGGGCGCAGTGCACACGAGGGGGCTGGA
CTTCGCCTGTGACATCTACATCTGGGCGCCCCTGGCCGGGACTTGTGGGGTCCTTCT
CCTGTCACTGGTTATCACCCTTTACTGCAAACGGGGCAGAAAGAAACTCCTGTATAT
ATTCAAACAACCATTTATGAGACCAGTACAAACTACTCAAGAGGAAGATGGCTGTA
GCTGCCGATTTCCAGAAGAAGAAGAAGGAGGATGTGAACTGAGAGTGAAGTTCAGC
AGGAGCGCAGACGCCCCCGCGTACAAGCAGGGCCAGAACCAGCTCTATAACGAGCT
CAATCTAGGACGAAGAGAGGAGTACGATGTTTGGACAAGAGACGTGGCCGGGACC
CTGAGATGGGGGGAAAGCCGAGAAGGAAGAACCCTCAGGAAGGCCTGTACAATGA
ACTGCAGAAAGATAAGATGGCGGAGGCCTACAGTGAGATTGGGATGAAAGGCGAG
CGCCGGAGGGGCAAGGGGCACGATGGCCTTTACCAGGGTCTCAGTACAGCCACCAA
GGACACCTACGACGCCCTTCACATGCAGGCCCTGCCCCCTCGCTAG SEQ ID NO: 43 (amino acid sequence for PSMA(6LH)-CAR, derived from antibody #1366)
MALPVTALLLPLALLLHAARPTVLTQSPAIMSASPGEKVTMTCRASSSVSSSYLHWYQQ
KSSASPKLWIYRTSNLASGVPARFSGSGSGTSYSLTISSLEAEDAATYYCQQYSGYPLTF
GAGTKLELKRGGGGSGGGGSGGGGSVKLQESGPGLVAPSQSLSITCTVSGFSLTDYGVS
WIRQPPGKGLEWLGVIWSDGNTYYNSPLKSRLSINKDNSKSQVFLKMNSLQTDDSAMY
YCARHKVYTMDYWGQGTSVTVSSTTTPAPRPPTPAPTIASQPLSLRPEACRPAAGGAVH -continued

SEQUENCES

TRGLDFACDIYIWAPLAGTCGVLLLSLVITLYCKRGRKKLLYIFKQPFMRPVQTTQEEDG
CSCRFPEEEEGGCELRVKFSRSADAPAYKQGQNQLYNELNLGRREEYDVLDKRRGRDP
EMGGKPRRKNPQEGLYNELQKDKMAEAYSEIGMKGERRRGKHDGLYQGLSTATKDT
YDALHMQALPPR

SEQ ID NO: 44 (nucleic acid sequence for PSMA(7LH)-CAR, derived from antibody #1352)
ATGGCCTTACCAGTGACCGCCTTGCTCCTGCCGCTGGCCTTGCTGCTCCATGCGGCT
CGACCTGACATCGTGATGACACAGTCTCACAAGTTCATGTCCACCTCTGTGGGCGAC
CGGGTGAACATCACATGCAAGGCCAGCCAGGATGTGGGCACCGCAGTGGCCTGGTA
TCAGCAGAAGCCCGGCCAGAGCCCTAAGTTTCTGATCTATTGGGCCTCCACCAGGCA
CACAGGCGTGCCTGACCGCTTCACAGGCAGCGGCTCCGGCACCGACTTCACCCTGA
CAATCTCCAATGTGCAGTCTGAGGACCTGGCCGATTACTTCTGCCACCAGTACACCT
CCTATCCATTCACATTTGGCTCTGGCACCAAGCTGGAGATGAAGAGGGGAGGAGGA
GGCTCCGGCGGAGGAGGCTCTGGCGGCGGCGGCAGCGTGAAGCTGCAGCAGTCCGG
ACCAGAGCTGGAGAAGCCAGGAGCCAGCGTGAAGATCAGCTGTAAGGCCTCTGGCT
ACAGCTTCACAGGCTATAACGTGAATTGGGTGAAGCAGTCTAACGGCAAGAGCCTG
GAGTGGATCGGCAATATCGACCCCTACCACGGCGGCACCACATATAACCAGAAGTT
TGAGGCCAAGGCCACCCTGACAGTGGATAAGAGCAGCAGCACCGCCTACATGCAGC
TGAAGTCCCTGACCTCTGAGGACAGCGCCGTGTACTATTGTGCCCGGAGCAGCCGGT
TTGATTATTGGGGCCAGGGCACCACACTGACCGTGTCTAGCACCACGACGCCAGCG
CCGCGACCACCAACACCGGCGCCCACCATCGCGTCGCAGCCCCTGTCCCTGCGCCCA
GAGGCGTGCCGGCCAGCGGCGGGGGGCGCAGTGCACACGAGGGGGCTGGACTTCG
CCTGTGACATCTACATCTGGGCGCCCCTGGCCGGGACTTGTGGGGTCCTTCTCCTGT
CACTGGTTATCACCCTTTACTGCAAACGGGGCAGAAAGAAACTCCTGTATATATTCA
AACAACCATTTATGAGACCAGTACAAACTACTCAAGAGGAAGATGGCTGTAGCTGC
CGATTTCCAGAAGAAGAAGAAGGAGGATGTGAACTGAGAGTGAAGTTCAGCAGGA
GCGCAGACGCCCCCGCGTACAAGCAGGGCCAGAACCAGCTCTATAACGAGCTCAAT
CTAGGACGAAGAGAGGAGTACGATGTTTTGGACAAGAGACGTGGCCGGGACCCTGA
GATGGGGGGAAAGCCGAGAAGGAAGAACCCTCAGGAAGGCCTGTACAATGAACTG
CAGAAAGATAAGATGGCGGAGGCCTACAGTGAGATTGGGATGAAAGGCGAGCGCC
GGAGGGGCAAGGGGCACGATGGCCTTTACCAGGGTCTCAGTACAGCCACCAAGGAC
ACCTACGACGCCCTTCACATGCAGGCCCTGCCCCCTCGCTAG SEQ ID NO: 45 (amino acid sequence for PSMA(7LH)-CAR, derived from antibody #1352)
MALPVTALLLPLALLLHAARPDIVMTQSHKFMSTSVGDRVNITCKASQDVGTAVAWYQ
QKPGQSPKFLIYWASTRHTGVPDRFTGSGSGTDFTLTISNVQSEDLADYFCHQYTSYPFT
FGSGTKLEMKRGGGGSGGGGSGGGGSVKLQQSGPELEKPGASVKISCKASGYSFTGYN
VNWVKQSNGKSLEWIGNIDPYHGGTTYNQKFEAKATLTVDKSSSTAYMQLKSLTSEDS
AVYYCARSSRFDYWGQGTTLTVSSTTTPAPRPPTPAPTIASQPLSLRPEACRPAAGGAVH
TRQLDFACDIYIWAPLAGTCGVLLLSLVITLYCKRGRKKLLYIFKQPFMRPVQTTQEEDG
CSCRFPEEEEGGCELRVKFSRSADAPAYKQGQNQLYNELNLGRREEYDVLDKRRGRDP
EMGGKPRRKNPQEGLYNELQKDKMAEAYSEIGMKGERRRGKHDGLYQGLSTATKDT
YDALHMQALPPR SEQ ID NO: 46 (nucleic acid sequence for PSMA(8LH)-CAR, derived from antibody #1207)
ATGGCCTTACCAGTGACCGCCTTGCTCCTGCCGCTGGCCTTGCTGCTCCATGCGGCT
CGACCTATCGTGCTGACCCAGAGCCCAGCCATCATGAGCGCCTCCCCAGGAGTGAA
GGTGACCATGACATGCAGGGCCAGCTCCTCTGTGGACAGCTCCTACCTGCACTGGTA
TCAGCAGAAGTCTGGCGCCAGCCCTCAAGTGTGGATCTACTCTACCAGCAACCTGGC
CTCTGGCGTGCCAGCACGCTTCTCCGGCTCTGGCAGCGGCACCTCCTATTCTCTGAC
AATCTCTAGCGTGGAGGCCGAGGATGCCGCCACATACTATTGCCAGCAGTACTCCG
GCTATCCCCTGACCTTTGGCGGCGGCACAAAGCTGGAGATCAAGAGGGGAGGAGGA
GGCAGCGGCGGAGGAGGCTCCGGCGGCGGCGGCTCTGTGAAGCTGCAGCAGAGCG
GACCAGGACTGGTGAAGCCTAGCCAGTCCCTGTCTCTGACCTGTGCCGTGACAGGCT
ACTCCATCACCTCTGACTATGCCTGGAACTGGATCAGAAAGTTCCCCGGCAATAAGC
TGGAGTGGATGGGCTACATCAGCTATTCCGGCAGAACCACATACAATCCTAGCCTG
GAGTCCCGGATCTCTATCACCAGAGACACAAGCAAGAACCAGTTCTTTCTGCAGCTG
AACAGCGTGACCACAGAGGATACCGCCACATACTATTGCGCCAGGTGTTACTATGG
CTCCTCTAGCCGCTGGTACGGCATGGATTATTGGGGCCGGGGCACATCCGTGGCCGT
GTCCTCTACCACGACGCCAGCGCCGCGACCACCAACACCGGCGCCCACCATCGCGT
CGCAGCCCCTGTCCCTGCGCCCAGAGGGCGTGCCGGCCAGCGGCGGGGGGCGCAGTG
CACACGAGGGGGCTGGACTTCGCCTGTGACATCTACATCTGGGCGCCCCTGGCCGG
GACTTGTGGGGTCCTTCTCCTGTCACTGGTTATCACCCTTTACTGCAAACGGGGCAG
AAAGAAACTCCTGTATATATTCAAACAACCATTTATGAGACCAGTACAAACTACTCA
AGAGGAAGATGGCTGTAGCTGCCGATTTCCAGAAGAAGAAGAAGGAGGATGTGAA
CTGAGAGTGAAGTTCAGCAGGAGCGCAGACGCCCCCGCGTACAAGCAGGGCCAGA
ACCAGCTCTATAACGAGCTCAATCTAGGACGAAGAGAGGAGTACGATGTTTTGGAC
AAGAGACGTGGCCGGGACCCTGAGATGGGGGGAAAGCCGAGAAGGAAGAACCCTC
AGGAAGGCCTGTACAATGAACTGCAGAAAGATAAGATGGCGGAGGCCTACAGTGA
GATTGGGATGAAAGGCGAGCGCCGGAGGGGCAAGGGGCACGATGGCCTTTACCAG
GGTCTCAGTACAGCCACCAAGGACACCTACGACGCCCTTCACATGCAGGCCCTGCC
CCCTCGCTAG SEQ ID NO: 47 (PSMA(8LH)-CAR, derived from antibody #1207)
MALPVTALLLPLALLLHAARPIVLTQSPAIMSASPGVKVTMTCRASSSVDSSYLHWYQQ
KSGASPQVWIYSTSNLASGVPARFSGSGSGTSYSLTISSVEAEDAATYYCQQYSGYPLTF
GGGTKLEIKRGGGGSGGGGSGGGGSVKLQQSGPGLVKPSQSLSLTCAVTGYSITSDYA

| SEQUENCES |
| --- |

```
WNWIRKFPGNKLEWMGYISYSGRITYNPSLESRISITRDTSKNQFFLQLNSVTTEDTATY
YCARCYYGSSSRWYGMDYWGRGTSVAVSSTTTPAPRPPTPAPTIASQPLSLRPEACRPA
AGGAVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYDVLD
KRRGRDPEMGGKPRRKNPQEGLYNELQKDKMAEAYSEIGMKGERRRGKGHDGLYQG
LSTATKDTYDALHMQALPPR

SEQ ID NO: 48 (nucleic acid sequence for CD8α signal peptide)
ATGGCCTTACCAGTGACCGCCTTGCTCCTGCCGCTGGCCTTGCTGCTCCACGCCGCC
AGGCCG SEQ ID NO: 49 (amino acid sequence for CD8α signal peptide)
MALPVTALLLPLALLLHAARP SEQ ID NO: 50 (nucleic acid sequence for anti-CD19-scFv)
GACATCCAGATGACACAGACTACATCCTCCCTGTCTGCCTCTCTGGGAGACAGAGTC
ACCATCAGTTGCAGGGCAAGTCAGGACATTAGTAAATATTTAAATTGGTATCAGCA
GAAACCAGATGGAACTGTTAAACTCCTGATCTACCATACATCAAGATTACACTCAG
GAGTCCCATCAAGGTTCAGTGGCAGTGGGTCTGGAACAGATTATTCTCTCACCATTA
GCAACCTGGAGCAAGAAGATATTGCCACTTACTTTTGCCAACAGGGTAATACGCTTC
CGTACACGTTCGGAGGGGGGACTAAGTTGGAAATAACAGGTGGCGGTGGCAGCGGC
GGTGGTGGTTCCGGAGGCGGCGGTTCTGAGGTGAAACTGCAGGAGTCAGGACCTGG
CCTGGTGGCGCCCTCACAGAGCCTGTCCGTCACATGCACTGTCTCAGGGGTCTCATT
ACCCGACTATGGTGTAAGCTGGATTCGCCAGCCTCCACGAAAGGGTCTGGAGTGGC
TGGGAGTAATATGGGGTAGTGAAACCACATACTATAATTCAGCTCTCAAATCCAGA
CTGACCATCATCAAGGACAACTCCAAGAGCCAAGTTTTCTTAAAAATGAACAGTCT
GCAAACTGATGACACAGCCATTTACTACTGTGCCAAACATTATTACTACGGTGGTAG
CTATGCTATGGACTACTGGGGTCAAGGAACCTCAGTCACCGTCTCCTCA SEQ ID NO: 51 (amino acid sequence for anti-CD19-scFv)
DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGGSGGGGSGGG
GSEVKLQESGPGLVAPSQSLSVTCTVSGVSLPDYGVSWIRQPPRKGLEWLGVIWGSETT
YYNSALKSRLTIIKDNSKSQVFLKMNSLQTDDTAIYYCAKHYYYGGSYAMDYWGQGT
SVTVSS SEQ ID NO: 52 (nucleic acid sequence for CD8α transmembrane)
ACCACGACGCCAGCGCCGCGACCACCAACACCGGCGCCCACCATCGCGTCGCAGCC
CCTGTCCCTGCGCCCAGAGGCGTGCCGGCCAGCGGCGGGGGGCGCAGTGCACACGA
GGGGGCTGGACTTCGCCTGTGATATCTACATCTGGGCGCCCCTGGCCGGGACTTGTG
GGGTCCTTCTCCTGTCACTGGTTATCACCCTTTACTGC SEQ ID NO: 53 (amino acid sequence for CD8α transmembrane)
TTTPAPRPPTPAPTIASQPLSLRPEACRPAAGGAVHTRGLDFACDIYIWAPLAGTCGVLLL
SLVITLYC SEQ ID NO: 54 (nucleic acid sequence for 4-1BB)
AAACGGGGCAGAAAGAAACTCCTGTATATATTCAAACAACCATTTATGAGACCAGT
ACAAACTACTCAAGAGGAAGATGGCTGTAGCTGCCGATTTCCAGAAGAAGAAGAAG
GAGGATGTGAACTG SEQ ID NO: 55 (nucleic acid sequence for CD3zeta)
GAGTGAAGTTCAGCAGGAGCGCAGACGCCCCCGCGTACAAGCAGGGCCAGAACCA
GCTCTATAACGAGCTCAATCTAGGACGAAGAGAGGAGTACGATGTTTTGGACAAGA
GACGTGGCCGGGACCCTGAGATGGGGGGGAAAGCCGAGAAGGAAGAACCCTCAGGA
AGGCCTGTACAATGAACTGCAGAAAGATAAGATGGCGGAGGCCTACAGTGAGATTG
GGATGAAAGGCGAGCGCCGGAGGGGCAAGGGGCACGATGGCCTTTACCAGGGTCT
CAGTACAGCCACCAAGGACACCTACGACGCCCTTCACATGCAGGCCCTGCCCCCTC
GC SEQ ID NO: 56 (nucleic acid sequence for T2A)
GAGGGCAGAGGCAGCCTGCTGACATGTGGCGACGTTGAAGAGAATCCTGGGCCC SEQ ID NO: 57 (nucleic acid sequence for IRF4 of the IRF4-CAR construct)
ATGAACCTGGAGGGCGGCGGCCGAGGCGGAGAGTTCGGCATGAGCGCGGTGAGCT
GCGGCAACGGGAAGCTCCGCCAGTGGCTGATCGACCAGATCGACAGCGGCAAGTAC
CCCGGGCTGGTGTGGGAGAACGAGGAGAAGAGCATCTTCCGCATCCCCTGGAAGCA
CGCGGGCAAGCAGGACTACAACCGCGAGGAGGACGCCGCGCTCTTCAAGGCTTGGG
CACTGTTTAAAGGAAAGTTCCGAGAAGGCATCGACAAGCCGGACCCTCCCACCTGG
AAGACGCGCCTGCGGTGCGCTTTGAACAAGAGCAATGACTTTGAGGAACTGGTTGA
GCGGAGCCAGCTGGACATCTCAGACCCGTACAAAGTGTACAGGATTGTTCCTGAGG
GAGCCAAAAAGGAGCCAAGCAGCTCACCTTGGAGGACCCGCAGATGTCCATGAGC
CACCCCTACACCATGACAACGCCTTACCCTTCGCTCCCAGCCCAGCAGGTTCACAAC
TACATGATGCCACCCCTCGACCGAAGCTGGAGGGACTACGTCCCGGATCAGCCACA
CCCGGAAATCCCGTACCAATGTCCCATGACGTTTGGACCCCGCGGCCACCACTGGCA
AGGCCCAGCTTGTGAAAATGGTTGCCAGGTGACAGGAACCTTTTATGCTTGTGCCCC
ACCTGAGTCCCAGGCTCCCGGAGTCCCCACAGAGCCAAGCATAAGGTCTGCCGAAG
```

SEQUENCES

CCTTGGCGTTCTCAGACTGCCGGCTGCACATCTGCCTGTACTACCGGGAAATCCTCG
TGAAGGAGCTGACCACGTCCAGCCCCGAGGGCTGCCGGATCTCCCATGGACATACG
TATGACGCCAGCAACCTGGACCAGGTCCTGTTCCCCTACCCAGAGGACAATGGCCA
GAGGAAAAACATTGAGAAGCTGCTGAGCCACCTGGAGAGGGGCGTGGTCCTCTGGA
TGGCCCCCGACGGGCTCTATGCGAAAAGACTGTGCCAGAGCAGGATCTACTGGGAC
GGGCCCCTGGCGCTGTGCAACGACCGGCCCAACAAACTGGAGAGAGACCAGACCTG
CAAGCTCTTTGACACACAGCAGTTCTTGTCAGAGCTGCAAGCGTTTGCTCACCACGG
CCGCTCCCTGCCAAGATTCCAGGTGACTCTATGCTTTGGAGAGGAGTTTCCAGACCC
TCAGAGGCAAAGAAAGCTCATCACAGCTCACGTAGAACCTCTGCTAGCCAGACAAC
TATATTATTTTGCTCAACAAAACAGTGGACATTTCCTGAGGGGCTACGATTTACCAG
AACACATCAGCAATCCAGAAGATTACCACAGATCTATCCGCCATTCCTCTATTCAAG
AATGA

SEQ ID NO: 58 (amino acid sequence for IRF4 of the IRF4-CAR construct)
MNLEGGGRGGEFGMSAVSCGNGKLRQWLIDQIDSGKYPGLVWENEEKSIFRIPWKHAG
KQDYNREEDAALFKAWALFKGKFREGIDKPDPPTWKTRLRCALNKSNDFEELVERSQL
DISDPYKVYRIVPEGAKKGAKQLTLEDPQMSMSHPYTMTTPYPSLPAQQVHNYMMPPL
DRSWRDYVPDQPHPEIPYQCPMTFGPRGHHWQGPACENGCQVTGTFYACAPPESQAPG
VPTEPSIRSAEALAFSDCRLHICLYYREILVKELTTSSPEGCRISHGHTYDASNLDQVLFPY
PEDNGQRKNIEKLLSHLERGVVLWMAPDGLYAKRLCQSRIYWDGPLALCNDRPNKLER
DQTCKLFDTQQFLSELQAFAHHGRSLPRFQVTLCFGEEFPDPQRQRKLITAHVEPLLARQ
LYYFAQQNSGHFLRGYDLPEHISNPEDYHRSIRHSSIQE SEQ ID NO: 59 (nucleic acid sequence for IRF-4-CD19-CAR; CD8α signal peptide-
anti-CD19-scFv-CD8α transmembrane-4-1BB-CD3zeta-T2A-IRF4)
ATGGCCTTACCAGTGACCGCCTTGCTCCTGCCGCTGGCCTTGCTGCTCCACGCCGCC
AGGCCGgacatccagatgacacagactacatcctccctgtctgcctctctgggagacagagt
caccatcagttgcagggcaagtcaggacattagtaaatatttaaattggtatcagcaga
aaccagatggaactgttaaactcctgattaccatacatcaagattacactcaggagtccc
atcaaggttcagtggcagtgggtctggaacagattattctctcaccattagcaacct
ggagcaagaagatattgccacttacttttgccaacagggtaatacgcttccgtacacgt
tcggaggggggactaagttggaaataacaggtggcggtggcagcggcggtggtggttccggaggcgg
cggttctgaggtgaaactgcaggagtcaggacctggcctggtggcgccctcacagagcct
gtccgtcacatgcactgtctcaggggtctcattacccgactatggtaagctggattcg
ccagcctccacgaaagggtctggagtggctgggagtaatatggggtagtgaaaccacatacta
taattcagctctcaaatccagactgaccatcatcaaggacaactccaagagccaagttttctt
aaaaatgaacagtctgcaaactgatgacacagccatttactactgtgccaaaca
ttattactacggtggtagctatgctatggactactggggtcaaggaacctcagtcaccgtctcctcaAC
CACGACGCCAGCGCCGCGACCACCAACACCGGCGCCCACCATCGCGTCGCAGCCCC
TGTCCCTGCGCCCAGAGGCGTGCCGGCCAGCGGCGGGGGGCGCAGTGCACACGAGG
GGGCTGGACTTCGCCTGTGATATCTACATCTGGGCGCCCCTGGCCGGGACTTGTGGG
GTCCTTCTCCTGTCACTGGTTATCACCCTTTACTGCaaacggggcagaaaga
aactcctgtatatattcaaacaaccatttatgagaccagtacaaactactcaagagg
aagatggctgtagctgccgatttccagaagaagaagaaggaggatgtgaactg
AGAGTGAAGTTCAGCAGGAGCGCAGACGCCCCCCGCGTACAAGCAGGGCCAGAACC
AGCTCTATAACGAGCTCAATCTAGGACGAAGAGAGGAGTACGATGTTTTGGACAAG
AGACGTGGCCGGGACCCTGAGATGGGGGGAAAGCCGAGAAGGAAGAACCCTCAGG
AAGGCCTGTACAATGAACTGCAGAAAGATAAGATGGCGGAGGCCTACAGTGAGATT
GGGATGAAAGGCGAGCGCCGGAGGGGCAAGGGGCACGATGGCCTTTACCAGGGTC
TCAGTACAGCCACCAAGGACACCTACGACGCCCTTCACATGCAGGCCCTGCCCCCTC
GCgagggcagaggcagctgctgacatgtggcgacgttgaagagaatcctgggcccATGAACCTGGAGG
GCGGCGGCCGAGGCGGAGAGTTCGGCATGAGCGCGGTGAGCTGCGGCAACGGGAAGCTCCG
CCAGTGGCTGATCGACCAGATCGACAGCGGCAAGTACCCCGGGCTGGTGTGGGAGA
ACGAGGAGAAGAGCATCTTCCGCATCCCCTGGAAGCACGCGGGCAAGCAGGACTAC
AACCGCGAGGAGGACGCCGCGCTCTTCAAGGCTTGGGCACTGTTTAAAGGAAAGTT
CCGAGAAGGCATCGACAAGCCGGACCCTCCCACCTGGAAGACGCGCCTGCGGTGCG
CTTTGAACAAGAGCAATGACTTTGAGGAACTGGTTGAGCGGAGCCAGCTGGACATC
TCAGACCCGTACAAAGTGTACAGGATTGTTCCTGAGGGAGCCAAAAAAGGAGCCAA
GCAGCTCACCTTGGAGGACCCGCAGATGTCCATGAGCCACCCCTACACCATGACAA
CGCCTTACCCTTCGCTCCCAGCCCAGCAGGTTCACAACTACATGATGCCACCCCTCG
ACCGAAGCTGGAGGGACTACGTCCCGGATCAGCCACACCCGGAAATCCCGTACCAA
TGTCCCATGACGTTTGGACCCCGCGGCCACCACTGGCAAGGCCCAGCTTGTGAAAAT
GGTTGCCAGGTGACAGGAACCTTTTATGCTTGTGCCCCACCTGAGTCCCAGGCTCCC
GGAGTCCCCACAGAGCCAAGCATAAGGTCTGCCGAAGCCTTGGCGTTCTCAGACTG
CCGGCTGCACATCTGCCTGTACTACCGGGAAATCCTCGTGAAGGAGCTGACCACGTC
CAGCCCCGAGGGCTGCCGGATCTCCCATGGACATACGTATGACGCCAGCAACCTGG
ACCAGGTCCTGTTCCCCTACCCAGAGGACAATGGCCAGAGGAAAAACATTGAGAAG
CTGCTGAGCCACCTGGAGAGGGGCGTGGTCCTCTGGATGGCCCCCGACGGGCTCTA
TGCGAAAAGACTGTGCCAGAGCAGGATCTACTGGGACGGGCCCCTGGCGCTGTGCA
ACGACCGGCCCAACAAACTGGAGAGAGACCAGACCTGCAAGCTCTTTGACACACAG
CAGTTCTTGTCAGAGCTGCAAGCGTTTGCTCACCACGGCCGCTCCCTGCCAAGATTC
CAGGTGACTCTATGCTTTGGAGAGGAGTTTCCAGACCCTCAGAGGCAAAGAAAGCT
CATCACAGCTCACGTAGAACCTCTGCTAGCCAGACAACTATATTATTTTGCTCAACA
AAACAGTGGACATTTCCTGAGGGGCTACGATTTACCAGAACACATCAGCAATCCAG
AAGATTACCACAGATCTATCCGCCATTCCTCTATTCAAGAATGA

SEQUENCES

SEQ ID NO: 60 (amino acid sequence for IRF-4-CD19-CAR; CD8α signal peptide-
anti-CD19-scFv-CD8 transmembrane-4-1BB-CD3zeta-T2A-IRF4)
MALPVTALLLPLALLLHAARPDIQMTQTTSSLSASLGDRVTISCRASQDISKYLNWYQ
QKPDGTVKLLIYHTSRLHSGVPSRFSGSGSGTDYSLTISNLEQEDIATYFCQQGNTL
PYTFGGGTKLEITGGGGSGGGGSGGGGSEVKLQESGPGLVAPSQSLSVTCTVSGVS
LPDYGVSWIRQPPRKGLEWLGVIWGSETTYYNSALKSRLTHIKDNSKSQVFLKMNS
LQTDDTAIYYCAKHYYYGGSYAMDYWGQGTSVTVSSTTTPAPRPPTPAPTIASQPLSL
RPEACRPAAGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYKQGQNQLYNELN
LGRREEYDVLDKRRGRDPEMGGKPRRKNPQEGLYNELQKDKMAEAYSEIGMKGERRR
GKGHDGLYQGLSTATKDTYDALHMQALPPREGRGSLLTCGDVEENPGPMNLEGGGR
GGEFGMSAVSCGNGKLRQWLIDQIDSGKYPGLVWENEEKSIFRIPWKHAGKQDYNREE
DAALFKAWALFKGKFREGIDKPDPPTWKTRLRCALNKSNDFEELVERSQLDISDPYKVY
RIVPEGAKKGAKQLTLEDPQMSMSHPYTMTTPYPSLPAQQVHNYMMPPLDRSWRDYV
PDQPHPEIPYQCPMTFGPRGHHWQGPACENGCQVTGTFYACAPPESQAPGVPTEPSIRSA
EALAFSDCRLHICLYYREILVKELTTSSPEGCRISHGHTYDASNLDQVLFPYPEDNGQRK
NIEKLLSHLERGVVLWMAPDGLYAKRLCQSRIYWDGPLALCNDRPNKLERDQTCKLFD
TQQFLSELQAFAHHGRSLPRFQVTLCFGEEFPDPQRQRKLITAHVEPLLARQLYYFAQQ
NSGHFLRGYDLPEHISNPEDYHRSIRHSSIQE SEQ ID NO: 61 (nucleic acid sequence for PSMA(445)-svFv of IRF4-PSMA(445)-CAR
construct)
GTCCAGCTCCAACAGCCGGGTGCTGCACTGGTTCGGCCAGGAGCTTCAGTGAGGCT
GTCCTGCAAGGCTTCTGGATACTCCTTCACCTACTACTGGATGAACTGGGTGATGCA
GAGGCCTGGCCAAGGCCTTGAGTGGATTGGCATGATTCATCCTTCCGATAGTGAAAC
TCGGTTAAGTCAGAAGTTCAGGGACAAGGCCACATTGACTGTAGACAAATCTTCCA
GCACAGTCTACATGCAACTCAACAGCCCGACATCTGATGACTCTGCAGTCTATTACT
GTGCAAGAGATGGTAACTTCCCTTACTATGCACTAGACTACTGGGGTCAAGGAACCT
CGGTCACCGTCTCCTCAGGTGGCGGTGGCAGCGGCGGTGGTGGTTCCGGAGGCGGC
GGTTCTGATGTTGTGCTGACCCAAGCTCCACTCTCCCTGCCTGTCAGTCTTGGAGATC
AAGCCTCCATCTCTTGCAGATCTAGTCAGAGCCTTGAATACAGTAATGGAAACACCT
ATTTACATTGGTACCTGCAGAAGCCAGGCCAGTCTCCAGAACTCCTGATCTACACAG
TTTCCAACCGATTTTCTGGGGTCCCAGACAGGTTCAGTGGCAGTGGATCAGGGACAG
ATTTCACACTCAAGATTCACAGAGTGGAGGCTGAGGATCTGGGAGTTTATTTCTGCT
CTCAAAGTACACATGTTCCCACGTTCGGAGGGGGGACCAAGCTGGAGATAAAACGG SEQ ID NO: 62 (amino acid sequence for PSMA(445)-svFv of IRF4-PSMA(445)-CAR
construct)
VQLQQPGAALVRPGASVRLSCKASGYSFTYYWMNWVMQRPGQGLEWIGMIHPSDSET
RLSQKFRDKATLIVDKSSSTVYMQLNSPTSDDSAVYYCARDGNFPYYALDYWGQGTS
VTVSSGGGGSGGGGSGGGGSDVVLTQAPLSLPVSLGDQASISCRSSQSLEYSNGNTYLH
WYLQKPGQSPELLIYTVSNRFSGVPDRFSGSGSGTDFTLKIHRVEAEDLGVYFCSQSTHV
PTFGGGTKLEIKR SEQ ID NO: 63 (nucleic acid sequence for IRF4-PSMA(445)-CAR; CD8α signal
peptide-PSMA (445)-scFv-CD8 transmembrane-4-1BB-CD3zeta-T2A-IRF4)
ATGGCCTTACCAGTGACCGCCTTGCTCCTGCCGCTGGCCTTGCTGCTCCATGCGGCT
CGACCTgtccagctccaacagccgggtgctgcactggttcggccaggagcttcagtgaggctgtcc
tgcaaggcttctggatactccttcacctactactggatgaactgggtgatgcagaggc
ctggccaaggccttgagtggattggcatgattcatccttccgatagtgaaactcggt
taagtcagaagttcagggacaaggccacattgactgtagacaaatcttccagcacagtc
tacatgcaactcaacagcccgacatctgatgactctgcagtctattactgtgcaagagatg
gtaacttcccttactatgcactagactactggggtcaaggaacctcggtcaccgtctcctcaggtg
gcggtggcagcggcggtggtggttccggaggcggcggttctgatgttgtgctgaccca
agctccactctccctgcctgtcagtcttggagatcaagcctccatctcttgcagatctagt
cagagccttgaatacagtaatggaaacacctatttacattggtacctgcagaagccaggccagtctc
cagaactcctgatctacacagtttccaaccgattttctggggtcccagacaggtt
cagtggcagtggatcagggacagatttcacactcaagattcacagagtggaggctgaggatc
tgggagtttatttctgctctcaaagtacacatgttcccacgttcggagggggg
aaacggACCACGACGCCAGCGCCGCGACCACCAACACCGGCGCCCACCATCGCGTCGC
AGCCCCTGTCCCTGCGCCCAGAGGCGTGCCGGCCAGCGGCGGGGGGCGCAGTGCAC
ACGAGGGGGCTGGACTTCGCCTGTGATATCTACATCTGGGCGCCCCTGGCCGGGACT
TGTGGGGTCCTTCTCCTGTCACTGGTTATCACCCTTTACTGCaaacggggca
gaaagaaactcctgtatatattcaaacaaccatttatgagaccagtacaaa
ctactcaagaggaagatggctgtagetgccgatttccagaagaagaagaaggagg
atgtgaactgAGAGTGAAGTTCAGCAGGAGCGCAGACGCCCCCGCGTACAAGCAGGGCC
AGAACCAGCTCTATAACGAGCTCAATCTAGGACGAAGAGAGGAGTACGATGTTTTG
GACAAGAGACGTGGCCGGGACCCTGAGATGGGGGGAAAGCCGAGAAGGAAGAACC
CTCAGGAAGGCCTGTACAATGAACTGCAGAAAGATAAGATGGCGGAGGCCTACAGT
GAGATTGGGATGAAAGGCGAGCGCCGGAGGGGCAAGGGGCACGATGGCCTTTACC
AGGGTCTCAGTACAGCCACCAAGGACACCTACGACGCCCTTCACATGCAGGCCCTG
CCCCCTCGCgagggcagaggcagcctgctgacatgtggcgacgttgaagagaatcctgggcccATGAACCTGGAGG
GCGGCGGCCGAGGCGGAGAGTTCGGCATGAGCGCGGTGAGCTGCGGCAACGGGAA
GCTCCGCCAGTGGCTGATCGACCAGATCGACAGCGGCAAGTACCCCGGGCTGGTGT
GGGAGAACGAGGAGAAGAGCATCTTCCGCATCCCCTGGAAGCACGCGGGCAAGCA
GGACTACAACCGCGAGGAGGACGCCGCGCTCTTCAAGGCTTGGGCACTGTTTAAAG
GAAAGTTCCGAGAAGGCATCGACAAGCCGGACCCTCCCACCTGGAAGACGCGCCTG -continued

---

SEQUENCES

```
CGGTGCGCTTTGAACAAGAGCAATGACTTTGAGGAACTGGTTGAGCGGAGCCAGCT
GGACATCTCAGACCCGTACAAAGTGTACAGGATTGTTCCTGAGGGAGCCAAAAAG
GAGCCAAGCAGCTCACCTTGGAGGACCCGCAGATGTCCATGAGCCACCCCTACACC
ATGACAACGCCTTACCCTTCGCTCCCAGCCCAGCAGGTTCACAACTACATGATGCCA
CCCCTCGACCGAAGCTGGAGGGACTACGTCCCGGATCAGCCACACCCGGAAATCCC
GTACCAATGTCCCATGACGTTTGGACCCCGCGGCCACCACTGGCAAGGCCCAGCTTG
TGAAAATGGTTGCCAGGTGACAGGAACCTTTTATGCTTGTGCCCCACCTGAGTCCCA
GGCTCCCGGAGTCCCCACAGAGCCAAGCATAAGGTCTGCCGAAGCCTTGGCGTTCT
CAGACTGCCGGCTGCACATCTGCCTGTACTACCGGGAAATCCTCGTGAAGGAGCTG
ACCACGTCCAGCCCCGAGGGCTGCCGGATCTCCCATGGACATACGTATGACGCCAG
CAACCTGGACCAGGTCCTGTTCCCCTACCCAGAGGACAATGGCCAGAGGAAAAACA
TTGAGAAGCTGCTGAGCCACCTGGAGAGGGGCGTGGTCCTCTGGATGGCCCCCGAC
GGGCTCTATGCGAAAAGACTGTGCCAGAGCAGGATCTACTGGGACGGGCCCCTGGC
GCTGTGCAACGACCGGCCCAACAAACTGGAGAGAGACCAGACCTGCAAGCTCTTTG
ACACACAGCAGTTCTTGTCAGAGCTGCAAGCGTTTGCTCACCACGGCCGCTCCCTGC
CAAGATTCCAGGTGACTCTATGCTTTGGAGAGGAGTTTCCAGACCCTCAGAGGCAA
AGAAAGCTCATCACAGCTCACGTAGAACCTCTGCTAGCCAGACAACTATATTATTTT
GCTCAACAAACAGTGGACATTTCCTGAGGGGCTACGATTTACCAGAACACATCAG
CAATCCAGAAGATTACCACAGATCTATCCGCCATTCCTCTATTCAAGAATGA
```

SEQ ID NO: 64 (amino acid sequence for IRF4-PSMA(445)-CAR; CD8α signal peptide-PSMA
(445)-scFv-CD8α transmembrane-4-1BB-CD3zeta-T2A-IRF4)
MALPVTALLLPLALLLHAARPVQLQQPGAALVRPGASVRLSCKASGYSFTYYWMN
WVMQRPGQGLEWIGMIHPSDSETRLSQKFRDKATLTVDKSSSTVYMQLNSPTSDD
SAVYYCARDGNFPYYALDYWGQGTSVTVSSGGGGSGGGGSGGGGSDVVLTQAPL
SLPVSLGDQASISCRSSQSLEYSNGNTYLHWYLQKPGQSPELLIYTVSNRFSGVPDR
FSGSGSGTDFTLKIHRVEAEDLGVYFCSQSTHVPTFGGGTKLEIKR**TTTPAPRPPTPA
PTIASQPLSLRPEACRPAAGGAVHTRGLDFACDIYIWAPLAGTCGVLLLSLVITLYC**KRG
RKKLLYIFKQPFMRPVQTTQEEDGCSCRFPEEEEGGCELRVKFSRSADAPAYKQGQ
NQLYNELNLGRREEYDVLDKRRGRDPEMGGKPRRKNPQEGLYNELQKDKMAEAYSEI
GMKGERRRGKGHDGLYQGLSTATKDTYDALHMQALPPREGRGSLLTCGDVEENPGP
MNLEGGGRGGEFGMSAVSCGNGKLRQWLIDQIDSGKYPGLVWENEEKSIFRIPWKHAG
KQDYNREEDAALFKAWALFKGKFREGIDKPDPPTWKTRLRCALNKSNDFEELVERSQL
DISDPYKVYRIVPEGAKKGAKQLTLEDPQMSMSHPYTMTTPYPSLPAQQVHNYMMPPL
DRSWRDYVPDQPHPEIPYQCPMTFGPRGHHWQGPACENGCQVTGTFYACAPPESQAPG
VPTEPSIRSAEALAFSDCRLHICLYYREILVKELTTSSPEGCRISHGHTYDASNLDQVLFPY
PEDNGQRKNIEKLLSHLERGVVLWMAPDGLYAKRLCQSRIYWDGPLALCNDRPNKLER
DQTCKLFDTQQFLSELQAFAHHGRSLPRFQVTLCFGEEFPDPQRQRKLITAHVEPLLARQ
LYYFAQQNSGHFLRGYDLPEHISNPEDYHRSIRHSSIQE

---

What is claimed is:

1. A recombinant nucleic acid sequence encoding a chimeric antigen receptor (CAR), wherein the CAR comprises a CD3 zeta signaling domain, a costimulatory signaling domain, a transmembrane domain, and a prostate-specific membrane antigen (PSMA) binding domain, wherein the PSMA binding domain comprises a heavy chain variable region (VH) and a light chain variable region (VL), wherein the VH and VL comprise the amino acid sequences of SEQ ID NOs: 12 and 14, 16 and 18, 20 and 22, 24 and 26, or 28 and 30, respectively.

2. The recombinant nucleic acid sequence of claim 1, wherein the VH and VL are encoded by the nucleic acid sequences of SEQ ID NOs: 11 and 13, 15 and 17, 19 and 21, 23 and 25, or 27 and 29, respectively.

3. The recombinant nucleic acid sequence of claim 1, wherein the PSMA binding domain is an antibody or an antigen-binding fragment thereof.

4. The recombinant nucleic acid sequence of claim 3, wherein the antigen-binding fragment is a single-chain variable fragment (scFv).

5. The recombinant nucleic acid sequence of claim 1, wherein the costimulatory signaling domain is 4-1BB.

6. The recombinant nucleic acid sequence of claim 1, wherein the CAR further comprises a CD8a domain.

7. The recombinant nucleic acid sequence of claim 1, wherein the CAR comprises the amino acid sequence of SEQ ID NO: 2, 4, 6, 8, 10, 39, 41, 43, 45, or 47.

8. The recombinant nucleic acid sequence of claim 1 comprising the nucleic acid sequence of SEQ ID NO: 1, 3, 5, 7, 9, 38, 40, 42, 44, or 46.

9. The recombinant nucleic acid sequence of claim 1, further encoding interferon regulatory factor 4 (IRF4) or a dominant negative TGFB receptor (TGFBRDN).

10. The recombinant nucleic sequence of claim 9 comprising the nucleic acid sequence of SEQ ID NO: 63.

11. The recombinant nucleic acid sequence of claim 1 further comprising one or more promoters.

12. The recombinant nucleic acid sequence of claim 11, wherein the one or more promoters are selected from group consisting of an EF1α promoter, a PGK promoter, a CMV promoter, or a CAG promoter.

13. A vector comprising the recombinant nucleic acid sequence of claim 1.

14. A genetically modified T cell comprising the vector of claim 13.

15. A genetically modified natural killer (NK) cell comprising a recombinant nucleic acid sequence encoding a chimeric antigen receptor (CAR) of claim 1.

* * * * *